(12) United States Patent
Xiao et al.

(10) Patent No.: US 7,354,922 B2
(45) Date of Patent: Apr. 8, 2008

(54) BRIDGED RING NK₁ ANTAGONISTS

(75) Inventors: Dong Xiao, Warren, NJ (US); Anandan Palani, Bridgewater, NJ (US); Cheng Wang, Summit, NJ (US); Hon-Chung Tsui, East Brunswick, NJ (US); Xianhai Huang, Warren, NJ (US); Sapna S. Shah, Jamesburg, NJ (US); Ashwin U. Rao, Avenel, NJ (US); Xiao Chen, Edison, NJ (US); Sunil Paliwal, Monroe Township, NJ (US); Neng-Yang Shih, Warren, NJ (US)

(73) Assignee: Schering Corporation, Kenilworth, NJ (US)

( * ) Notice: Subject to any disclaimer, the term of this patent is extended or adjusted under 35 U.S.C. 154(b) by 0 days.

(21) Appl. No.: 11/291,363

(22) Filed: Dec. 1, 2005

(65) Prior Publication Data

US 2006/0258665 A1    Nov. 16, 2006

Related U.S. Application Data

(60) Provisional application No. 60/635,971, filed on Dec. 14, 2004.

(51) Int. Cl.
| | |
|---|---|
| A01N 43/58 | (2006.01) |
| A01N 43/60 | (2006.01) |
| C07D 245/00 | (2006.01) |
| C07D 241/36 | (2006.01) |
| C07D 471/00 | (2006.01) |

(52) U.S. Cl. .................. 514/249; 540/460; 544/349
(58) Field of Classification Search .............. 540/460; 514/249; 544/349
See application file for complete search history.

(56) References Cited

U.S. PATENT DOCUMENTS

| | | |
|---|---|---|
| 5,620,989 A | 4/1997 | Harrison et al. |
| 5,661,162 A | 8/1997 | MacLeod et al. |
| 5,760,018 A | 6/1998 | Baker et al. |
| 6,329,401 B1 | 12/2001 | Mendel et al. |

OTHER PUBLICATIONS

West, Anthony R., Solid State Chemistry and its Applications, Wiley, New York, 1988, pp. 358 & 365.*
Ahmed et al., Journal of Medicinal Chemistry, 1976, vol. 19, pp. 117-122.*
Saria et al., European Journal of Pharmacology, 1999, vol. 375, pp. 51-60.*
Wu, X., et al., "Generation of Cyclopenta[c]piperidines and Pyrrolo(3,4-c)piperidines-Potential Substance P Antagonists-from Adducts of Cyclic Dienophiles and 5-Chloro-6-methyl-3-phenyl-2H-1,4-oxazin-2-one", Tetrahedron, 56, 6279-6290 (2000).
Rombouts, F., et al. "Synthesis and conformational analysis of Substance P antagonist analogues based on a 1,7-nephthyridine scaffold", Tetrahedron, 59, 4721-4731 (2003).
PCT International Search Report dated Mar. 30, 2006 for Corresponding PCT Application No. PCT/US2005/044647.

* cited by examiner

*Primary Examiner*—Margaret D. Seaman
*Assistant Examiner*—Niloofar Rahmani
(74) *Attorney, Agent, or Firm*—Serena Farquharson-Torres; Thomas A. Blinka

(57) ABSTRACT

A compound having the general structure shown in Formula (I):

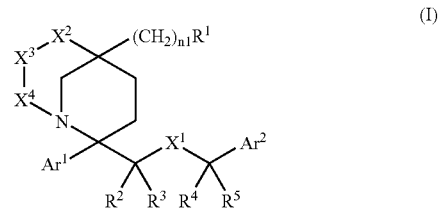

or pharmaceutically acceptable salts and/or solvates thereof are useful in treating diseases or conditions mediated by NK₁ receptors, for example various physiological disorders, symptoms or diseases, including emesis, depression, anxiety and cough.

30 Claims, No Drawings

US 7,354,922 B2

BRIDGED RING NK₁ ANTAGONISTS

This application claims the benefit of U.S. Provisional Application No. 60/635,971 filed Dec. 14, 2004.

FIELD OF THE INVENTION

The present invention relates to novel neurokinin-1 ($NK_1$ or NK-1) receptor antagonists, pharmaceutical compositions comprising such compounds, and methods of treatment using such compounds, to treat $NK_1$ receptor mediated diseases and conditions, including, for example, emesis, depression, anxiety and cough.

BACKGROUND OF THE INVENTION

Tachykinins are peptide ligands for neurokinin receptors. Neurokinin receptors, such as $NK_1$, $NK_2$ and $NK_3$, are involved in a variety of biological processes. They can be found in a mammal's nervous and circulatory systems, as well as in peripheral tissues. Consequently, the modulation of these types of receptors has been studied to potentially treat or prevent various mammalian disease states. For instance, $NK_1$ receptors have been reported to be involved in microvascular leakage and mucus secretion. Representative types of neurokinin receptor antagonists and the disorders that can be treated with them include, for example, sleep, pain, migraine, emesis, nociception and inflammation; see, for example, U.S. Pat. Nos. 6,329,401, 5,760,018, 5,620,989, 5,760,018, 5,661,162, 5,620,989, Wu et al., *Tetrahedron*, 56, 6279-6290 (2000), Rombouts et al., *Tetrahedron*, 59, 4721-4731 (2003), and Rogiers et al., *Tetrahedron*, 57, 8971-8981 (2001).

It would be beneficial to provide a $NK_1$ antagonist that is potent, selective, and possesses beneficial therapeutic and pharmacological properties, and good metabolic stability. It would further be beneficial to provide a $NK_1$ antagonist that is effective for treating a variety of physiological disorders, symptoms and diseases, while minimizing side effects. This invention provides such $NK_1$ antagonists.

SUMMARY OF THE INVENTION

In one embodiment, the present invention is directed to a compound of Formula (I):

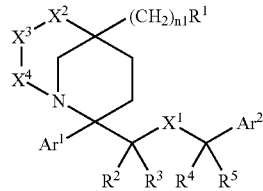

(I)

or a pharmaceutically acceptable salt, solvate and/or ester thereof, wherein:

$Ar^1$ and $Ar^2$ are each independently selected from the group consisting of aryl substituted with 0 to 3 substituents $R^6$ and heteroaryl substituted with 0 to 3 substituents $R^6$;

$X^1$ is —O— or —N($R^7$)—;
$X^2$ is —O—, —N($R^8$)—, or —C($R^9$)$_2$—;
$X^3$ is —C($R^9$)$_2$—, —C(O)—, or —C(=N—$R^{10}$)—;
$X^4$ is —N($R^{11}$)— or —C($R^9$)$_2$—;

with the proviso that when $X^3$ is —C($R^9$)$_2$—, at least one of $X^2$ and $X^4$ is also —C($R^9$)$_2$—;

n1 is an integer of from 0 to 4;

$R^1$ is selected from the group consisting of H, —OH, alkyl, alkyl substituted with one or more hydroxyl groups, —O-alkyl, —O-alkyl-cycloalkyl, heteroaryl or aryl substituted with 0 to 3 substituents $R^6$, —N($R^7$)$_2$, —N($R^{11}$)C(O)$R^{12}$, heterocyclyl substituted with 0 to 3 substituents $R^{13}$, —N($R^{11}$)C(O)N($R^{14}$)$_2$, —OC(O)N($R^{14}$)$_2$, —C(O)N($R^{14}$)$_2$, —C(O)$R^{12}$, —OC(O)$R^{12}$, —C(O)O$R^{15}$, —CN, —CH$_2$N$_3$, —O-alkyl-aryl, —O—N=C($R^{12}$)$_2$, —S—$R^{12}$, —S(O)—$R^{12}$, —S(O$_2$)—$R^{12}$, and N($R^{11}$)S(O$_2$)—$R^{12}$; or when $X^2$ is —N($R^8$)—, $R^1$ and $R^8$ together can form a group $X^5$ as shown in Formula (IA):

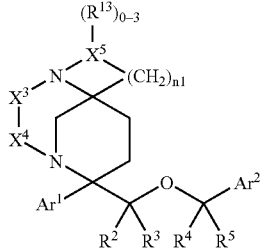

(IA)

wherein $X^5$ is selected from the group consisting of —C(O)—, —(CH$_2$)$_{n2}$—O—, —(CH$_2$)$_{n2}$—, —(CH$_2$)$_{n2}$—C(O)—N($R^{13}$)—, —(CH$_2$)$_{n2}$—N($R^{13}$)—, and —C(O)—N($R^{13}$)—C(O)—;

n2 is an integer of from 1 to 3;

with the proviso that:
(a) when $X^5$ is —C(O)—, n1 is 2 or 3;
(b) when $X^5$ is —(CH$_2$)$_{n2}$—O—, n2 is 2 or 3; and
(c) when $X^5$ is —(CH$_2$)$_{n2}$—, n1 is 2 or 3;

$R^2$, $R^3$, $R^4$, and $R^5$ are each independently selected from the group consisting of H, alkyl, haloalkyl, cycloalkyl, heterocyclyl substituted with 0 to 3 substituents $R^{13}$, and aryl or heteroaryl substituted with 0 to 3 substituents $R^6$;

each $R^6$ is independently selected from the group consisting of halogen, alkyl, —O-alkyl, haloalkyl, —O-haloalkyl, —CN, —OH, unsubstituted heteroaryl, and heteroaryl substituted with at least one alkyl or haloalkyl;

$R^7$ is selected from the group consisting of H, alkyl, haloalkyl, cycloalkyl, heterocyclyl substituted with 0 to 3 substituents $R^{13}$, aryl substituted with 0 to 3 substituents $R^6$, -alkyl-aryl wherein the aryl moiety is substituted with 0 to 3 substituents $R^6$, and heteroaryl substituted with 0 to 3 substituents $R^6$;

$R^8$ is selected from the group consisting of H, alkyl, -alkyl-cycloalkyl, —C(O)N($R^{14}$)$_2$, —C(O)$R^{12}$, and aryl or heteroaryl substituted with 0 to 3 substituents $R^6$;

each $R^9$ is independently selected from the group consisting of H, alkyl, haloalkyl, cycloalkyl, heterocyclyl, aryl, and heteroaryl;

$R^{10}$ is alkyl or aryl; or when $X^3$ is —C(=N—$R^{10}$) and $X^2$ is —N($R^8$)—, $R^8$ and $R^{10}$ together can form a group $X^6$ as shown in Formula (IB):

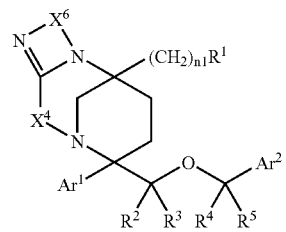

(IB)

wherein $X^6$ is —N($R^{13}$)—C(O)—;

each $R^{11}$ is independently selected from the group consisting of H and alkyl;

$R^{12}$ is selected from the group consisting of H, alkyl, aryl, and heteroaryl, wherein said aryl or heteroaryl are substituted with 0 to 3 substituents $R^6$;

each $R^{13}$ is independently selected from H, alkyl, aryl, or -alkyl-aryl;

each $R^{14}$ is independently selected from H, alkyl, aryl, heteroaryl, or heterocyclyl, wherein said heterocyclyl is substituted with 0 to 3 substituents $R^{13}$, and wherein each of said aryl and heteroaryl is independently substituted with 0 to 3 substituents $R^6$; or two substituents $R^{14}$, together with the nitrogen atom to which they are attached, form a heterocyclyl ring substituted with 0 to 3 substituents $R^{13}$; and $R^{15}$ is selected from the group consisting of H, alkyl, and aryl substituted with 0 to 3 substituents $R^6$.

In another embodiment, the present invention is directed to a pharmaceutical composition comprising a therapeutically effective amount of at least one compound of Formula (I), or a pharmaceutically acceptable salt, solvate, and/or ester thereof, and at least one pharmaceutically acceptable carrier.

In another embodiment, the present invention is directed to a kit comprising two or more containers in a single package, wherein each container in the package comprises a pharmaceutical composition. At least one container of the package comprises an effective amount of the compound of Formula (I), or a pharmaceutically acceptable salt, solvate, and/or ester thereof in a pharmaceutically acceptable carrier, and at least one other container of the package comprises another therapeutic agent in a pharmaceutically acceptable carrier. The pharmaceutical compositions of the kit may be used in combination.

In another embodiment, the present invention is directed to a method for affecting an $NK_1$ receptor in a patient. The method comprises administering to the patient an effective amount of at least one compound of Formula (I), or a pharmaceutically acceptable salt, solvate, and/or ester thereof.

In another embodiment, the present invention is directed to a method for treating an $NK_1$ receptor mediated condition or disease (i.e., a disease associated with an $NK_1$ receptor, or a disease involving an $NK_1$ receptor in part of the disease process) in a patient in need of such treatment. The method comprises administering to the patient an effective amount of at least one compound of Formula (I), or a pharmaceutically acceptable salt, solvate, and/or ester thereof.

Other features and advantages of the invention will be apparent from the following detailed description, and from the claims.

DETAILED DESCRIPTION OF THE INVENTION

In a first embodiment, the present invention is directed to a compound of Formula (I), or a pharmaceutically acceptable salt, solvate, and/or ester thereof, as described herein.

In another embodiment of the compounds of Formula (I),
$Ar^1$ is aryl;
$Ar^2$ is aryl substituted with 0 to 3 substituents $R^6$;
$X^1$ is —O—;
$X^2$ is —O—, —N($R^8$)—, or —C($R^9$)$_2$—;
$X^3$ is —C($R^9$)$_2$—, —C(O)—, or —C(=N—$R^{10}$)—;
$X^4$ is —N($R^{11}$)— or —C($R^9$)$_2$—;
with the proviso that when $X^3$ is —C($R^9$)$_2$—, at least one of $X^2$ and $X^4$ is also —C($R^9$)$_2$—;
n1 is an integer of from 0 to 3;

$R^1$ is selected from the group consisting of H, —OH, $(C_{1-6})$alkyl, $(C_{1-6})$alkyl substituted with one or more hydroxyl groups, —O-alkyl, —O—$(C_{1-6})$alkyl-$(C_{3-6})$cycloalkyl, heteroaryl substituted with 0 to 3 substituents $R^6$, —N($R^7$)$_2$, —N($R^{11}$)C(O)$R^{12}$, heterocyclyl substituted with 0 to 3 substituents $R^{13}$, —N($R^{11}$)C(O)N($R^{14}$)$_2$, —OC(O)N($R^{14}$)$_2$, —C(O)N($R^{14}$)$_2$, —OC(O)$R^{12}$, —C(O)$R^{12}$, —C(O)O$R^{15}$, —CN, —CN$_3$, —O-alkyl-aryl, —O—N=C($R^{12}$)$_2$, —S—$R^{12}$, —S(O$_2$)—$R^{12}$, and N($R^{11}$)S(O$_2$)—$R^{12}$; or when $X^2$ is —N($R^8$)—, $R^1$ and $R^8$ together can form a group $X^5$ as shown in Formula (IA):

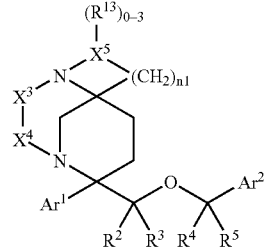

(IA)

wherein $X^5$ is selected from the group consisting of —C(O)—, —(CH$_2$)$_{n2}$—O—, a covalent bond, —(CH$_2$)$_{n2}$—C(O)—N($R^{13}$)—, and —C(O)—N($R^{13}$)—C(O)—;
n2 is an integer of from 1 to 3;
with the proviso that:
(a) when $X^5$ is —C(O)—, n1 is 2;
(b) when $X^5$ is —(CH$_2$)$_{n2}$—O—, n1 is 1 and n2 is 2;
(c) when $X^5$ is —(CH$_2$)$_{n2}$—, n1 is 2;
(d) when $X^5$ is —(CH$_2$)$_{n2}$—C(O)—N($R^{13}$)—, n1 and n2 are both 1; and
(e) when $X^5$ is —C(O)—N($R^{13}$)—C(O)—, n1 is 0;
$R^2$ and $R^3$ are H;
$R^4$ and $R^5$ are each independently H or $(C_{1-6})$alkyl;
each $R^6$ is independently $(C_{1-6})$alkyl or halo$(C_{1-6})$alkyl;
$R^7$ is selected from the group consisting of H, $(C_{3-6})$cycloalkyl, and —$(C_{1-6})$alkyl-aryl wherein the aryl moiety is substituted with 0 to 3 substituents $R^6$;
$R^8$ is selected from the group consisting of H, $(C_{1-6})$alkyl, —$(C_{1-6})$alkyl-$(C_{3-6})$cycloalkyl, —C(O)N($R^{14}$)$_2$, and —C(O)$R^{12}$;
$R^9$ is H;
$R^{10}$ is $(C_{1-6})$alkyl or aryl; or
when $X^3$ is —C(=N—$R^{10}$) and $X^2$ is —N($R^8$)—, $R^8$ and $R^{10}$ together can form a group $X^6$ as shown in Formula (IB):

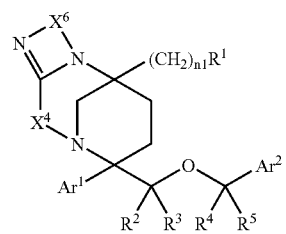

(IB)

wherein $X^6$ is —N($R^{13}$)—C(O)—;
$R^{12}$ is selected from the group consisting of $(C_{1-6})$alkyl and heteroaryl substituted with 0 to 3 substituents $R^6$;
each $R^{14}$ is independently H or heteroaryl; or
two $R^{14}$, together with the nitrogen atom to which they are attached, form a heterocyclyl ring substituted with 0 to 5 substituents $R^{13}$; and
$R^{15}$ is H or $(C_{1-6})$alkyl.

In another embodiment of the compounds of Formula (I), $X^2$ is —N($R^8$)—, $X^3$ is —C(O)—, and $X^4$ is —C($R^9$)$_2$—.

In another embodiment of the compounds of Formula (I), $X^2$, $X^3$, and $X^4$ are each —C($R^9$)$_2$—.

In another embodiment of the compounds of Formula (I), $X^2$ is —N($R^8$)—, and $X^3$ and $X^4$ are each —C($R^9$)$_2$—.

In another embodiment of the compounds of Formula (I), $X^2$ is —O—, $X^3$ is —C(O)—, and $X^4$ is —C($R^9$)$_2$—.

In another embodiment of the compounds of Formula (I), $X^2$ is —N($R^8$)—, $X^3$ is —C(=N—$R^{10}$)—, and $X^4$ is —C($R^9$)$_2$—.

In another embodiment of the compounds of Formula (I), $X^2$ and $X^4$ are each —N($R^8$)—, and $X^3$ is —C(O)—.

In another embodiment, the compounds of Formula (I) have a structure according to Formula (IA).

In another embodiment, the compounds of Formula (I) have a structure according to Formula (IA), wherein $X^5$ is —C(O)—.

In another embodiment, the compounds of Formula (I) have a structure according to Formula (IA), wherein $X^5$ is —C(O)— and n1 is 2 or 3.

In another embodiment, the compounds of Formula (I) have a structure according to Formula (IA), wherein $X^5$ is —(CH$_2$)$_{n2}$—O—.

In another embodiment, the compounds of Formula (I) have a structure according to Formula (IA), wherein $X^5$ is —(CH$_2$)$_{n2}$—O—, n1 is 1 or 2, and n2 is 2 or 3.

In another embodiment, the compounds of Formula (I) have a structure according to Formula (IA), wherein $X^5$ is —(CH$_2$)$_{n2}$—O—, n1 is 1, and n2 is 2.

In another embodiment, the compounds of Formula (I) have a structure according to Formula (IA), wherein $X^5$ is a covalent bond, and n1 is 3 or 4.

In another embodiment, the compounds of Formula (I) have a structure according to Formula (IA), wherein $X^5$ is a covalent bond, and n1 is 3.

In another embodiment, the compounds of Formula (I) have a structure according to Formula (IA), wherein $X^5$ is —(CH$_2$)$_{n2}$—C(O)—N($R^{13}$)—.

In another embodiment, the compounds of Formula (I) have a structure according to Formula (IA), wherein $X^5$ is —(CH$_2$)$_{n2}$—C(O)—N($R^{13}$)—, n1 is 1, and n2 is 2.

In another embodiment, the compounds of Formula (I) have a structure according to Formula (IA), wherein $X^5$ is —(CH$_2$)$_{n2}$—C(O)—N($R^{13}$)—, n1 is 2, and n2 is 2.

In another embodiment, the compounds of Formula (I) have a structure according to Formula (IA), wherein $X^5$ is —C(O)—N($R^{13}$)—C(O)—.

In another embodiment, the compounds of Formula (I) have a structure according to Formula (IB), wherein $X^6$ is —N($R^{13}$)—C(O)—.

In another embodiment of the compounds of Formula (I), said compounds have a structure according to the following Formula (II):

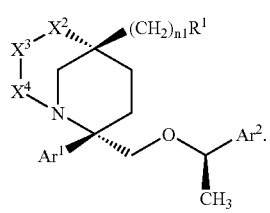

(II)

In another embodiment of the compounds of Formula (I), said compounds have structure according to the following Formula (III):

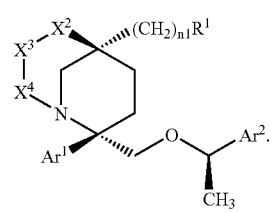

(III)

In another embodiment of the compounds of Formula (I), said compounds have a structure selected from the group consisting of:

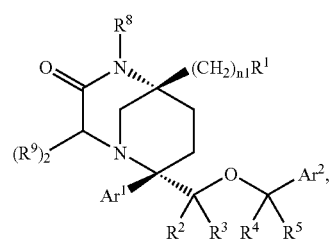

(IV)

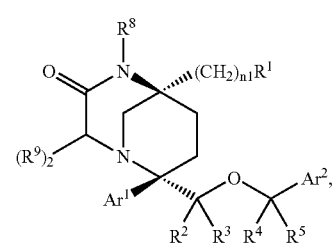

(V)

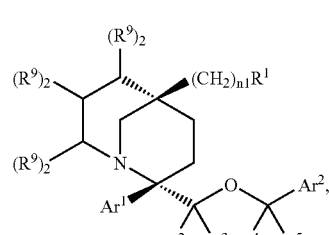

(VI)

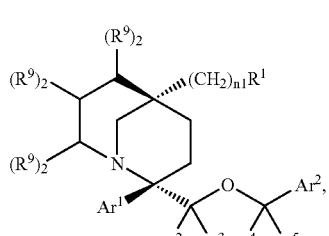

(VII)

-continued
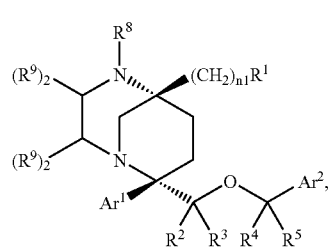
(VIII)
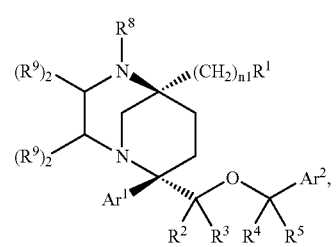
(IX)
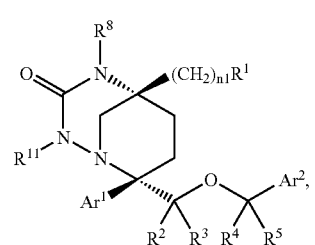
(X)
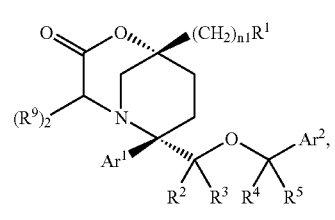
(XI)
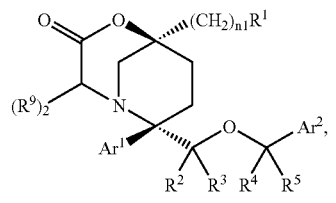
(XII)
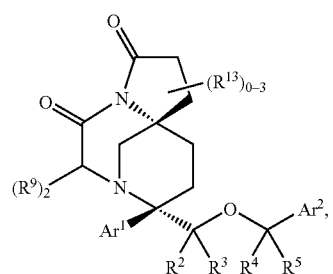
(XIII)
-continued
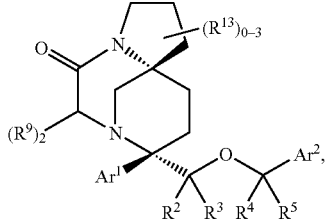
(XIV)
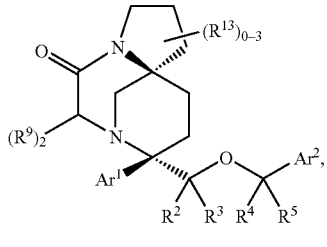
(XV)
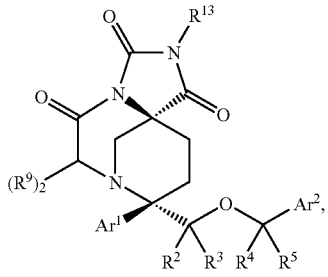
(XVI)
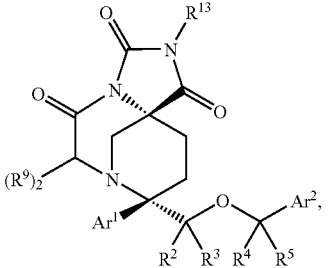
(XVII)
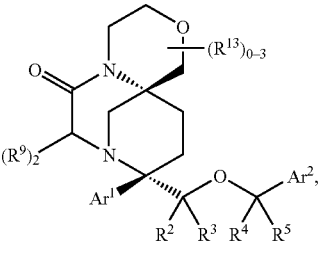
(XVIII)
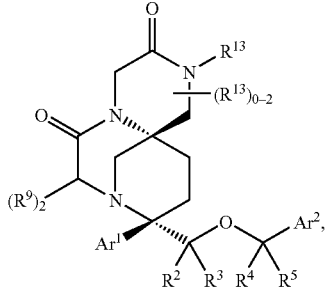
(XIX)

-continued

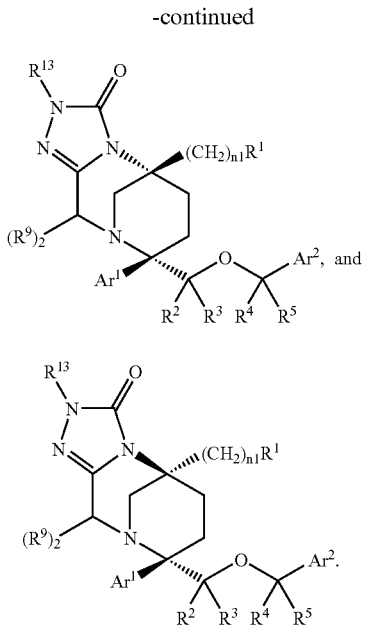
(XX)

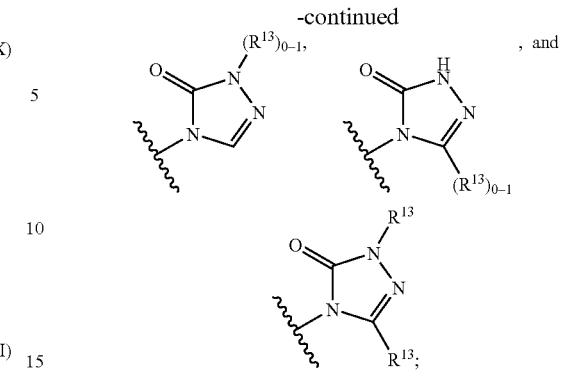

$R^2$, $R^3$ and $R^4$ are each H;
$R^5$ is $(C_{1-6})$alkyl;
each $R^6$ is independently H, $(C_{1-6})$alkyl, or $(C_{1-6})$haloalkyl;
$R^7$ is H, $(C_{1-6})$alkyl, $(C_{3-6})$cycloalkyl, or —$(C_{1-6})$alkyl-phenyl;
$R^8$ is H, $(C_{1-6})$alkyl, or —$(C_{1-6})$alkyl-$(C_{3-6})$cycloalkyl;
each $R^9$ is independently H or $(C_{1-6})$alkyl;
$R^{11}$ is H or $(C_{1-6})$alkyl;
$R^{13}$ is H or $(C_{1-6})$alkyl;

(XXI)

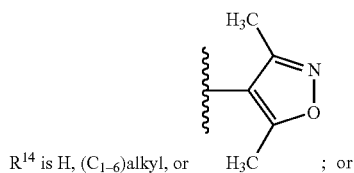

$R^{14}$ is H, $(C_{1-6})$alkyl, or  ; or two $R^{14}$ groups, together with the nitrogen atom to which they are shown attached, form

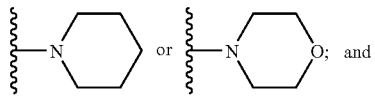

In another embodiment of the compounds of Formula (I), said compounds have the structure of Formula (IV), and $Ar^1$ and $Ar^2$ are both phenyl substituted with 0 to 3 substituents $R^6$;

$R^1$ is selected from the group consisting of H, —OH, $(C_{1-6})$alkyl, —$(C_{1-6})$alkyl-OH, —O—$(C_{1-6})$alkyl, —O—$(C_{1-6})$alkyl-$(C_{3-6})$cycloalkyl, —N$(R^7)_2$, —N$(R^{11})$C(O)N$(R^{14})_2$, —OC(O)N$(R^{14})_2$, —OC(O)—$(C_{1-6})$alkyl, —C(O)OH, —C(O)—O—$(C_{1-6})$alkyl, —CN, —CN$_3$, —O—$(C_{1-6})$alkyl-phenyl, —O—N=C(($C_{1-6})$alkyl$)_2$, —S—$(C_{1-6})$alkyl, —S(O$_2$)—$(C_{1-6})$alkyl, and N$(R^{11})$S(O$_2$)—$(C_{1-6})$alkyl, n1 is 0 or 1.

In another embodiment of the compounds of Formula (I), said compounds have the structure of Formula (V), and $Ar^1$ and $Ar^2$ are both phenyl substituted with 0 to 3 substituents $R^6$;

$R^1$ is selected from the group consisting of H, —OH, $(C_{1-6})$alkyl, —$(C_{1-6})$alkyl-OH, —O—$(C_{1-6})$alkyl, —O—$(C_{1-6})$alkyl-$(C_{3-6})$cycloalkyl, —N$(R^7)_2$, —N$(R^{11})$C(O)N$(R^{14})_2$, —OC(O)N$(R^{14})_2$, —OC(O)—$(C_{1-6})$alkyl, —C(O)OH, —C(O)—O—$(C_{1-6})$alkyl, —CN, —CN$_3$, —O—$(C_{1-6})$alkyl-phenyl, —O—N=C(($C_{1-6})$alkyl$)_2$, —S—$(C_{1-6})$alkyl, —S(O$_2$)—$(C_{1-6})$alkyl, and N$(R^{11})$S(O$_2$)—$(C_{1-6})$alkyl,

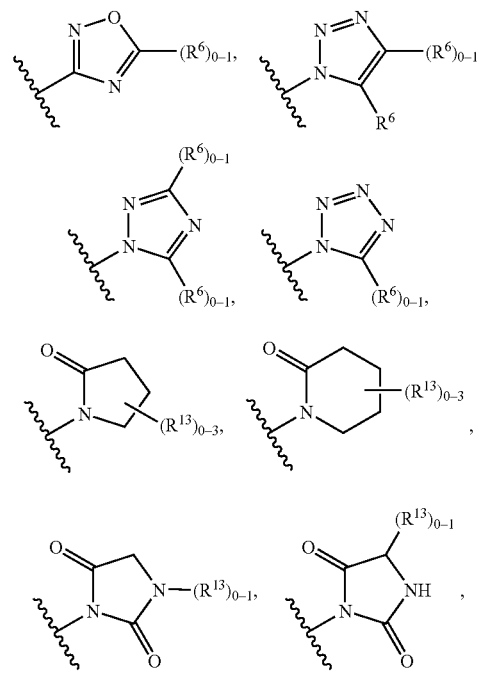

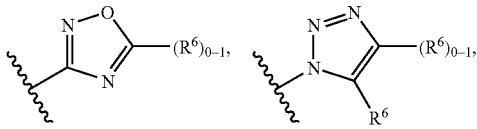

-continued

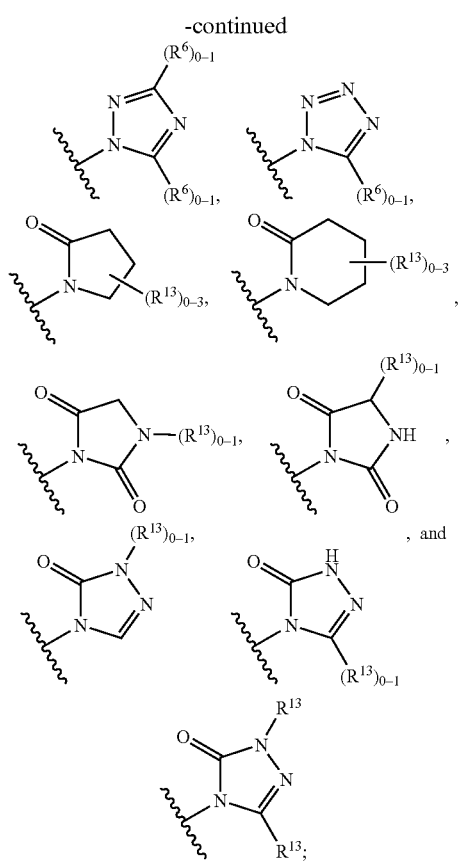

$R^2$, $R^3$ and $R^4$ are each H;
$R^5$ is $(C_{1-6})$alkyl;
each $R^6$ is independently H, $(C_{1-6})$alkyl, or $(C_{1-6})$haloalkyl;
$R^7$ is H, $(C_{1-6})$alkyl, $(C_{3-6})$cycloalkyl, or —$(C_{1-6})$alkyl-phenyl;
$R^8$ is H, $(C_{1-6})$alkyl, or —$(C_{1-6})$alkyl-$(C_{3-6})$cycloalkyl;
each $R^9$ is independently H or $(C_{1-6})$alkyl;
$R^{11}$ is H or $(C_{1-6})$alkyl;
$R^{13}$ is H or $(C_{1-6})$alkyl;

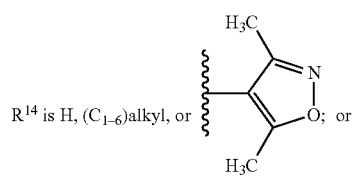

two $R^{14}$ groups, together with the nitrogen atom to which they are shown attached, form

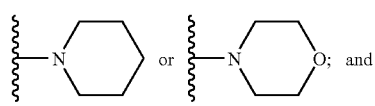

n1 is 0 or 1.

In another embodiment of the compounds of Formula (I), said compounds have the structure of Formula (VI), and $Ar^1$ and $Ar^2$ are both phenyl substituted with 0 to 3 substituents $R^6$;
$R^1$ is selected from the group consisting of H, —$N(R^7)_2$, —$N(R^{11})C(O)N(R^{14})_2$, —$OC(O)N(R^{14})_2$, —$N(R^{11})C(O)$—$(C_{1-6})$alkyl, —CN,

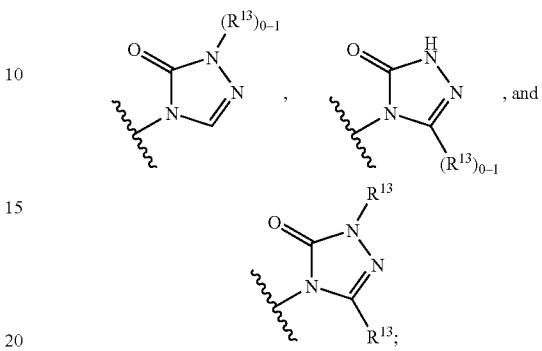

$R^2$, $R^3$ and $R^4$ are each H;
$R^5$ is $(C_{1-6})$alkyl;
each $R^6$ is independently H, $(C_{1-6})$alkyl, or $(C_{1-6})$haloalkyl;
$R^7$ is H or $(C_{1-6})$alkyl;
each $R^9$ is independently H or $(C_{1-6})$alkyl;
$R^{11}$ is H or $(C_{1-6})$alkyl;
$R^{13}$ is H or $(C_{1-6})$alkyl;
$R^{14}$ is H or $(C_{1-6})$alkyl; and
n1 is 0.

In another embodiment of the compounds of Formula (I), said compounds have the structure of Formula (VII), and $Ar^1$ and $Ar^2$ are both phenyl substituted with 0 to 3 substituents $R^6$;
$R^1$ is selected from the group consisting of H, —$N(R^7)_2$, —$N(R^{11})C(O)N(R^{14})_2$, —$OC(O)N(R^{14})_2$, —$N(R^{11})C(O)$—$(C_{1-6})$alkyl, —CN,

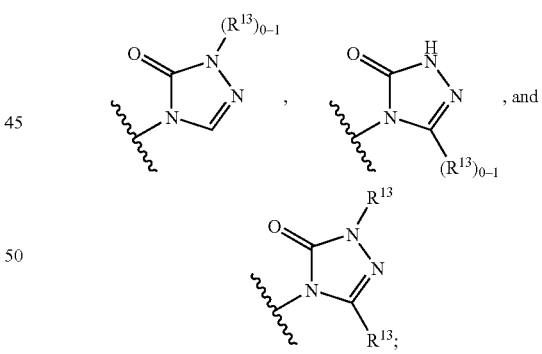

$R^2$, $R^3$ and $R^4$ are each H;
$R^5$ is $(C_{1-6})$alkyl;
each $R^6$ is independently H, $(C_{1-6})$alkyl, or $(C_{1-6})$haloalkyl;
$R^7$ is H or $(C_{1-6})$alkyl;
each $R^9$ is independently H or $(C_{1-6})$alkyl;
$R^{11}$ is H or $(C_{1-6})$alkyl;
$R^{13}$ is H or $(C_{1-6})$alkyl;
$R^{14}$ is H or $(C_{1-6})$alkyl; and
n1 is 0.

In another embodiment of the compounds of Formula (I), said compounds have the structure of Formula (VIII), and Ar$^1$ and Ar$^2$ are both phenyl substituted with 0 to 3 substituents R$^6$;
R$^1$ is selected from the group consisting of H, —OH, (C$_{1-6}$)alkyl, hydroxy-(C$_{1-6}$)alkyl-, —C(O)N(R$^{14}$)$_2$, —OC(O)—(C$_{1-6}$)alkyl, and —C(O)—(C$_{1-6}$)alkyl;
R$^2$, R$^3$ and R$^4$ are each H;
R$^5$ is (C$_{1-6}$)alkyl;
each R$^6$ is independently H, (C$_{1-6}$)alkyl, or (C$_{1-6}$)haloalkyl;
R$^8$ is H or (C$_{1-6}$)alkyl;
each R$^9$ is independently H or (C$_{1-6}$)alkyl;
R$^{14}$ is H or (C$_{1-6}$)alkyl; and
n1 is 0 or 1.

In another embodiment of the compounds of Formula (I), said compounds have the structure of Formula (IX), and
Ar$^1$ and Ar$^2$ are both phenyl substituted with 0 to 3 substituents R$^6$;
R$^1$ is selected from the group consisting of H, —OH, (C$_{1-6}$)alkyl, hydroxy-(C$_{1-6}$)alkyl-, —C(O)N(R$^{14}$)$_2$, —OC(O)—(C$_{1-6}$)alkyl, and —C(O)—(C$_{1-6}$)alkyl;
R$^2$, R$^3$ and R$^4$ are each H;
R$^5$ is (C$_{1-6}$)alkyl;
each R$^6$ is independently H, (C$_{1-6}$)alkyl, or (C$_{1-6}$)haloalkyl;
R$^8$ is H or (C$_{1-6}$)alkyl;
each R$^9$ is independently H or (C$_{1-6}$)alkyl;
R$^{14}$ is H or (C$_{1-6}$)alkyl; and
n1 is 0 or 1.

In another embodiment of the compounds of Formula (I), said compounds have the structure of Formula (X), and
Ar$^1$ and Ar$^2$ are both phenyl substituted with 0 to 3 substituents R$^6$;
R$^1$ is selected from the group consisting of H or (C$_{1-6}$)alkyl;
R$^2$, R$^3$ and R$^4$ are each H;
R$^5$ is (C$_{1-6}$)alkyl;
each R$^6$ is independently H, (C$_{1-6}$)alkyl, or (C$_{1-6}$)haloalkyl;
R$^8$ and R$^{11}$ are H or (C$_{1-6}$)alkyl;
each R$^9$ is independently H or (C$_{1-6}$)alkyl; and
n1 is 0.

In another embodiment of the compounds of Formula (I), said compounds have the structure of Formula (XI), and
Ar$^1$ and Ar$^2$ are both phenyl substituted with 0 to 3 substituents R$^6$;
R$^1$ is selected from the group consisting of H, —OH, (C$_{1-6}$)alkyl, —(C$_{1-6}$)alkyl-OH, and —O—(C$_{1-6}$)alkyl;
R$^2$, R$^3$ and R$^4$ are each H;
R$^5$ is (C$_{1-6}$)alkyl;
each R$^6$ is independently H, (C$_{1-6}$)alkyl, or (C$_{1-6}$)haloalkyl;
each R$^9$ is independently H or (C$_{1-6}$)alkyl; and
n1 is 0 or 1.

In another embodiment of the compounds of Formula (I), said compounds have the structure of Formula (XII), and
Ar$^1$ and Ar$^2$ are both phenyl substituted with 0 to 3 substituents R$^6$;
R$^1$ is selected from the group consisting of H, —OH, (C$_{1-6}$)alkyl, —(C$_{1-6}$)alkyl-OH, and —O—(C$_{1-6}$)alkyl;
R$^2$, R$^3$ and R$^4$ are each H;
R$^5$ is (C$_{1-6}$)alkyl;
each R$^6$ is independently H, (C$_{1-6}$)alkyl, or (C$_{1-6}$)haloalkyl;
each R$^9$ is independently H or (C$_{1-6}$)alkyl; and
n1 is 0 or 1.

In another embodiment of the compounds of Formula (I), said compounds have the structure of Formula (XIII), and
Ar$^1$ and Ar$^2$ are both phenyl substituted with 0 to 3 substituents R$^6$;
R$^2$, R$^3$ and R$^4$ are each H;
R$^5$ is (C$_{1-6}$)alkyl;
each R$^6$ is independently H, (C$_{1-6}$)alkyl, or (C$_{1-6}$)haloalkyl;
each R$^9$ is independently H or (C$_{1-6}$)alkyl; and
each R$^{13}$ is independently H or (C$_{1-6}$)alkyl.

In another embodiment of the compounds of Formula (I), said compounds have the structure of Formula (XIV), and
Ar$^1$ and Ar$^2$ are both phenyl substituted with 0 to 3 substituents R$^6$;
R$^2$, R$^3$ and R$^4$ are each H;
R$^5$ is (C$_{1-6}$)alkyl;
each R$^6$ is independently H, (C$_{1-6}$)alkyl, or (C$_{1-6}$)haloalkyl;
each R$^9$ is independently H or (C$_{1-6}$)alkyl; and
each R$^{13}$ is independently H or (C$_{1-6}$)alkyl.

In another embodiment of the compounds of Formula (I), said compounds have the structure of Formula (XV), and
Ar$^1$ and Ar$^2$ are both phenyl substituted with 0 to 3 substituents R$^6$;
R$^2$, R$^3$ and R$^4$ are each H;
R$^5$ is (C$_{1-6}$)alkyl;
each R$^6$ is independently H, (C$_{1-6}$)alkyl, or (C$_{1-6}$)haloalkyl;
each R$^9$ is independently H or (C$_{1-6}$)alkyl; and
each R$^{13}$ is independently H or (C$_{1-6}$)alkyl.

In another embodiment of the compounds of Formula (I), said compounds have the structure of Formula (XVI), and
Ar$^1$ and Ar$^2$ are both phenyl substituted with 0 to 3 substituents R$^6$;
R$^2$, R$^3$ and R$^4$ are each H;
R$^5$ is (C$_{1-6}$)alkyl;
each R$^6$ is independently H, (C$_{1-6}$)alkyl, or (C$_{1-6}$)haloalkyl;
each R$^9$ is independently H or (C$_{1-6}$)alkyl; and
each R$^{13}$ is independently H or (C$_{1-6}$)alkyl.

In another embodiment of the compounds of Formula (I), said compounds have the structure of Formula (XVII), and
Ar$^1$ and Ar$^2$ are both phenyl substituted with 0 to 3 substituents R$^6$;
R$^2$, R$^3$ and R$^4$ are each H;
R$^5$ is (C$_{1-6}$)alkyl;
each R$^6$ is independently H, (C$_{1-6}$)alkyl, or (C$_{1-6}$)haloalkyl;
each R$^9$ is independently H or (C$_{1-6}$)alkyl; and
each R$^{13}$ is independently H or (C$_{1-6}$)alkyl.

In another embodiment of the compounds of Formula (I), said compounds have the structure of Formula (XVIII), and
Ar$^1$ and Ar$^2$ are both phenyl substituted with 0 to 3 substituents R$^6$;
R$^2$, R$^3$ and R$^4$ are each H;
R$^5$ is (C$_{1-6}$)alkyl;
each R$^6$ is independently H, (C$_{1-6}$)alkyl, or (C$_{1-6}$)haloalkyl;
each R$^9$ is independently H or (C$_{1-6}$)alkyl; and
each R$^{13}$ is independently H or (C$_{1-6}$)alkyl.

In another embodiment of the compounds of Formula (I), said compounds have the structure of Formula (XIX), and
Ar$^1$ and Ar$^2$ are both phenyl substituted with 0 to 3 substituents R$^6$;
R$^2$, R$^3$ and R$^4$ are each H;
R$^5$ is (C$_{1-6}$)alkyl;
each R$^6$ is independently H, (C$_{1-6}$)alkyl, or (C$_{1-6}$)haloalkyl;

each $R^9$ is independently H or $(C_{1-6})$alkyl; and
each $R^{13}$ is independently H, $(C_{1-6})$alkyl, or —$(C_{1-6})$alkyl-$(C_{6-12})$aryl.

In another embodiment of the compounds of Formula (I), said compounds have the structure of Formula (XX), and
$Ar^1$ and $Ar^2$ are both phenyl substituted with 0 to 3 substituents $R^6$;
$R^1$ is H, $(C_{1-6})$alkyl, —O—$(C_{1-6})$alkyl, or —O—$(C_{1-6})$alkyl-$(C_{6-12})$aryl;
$R^2$, $R^3$ and $R^4$ are each H;
$R^5$ is $(C_{1-6})$alkyl;
each $R^6$ is independently H, $(C_{1-6})$alkyl, or $(C_{1-6})$haloalkyl;
each $R^9$ is independently H or $(C_{1-6})$alkyl;
$R^{13}$ is independently H or $(C_{1-6})$alkyl; and
n1 is 0 or 1.

In another embodiment of the compounds of Formula (I), said compounds have the structure of Formula (XXI), and
$Ar^1$ and $Ar^2$ are both phenyl substituted with 0 to 3 substituents $R^6$;
$R^1$ is H, $(C_{1-6})$alkyl, —O—$(C_{1-6})$alkyl, or —O—$(C_{1-6})$alkyl-$(C_{6-12})$aryl;
$R^2$, $R^3$ and $R^4$ are each H;
$R^5$ is $(C_{1-6})$alkyl;
each $R^6$ is independently H, $(C_{1-6})$alkyl, or $(C_{1-6})$haloalkyl;
each $R^9$ is independently H or $(C_{1-6})$alkyl;
$R^{13}$ is independently H or $(C_{1-6})$alkyl; and
n1 is 0 or 1.

In yet another embodiment of the compounds of Formula (I), $Ar^1$ and $Ar^2$ are independently unsubstituted phenyl, tolyl, unsubstituted pyridyl, xylyl, fluorophenyl, difluorophenyl, chlorophenyl, dichlorophenyl, trifluoromethylphenyl, or bis(trifluoromethyl)phenyl.

In yet another embodiment of the compounds of Formula (I), $Ar^1$ is unsubstituted phenyl and $Ar^2$ is bis(trifluoromethyl)phenyl.

In yet another embodiment of the compounds of Formula (I), $Ar^1$ is unsubstituted phenyl and $Ar^2$ is 3,5-bis(trifluoromethyl)phenyl.

In yet another embodiment of the compounds of Formula (I), $X^1$ is —NH—, —N(CH$_3$)—, —N(CH$_2$CH$_3$)—, —N(CF$_3$)—, —N(phenyl)-, or —N(benzyl)-.

In yet another embodiment of the compounds of Formula (I), $X^2$ is —NH—, —N(C(O)NH$_2$)—, —N(C(O)NH(CH$_3$))—, —N(C(O)N(CH$_3$)$_2$)—, —N(C(O)CH$_3$)—, —N(C(O)CH$_2$CH$_3$)—, —N(CH$_3$)—, —N(CH$_2$CH$_3$)—, —N(CH$_2$-cyclopropyl)-, —N(CH$_2$-cyclopentyl)-, —N(CH$_2$-cyclohexyl)-, —N(phenyl)-, —N(tolyl)-, —N(xylyl)-, —N(pyridyl)-, or —N(C(O)phenyl)-.

In yet another embodiment of the compounds of Formula (I), $X^2$ is —CH$_2$—, —CH(CH$_3$)—, —C(CH$_3$)$_2$—, —CH(CF$_3$)—, —C(CF$_3$)$_2$—, —CH(cyclopropyl)-, —CH(pyrrolidinonyl)-, —CH(tetrahydrofuranyl)-, —CH(phenyl)-, or —CH(pyridyl)-.

In yet another embodiment of the compounds of Formula (I), $X^3$ is —CH$_2$—, —CH(CH$_3$)—, —C(CH$_3$)$_2$—, —CH(CF$_3$)—, —C(CF$_3$)$_2$—, —CH(cyclopropyl)-, —CH(pyrrolidinonyl)-, —CH(tetrahydrofuranyl)-, —CH(phenyl)-, or —CH(pyridyl)-.

In yet another embodiment of the compounds of Formula (I), $X^3$ is carbonyl.

In yet another embodiment of the compounds of Formula (I), $X^4$ is —NH—, —N(CH$_3$)—, or —N(CH$_2$CH$_3$)—.

In yet another embodiment of the compounds of Formula (I), $X^2$, $X^3$, and $X^4$ are each —CH$_2$—.

In yet another embodiment of the compounds of Formula (I), $X^2$ is —NH—, $X^3$ is carbonyl, and $X^4$ is —CH$_2$—.

In yet another embodiment of the compounds of Formula (I), $X^2$ is —N(CH$_3$)—, $X^3$ is carbonyl, and $X^4$ is —CH$_2$—.

In yet another embodiment of the compounds of Formula (I), $X^2$ is —N(CH$_2$cyclopropyl)-, $X^3$ is carbonyl, and $X^4$ is —CH$_2$—.

In yet another embodiment of the compounds of Formula (I), $X^2$ is —O—, $X^3$ is carbonyl, and $X^4$ is —CH$_2$—.

In yet another embodiment of the compounds of Formula (I), $X^2$ is —N(C(O)NH$_2$)— and $X^3$ and $X^4$ are both —CH$_2$—.

In yet another embodiment of the compounds of Formula (I), $X^2$ is —N(C(O)CH$_3$)— and $X^3$ and $X^4$ are both —CH$_2$—.

In yet another embodiment of the compounds of Formula (I), $X^3$ is carbonyl and $X^2$ and $X^4$ are both —NH—.

In yet another embodiment of the compounds of Formula (I), $X^5$ is —(CH$_2$)$_2$—O—.

In yet another embodiment of the compounds of Formula (I), $X^5$ is —(CH$_2$)$_3$—O—.

In yet another embodiment of the compounds of Formula (I), $X^5$ is —(CH$_2$)—C(O)—NH—.

In yet another embodiment of the compounds of Formula (I), $X^5$ is —(CH$_2$)—C(O)—N(($C_{1-6}$)alkyl)-, wherein ($C_{1-6}$) alkyl is methyl, ethyl, n-propyl, isopropyl, n-butyl, tert-butyl, isobutyl, sec-butyl, n-pentyl, or n-hexyl.

In yet another embodiment of the compounds of Formula (I), $X^5$ is —(CH$_2$)—C(O)—N(phenyl)-.

In yet another embodiment of the compounds of Formula (I), $X^5$ is —(CH$_2$)—C(O)—N(CH$_2$-phenyl)-.

In yet another embodiment of the compounds of Formula (I), $R^1$ is H, —OH, methyl, ethyl, n-propyl, isopropyl, n-butyl, tert-butyl, isobutyl, sec-butyl, —CH$_2$—OH, —CH$_2$CH$_2$—OH, —CH(OH)CH$_3$, —CH(OH)CH$_2$CH$_2$—OH, —O—CH$_3$, —O—CH$_2$CH$_3$, —O—CH$_2$CH$_2$CH$_3$, —O—CH(CH$_3$)$_2$, —O—CH$_2$-cyclopropyl, —O—CH$_2$-cyclobutyl, —O—CH$_2$-cyclopentyl, —O—CH$_2$-cyclohexyl, —O—CH$_2$CH$_2$-cyclopropyl, pyridyl, oxadiazolyl, triazolyl, tetrazolyl,

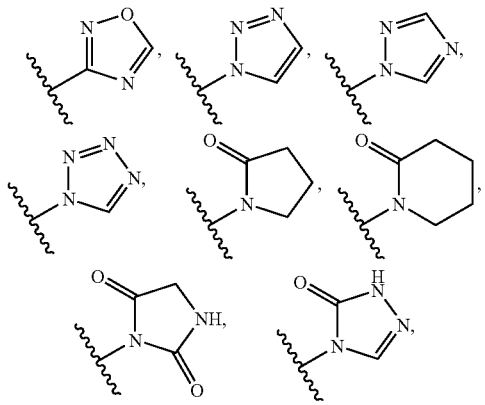

phenyl, —NH$_2$, —N(CH$_3$)$_2$, —NH(CH$_3$), —NH(benzyl), —N(benzyl)$_2$, —NH—C(O)—CH$_3$, —N(CH$_3$)—C(O)—CH$_3$, —NH—C(O)—CH$_2$CH$_3$, —N(CH$_3$)—C(O)—CH$_2$CH$_3$, —NH—C(O)—NH$_2$, —NH—C(O)—N(CH$_3$)$_2$, —N(CH$_3$)—C(O)—NH$_2$, —N(CH$_3$)—C(O)—N(CH$_3$)$_2$, —O—C(O)—N(CH$_3$)$_2$, —O—C(O)—NH$_2$, —C(O)—N(CH$_3$)$_2$, —C(O)—NH$_2$, —C(O)—CH$_3$, —C(O)-phenyl, —C(O)-pyridyl, —O—C(O)—CH$_3$, —O—C(O)-phenyl, —O—C(O)-pyridyl, —C(O)—OH, —C(O)—OCH$_3$, —C(O)—OCH₂CH₃, —C(O)—O-phenyl, —CN, —CN₃, —O—CH₂-phenyl, —O—CH(phenyl)CH₃, —O—CH₂CH₂-phenyl, —O—N═C(CH₃)₂, —O—N═CH(CH₃), —S—CH₃, —S—CH₂CH₃, —S—CH₂CH₂CH₃, —S—CH(CH₃)₂, —S-phenyl, —S(O)—CH₃, —S(O)—CH₂CH₃, —S(O)—CH₂CH₂CH₃, —S(O)—CH(CH₃)₂, —S(O)-phenyl, —S(O₂)—CH₃, —S(O₂)—CH₂CH₃, —S(O₂)—CH₂CH₂CH₃, —S(O₂)—CH(CH₃)₂, —S(O₂)-phenyl, —NH—S(O₂)—CH₃, —N(CH₃)—S(O₂)—CH₃, —NH—S(O₂)-phenyl, or —N(CH₃)—S(O₂)-phenyl.

In yet another embodiment of the compounds of Formula (I), $R^2$, $R^3$, $R^4$, and $R^5$ are independently H, —CH₃, —CF₃, cyclopropyl, oxadiazolyl, triazolyl, tetrazolyl, pyridyl, or phenyl.

In yet another embodiment of the compounds of Formula (I), each $R^6$ is independently fluorine, chlorine, methyl, ethyl, n-propyl, isopropyl, —O—CH₃, —O—CH₂CH₃, —CF₃, —OCF₃, —CN, —OH, or —NO₂.

In yet another embodiment of the compounds of Formula (I), $R^7$ is H, methyl, ethyl, n-propyl, isopropyl, —CF₃, cyclopropyl, oxadiazolyl, triazolyl, tetrazolyl, pyridyl, or phenyl.

In yet another embodiment of the compounds of Formula (I), $R^8$ is H, methyl, ethyl, n-propyl, isopropyl, —CH₂-cyclopropyl, —CH₂-cyclobutyl, —CH₂-cyclopentyl, —CH₂-cyclohexyl, —C(O)—N(CH₃)₂, —C(O)—NH₂, —C(O)—CH₃, —C(O)-phenyl, —C(O)-pyridyl, phenyl, pyridyl, oxadiazolyl, triazolyl, or tetrazolyl.

In yet another embodiment of the compounds of Formula (I), $R^9$ is H, methyl, ethyl, n-propyl, —CF₃, cyclopropyl, phenyl, pyridyl, oxadiazolyl, triazolyl, or tetrazolyl.

In yet another embodiment of the compounds of Formula (I), $R^{10}$ is —CH₃ or phenyl.

In yet another embodiment of the compounds of Formula (I), $R^{11}$ is H or —CH₃.

In yet another embodiment of the compounds of Formula (I), $R^{12}$ is H, —CH₃, —CH₂CH₃, —CH₂CH₂CH₃, —CH(CH₃)₂, phenyl, tolyl, trifluoromethylphenyl, bis(trifluormethyl)phenyl, or pyridyl.

In yet another embodiment of the compounds of Formula (I), each $R^{13}$ is independently H, —CH₃, —CH₂CH₃, —CH₂CH₂CH₃, —CH(CH₃)₂, or —CH₂-phenyl, or two substituents $R^{13}$, together with the carbon atom to which they are attached form a carbonyl group.

In yet another embodiment of the compounds of Formula (I), each $R^{14}$ is independently H, —CH₃, —CH₂CH₃, —CH₂CH₂CH₃, —CH(CH₃)₂, phenyl, tolyl, trifluoromethylphenyl, bis(trifluormethyl)phenyl, or pyridyl.

In yet another embodiment of the compounds of Formula (I), two substituents $R^{14}$, together with the nitrogen atom to which they are attached form a piperidyl, morpholinyl, pyrrolidyl, or piperazyl ring, and each of said piperidyl, morpholinyl, pyrrolidyl, or piperazyl rings can be unsubstituted or optionally substituted with 1 to 4 —CH₃, —CH₂CH₃, —CH₂CH₂CH₃, —CH(CH₃)₂, or —CH₂-phenyl groups.

In yet another embodiment of the compounds of Formula (I), two substituents $R^{14}$, together with the nitrogen atom to which they are attached form a piperidyl, morpholinyl, pyrrolidyl, or piperazyl ring, and 1 or 2 ring carbon atoms of said piperidyl, morpholinyl, pyrrolidyl, or piperazyl rings can form a carbonyl group.

In yet another embodiment of the compounds of Formula (I), $R^{15}$ is H, —CH₃, —CH₂CH₃, —CH₂CH₂CH₃, —CH(CH₃)₂, phenyl, tolyl, trifluoromethylphenyl, bis(trifluormethyl)phenyl, fluorophenyl, or bis(fluoro)phenyl.

In an additional embodiment, the compounds of Formula (I) can have one of the following structures, or can be a racemic mixture of one of the following structures:

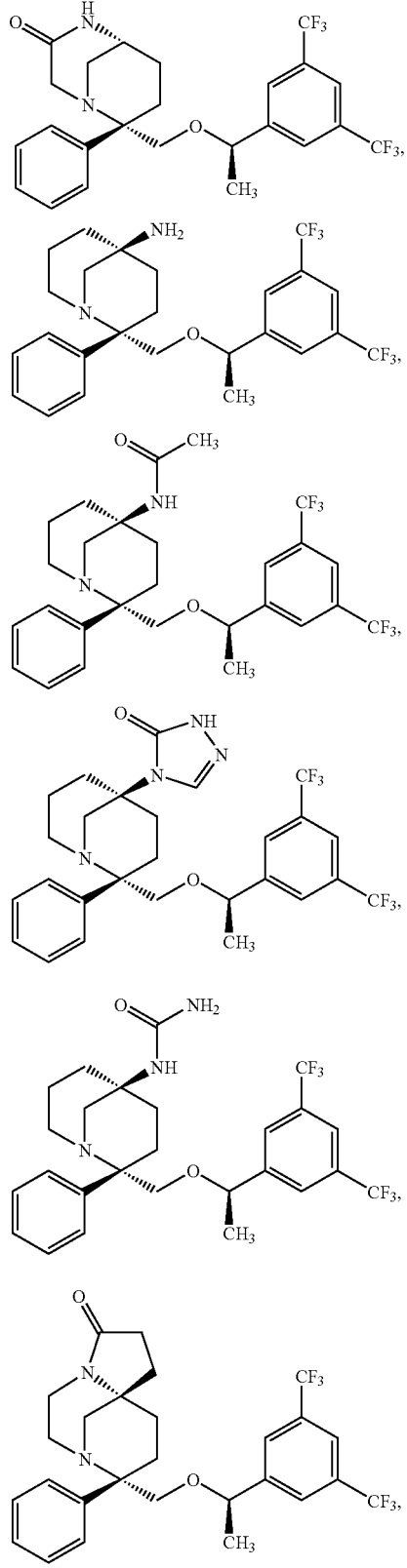

-continued
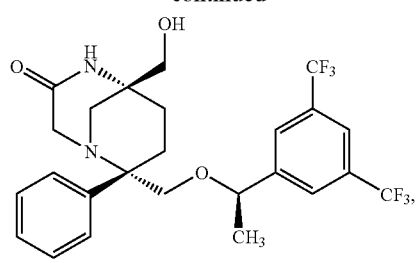
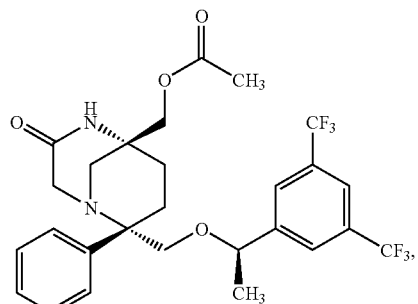
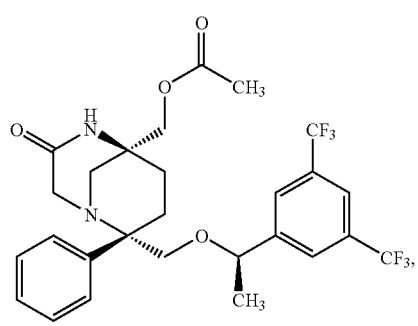
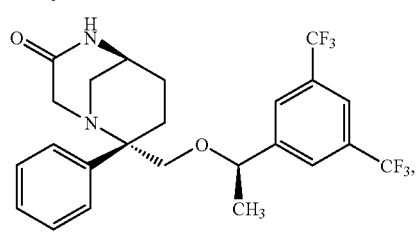
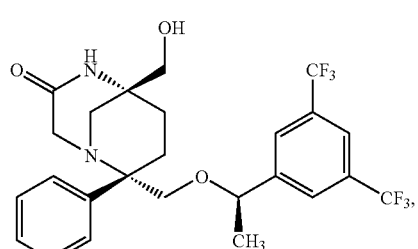
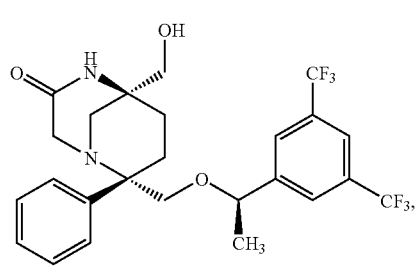
-continued
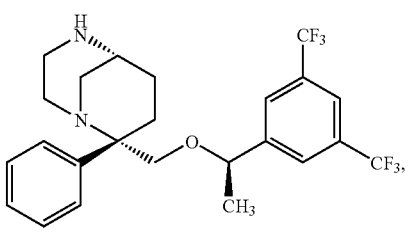
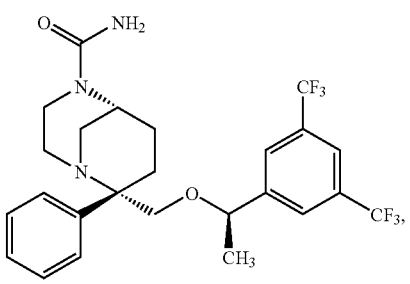
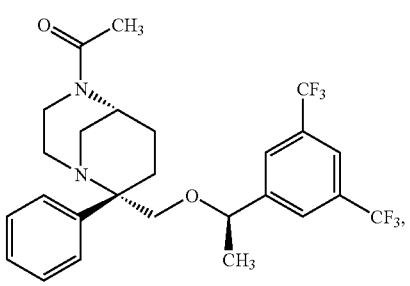
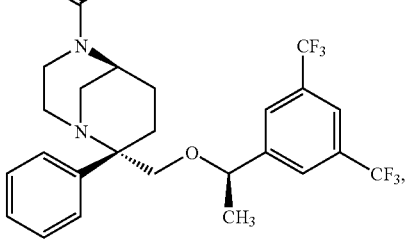
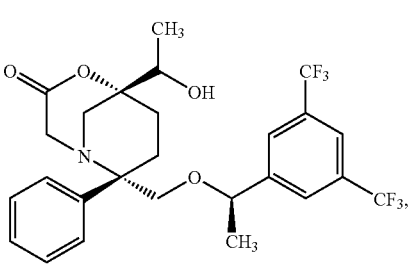
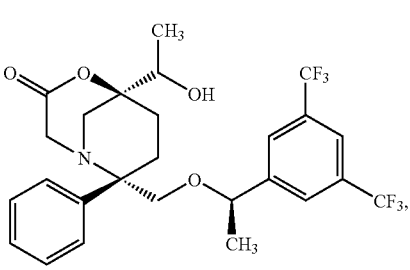

-continued
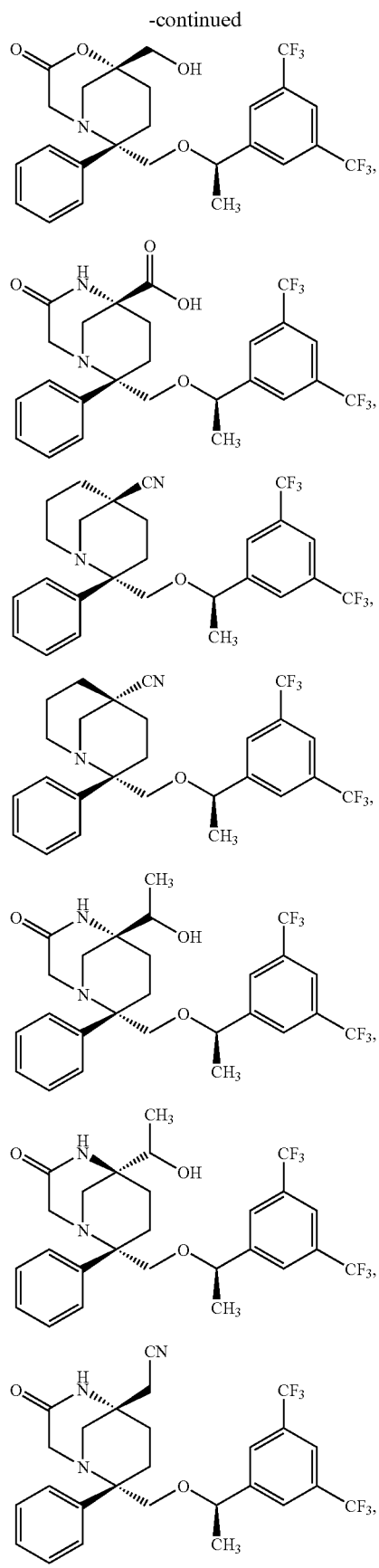
-continued
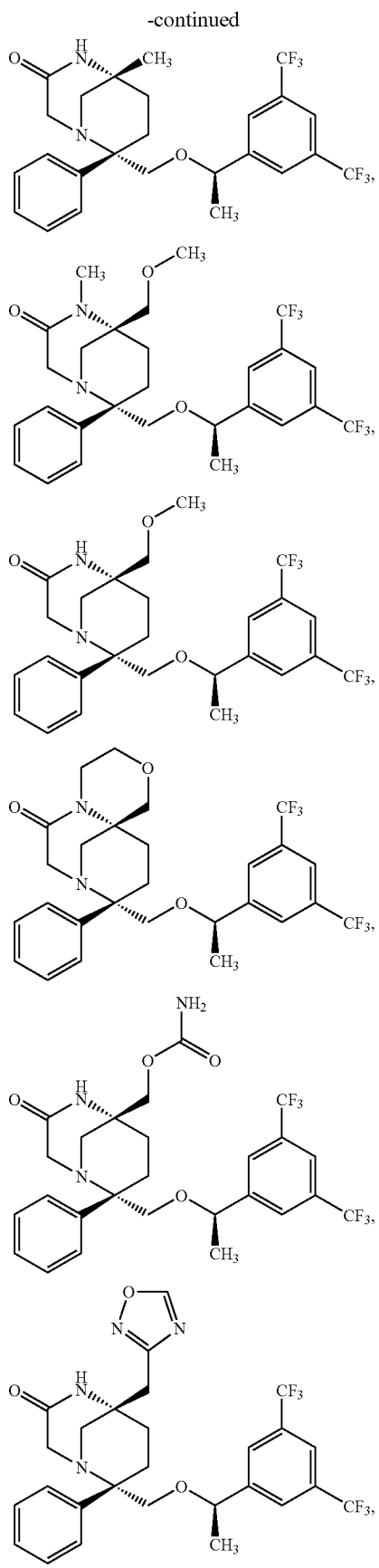

-continued
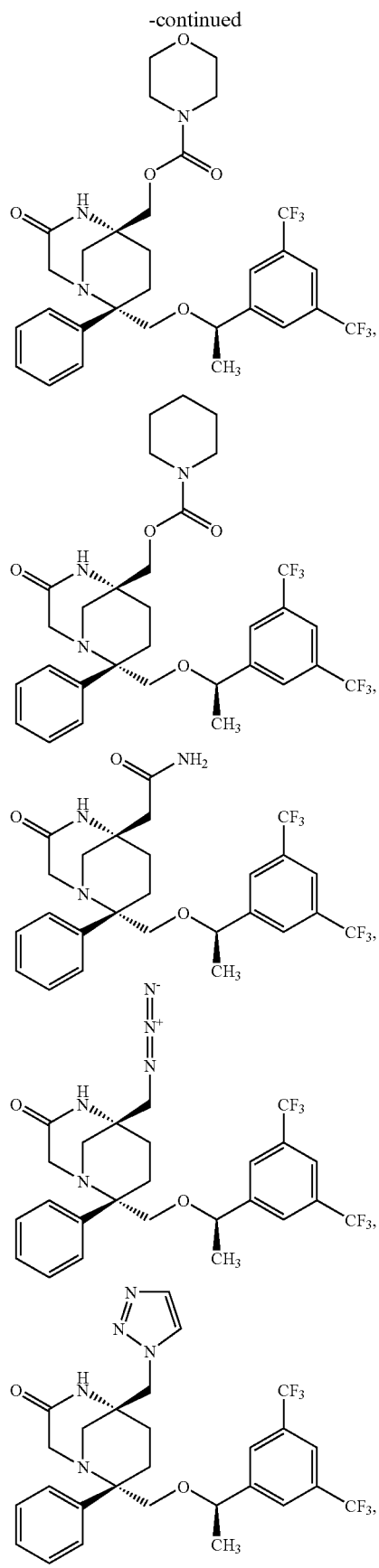
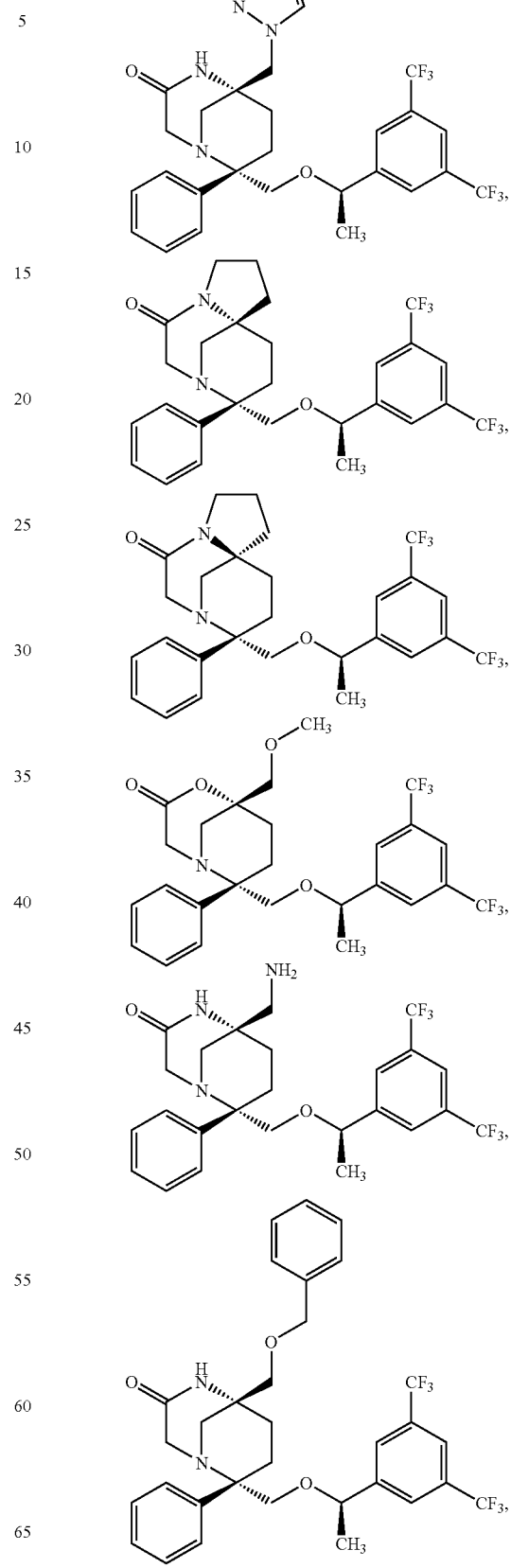

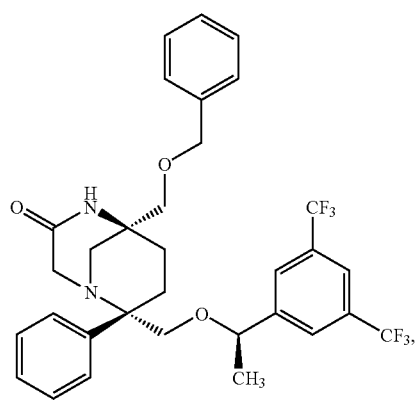
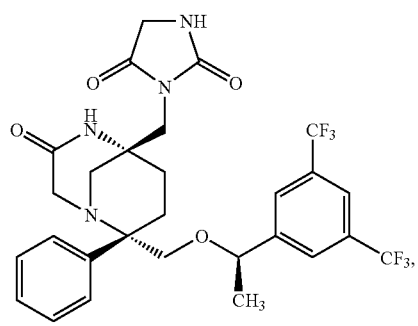
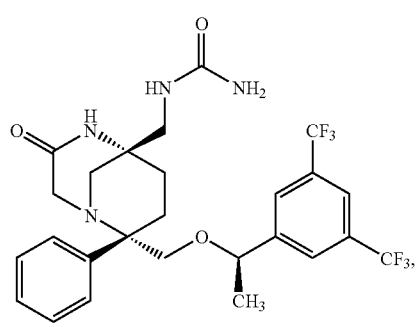
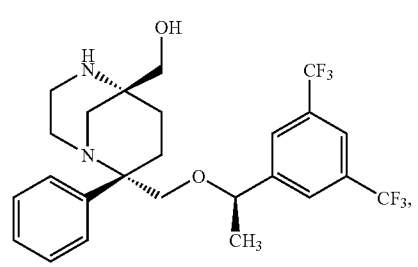
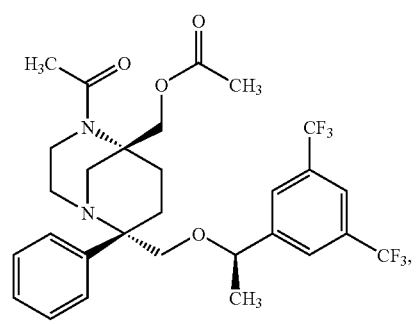
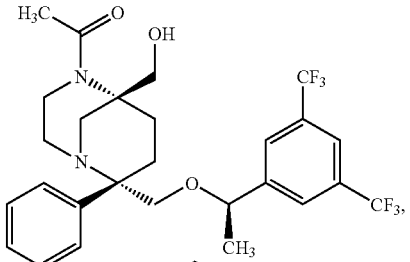
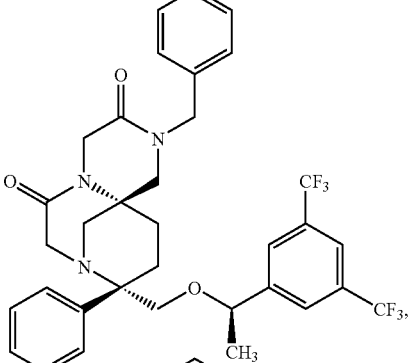
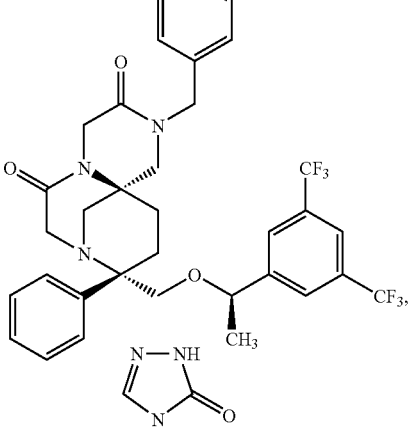
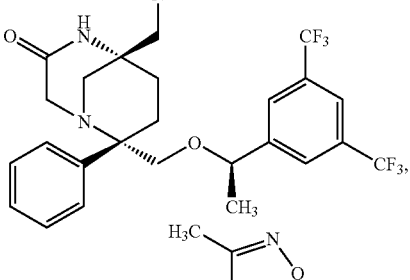
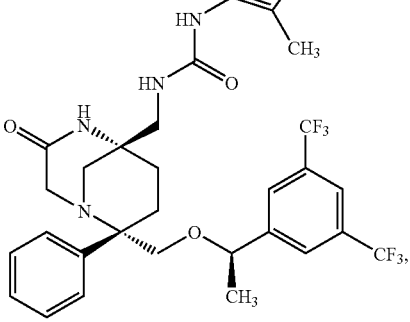

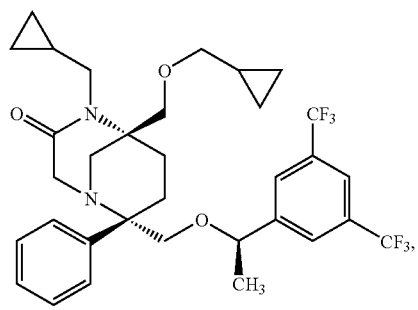
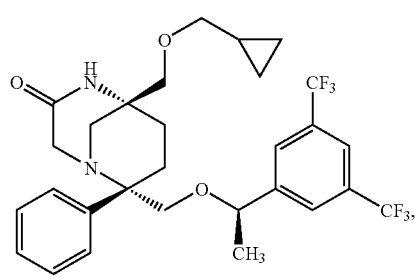
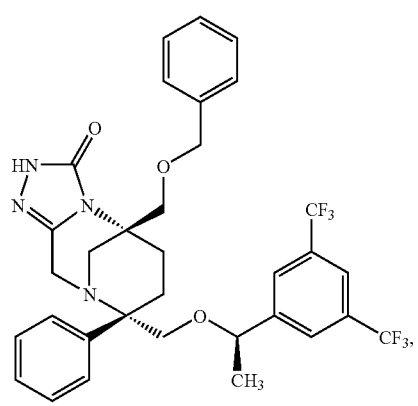
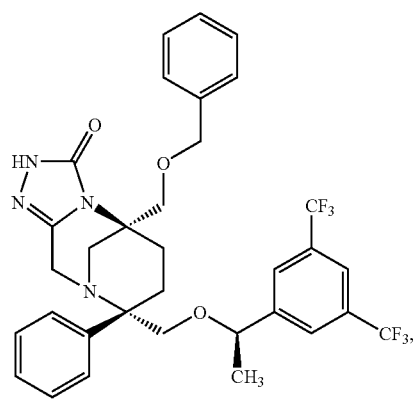
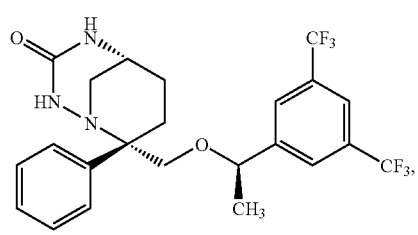
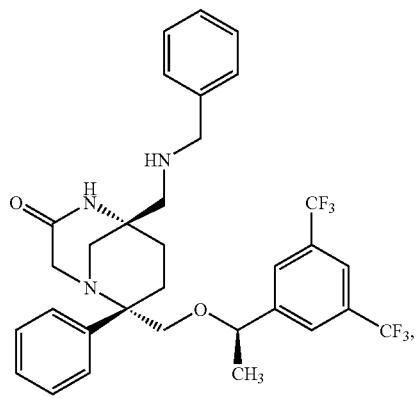
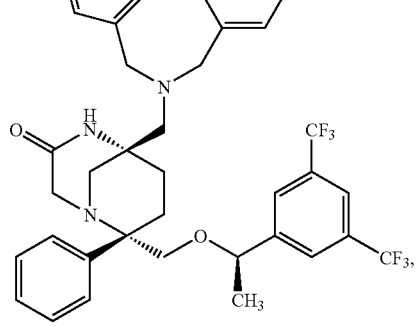
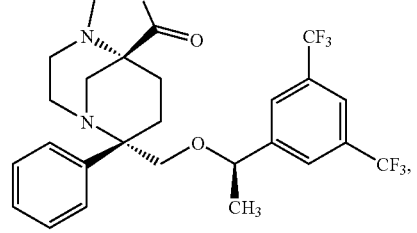
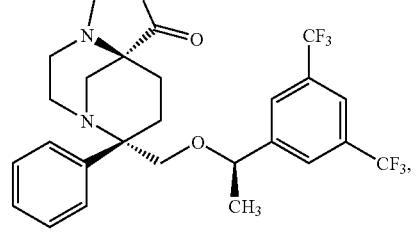
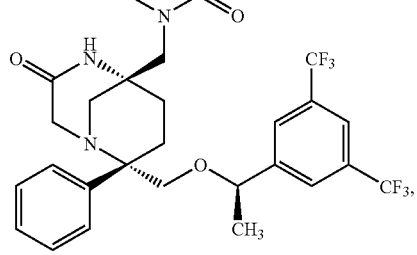

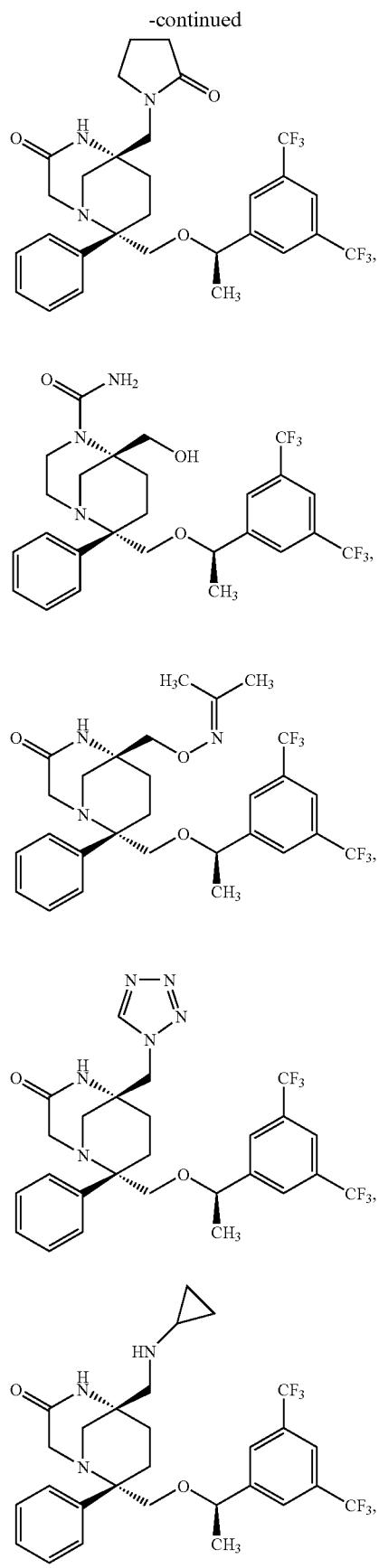
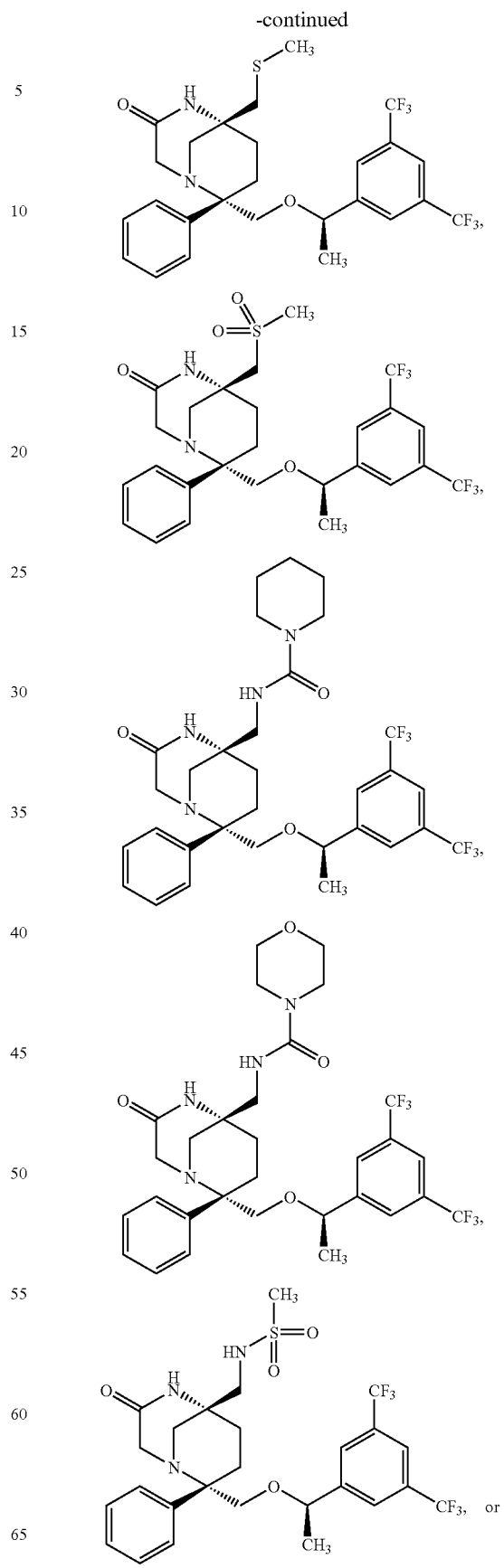

-continued

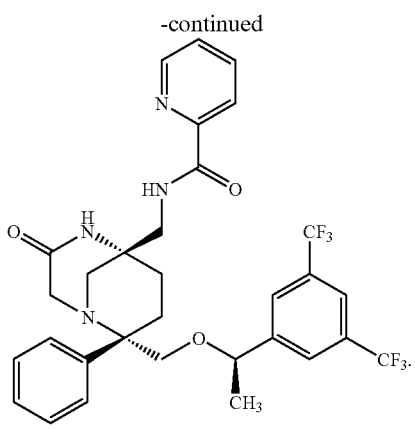

In still an additional embodiment, the present invention is directed to a method of treating a disease (or disorder or condition) in a patient in need of such treatment, wherein the disease is selected from the group consisting of: (1) respiratory diseases (e.g., chronic lung disease, bronchitis, pneumonia, asthma, allergy, cough and bronchospasm), (2) inflammatory diseases (e.g., arthritis and psoriasis), (3) skin disorders (e.g., atopic dermatitis and contact dermatitis), (4) ophthalmalogical disorders (e.g., retinitis, ocular hypertension and cataracts), (5) central nervous system conditions, such as depressions (e.g., neurotic depression), anxieties (e.g., general anxiety, social anxiety and panic anxiety disorders), phobias (e.g., social phobia), and bipolar disorder, (6) addictions (e.g., alcohol dependence and psychoactive substance abuse), (7) epilepsy, (8) nociception, (9) psychosis, (10) schizophrenia, (11) Alzheimer's disease, (12) AIDS related dementia, (13) Towne's disease, (14) stress related disorders (e.g., post traumatic stress disorder), (15) obsessive/compulsive disorders, (16) eating disorders (e.g., bulimia, anorexia nervosa and binge eating), (17) sleep disorders, (18) mania, (19) premenstrual syndrome, (20) gastrointestinal disorders (e.g., irritable bowel syndrome, Crohn's disease, colitis, and emesis), (21) atherosclerosis, (22) fibrosing disorders (e.g., pulmonary fibrosis), (23) obesity, (24) Type II diabetes, (25) pain related disorders (e.g., headaches, such as migraines, neuropathic pain, post-operative pain, and chronic pain syndromes), (26) bladder and genitourinary disorders (e.g., interstitial cystitis and urinary incontinence), (27) emesis (e.g., chemotherapy-induced (e.g., induced by cisplatin, doxorubicin, and taxane), radiation-induced, motion sickness, ethanol-induced, and post operative nausea and vomiting), and (28) nausea, comprising administering to the patient an effective amount of at least one (e.g., one) compound of Formula (I) or a pharmaceutically acceptable salt, solvate, and/or ester thereof.

In still an additional embodiment, the present invention is directed to a method of treating a disease (or disorder or condition) in a patient in need of such treatment, wherein the disease is selected from the group consisting of: respiratory diseases (e.g., cough), depression, anxiety, phobia, bipolar disorder, alcohol dependence, psychoactive substance abuse, nociception, psychosis, schizophrenia, stress related disorders, obsessive/compulsive disorder, bulimia, anorexia nervosa, binge eating, sleep disorders, mania, premenstrual syndrome, gastrointestinal disorders, obesity, pain related disorders (e.g., headaches, such as migraines, neuropathic pain, post-operative pain, and chronic pain syndromes), bladder disorders, genitourinary disorders, emesis and nausea, comprising administering to the patient an effective amount of at least one compound of Formula I or a pharmaceutically acceptable salt, solvate, and/or ester thereof.

In still an additional embodiment, the present invention also is directed to a method of treating a disease (or disorder or condition) wherein there is microvascular leakage and mucus secretion in a patient in need of such treatment, comprising administering to the patient an effective amount of at least one compound of Formula (I) or a pharmaceutically acceptable salt, solvate, and/or ester thereof.

In still an additional embodiment, the present invention also is directed to a method of treating asthma, emesis, nausea, depressions, anxieties, cough and pain related disorders in a patient in need of such treatment comprising administering to the patient an effective amount of at least one compound of Formula (I) or a pharmaceutically acceptable salt, solvate, and/or ester thereof.

In still an additional embodiment, the present invention also is directed to a method of treating emesis, depression, anxiety, and cough in a patient in need of such treatment comprising administering to the patient an effective amount of at least one compound of Formula I or a pharmaceutically acceptable salt, solvate, and/or ester thereof.

In still an additional embodiment, the present invention also is directed to a method for antagonizing an effect of a Substance P at a neurokinin-1 receptor site in a patient in need of such treatment, comprising administering to the patient at least one compound of Formula (I) or a pharmaceutically acceptable salt, solvate, and/or ester thereof.

In still an additional embodiment, the present invention also is directed to a method for the blockade of $NK_1$ receptors in a patient in need of such treatment, comprising administering to the patient at least one compound of Formula (I) or a pharmaceutically acceptable salt, solvate, and/or ester thereof.

In still an additional embodiment, the present invention also is directed to a method for treating depression and/or anxiety in a patient in need of such treatment comprising administering to the patient an effective amount of one or more compounds of Formula I or a pharmaceutically acceptable salt, solvate, and/or ester thereof, in combination with an effective amount of one or more anti-depressant agents and/or one or more anti-anxiety agents.

In still an additional embodiment, the present invention also is directed to a method of treating an $NK_1$ receptor mediated disease (or disorder or condition) in a patient in need of such treatment comprising administering to the patient an effective amount of one or more compounds of Formula (I) or a pharmaceutically acceptable salt, solvate, and/or ester thereof, in combination with an effective amount of one or more selective serotonin reuptake inhibitors ("SSRIs").

In still an additional embodiment, the present invention also is directed to a method of treating depression and/or anxiety in a patient in need of such treatment comprising administering to the patient an effective amount of one or more compounds of Formula (I) or a pharmaceutically acceptable salt, solvate, and/or ester thereof, in combination with an effective amount of one or more selective serotonin reuptake inhibitors.

In yet an additional embodiment, the present invention also is directed to a method of treating an $NK_1$ receptor mediated disease (or disorder or condition) in a patient in need of such treatment comprising administering to the patient an effective amount of at least one compound of Formula (I) or a pharmaceutically acceptable salt, solvate, and/or ester thereof, in combination with at least one therapeutic agent selected from the group consisting of: other types of $NK_1$ receptor antagonists (e.g., $NK_1$ receptor antagonists other than those according to Formula (I) of the present invention), prostanoids, $H_1$ receptor antagonists, α-adrenergic receptor agonists, dopamine receptor agonists, melanocortin receptor agonists, endothelin receptor antagonists, endothelin converting enzyme inhibitors, angiotensin II receptor antagonists, angiotensin converting enzyme inhibitors, neutral metalloendopeptidase inhibitors, $ET_A$ antagonists, renin inhibitors, serotonin 5-$HT_3$ receptor antagonists (e.g., ondansetron), serotonin 5-$HT_{2c}$ receptor agonists, nociceptin receptor agonists, glucocorticoids (e.g., dexamethasone), rho kinase inhibitors, potassium channel modulators and inhibitors of multi-drug resistance protein 5.

In yet an additional embodiment, the invention also is directed to a method for treating an $NK_1$ mediated disease (or disorder or condition) in a patient in need of such treatment comprising administering to the patient an effective amount of at least one compound of Formula (I) a pharmaceutically acceptable salt, solvate, and/or ester thereof, in combination with at least one therapeutic agent selected from the group consisting of: prostanoids, such as prostaglandin E1; α-adrenergic agonists, such as phentolamine mesylate; dopamine receptor agonists, such as apomorphine; angiotensin II antagonists, such as losartan, irbesartan, valsartan and candesartan; $ET_A$ antagonists, such as bosentan and ABT-627; serotonin 5-$HT_3$ receptor antagonists, such as ondansetron; and glucocorticoids, such as dexamethasone.

In yet an additional embodiment, the invention also is directed to a method for treating an $NK_1$ mediated disease (or disorder or condition) in a patient in need of such treatment comprising administering to the patient an effective amount of at least one compound of Formula I or a pharmaceutically acceptable salt, solvate, and/or ester thereof, in combination with an effective amount of at least one therapeutic agent selected from the group consisting of: other types of $NK_1$ receptor antagonists, SSRIs, dopamine receptor agonists, serotonin 5-$HT_3$ receptor antagonists, serotonin 5-$HT_{2c}$ receptor agonists, nociceptin receptor agonists, glucocorticoids and inhibitors of multi-drug resistance protein 5.

In yet an additional embodiment, the invention also is directed to a method for treating emesis, nausea and/or vomiting in a patient in need of such treatment comprising administering to the patient an effective amount of at least one compound of Formula (I) or a pharmaceutically acceptable salt, solvate, and/or ester thereof, in combination with an effective amount of at least one serotonin 5-$HT_3$ receptor antagonist (e.g., ondansetron) and/or at least one glucocorticoid (e.g., dexamethasone).

In still yet an additional embodiment, the present invention also is directed to a kit comprising, in separate containers in a single package, pharmaceutical compositions for use in combination to treat an $NK_1$ receptor mediated disease (or disorder or condition), wherein one container comprises a pharmaceutical composition comprising an effective amount of at least one compound of Formula I or a pharmaceutically acceptable salt, solvate, and/or ester thereof, in a pharmaceutically acceptable carrier, and wherein, a separate container comprises a pharmaceutical composition comprising at least one other therapeutic agent in a pharmaceutically acceptable carrier, said at least one other therapeutic agent being selected from the group consisting of: SSRIs, other types of $NK_1$ receptor antagonists, prostanoids, $H_1$ receptor antagonists, α-adrenergic receptor agonists, dopamine receptor agonists, melanocortin receptor agonists, endothelin receptor antagonists, endothelin converting enzyme inhibitors, angiotensin II receptor antagonists, angiotensin converting enzyme inhibitors, neutral metalloendopeptidase inhibitors, $ET_A$ antagonists, renin inhibitors, serotonin 5-$HT_3$ receptor antagonists, serotonin 5-$HT_{2c}$ receptor agonists, nociceptin receptor agonists, glucocorticoids, rho kinase inhibitors, potassium channel modulators and inhibitors of multi-drug resistance protein 5.

In still yet an additional embodiment, the present invention also is directed to a kit comprising, in separate containers in a single package, pharmaceutical compositions for use in combination to treat depression and/or anxiety, wherein one container comprises a pharmaceutical composition comprising an effective amount of at least one compound of Formula I or a pharmaceutically acceptable salt, solvate, and/or ester thereof, in a pharmaceutically acceptable carrier, and wherein a separate second container comprises a pharmaceutical composition comprising an antidepressant agent in a pharmaceutically acceptable carrier, and/or a separate third container comprises a pharmaceutical composition comprising an antianxiety agent in a pharmaceutically acceptable carrier.

In still yet an additional embodiment, the present invention also is directed to a kit comprising, in separate containers in a single package, pharmaceutical compositions for use in combination to treat depression and/or anxiety, wherein one container comprises a pharmaceutical composition comprising an effective amount of at least one compound of Formula I or a pharmaceutically acceptable salt, solvate, and/or ester thereof, in a pharmaceutically acceptable carrier, and wherein a separate second container comprises a pharmaceutical composition comprising an antidepressant agent and/or an antianxiety agent in a pharmaceutically acceptable carrier.

In still yet an additional embodiment, the present invention also is directed to a kit comprising, in separate containers in a single package, pharmaceutical compositions for use in combination to treat an $NK_1$ receptor mediated disease, wherein one container comprises a pharmaceutical composition comprising an effective amount of at least one compound of Formula (I) or a pharmaceutically acceptable salt, solvate, and/or ester thereof, in a pharmaceutically acceptable carrier, and wherein, a separate container comprises a pharmaceutical composition comprising at least one SSRI in a pharmaceutically acceptable carrier.

In still yet an additional embodiment, the present invention also is directed to a kit comprising, in separate containers in a single package, pharmaceutical compositions for use in combination to treat depression and/or anxiety, wherein one container comprises a pharmaceutical composition comprising an effective amount of at least one compound of Formula (I) or a pharmaceutically acceptable salt, solvate, and/or ester thereof, in a pharmaceutically acceptable carrier, and wherein a separate second container comprises a pharmaceutical composition comprising at least one SSRI in a pharmaceutically acceptable carrier.

In still yet an additional embodiment, the present invention also is directed to a kit comprising, in separate containers in a single package, pharmaceutical compositions for use in combination to treat emesis and/or nausea, wherein one container comprises a pharmaceutical composition comprising an effective amount of at least one compound of Formula (I) or a pharmaceutically acceptable salt, solvate, and/or ester thereof, in a pharmaceutically acceptable carrier, and wherein, a separate second container comprises a pharmaceutical composition comprising at least one serotonin 5-HT$_3$ receptor antagonist in a pharmaceutically acceptable carrier, and/or wherein a separate third container comprises a pharmaceutical composition comprising at least one glucocorticoid in a pharmaceutically acceptable carrier.

In still yet an additional embodiment, the present invention also is directed to a kit comprising, in separate containers in a single package, pharmaceutical compositions for use in combination to treat emesis and/or nausea, wherein one container comprises a pharmaceutical composition comprising an effective amount of at least one compound of Formula (I) or a pharmaceutically acceptable salt, solvate, and/or ester thereof, in a pharmaceutically acceptable carrier, and wherein, a separate second container comprises ondansetron, and/or wherein a separate third container comprises dexamethasone.

Another aspect of the invention is to provide a kit comprising, in separate containers in a single package, pharmaceutical compositions for use in combination to treat an NK$_1$ receptor mediated disease, wherein one container comprises a pharmaceutical composition comprising an effective amount of at least one compound of Formula (I) in a pharmaceutically acceptable carrier, and wherein, a separate container comprises a pharmaceutical composition comprising at least one therapeutic agent in a pharmaceutically acceptable carrier, the therapeutic agent being selected from the group consisting of: other types of NK$_1$ receptor antagonists, SSRIs, dopamine receptor agonists, serotonin 5-HT$_3$ receptor antagonists, serotonin 5-HT$_{2c}$ receptor agonists, nociceptin receptor agonists, glucocorticoids and inhibitors of multi-drug resistance protein 5.

Except where stated otherwise, the following definitions apply throughout the specification and claims. When any variable occurs more than one time in any moiety, its definition on each occurrence is independent of its definition at every other occurrence. A moiety (e.g., "alkyl", "aryl", "heteroaryl", etc.) described as substituted with one or more substituents (e.g., alkyl substituted with one or more hydroxyl groups), includes substitution with 1, 2, 3, etc. substituents, provided that the resulting substituted moiety results in a stable compound (where the term "stable" has the meaning provided herein). Likewise, moieties (e.g., aryl or heteroaryl) which are described as substituted with "0 to 3" substituents include unsubstituted moieties (i.e., "0" substituents), and moieties substituted with 1, 2, or 3 such substituents, provided that the resulting substituted moiety results in a stable compound. Chemical names, common names, and chemical structures may be used interchangeably to describe the same structure. These definitions apply regardless of whether a term is used by itself or in combination with other terms, unless otherwise indicated. Hence, the definition of "alkyl" applies to "alkyl" as well as the "alkyl" portions of "hydroxyalkyl," "haloalkyl," "alkoxy," etc.

Ac means acetyl.
Bn means benzyl.
Boc means t-butoxycarbonyl.
Bu means butyl.
t-Bu or Bu$^t$ means tertiary-butyl.
n-Bu means normal-butyl.
Cbz means carbobenzoxy (i.e., Ph-CH$_2$—O—C(O)—).
DCE means dichloroethane.
DIEA means diisopropylethyl amine.
DMF means dimethylformamide.
DMAP means dimethylamino pyridine.
DMSO means dimethylsulfoxide.
Et means ethyl.
Et$_3$N means triethyl amine.
EtOAc mean ethyl acetate.
Et$_2$O means diethyl ether.
KOtBu means potassium t-butoxide.
LAH means LiAlH$_4$.
LCMS means liquid chromatography mass spectroscopy.
LiHMDS means lithium hexamethyldisilazide.
Me means methyl.
MeOH means methanol.
Ms means methanesulfonyl.
MsCl means methanesulfonyl chloride
MS means mass spectroscopy.
Ni (Ra) means Raney Ni.
Ph means phenyl
i-Pr means isopropyl.
PPTS means pyridinium p-toluenesulfonic acid.
TBAF means tetrabutylammonium fluoride.
Tempo means 2,2,6,6-tetramethylpiperidinyl-1-oxyl.
TFA means trifluoroacetic acid.
TMS means trimethylsilyl.
pTSA means p-toluene sulfonic acid.
THF means tetrahydrofuran.
TLC means Thin Layer Chromatography.
TMSNCO means trimethylsilylisocyanate.
TosMIC means toluenesulfonylmethylisocyanate.
"Patient" includes both human and animals.
"Mammal" means humans and other mammalian animals.

Portions of chemical formulae enclosed in parentheses and/or brackets denote pendant groups. For example, —C(O)— refers to a carbonyl group (i.e.,

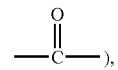

),

—N(alkyl)- refers to a divalent amine group with a pendant alkyl group (i.e.,

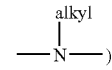

)

and —C(=NOCH$_3$)—CH$_3$ refers to

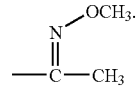

"Alkyl" means an aliphatic hydrocarbon group, which may be straight or branched and comprising about 1 to about 20 carbon atoms in the chain. Preferred alkyl groups contain about 1 to about 12 carbon atoms in the chain. More preferred alkyl groups contain about 1 to about 6 carbon atoms in the chain. Branched means that one or more lower alkyl groups such as methyl, ethyl or propyl, are attached to a linear alkyl chain. "Lower alkyl" means a group having about 1 to about 6 carbon atoms in the chain that may be straight or branched. The term "substituted alkyl" means that the alkyl group may be substituted by one or more substituents which may be the same or different, each substituent being independently selected from the group consisting of halo, alkyl, aryl, cycloalkyl, cyano, hydroxy, alkoxy, alkylthio, amino, —NH(alkyl), —NH(cycloalkyl), —N(alkyl)$_2$, carboxy and —C(O)O-alkyl. Non-limiting examples of suitable alkyl groups include methyl, ethyl, n-propyl, isopropyl and t-butyl.

"Alkenyl" means an aliphatic hydrocarbon group containing at least one carbon-carbon double bond and which may be straight or branched and comprising about 2 to about 15 carbon atoms in the chain. Preferred alkenyl groups have about 2 to about 12 carbon atoms in the chain, and more preferably about 2 to about 6 carbon atoms in the chain. Branched means that one or more lower alkyl groups such as methyl, ethyl or propyl, are attached to a linear alkenyl chain. "Lower alkenyl" means that there are about 2 to about 6 carbon atoms in the chain, which may be straight or branched. The term "alkenyl" includes substituted alkenyl which means that the alkenyl group may be substituted by one or more substituents which may be the same or different, each substituent being independently selected from the group consisting of halo, alkyl, aryl, cycloalkyl, cyano, alkoxy and —S(alkyl). Non-limiting examples of suitable alkenyl groups include ethenyl (i.e., vinyl), propenyl, n-butenyl, 3-methylbut-2-enyl, n-pentenyl, octenyl and decenyl.

"Alkynyl" means an aliphatic hydrocarbon group containing at least one carbon-carbon triple bond and which may be straight or branched and comprising about 2 to about 15 carbon atoms in the chain. Preferred alkynyl groups have about 2 to about 12 carbon atoms in the chain, and more preferably about 2 to about 4 carbon atoms in the chain. Branched means that one or more lower alkyl groups such as methyl, ethyl or propyl are attached to a linear alkynyl chain. "Lower alkynyl" means about 2 to about 6 carbon atoms in the chain that may be straight or branched. Non-limiting examples of suitable alkynyl groups include ethynyl, propynyl, 2-butynyl, and 3-methylbutynyl. The term "substituted alkynyl" means that the alkynyl group may be substituted by one or more substituents which may be the same or different, each substituent being independently selected from the group consisting of alkyl, aryl and cycloalkyl.

"Aryl" means an aromatic monocyclic or multicyclic ring system comprising about 6 to about 14 carbon atoms, preferably about 6 to about 10 carbon atoms. The aryl group can be optionally substituted with one or more "ring system substituents" which may be the same or different, and are as defined herein. Non-limiting examples of suitable aryl groups include phenyl and naphthyl.

"Heteroaryl" means an aromatic monocyclic or multicyclic ring system comprising about 5 to about 14 ring atoms, preferably about 5 to about 10 ring atoms, in which one or more of the ring atoms is an element other than carbon, for example nitrogen, oxygen or sulfur, alone or in combination. Preferred heteroaryls contain about 5 to about 6 ring atoms. The "heteroaryl" can be optionally substituted by one or more "ring system substituents" which may be the same or different, and are as defined herein. The prefix aza, oxa, or thia before the heteroaryl root name means that at least a nitrogen, oxygen or sulfur atom, respectively, is present as a ring atom. A nitrogen atom of a heteroaryl can be optionally oxidized to the corresponding N-oxide. Non-limiting examples of suitable heteroaryls include pyridyl, pyrazinyl, furanyl, thienyl, pyrimidinyl, pyridone (including N-substituted pyridones), isoxazolyl, isothiazolyl, oxazolyl, thiazolyl, pyrazolyl, furazanyl, pyrrolyl, pyrazolyl, triazolyl, 1,2,4-thiadiazolyl, pyrazinyl, pyridazinyl, quinoxalinyl, phthalazinyl, oxindolyl, imidazo[1,2-a]pyridinyl, imidazo[2,1-b]thiazolyl, benzofurazanyl, indolyl, azaindolyl, benzimidazolyl, benzothienyl, quinolinyl, imidazolyl, thienopyridyl, quinazolinyl, thienopyrimidyl, pyrrolopyridyl, imidazopyridyl, isoquinolinyl, benzoazaindolyl, 1,2,4-triazinyl, benzothiazolyl, tetrazolyl and the like. The term "heteroaryl" also refers to partially saturated heteroaryl moieties such as, for example, tetrahydroisoquinolyl, tetrahydroquinolyl, and the like.

"Aralkyl", "arylalkyl", or "-alkyl-aryl" means a group in which the aryl and alkyl portions are as previously described. Preferred aralkyls comprise a lower alkyl group. Non-limiting examples of suitable aralkyl groups include benzyl, 2-phenethyl, and naphthalenylmethyl. The bond to the parent moiety is through the alkyl.

"Alkylaryl" or "-aryl-alkyl" means a group in which the alkyl and aryl portions are as previously described. Preferred alkylaryls comprise a lower alkyl group. A non-limiting example of a suitable alkylaryl group is tolyl. The bond to the parent moiety is through the aryl.

"Cycloalkyl" means a non-aromatic mono- or multicyclic ring system comprising about 3 to about 10 carbon atoms, preferably about 5 to about 10 carbon atoms. Preferred cycloalkyl rings contain about 5 to about 7 ring atoms. The cycloalkyl can be optionally substituted with one or more "ring system substituents" which may be the same or different, and are as defined above. Non-limiting examples of suitable monocyclic cycloalkyls include cyclopropyl, cyclopentyl, cyclohexyl, cycloheptyl, and the like. Non-limiting examples of suitable multicyclic cycloalkyls include 1-decalinyl, norbornyl, adamantyl and the like, as well as partially saturated species such as, for example, indanyl, tetrahydronaphthyl and the like.

"Halogen" means fluorine, chlorine, bromine, or iodine. Preferred halogens are fluorine, chlorine and bromine. "Halogen" or "halo" substituted groups (e.g., haloalkyl groups) refers to groups substituted with one or more fluorine, chlorine, bromine, and/or iodine atoms. Preferred haloalkyl groups are those in which one or more hydrogen atoms of the alkyl group have been replaced with chlorine or fluorine. Non-limiting examples of haloalkyl groups include —$CFH_2$, —$CHF_2$, —$CF_3$, —$CH_2Cl$, etc.

"Ring system substituent" means a substituent attached to an aromatic or non-aromatic ring system, which, for example, replaces an available hydrogen on the ring system. Ring system substituents may be the same or different, each being independently selected from the group consisting of alkyl, alkenyl, alkynyl, aryl, heteroaryl, aralkyl, alkylaryl, heteroaralkyl, heteroarylalkenyl, heteroarylalkynyl, alkylheteroaryl, hydroxy, hydroxyalkyl, alkoxy, aryloxy, aralkoxy, acyl, aroyl, halo, nitro, cyano, carboxy, alkoxycarbonyl, aryloxycarbonyl, aralkoxycarbonyl, alkylsulfonyl, arylsulfonyl, heteroarylsulfonyl, alkylthio, arylthio, heteroarylthio, aralkylthio, heteroaralkylthio, cycloalkyl, —C(=N—CN)—$NH_2$, —C(=NH)—$NH_2$, —C(=NH)—NH(alkyl), $Y_1Y_2N$—, $Y_1Y_2$N-alkyl-, $Y_1Y_2$NC(O)—, $Y_1Y_2NSO_2$— and —$SO_2NY_1Y_2$, wherein $Y_1$ and $Y_2$ can be the same or different and are independently selected from the group consisting of hydrogen, alkyl, aryl, cycloalkyl, and aralkyl. "Ring system substituent" may also mean a single moiety that simultaneously replaces two available hydrogens on two adjacent carbon atoms (one H on each carbon) on a ring system. Examples of such moieties are methylenedioxy, ethylenedioxy, —C($CH_3$)$_2$— and the like which form moieties such as, for example:

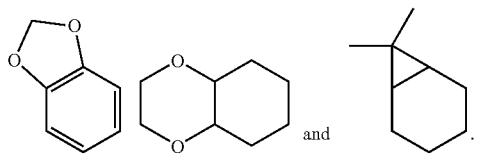

"Heterocyclyl" means a non-aromatic monocyclic or multicyclic ring system comprising about 3 to about 10 ring atoms, preferably about 5 to about 10 ring atoms, in which one or more of the atoms in the ring system is an element other than carbon, for example nitrogen, oxygen or sulfur, alone or in combination. A heterocyclyl ring can be completely saturated or partially unsaturated. There are no adjacent oxygen and/or sulfur atoms present in the heterocyclyl ring system. Preferred heterocyclyls contain about 5 to about 6 ring atoms. The prefix aza, oxa, or thia before the heterocyclyl root name means that at least a nitrogen, oxygen, or sulfur atom respectively is present as a ring atom. Any —NH in a heterocyclyl ring may be present in protected form such as, for example, an —N(Boc), —N(CBz), —N(Tos) group and the like; such protected functional groups are also considered part of this invention. The heterocyclyl can be optionally substituted by one or more "ring system substituents" which may be the same or different, and are as defined herein. The nitrogen or sulfur atom of the heterocyclyl can be optionally oxidized to the corresponding N-oxide, S-oxide or S,S-dioxide. Non-limiting examples of suitable monocyclic heterocyclyl rings include tetrahydrofuran, tetrahydrothiophene, thiazoline, 2,4-dihydro-[1,2,3]-triazole-3-one, 3,4-dihydro-2H-pyrrole, 2,3-dihydro-1H-pyrrole, 1,2-dihydropyridyl, 2,3-dihydrofuran, morpholine, piperazine, pyrrolidine, pyrrolidinone, piperadinone, 3,4-dihydro-2H-pyran, tetrahydropyran, 1,4-dioxane, lactams, lactones, and the like.

It should be noted that in hetero-atom containing ring systems of this invention, there are no hydroxyl groups on carbon atoms adjacent to a N, O or S, as well as there are no N or S groups on carbon adjacent to another heteroatom. Thus, for example, in the ring:

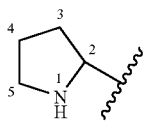

—OH is not attached directly to carbons marked 2 and 5.

It should also be noted that tautomeric forms such as, for example, the moieties:

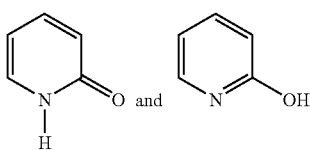

are considered equivalent in certain embodiments of this invention.

"Heteroaralkyl" means an -alkyl-heteroaryl group in which the heteroaryl and alkyl are as previously described. Preferred heteroaralkyls contain a lower alkyl group. Non-limiting examples of suitable aralkyl groups include pyridylmethyl, and quinolin-3-ylmethyl. The bond to the parent moiety is through the alkyl.

"Hydroxyalkyl" means an -alkyl-OH group in which alkyl is as previously defined. The "alkyl" portion of the hydroxyalkyl is preferably a lower alkyl. Non-limiting examples of suitable hydroxyalkyl groups include hydroxymethyl and 2-hydroxyethyl. The bond to the parent moiety is through the alkyl.

"Acyl" means a —C(O)—H, —C(O)-alkyl or —C(O)-cycloalkyl group in which the various groups are as previously described. The bond to the parent moiety is through the carbonyl. Preferred acyls contain a lower alkyl. Non-limiting examples of suitable acyl groups include formyl, acetyl and propanoyl.

"Aroyl" means an —C(O)-aryl group in which the aryl group is as previously described. The bond to the parent moiety is through the carbonyl. Non-limiting examples of suitable groups include benzoyl and 1-naphthoyl.

"Alkoxy" means an —O-alkyl group in which the alkyl group is as previously described. Non-limiting examples of suitable alkoxy groups include methoxy, ethoxy, n-propoxy, isopropoxy, and n-butoxy. The bond to the parent moiety is through the ether oxygen.

"Aryloxy" means an —O-aryl group in which the aryl group is as previously described. Non-limiting examples of suitable aryloxy groups include phenoxy and naphthoxy. The bond to the parent moiety is through the ether oxygen.

"Aralkyloxy" mean a —O-alkyl-aryl group in which the aralkyl group is as previously described. Non-limiting examples of suitable aralkyloxy groups include benzyloxy and 1- or 2-naphthalenemethoxy. The bond to the parent moiety is through the ether oxygen.

"Alkylthio" means an —S-alkyl group in which the alkyl group is as previously described. Non-limiting examples of suitable alkylthio groups include methylthio and ethylthio. The bond to the parent moiety is through the sulfur.

"Arylthio" means an —S-aryl group in which the aryl group is as previously described. Non-limiting examples of suitable arylthio groups include phenylthio and naphthylthio. The bond to the parent moiety is through the sulfur.

"Aralkylthio" means an —S-aralkyl or —S-alkyl-aryl group in which the aralkyl group is as previously described. Non-limiting example of a suitable aralkylthio group is benzylthio. The bond to the parent moiety is through the sulfur.

"Alkoxycarbonyl" means an —C(O)—O-alkyl group. Non-limiting examples of suitable alkoxycarbonyl groups include methoxycarbonyl and ethoxycarbonyl. The bond to the parent moiety is through the carbonyl.

"Aryloxycarbonyl" means a —C(O)—O-aryl group. Non-limiting examples of suitable aryloxycarbonyl groups include phenoxycarbonyl and naphthoxycarbonyl. The bond to the parent moiety is through the carbonyl.

"Aralkoxycarbonyl" means an —C(O)—O-alkyl-aryl group. Non-limiting example of a suitable aralkoxycarbonyl group is benzyloxycarbonyl. The bond to the parent moiety is through the carbonyl.

"Alkylsulfonyl" means a —S(O₂)-alkyl group. Preferred groups are those in which the alkyl group is lower alkyl. The bond to the parent moiety is through the sulfonyl.

"Arylsulfonyl" means an —S(O₂)-aryl group. The bond to the parent moiety is through the sulfonyl.

The term "substituted" means that one or more hydrogens on the designated atom is replaced with a selection from the indicated group, provided that the designated atom's normal valency under the existing circumstances is not exceeded, and that the substitution results in a stable compound. Combinations of substituents and/or variables are permissible only if such combinations result in stable compounds. A "stable compound" or "stable structure" means a compound that is sufficiently robust to survive isolation to a useful degree of purity from a reaction mixture, and formulation into an efficacious therapeutic agent.

The term "optionally substituted" means optional substitution with the specified groups, radicals or moieties.

The term "isolated" or "in isolated form" for a compound refers to the physical state of said compound after being isolated from a synthetic process or natural source or combination thereof. The term "purified" or "in purified form" for a compound refers to the physical state of said compound after being obtained from a purification process or processes described herein or well known to the skilled artisan, in sufficient purity to be characterizable by standard analytical techniques described herein or well known to the skilled artisan.

It should also be noted that any heteroatom with unsatisfied valences in the text, schemes, examples, and Tables herein is assumed to have one or more hydrogen atoms to satisfy the valences.

When a ring system (e.g., cycloalkyl, heterocyclyl, aryl, or heteroaryl) is substituted with a number of substituents varying within an expressly defined range, it is understood that the total number of substituents does not exceed the normal available valencies under the existing conditions. Thus, for example, a phenyl ring substituted with "n" substituents (where "n" ranges from 0 to 5) can have 0 to 5 substituents, whereas it is understood that a pyridinyl ring substituted with "n" substituents has a number of substituents ranging from 0 to 4.

When a functional group in a compound is termed "protected", this means that the group is in modified form to preclude undesired side reactions at the protected site when the compound is subjected to a reaction. Suitable protecting groups will be recognized by those with ordinary skill in the art as well as by reference to standard textbooks such as, for example, T. W. Greene et al, *Protective Groups in Organic Synthesis* (1991), Wiley, N.Y., herein incorporated by reference.

When any variable (e.g., aryl, heterocyclyl, $R^{13}$, etc.) occurs more than one time in any constituent or in Formula (I), its definition on each occurrence is independent of its definition at every other occurrence.

As used herein, the term "composition" is intended to encompass a product comprising the specified ingredients in the specified amounts, as well as any product which results, directly or indirectly, from combination of the specified ingredients in the specified amounts.

"Alkylheteroaryl" means an alkyl group attached to a parent moiety via a heteroaryl group.

"Alkylsulfinyl" means a —S(O)-alkyl group. Preferred groups are those in which the alkyl group is lower alkyl. The bond to the parent moiety is through the sulfinyl.

"Aralkenyl" means an -alkenyl-aryl group in which the aryl and alkenyl are as previously described. Preferred aralkenyls contain a lower alkenyl group. Non-limiting examples of suitable aralkenyl groups include 2-phenethenyl and 2-naphthylethenyl. The bond to the parent moiety is through the alkenyl.

"Arylsulfinyl" means an —S(O)-aryl group. Non-limiting examples of suitable arylsulfinyl groups include phenylsulfinyl and naphthylsulfinyl. The bond to the parent moiety is through the sulfinyl.

A carbamate group means a —O—C(O)—N(alkyl or aryl)-group, and a urea group means a —N(alkyl or aryl)-C(O)—N(alkyl or aryl)-group. Representative carbamate and urea groups may include the following:

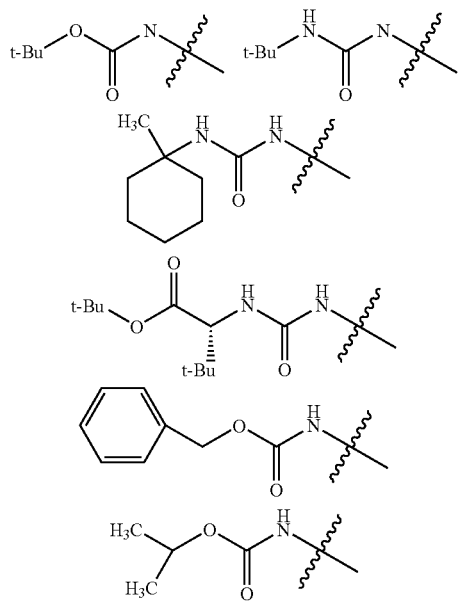

"Cycloalkenyl" means a non-aromatic mono or multicyclic ring system comprising about 3 to about 10 carbon atoms, preferably about 5 to about 10 carbon atoms, which contains at least one carbon-carbon double bond. Preferred cycloalkenyl rings contain about 5 to about 7 ring atoms. The cycloalkenyl can be optionally substituted with one or more "ring system substituents" which may be the same or different, and are as defined above. Non-limiting examples of suitable monocyclic cycloalkenyls include cyclopentenyl, cyclohexenyl, cycloheptenyl, and the like. A non-limiting example of a suitable multicyclic cycloalkenyl is norbornylenyl.

"Heteroaralkylthio" means an —S-alkyl-heteroaryl group wherein the group is attached to the parent moiety through the sulfur.

"Heteroarylsulfinyl" means a —S(O)-heteroaryl group wherein the heteroaryl is as defined herein and the heteroarylsulfinyl group is attached to the parent moiety through the sulfinyl.

"Heteroarylsulfonyl" means a —S($O_2$)-heteroaryl group wherein the heteroaryl is as defined herein and the heteroarylsulfonyl group is attached to the parent moiety through the sulfonyl.

"Heteroarylthio" means an —S-heteroaryl group wherein the heteroaryl is as defined herein and the heteroaryl group is attached to the parent moiety through the sulfur.

"Sulfonamide" means a sulfonyl group attached to a parent moiety through an amide.

As is well known in the art, a bond drawn from a particular atom wherein no moiety is depicted at the terminal end of the bond indicates a methyl group bound through that bond to the atom. For example:

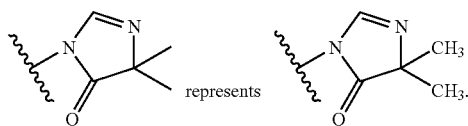
represents

It should also be noted that throughout the specification and Claims appended hereto, that any formula, compound, moiety or chemical illustration with unsatisfied valences is assumed to have the hydrogen atom to satisfy the valences unless the context indicates a bond.

With reference to the number of moieties (e.g., substituents, groups or rings) in a compound, unless otherwise defined, the phrases "one or more" and "at least one" mean that there can be as many moieties as chemically permitted, and the determination of the maximum number of such moieties is well within the knowledge of those skilled in the art.

The wavy line "∼∼∼" as a bond generally indicates a mixture of, or either of, the possible isomers, e.g., containing (R)- and (S)-stereochemistry. For example,

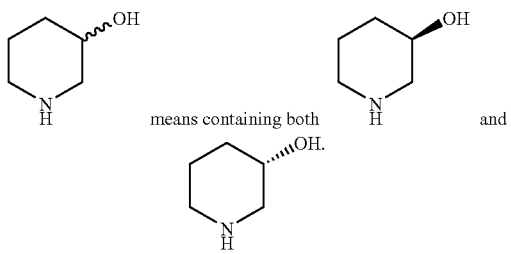
means containing both             and

Similarly, when the stereochemistry in a structure is not expressly indicated, (e.g., a straight line "——" is used at a chiral center, rather than "◀━" or "⋯⋯⋯" the structure can have a mixture of, or any of the individual possible stereochemical configurations having the indicated connectivity (e.g., all possible enantiomers), as well as mixtures of such stereoisomers (e.g., racemic mixtures). For example,

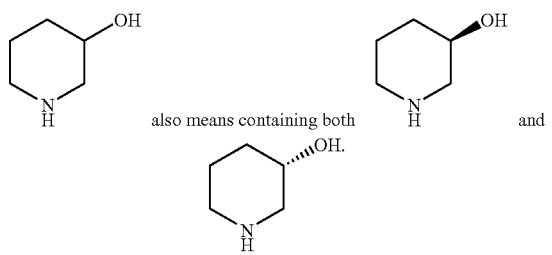
also means containing both         and

Lines drawn into the ring systems, such as, for example:

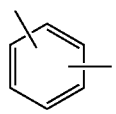

indicate that the indicated line (bond) may be attached to any of the substitutable ring carbon atoms.

Prodrugs and solvates of the compounds of the invention are also contemplated herein. The term "prodrug", as employed herein, denotes a compound that is a drug precursor, which, upon administration to a subject, undergoes chemical conversion by metabolic or chemical processes to yield a compound of Formula (I) or a salt and/or solvate thereof. A discussion of prodrugs is provided in T. Higuchi and V. Stella, *Pro-drugs as Novel Delivery Systems* (1987) Volume 14 of the A.C.S. Symposium Series, and in *Bioreversible Carriers in Drug Design*, (1987) Edward B. Roche, ed., American Pharmaceutical Association and Pergamon Press, both of which are incorporated herein by reference thereto.

"Solvate" means a physical association of a compound of this invention with one or more solvent molecules. This physical association involves varying degrees of ionic and covalent bonding, including hydrogen bonding. In certain instances, the solvate will be capable of isolation, for example, when one or more solvent molecules are incorporated in the crystal lattice of the crystalline solid. "Solvate" encompasses both solution-phase and isolatable solvates. Non-limiting examples of suitable solvates include ethanolates, methanolates, and the like. A "hydrate" is a solvate wherein the solvent molecule is $H_2O$.

One or more compounds of the present invention may also exist as, or optionally convert to, a solvate. Preparation of solvates is generally known. Thus, for example, M. Caira et al, *J. Pharmaceutical Sci.*, 93(3), 601-611 (2004) describes the preparation of the solvates of the antifungal fluconazole in ethyl acetate as well as from water. Similar preparations of solvates, hemisolvate, hydrates and the like are described by E. C. van Tonder et al, *AAPS PharmSciTech.*, 5(1), article 12 (2004); and A. L. Bingham et al, *Chem. Commun.*, 603-604 (2001). A typical, non-limiting, process involves dissolving the inventive compound in desired amounts of the desired solvent (organic or water or mixtures thereof) at a higher than ambient temperature, and cooling the solution at a rate sufficient to form crystals which are then isolated by standard methods. Analytical techniques such as, for example infrared spectroscopy, show the presence of the solvent (or water) in the crystals as a solvate (or hydrate).

"Effective amount" or "therapeutically effective amount" is meant to describe an amount of compound or a composition of the present invention effective in antagonizing the neurokinin-1 receptor and thus producing the desired therapeutic effect in a suitable patient.

The term "pharmaceutical composition" is also intended to encompass both the bulk composition and individual dosage units comprised of more than one (e.g., two) pharmaceutically active agents such as, for example, a compound of the present invention and an additional agent selected from the lists of the additional agents described herein, along with any pharmaceutically inactive excipients. The bulk composition and each individual dosage unit can contain fixed amounts of the afore-said "more than one pharmaceutically active agents". The bulk composition is material that has not yet been formed into individual dosage units. An illustrative dosage unit is an oral dosage unit such as tablets, pills and the like. Similarly, the herein-described method of treating a patient by administering a pharmaceutical composition of the present invention is also intended to encompass the administration of the afore-said bulk composition and individual dosage units.

The compounds of Formula (I) form salts that are also within the scope of this invention. Reference to a compound of Formula (I) herein is understood to include reference to salts thereof, unless otherwise indicated. The term "salt(s)", as employed herein, denotes acidic salts formed with inorganic and/or organic acids, as well as basic salts formed with inorganic and/or organic bases. In addition, when a compound of Formula (I) contains both a basic moiety, such as, but not limited to a pyridine or imidazole, and an acidic moiety, such as, but not limited to a carboxylic acid, zwitterions ("inner salts") may be formed and are included within the term "salt(s)" as used herein. Pharmaceutically acceptable (i.e., non-toxic, physiologically acceptable) salts are preferred, although other salts are also useful. Salts of the compounds of the Formula (I) may be formed, for example, by reacting a compound of Formula (I) with an amount of acid or base, such as an equivalent amount, in a medium such as one in which the salt precipitates or in an aqueous medium followed by lyophilization.

Exemplary acid addition salts include acetates, adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides, hydrobromides, hydroiodides, 2-hydroxyethanesulfonates, lactates, maleates, methanesulfonates, methyl sulfates, 2-naphthalenesulfonates, nicotinates, nitrates, oxalates, pamoates, pectinates, persulfates, 3-phenylpropionates, phosphates, picrates, pivalates, propionates, salicylates, succinates, sulfates, sulfonates (such as those mentioned herein), tartarates, thiocyanates, toluenesulfonates (also known as tosylates,) undecanoates, and the like.

Exemplary basic salts include ammonium salts, alkali metal salts such as sodium, lithium, and potassium salts, alkaline earth metal salts such as calcium and magnesium salts, aluminum salts, zinc salts, salts with organic bases (for example, organic amines) such as benzathines, diethylamine, dicyclohexylamines, hydrabamines (formed with N,N-bis(dehydroabietyl)ethylenediamine), N-methyl-D-glucamines, N-methyl-D-glucamides, t-butyl amines, piperazine, phenylcyclohexylamine, choline, tromethamine, and salts with amino acids such as arginine, lysine and the like. Basic nitrogen-containing groups may be quaternized with agents such as lower alkyl halides (e.g. methyl, ethyl, propyl, and butyl chlorides, bromides and iodides), dialkyl sulfates (e.g. dimethyl, diethyl, dibutyl, and diamyl sulfates), long chain halides (e.g. decyl, lauryl, myristyl and stearyl chlorides, bromides and iodides), aralkyl halides (e.g. benzyl and phenethyl bromides), and others. Acids (and bases) which are generally considered suitable for the formation of pharmaceutically useful salts from basic (or acidic) pharmaceutical compounds are discussed, for example, by S. Berge et al, *Journal of Pharmaceutical Sciences* (1977) 66(1) 1-19; P. Gould, *International J. of Pharmaceutics* (1986) 33 201-217; Anderson et al, *The Practice of Medicinal Chemistry* (1996), Academic Press, New York; in *The Orange Book* (Food & Drug Administration, Washington, D.C. on their website); and P. Heinrich Stahl, Camille G. Wermuth (Eds.), *Handbook of Pharmaceutical Salts: Properties, Selection, and Use*, (2002) Int'l. Union of Pure and Applied Chemistry, pp. 330-331, each of which is incorporated herein by reference.

All such acid salts and base salts are intended to be pharmaceutically acceptable salts within the scope of the invention and all acid and base salts are considered equivalent to the free forms of the corresponding compounds for purposes of the invention.

Compounds of Formula (I) and salts, solvates and prodrugs thereof, may exist in their tautomeric form (for example, as an amide or imino ether). All such tautomeric forms are contemplated herein as part of the present invention.

Polymorphic forms of the compounds of Formula (I), and of the salts, solvates, and/or prodrugs thereof, are intended to be included in the present invention.

All stereoisomers (for example, geometric isomers, optical isomers and the like) of the present compounds (including those of the salts, solvates and prodrugs of the compounds as well as the salts and solvates of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this invention. Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the IUPAC 1974 Recommendations. The use of the terms "salt", "solvate" "prodrug" and the like, is intended to apply equally to the salt, solvate and prodrug of enantiomers, stereoisomers, rotamers, tautomers, racemates or prodrugs of the inventive compounds.

Compounds of Formula (I) are effective antagonists of the $NK_1$ receptor, and have an effect on its endogenous agonist, Substance P, at the $NK_1$ receptor site, and therefore, can be useful in treating diseases, disorders, or conditions caused or aggravated by the activity of the receptor.

The in vitro and in vivo $NK_1$, $NK_2$ and $NK_3$ activities of the compounds of Formula (I) can be determined by various procedures known in the art, such as a test for their ability to inhibit the activity of the $NK_1$ agonist Substance P. The percent inhibition of neurokinin agonist activity is the difference between the percent of maximum specific binding ("MSB") and 100%. The percent of MSB is defined by the following equation, wherein "dpm" represents "disintegrations per minute":

$$\% MSB = \frac{(dpm \text{ of unknown}) - (dpm \text{ of nonspecific binding})}{(dpm \text{ of total binding}) - (dpm \text{ of nonspecific binding})} \times 100.$$

The concentration at which the compound produces 50% inhibition of binding is then used to determine an inhibition constant ("$K_i$") using the Chang-Prusoff equation.

In vivo activity may be measured by inhibition of an agonist-induced foot tapping in a gerbil, as described in *Science*, 281, 1640-1695 (1998), which is herein incorporated by reference in its entirety. It will be recognized that compounds of Formula (I) can exhibit $NK_1$ antagonist activities of varying degrees. For instance, certain compounds can exhibit stronger $NK_1$ antagonist activities than others.

The compounds of the present invention exhibit potent affinities for the $NK_1$ receptor as measured by $K_i$ values (in nM). The activities (potencies) for the compounds of the invention are determined by measuring their $K_i$ values. The smaller the $K_i$ value, the more active is a compound for antagonizing the $NK_1$ receptor. Compounds of the invention exhibit a wide range of activities. The $NK_1$ average $K_i$ values for compounds of Formula (I) generally range from 0.01 nM to about 1000 nM, preferably, from about 0.05 nM to about 100 nM, with values of from about 0.05 nM to about 20 nM being more preferred. Even more preferred are compounds having average $K_i$ values of from 0.05 nM to about 5 nM for the $NK_1$ receptor. Especially preferred compounds have $NK_1$ average $K_i$ values of from 0.05 nM to about 1 nM. Even more especially preferred compounds have $NK_1$ average $K_i$ values of from 0.05 nM to about 0.2 nM. Examples 3a, 4, 5, 8, 12, 15, 16, 20, 30, 32, 33, 34, 38, 47, 49, 51, and 57 have $K_i$ values, respectively, of 0.15, 0.11, 0.1, 0.12, 0.13, 0.09, 0.16, 0.15, 0.11, 0.11, 0.13, 0.07, 0.12, 0.12, 0.16, 0.12, and 0.12.

Compounds of the Formula (I) have a number of utilities. For instance, the inventive compounds can be useful as antagonists of neurokinin receptors, particularly, $NK_1$ receptors in a mammal, such as a human. As such, they may be useful in treating and preventing one or more of a variety of mammalian (human and animal) disease states (physiological disorders, symptoms and diseases) in a patient in need of such treatment, wherein the disease states are selected from the group consisting of: (1) respiratory diseases (e.g., chronic lung disease, bronchitis, pneumonia, asthma, allergy, cough and bronchospasm), (2) inflammatory diseases (e.g., arthritis and psoriasis), (3) skin disorders (e.g., atopic dermatitis and contact dermatitis), (4) ophthalmologic disorders (e.g., retinitis, ocular hypertension and cataracts), (5) central nervous system conditions, such as depressions (e.g., neurotic depression), anxieties (e.g., general anxiety, social anxiety and panic anxiety disorders), phobias (e.g., social phobia), and bipolar disorder, (6) addictions (e.g., alcohol dependence and psychoactive substance abuse), (7) epilepsy, (8) nociception, (9) psychosis, (10) schizophrenia, (11) Alzheimer's disease, (12) AIDs related dementia, (13) Towne's disease, (14) stress related disorders (e.g., post traumatic stress disorder), (15) obsessive/compulsive disorders, (16) eating disorders (e.g., bulimia, anorexia nervosa and binge eating), (17) sleep disorders, (18) mania, (19) premenstrual syndrome, (20) gastrointestinal disorders (e.g., irritable bowel syndrome, Crohn's disease, colitis, and emesis), (21) atherosclerosis, (22) fibrosing disorders (e.g., pulmonary fibrosis), (23) obesity, (24) Type II diabetes, (25) pain related disorders (e.g., headaches, such as migraines, neuropathic pain, post-operative pain, and chronic pain syndromes), (26) bladder and genitourinary disorders (e.g., interstitial cystitis and urinary incontinence), (27) emesis (e.g., chemotherapy-induced (e.g., induced by cisplatin, doxorubicin, and taxane), radiation-induced, motion sickness, ethanol-induced, and post operative nausea and vomiting), and (28) nausea. Preferably, the inventive compounds can be useful in treating and preventing one of the following mammalian (e.g., human) disease states in a patient in need of such treatment: respiratory diseases (e.g., cough), depression, anxiety, phobia, and bipolar disorder, alcohol dependence, psychoactive substance abuse, nociception, psychosis, schizophrenia, stress related disorders, obsessive/compulsive disorder, bulimia, anorexia nervosa and binge eating, sleep disorders, mania, premenstrual syndrome, gastrointestinal disorders, obesity, pain related disorders, bladder disorders, genitourinary disorders, emesis and nausea. In particular, the compounds according to Formula (I) are useful for treating disease states related to microvascular leakage and mucus secretion. Consequently, the compounds of the invention are especially useful in the treatment and prevention of asthma, emesis, nausea, depressions, anxieties, cough and pain related disorders, more especially, emesis, depression, anxiety and cough.

In another aspect, the invention relates to pharmaceutical compositions comprising at least one compound (e.g., one to three compounds, preferably, one compound) represented by Formula (I) and at least one pharmaceutically acceptable excipient or carrier. The invention also relates to the use of such pharmaceutical compositions in the treatment of mammalian (e.g., human) disease states, such as those listed above.

In still another aspect of the invention, a method is provided for antagonizing the effects of a Substance P at a neurokinin-1 receptor site or for the blockade of one or more neurokinin-1 receptors in a mammal (i.e., a patient, e.g., a human) in need of such treatment, comprising administering to the mammal an effective amount of at least one (e.g., one) compound according to Formula (I).

In another aspect of the invention, an effective amount of one or more of the inventive $NK_1$ receptor antagonists may be combined with an effective amount of one or more anti-depressant agents and/or one or more anti-anxiety agents (e.g., gepirone, gepirone hydrochloride, nefazodone, and nefazodone hydrochloride (e.g., Serzone®) to treat depression and/or anxiety. U.S. Pat. No. 6,117,855 (2000), the disclosure of which is incorporated herein by reference, discloses a method for treating or preventing depression or anxiety with a combination therapy of a specific $NK_1$ receptor antagonist together with an anti-depressant and/or anti-anxiety agent. Thus, anti-depressant and/or anti-anxiety agents, such as those disclosed in U.S. Pat. No. 6,117,855 (2000), can be combined with one or more (e.g., one) compounds of the Formula (I) to treat depression and/or anxiety disease states in a mammal, preferably, a human.

In still another aspect of the invention, an effective amount of one or more (e.g., one) of the inventive $NK_1$ receptor antagonists may be combined with an effective amount of one or more (e.g., one) selective serotonin reuptake inhibitors ("SSRIs") to treat a variety of mammalian disease states, such as those described above. SSRIs alter the synaptic availability of serotonin through their inhibition of presynaptic reaccumulation of neuronally released serotonin. U.S. Pat. No. 6,162,805 (2000), the disclosure of which is incorporated herein by reference, discloses a method for treating obesity with a combination therapy of a $NK_1$ receptor antagonist and an SSRI. One or more inventive compound(s) of the Formula (I) can be combined together with an SSRI(s) in a single pharmaceutical composition, or it can be administered simultaneously, concurrently or sequentially with an SSRI. This combination may be useful in the treatment and prevention of obesity or another of the above-identified human and animal disease states. In particular, an effective amount of at least one (e.g., one) compound having the Formula (I), alone or together with an effective amount of at least one (e.g., one) selective serotonin reuptake inhibitor, can be useful in the treatment and prevention of depression, and/or anxiety.

Numerous chemical substances are known to alter the synaptic availability of serotonin through their inhibition of presynaptic reaccumulation of neuronally released serotonin. Representative SSRIs include, without limitation, the following: fluoxetine, fluoxetine hydrochloride (e.g., Prozac®), fluvoxamine, fluvoxamine maleate (e.g. Luvox®), paroxetine, paroxetine hydrochloride (e.g., Paxil®), sertraline, sertraline hydrochloride (e.g., Zoloft®), citalopram, citalopram hydrobromide (e.g., Celexa™), duloxetine, duloxetine hydrochloride, venlafaxine, and venlafaxine hydrochloride (e.g., Effexor®). Further SSRIs include those disclosed in U.S. Pat. No. 6,162,805 (2000). Other compounds can readily be evaluated to determine their ability to inhibit serotonin reuptake selectively. Thus, one aspect of the invention relates to a pharmaceutical composition comprising at least one (e.g., one) $NK_1$ receptor antagonist having the Formula (I), at least one (e.g., one) SSRI, and at least one pharmaceutically acceptable excipient or carrier. Another aspect of the invention relates to a method of treating the above identified mammalian (e.g., human) disease states, the method comprising administering to a patient in need of such treatment an effective amount of a pharmaceutical composition comprising at least one (e.g., one) $NK_1$ receptor antagonist having the Formula (I) in combination with at least one (e.g., one) SSRI, such as one of those recited above, and at least one pharmaceutically acceptable excipient or carrier.

In a preferred aspect, the invention relates to a method of treating depression and anxiety, the method comprising administering to a patient in need of such treatment an effective amount of at least one (e.g., one) $NK_1$ receptor antagonist having the Formula (I) in combination with at least one (e.g., one) SSRI, such as one of those described above. When an inventive $NK_1$ receptor antagonist is combined with an SSRI for administration to a patient in need of such treatment, the two active ingredients can be administered simultaneously, consecutively (one after the other within a relatively short period of time), or sequentially (first one and then the other over a period of time). In general, when the two active ingredients are administered consecutively or sequentially, the inventive $NK_1$ receptor antagonist is preferably administered before the administration of the SSRI.

It is another embodiment of the invention to treat a patient suffering from multiple ailments with a combination therapy, the therapy comprising administering to a patient (e.g., a mammal, preferably a human) in need of such treatment at least one compound of Formula (I), and at least one other active ingredient (i.e., drug) used for treating one or more of the ailments being suffered by the patient. The compounds of Formula (I) and the other active ingredients can be administered sequentially, concurrently and/or simultaneously. The compounds of Formula (I) and the other active ingredients can be administered separately in any suitable dosage form. Preferably, administration is accomplished using an oral dosage forms or using a transdermal patches. The compounds of Formula (I) and the other active ingredients can be formulated together and administered in one combined dosage form.

Thus, the compounds of the invention may be employed alone or in combination with other active agents. Combination therapy includes the administration of two or more active ingredients to a patient in need of treatment. In addition to the above described $NK_1$ receptor antagonist/SSRI combination therapy, the compounds having the Formula (I) may be combined with one or more other active agents, such as the following: other types of $NK_1$ receptor antagonists (e.g., those that are disclosed in neurokinin receptor antagonist patents cited above), prostanoids, $H_1$ receptor antagonists, α-adrenergic receptor agonists, dopamine receptor agonists, melanocortin receptor agonists, endothelin receptor antagonists, endothelin converting enzyme inhibitors, angiotensin II receptor antagonists, angiotensin converting enzyme inhibitors, neutral metalloendopeptidase inhibitors, $ET_A$ antagonists, renin inhibitors, serotonin 5-$HT_3$ receptor antagonists (e.g., ondansetron, ondansetron hydrochloride (e.g., Zolfran®), palonosetron, granisetron, and granisetron hydrochloride (e.g., Kytril®), serotonin 5-$HT_{2c}$ receptor agonists, nociceptin receptor agonists, glucocorticoids (e.g., dexamethasone), rho kinase inhibitors, potassium channel modulators and/or inhibitors of multi-drug resistance protein 5.

Particularly useful therapeutic agents for combination therapy with compounds of the invention are the following: prostanoids, such as prostaglandin $E_1$; α-adrenergic agonists, such as phentolamine mesylate; dopamine receptor agonists, such as apomorphine; angiotensin II antagonists, such as losartan, irbesartan, valsartan and candesartan; $ET_A$ antagonists, such as bosentan and ABT-627; serotonin 5-$HT_3$ receptor antagonists, such as ondansetron; and glucocorticoids, such as dexamethasone. In preferred embodiments of the invention, the inventive compounds can be combined with: other types of $NK_1$ receptor antagonists, SSRIs, dopamine receptor agonists, serotonin 5-$HT_3$ receptor antagonists, serotonin 5-$HT_{2c}$ receptor agonists, nociceptin receptor agonists, glucocorticoids and/or inhibitors of multi-drug resistance protein 5.

Another embodiment of this invention is directed to a method for treating a physiological disorder, symptom or disease in a patient in need of such treatment, comprising administering to the patient an effective amount of at least one compound of Formula (I), and an effective amount of at least one active ingredient selected from the group consisting of: other $NK_1$ receptor antagonists, selective serotonin reuptake inhibitors, dopamine receptor agonists, serotonin 5-$HT_3$ receptor antagonists, serotonin 5-$HT_{2c}$ receptor agonists, nociceptin receptor agonists, glucocorticoids and inhibitors of multidrug resistance protein 5, wherein the physiological disorder, symptom or disease is selected from the group consisting of: a respiratory disease, depression, anxiety, phobia, bipolar disorder, alcohol dependence, psychoactive substance abuse, nociception, psychosis, schizophrenia, stress related disorder, obsessive/compulsive disorder, bulimia, anorexia nervosa, binge eating, sleep disorder, mania, premenstrual syndrome, gastrointestinal disorder, obesity, headache, neuropathic pain, post-operative pain, chronic pain syndrome, bladder disorder, genitourinary disorder, cough, emesis and nausea.

It is yet another embodiment of the invention to treat a patient suffering from chemotherapy-induced nausea and vomiting or emesis, for example as the result of treatment with chemotherapy agents such as cisplatin, doxorubicin, and taxane. Treatments can comprise administering to a patient in need of such treatment an effective amount of at least one $NK_1$ receptor antagonist of Formula (I), optionally in combination with other agents, such as serotonin 5-$HT_3$ receptor antagonists (e.g., ondansetron) and/or glucocorticoids (e.g., dexamethasone). The $NK_1$ receptor antagonist of Formula (I) may be administered in an intravenous solution containing dextrose or sodium chloride, in oral form (e.g., as a pill or capsule), or as a combination of an intravenous and oral administration. For example, the intravenous solution comprising the $NK_1$ receptor antagonist of Formula (I) may be administered to the patient before, during, or after administration of the chemotherapy agent, followed by administration of the $NK_1$ receptor antagonist of Formula (I) in oral form. Such treatment may also include repeated administration of the $NK_1$ receptor antagonist of Formula (I) over a period of days or weeks to reduce or prevent emesis.

For intravenous formulations of the $NK_1$ receptor antagonist of Formula (I), the compound of Formula (I) may be stored in the form of a solid (e.g., powder), optionally in combination with one or more other agents (e.g., serotonin 5-$HT_3$ receptor antagonists or glucocorticoids), then reconstituted by the addition of a suitable liquid. Alternatively, the compound of Formula (I) may be stored as a solution or suspension (e.g., in a single use vial, a multi-use vial, or in a ready-to-use vial), optionally in combination with one or more other agents described herein. Alternatively, the solution or suspension of the compound of Formula (I) may be mixed, prior to administration, with the optional other agents, or the solution or suspension of the compound of Formula (I) may be administered separately from the solution or suspension of the other optional agents.

Oral formulations of the $NK_1$ receptor antagonist of Formula (I) may be in the form of a pill or capsule. If combined with one or more agents (e.g., serotonin 5-$HT_3$ receptor antagonists or glucocorticoids), the compound of Formula (I) and the one or more agents may be mixed together with pharmaceutically acceptable excipients, or may be combined in a layered structure (e.g., bilayer pill) to segregate the various active ingredients. Alternatively, the compound of Formula (I) and the optional other agents may be administered separately.

Pharmaceutical compositions may contain from about 0.1 to about 99.9 weight percent, or from about 5 to about 95 weight percent, or from about 20 to about 80 weight percent of active ingredient (compound of the Formula (I)). For preparing pharmaceutical compositions from the compounds described by this invention, inert, pharmaceutically acceptable carriers can be either solid or liquid. Solid form preparations include powders, tablets, dispersible granules, capsules, cachets and suppositories. The powders and tablets may be comprised of from about 5 to about 95 percent active ingredient: Suitable solid carriers are known in the art, e.g. magnesium carbonate, magnesium stearate, talc, sugar or lactose. Tablets, powders, cachets and capsules can be used as solid dosage forms suitable for oral administration. Examples of pharmaceutically acceptable carriers and methods of manufacture for various compositions may be found in A. Gennaro (ed.), Remington: *The Science and Practice of Pharmacy*, 20$^{th}$ Edition, (2000), Lippincott Williams & Wilkins, Baltimore, Md., herein incorporated by reference.

Liquid form preparations include solutions, suspensions and emulsions, for example, water or water-propylene glycol solutions for parenteral injection or addition of sweeteners and opacifiers for oral solutions, suspensions, and emulsions. Liquid form preparations may also include solutions for intranasal administration.

Aerosol preparations suitable for inhalation may include solutions and solids in powder form, which may be in combination with a pharmaceutically acceptable carrier, such as an inert compressed gas, e.g. nitrogen.

Also included are solid form preparations that are intended to be converted, shortly before use, to liquid form preparations for either oral or parenteral administration. Such liquid forms include solutions, suspensions and emulsions.

The compounds of the invention may also be deliverable transdermally. The transdermal compositions can take the form of creams, lotions, aerosols and/or emulsions and can be included in a transdermal patch of the matrix or reservoir type as are conventional in the art for this purpose.

Preferably, the pharmaceutical preparation is in a unit dosage form. In such form, the preparations subdivided into suitably sized unit doses containing appropriate quantities of the active component, e.g., an effective amount to achieve the desired purpose.

The quantity of active compound in a unit dose of preparation may be varied or adjusted from about 0.01 mg to about 4000 mg, preferably from about 0.02 mg to about 1000 mg, more preferably from about 0.3 mg to about 500 mg, and most preferably from about 0.04 mg to about 250 mg according to the particular application.

The actual dosage employed may be varied depending upon the requirements of the patient and the severity of the condition being treated. Determination of the proper dosage regimen for a particular situation is within the skill in the art. For convenience, the total daily dosage may be divided and administered in portions during the day as required.

The amount and frequency of administration of the compounds of the invention and/or the pharmaceutically acceptable salts thereof will be regulated according to the judgment of the attending clinician considering such factors as age, condition and size of the patient as well as severity of the symptoms being treated. A typical recommended daily dosage regimen for oral administration can range from about 0.02 mg/day to about 2000 mg/day, in two to four divided doses.

The pharmaceutical compositions of the invention may be administered from about 1 to about 5 times per day, or alternatively, as a continuous infusion. Such administration can be used as a chronic or acute therapy.

The quantity of $NK_1$ receptor antagonist in combination with a selective serotonin reuptake inhibitor ("SSRI") in a unit dose of preparation may be from about 10 to about 300 mg of $NK_1$ receptor antagonist combined with from about 10 to about 100 mg of SSRI. In another combination, the quantity of $NK_1$ receptor antagonist in combination with a SSRI in a unit dose of preparation may be from about 50 to about 300 mg of $NK_1$ receptor antagonist combined with from about 10 to about 100 mg of SSRI. In another combination, the quantity of $NK_1$ receptor antagonist in combination with SSRI in a unit dose of preparation may be from about 50 to about 300 mg of $NK_1$ receptor antagonist combined with from about 20 to about 50 mg of SSRI.

The actual dosage employed may be varied depending upon the requirements of the patient and the severity of the condition being treated. Determination of the proper dosage regimen for a particular situation is within the skill of the art. For convenience, the total daily dosage may be divided and administered in portions during the day as required. Upon improvement of a patient's condition, a maintenance dose of a compound, composition or combination of the invention may be administered, if necessary. Subsequently, the dosage or frequency of administration, or both, may be reduced, as a function of the symptoms, to a level at which the improved condition is retained. When the symptoms have been alleviated to the desired level, treatment should cease. Patients may, however, require intermittent treatment on a long-term basis upon any recurrence of disease symptoms.

Specific dosage and treatment regimens for any particular patient may be varied and will depend upon a variety of factors, including the activity of the specific compound employed, the age, body weight, general health status, sex and diet of the patient, the time of administration, the rate of excretion, the specific drug combination, the severity and course of the symptoms being treated, the patient's disposition to the condition being treated and the judgment of the treating physician. Determination of the proper dosage regimen for a particular situation is within the skill of the art.

EXAMPLES

The invention disclosed herein is exemplified by the following preparations and examples, which should not be construed to limit the scope of the disclosure. Alternative mechanistic pathways and analogous structures may be apparent to those skilled in the art.

Preparation of Examples 1a and 1b

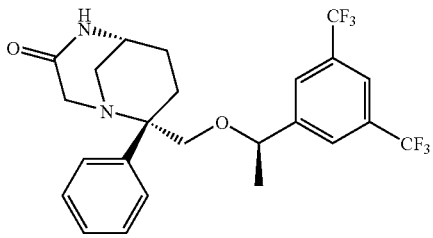

Example 1a

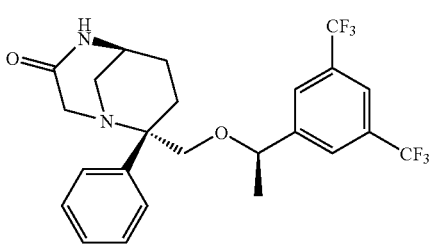

Example 1b

Step 1:

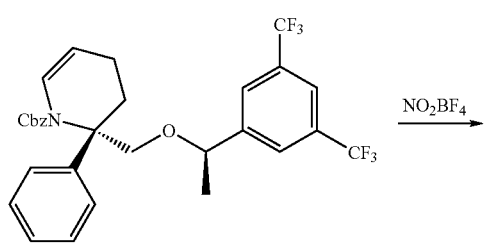

Compound i

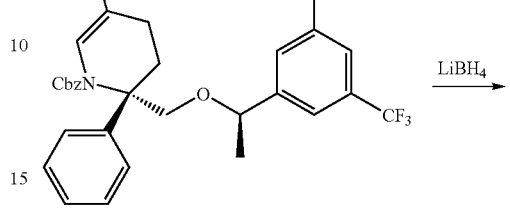

Compound ii

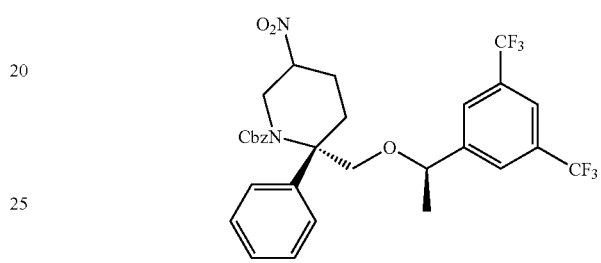

Compound iii

Compound i (i.e., Compound 45 of U.S. Published Application 2003/158173 A1, Ser. No. 10/321,687; herein incorporated by reference in its entirety) (20.0 g, 35.5 mmol) was dissolved in 300 mL of THF and cooled to −30° C. NO$_2$BF$_4$ (9.5 g, 68.8 mmol) was then added in one portion. The solution was allowed to warm to 23° C. and stirred for 3 h. Then 200 mL of saturated NaHCO$_3$ solution was added, and the mixture was stirred for 30 min. The organic and aqueous phases were then separated. The aqueous phase was extracted three times with 30 mL of Et$_2$O. The combined organic phases were dried and concentrated to give Compound ii, which was used without further purification.

Step 2:

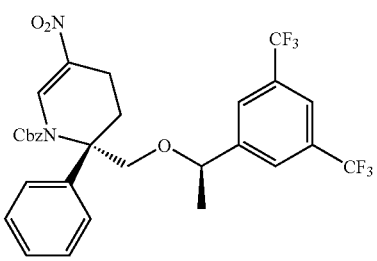

Compound ii

To a solution of Compound ii in anhydrous THF (355 mL) at 0° C. was added a solution of LiBH$_4$ (2.0 M in THF, 8.875 mL, 17.75 mmol), dropwise. After stirring for 10 min, the solution was quenched with saturated NH$_4$Cl solution (100 mL). The layers were separated and the aqueous layer was extracted three times with Et$_2$O (50 mL each). The combine organic layers were washed with brine, dried, and concentrated. The resulting residue was dissolved in 50 mL CH$_2$Cl$_2$ and was passed through a short pad of silica gel to give the desired product, Compound iii (16.1 g, 65%).

Step 3:

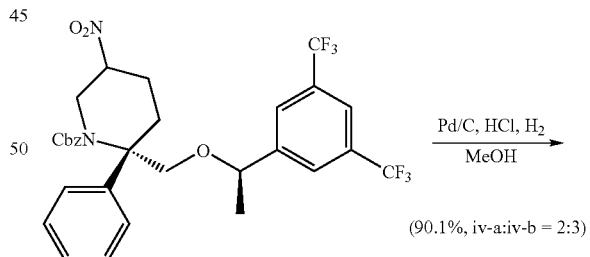

Compound iii (90.1%, iv-a:iv-b = 2:3)

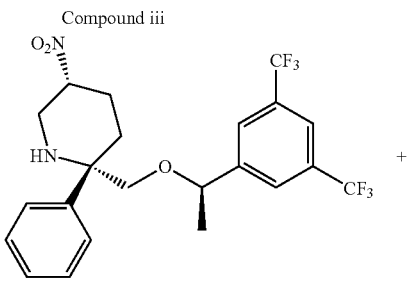

Compound iv-a

+

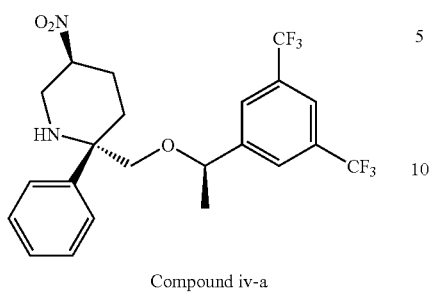

Compound iv-a

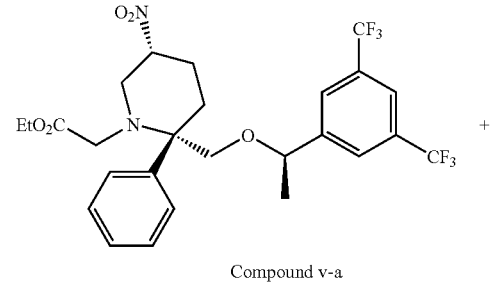

Compound v-a

+

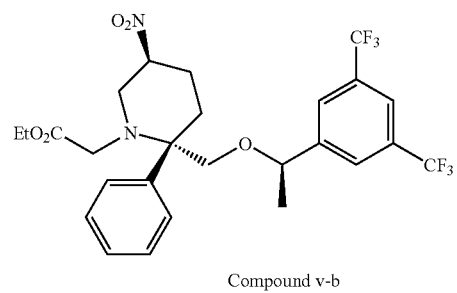

Compound v-b

Compound iii (10.46 g, 17.1 mmol, 1.0 equiv.) was dissolved in methanol (70 mL). After flushing the resulting solution with nitrogen for 15 minutes, 10% Pd/C (701 mg, 0.65 mmol, 0.038 equiv.) was added. The reaction vessel was then held under vacuum, and then refilled with nitrogen gas (3×). Concentrated hydrochloric acid (7.1 mL, 12N, 85.5 mmol, 5.0 equiv.) was syringed into the solution, causing the Pd/C to solidify. A hydrogen balloon was attached to the reaction vessel and filled with hydrogen. After stirring the resulting reaction mixture at room temperature for 1 h, TLC analysis (EtOAc/Hexane=20%) indicated little reaction had occurred, so another portion of 10% Pd/C (701 mg, 0.65 mmol, 0.038 equiv.) and concentrated HCl (1.2 mL, 12N, 14.4 mmol, 0.84 equiv.) were added. Hydrogenation of the reaction mixture was allowed to continue for an additional hour. TLC analysis then showed that Compound iii was completely consumed. The reaction mixture was diluted with methanol, carefully filtered through a celited funnel (i.e., a funnel containing a pad of CELITE), and the residue was thoroughly washed with methanol. The filtrate was neutralized with Et$_3$N (15 mL), stirred at room temperature overnight, and concentrated to dryness. The concentrated residue was dissolved into EtOAc, and then washed with saturated NaHCO$_3$ aqueous solution. The resulting two layers were separated, and the aqueous layer was further extracted with EtOAc. The combined organic layers were dried over anhydrous Na$_2$SO$_4$, filtered and concentrated to afford a crude product, which was purified using a BIOTAGE apparatus (Et$_2$O/Hexane=10% to 50%) to give Compound iv-a (2.55 g) and Compound iv-b (3.85 g), as well as a mixture of Compounds iv-a and iv-b (0.94 g). Total yield: 90.1%.

Step 4:

To a solution of Compound iv-b (2.4 g, 5.04 mmol, 1 equiv) in glacial acetic acid (20 mL) was added a solution of glyoxylic acid ethyl ester in toluene (6 mL, 45-50 wt. %). The mixture was cooled to 0° C. with an ice bath, and then sodium cyanoborohydride (1.5 g, 23.9 mmol, 4.7 equiv.) was added in several small portions. The ice bath was removed 10 minutes after the addition of the sodium cyanoborohydride was complete to allow the reaction mixture to warm to room temperature. After stirring the reaction mixture at room temperature for 4.5 h, some of the acetic acid was removed under vacuum, and then the reaction mixture was diluted with EtOAc, neutralized with an aqueous NaOH (2N) solution, then washed with an aqueous saturated NaHCO$_3$ solution. The neutralized and washed mixture was extracted with EtOAc, and the combined organic layers were dried over anhydrous Na$_2$SO$_4$, filtered and concentrated to give a crude product, which was purified with a BIOTAGE apparatus (EtOAc/Hexane=10%) to give Compound v-a (0.85 g) and Compound v-b (1.07 g). Total yield: 68%.

Step 5:

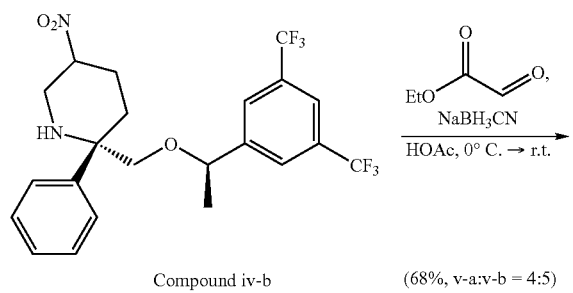

Compound iv-b (68%, v-a:v-b = 4:5)

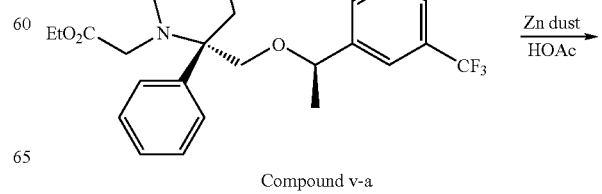

Compound v-a

Preparation of Examples 2a and 3a

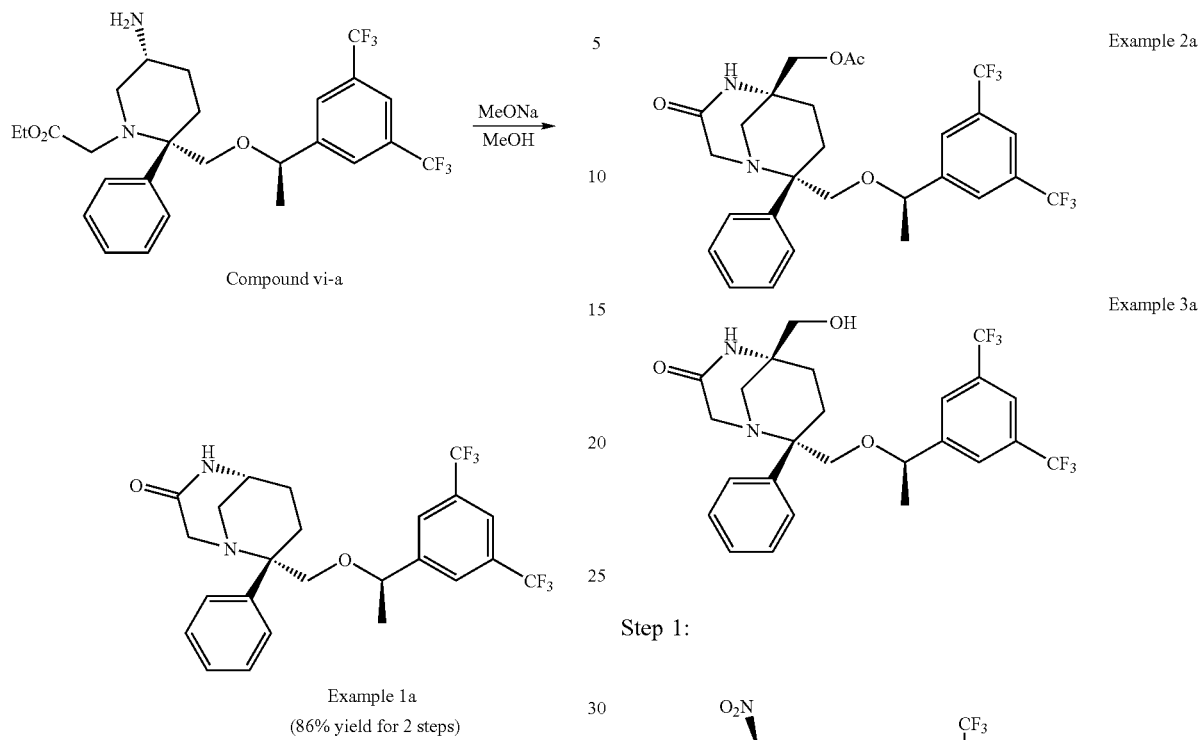

To a solution of ester Compound v-a (402.5 mg, 0.716 mmol, 1 equiv) in glacial acetic acid (4 mL) at 0° C., zinc dust (468 mg, 7.16 mmol, 10 equiv.) was added. The reaction mixture was stirred at room temperature for 2 h, until TLC analysis (MeOH/CH$_2$Cl$_2$=10%) showed that the starting material Compound v-a was completely consumed. The reaction mixture was then diluted with EtOAc, and passed through a celited funnel. The CELITE pad was thoroughly washed with EtOAc. The filtrate was then concentrated to dryness to give crude Compound vi-a as a yellow oil. The crude Compound vi-a was dissolved in EtOAc, neutralized with saturated NaHCO$_3$ aqueous solution, then the aqueous and organic layers were separated. The aqueous layer was further extracted with EtOAc. The combined organic layers were dried over anhydrous Na$_2$SO$_4$, filtered, and concentrated. The resulted crude product was dissolved in anhydrous methanol (37 mL), treated with anhydrous sodium methoxide (150 mg, 2.78 mmol, 3.9 equiv.), then heated at 88° C. overnight. TLC analysis indicated that the reaction was complete. The reaction mixture was then concentrated to dryness, and the resulting residue was dissolved into EtOAc, washed with saturated aqueous NH$_4$Cl solution, and saturated aqueous NaHCO$_3$ solution. The organic layer was dried over anhydrous Na$_2$SO$_4$, filtered, and concentrated to give the crude product, which was purified with a BIOTAGE apparatus (MeOH/CH$_2$Cl$_2$=2%) to give Example 1a (300 mg, 86% yield). Electrospray MS [M+1]$^+$ 487.1.

Example 1b was prepared using a procedure similar to the procedure used to prepare Example 1a, except that Compound v-b was used in place of Compound v-a in Step 3 (14.6% yield). Electrospray MS [M+1]$^+$ 559.1.

Step 1:

To a solution of ester Compound v-b (563 mg, 1 mmol, 1 equiv.) in anhydrous DMF (5 mL), paraformaldehyde (258 mg) was added. The resulting pale suspension was cooled to 0° C., and a 1.0 M solution of TBAF in THF (0.1 mL, 0.1 mmol, 0.1 equiv.) was syringed in. The solution was stirred at 0° C. for 30 minutes, then at room temperature for 3 h. TLC analysis (EtOAc/Hexane=20%) showed that the reaction was complete. The solution was diluted with EtOAc, and passed through a silica gel plug by flashing with EtOAc. The filtrate was concentrated to give the crude product, which was purified with a BIOTAGE apparatus (EtOAc/Hexane=10%, 20%, 50%) to give Compound vii-a (234.2 mg) and Compound vii-b (210 mg, 73%).

Step 2:

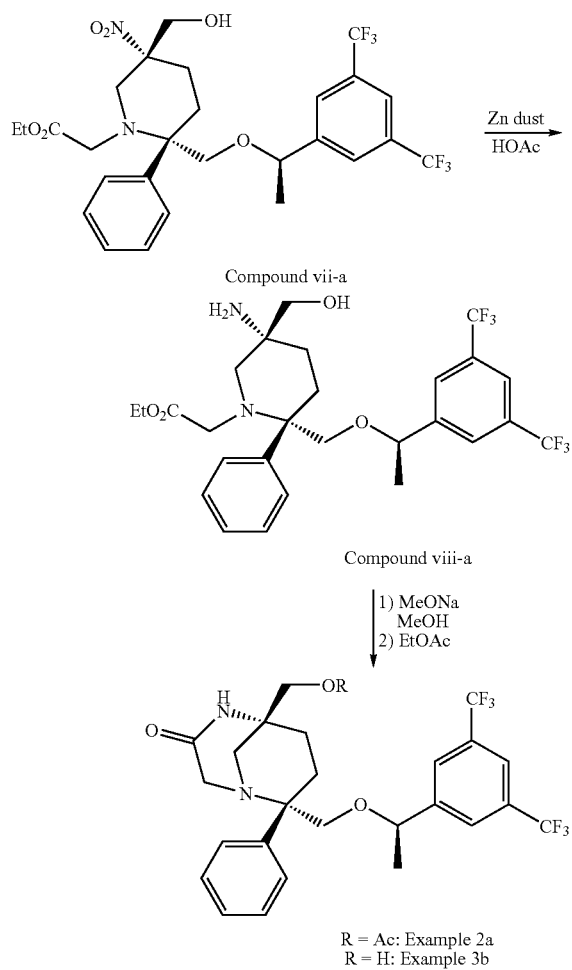

To a solution of ester Compound vii-a (107.8 mg, 0.182 mmol, 1 equiv.) in glacial acetic acid (1.5 mL) at 0° C., zinc dust (119 mg, 1.82 mmol, 10 equiv.) was added. The reaction mixture was stirred at room temperature for 2 h, until TLC analysis (MeOH/CH$_2$Cl$_2$=10%) showed that the starting material Compound vii-a was completely consumed. The mixture was then diluted with EtOAc, and passed through a celited funnel. The CELITE pad was thoroughly washed with EtOAc, and the filtrate was concentrated to dryness to give crude Compound viii-a as a yellow oil. The crude Compound viii-a was then dissolved in EtOAc, neutralized with a saturated aqueous NaHCO$_3$ solution and the aqueous and organic layers were separated. The aqueous layer was further extracted with EtOAc, and the combined organic layers were dried over anhydrous Na$_2$SO$_4$, filtered, and concentrated. The resulting crude product was dissolved in anhydrous methanol (10 mL), treated with anhydrous sodium methoxide (32 mg, 0.60 mmol, 3.9 equiv.), then heated at 88° C. for 2 h. TLC analysis indicated that the reaction was complete. The reaction mixture was then concentrated to dryness, and dissolved into EtOAc (which served as an acetylation reagent in the presence of NaOMe), washed with saturated aqueous NH$_4$Cl solution, and saturated aqueous NaHCO$_3$ solution. The organic layer was dried over anhydrous Na$_2$SO$_4$, filtered, and concentrated to give the crude product, which was purified with a BIOTAGE apparatus (MeOH/CH$_2$Cl$_2$=2%) to give Example 2a (20 mg, 19.70% yield), Electrospray MS [M+1]$^+$ 559.1; and Example 3a (75.5 mg, 80.4% yield). Electrospray MS [M+1]$^+$ 517.1.

Preparation of Examples 2b and 3b

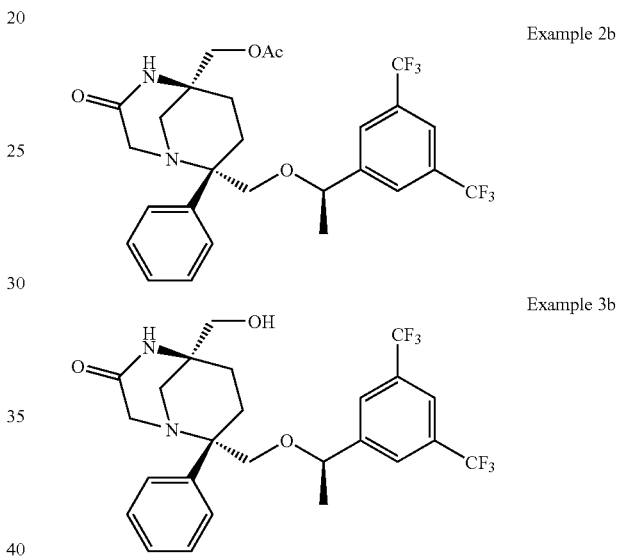

Example 2b was prepared using a procedure similar to the procedure used to prepare Example 2a, except that Compound vii-b was used in place of Compound vii-a in Step 2 (11.2% yield). Electrospray MS [M+1]$^+$ 559.1.

Example 3b was prepared using a procedure similar to the procedure used to prepare Example 3a, except that Compound vii-b was used in place of Compound vii-a in Step 2 (46.3% yield). Electrospray MS [M+1]$^+$ 517.1.

Preparation of Example 4

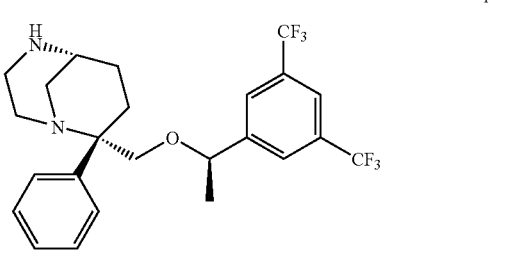

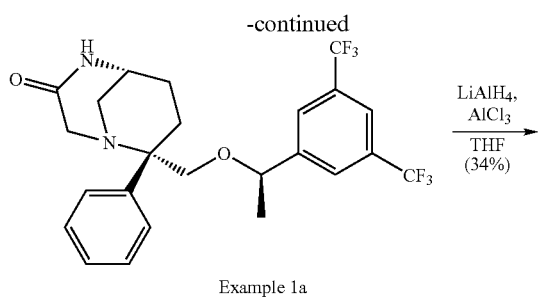

Example 1a

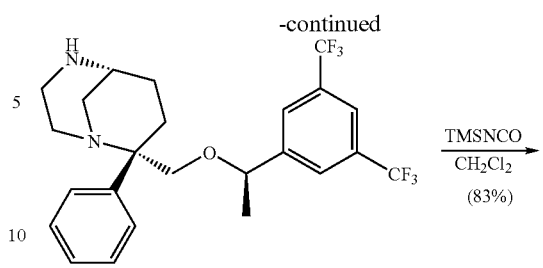

Example 4

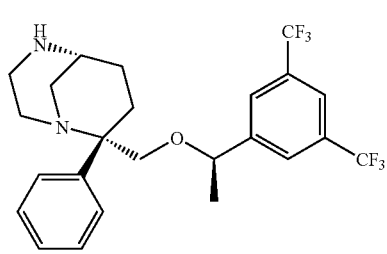

Example 4

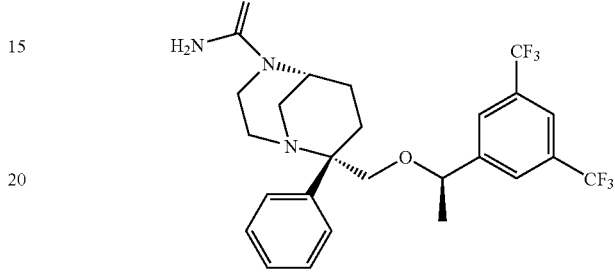

Example 5

To a solution of anhydrous AlCl₃ (80 mg, 0.6 mmol, 4.9 equiv.) in anhydrous THF (1 mL) at 0° C., was added a 1.0 M solution of LiAlH₄ in ethyl ether (1.8 mL, 1.8 mmol, 14.6 equiv.). After the resulting mixture was stirred at room temperature for 30 minutes, it was cooled to −78° C. before a solution of Example 1a (60 mg, 0.123 mmol, 1 equiv.) in anhydrous THF (1 mL) was syringed in. Residues of Example 1a were rinsed from the syringe into the reaction mixture with 2×0.5 mL of dry THF. The reaction mixture was stirred at room temperature overnight. After TLC analysis (MeOH/CH₂Cl₂=10%) indicated the reaction was complete, the reaction mixture was diluted with EtOAc, quenched with saturated aqueous Rochelle's salt solution, and the aqueous and organic layers were separated. The aqueous layer was further extracted with EtOAc, and the combined organic layers were dried over anhydrous Na₂SO₄, filtered and concentrated to give a crude product, which was purified by chromatography in a silica column (MeOH/CH₂Cl₂=2%, 5%, 10%) to give purified Example 4 (20 mg, 34% yield). Electrospray MS [M+1]⁺ 473.1.

Preparation of Example 5

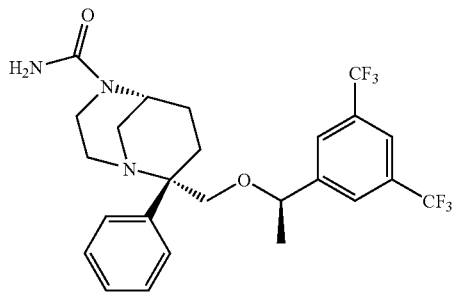

Example 5

To a solution of Example 4 (20 mg, 0.042 mmol, 1 equiv.) in anhydrous CH₂Cl₂ (1 mL), was added trimethylsilyl isocyanate (0.1 mL, 0.739 mmol, 17.6 equiv.). The resulting reaction mixture was stirred at room temperature overnight. TLC analysis (MeOH/CH₂Cl₂=10%) indicated the reaction was complete. The solvent was then evaporated under vacuum, and the crude product was purified by Prep. TLC (5 mm; MeOH/CH₂Cl₂=10%) to give Example 5 (18 mg, 83% yield).

Preparation of Example 6

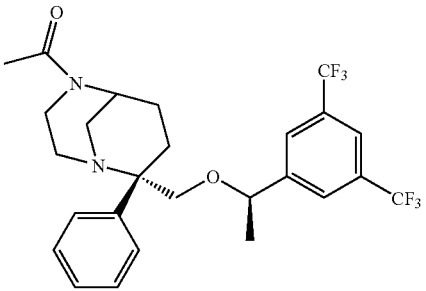

Example 6

Step 1:

Compound ix

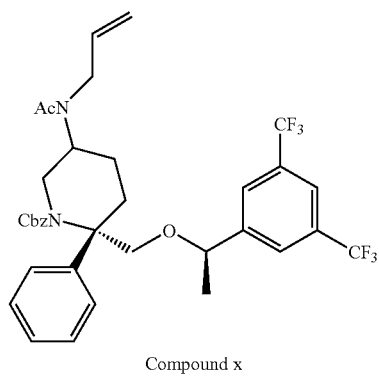

Compound x

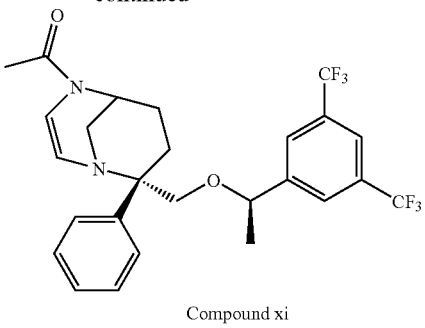

Compound xi

A solution of Compound ix (i.e., Compound 47 of U.S. Published Application 2003/158173 A1, Ser. No. 10/321, 687) (1.076 g, 1.86 mmol, 1.0 equiv.) in dry dichloroethane (15 mL) was treated with allylamine (0.17 mL, 2.22 mmol, 1.2 equiv.), sodium triacetoxyborohydride (670 mg, 3.16 mmol, 1.7 equiv.), glacial acetic acid (0.13 mL, 2.22 mmol, 1.2 equiv.) and molecular sieves (4 Å). The resulting cloudy solution was stirred at room temperature overnight. The mixture was then partitioned between 50 mL of EtOAc and 50 mL of NH$_4$Cl solution, and the organic layer was separated, dried, and concentrated in vacuo. The crude product was then dissolved in dry dichloromethane (10 mL). The resulting colorless solution was cooled to 0° C., and acetyl chloride (0.158 mL, 2.23 mmol, 1.2 equiv.) was added, followed by DIEA (0.49 mL, 2.79 mmol, 1.5 equiv.). The solution was stirred for 30 minutes until TLC analysis (EtOAc/Hexane=2:1) showed that the reaction was complete. The solution was then partitioned between 50 mL of EtOAc and 50 mL of NH$_4$Cl solution, and the organic layer was separated, dried, and concentrated in vacuo, to give the crude product, which was purified with a BIOTAGE apparatus to give Compound x (489 mg, 39.7% yield).

Step 2:

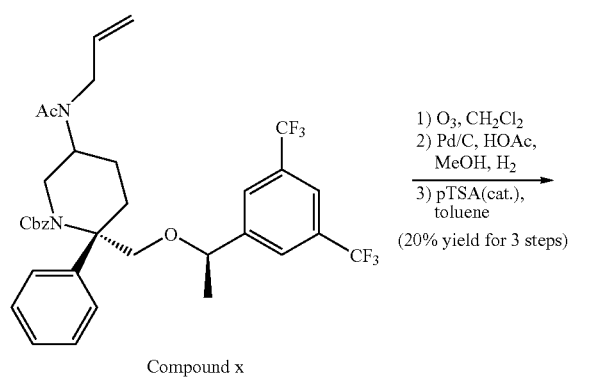

Compound x

O$_3$ was bubbled through a solution of Compound x (489 mg, 0.74 mmol, 1 equiv.) in anhydrous dichloromethane (15 mL) at −78° C., until the solution turned blue. The solution was then flushed with nitrogen gas to remove excess O$_3$. Once the blue solution turned colorless, a small amount of dimethylsulfide was added. The resulting reaction mixture was stirred at room temperature 30 minutes. TLC analysis (EtOAc/Hexane=50%) showed only the product. The solvent was evaporated, and the crude product was purified with a BIOTAGE apparatus (EtOAc/Hexane=20%, 50%) to give the pure product. The product was dissolved in dry MeOH (10 mL), and treated with molecular sieves (4 Å), 10% Pd/C and a few drops of HOAc, and hydrogenated. No cyclization occurred. However, the Cbz group was removed. The resulting mixture was then diluted with MeOH and passed through a celited funnel. The filtrate was concentrated to dryness, dissolved in dry toluene, treated with pTSA (2 mg, cat.) and heated at 88° C. overnight until the reaction was complete. The mixture was then concentrated to give the crude product, which was purified with a BIOTAGE apparatus (EtOAc/Hexane=50%) to give a mixture of two diastereomers, Compound xi (76 mg, 20% yield).

Step 3:

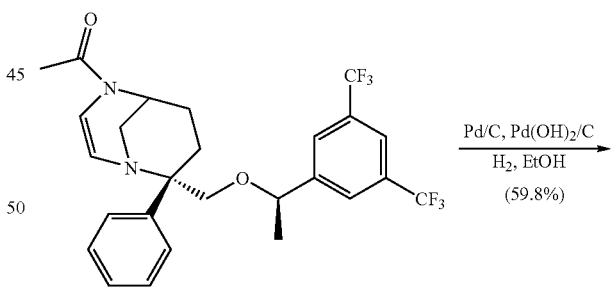

Compound xi

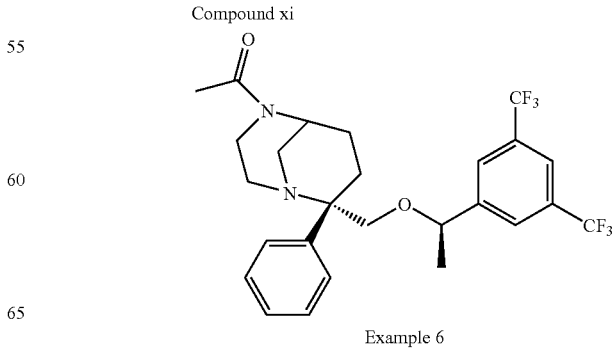

Example 6

Hydrogenation of a solution of Compound xi (30 mg, 0.0585 mmol, 1 equiv.) in EtOH (2 mL) in the presence of 10% Pd/C (30 mg, 0.028 mmol, 0.48 equiv.) yielded no product. After adding 20% Pd(OH)$_2$/C (30 mg, 0.043 mmol, 0.73 equiv.), the hydrogenation was complete after 4 h. The reaction mixture was diluted with MeOH and passed through a celited funnel, and the CELITE pad was washed thoroughly with MeOH. The filtrate was concentrated to dryness to give the crude product, which was purified by Prep. TLC (EtOAc/Hexane=2:1) to give Example 6 (mixture of diastereomers) (18 mg, 59.8% yield). Electrospray MS [M+1]$^+$ 515.1.

Preparation of Example 7

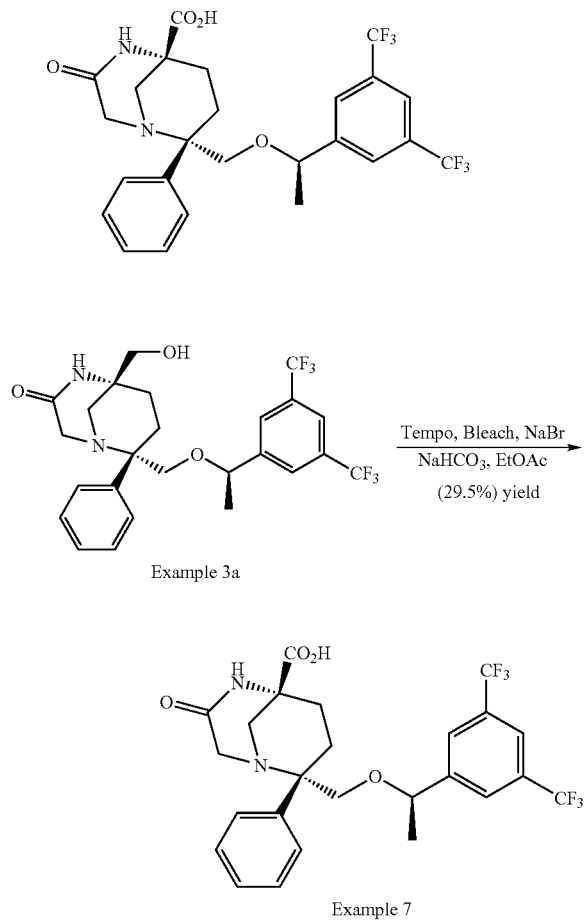

To a solution of Example 3a (142 mg, 0.275 mmol, 1 equiv.) in EtOAc (1 mL) and saturated NaHCO$_3$ aqueous solution (1 mL) at 0° C., was added NaBr (54 mg, 0.524 mmol, 1.9 equiv.) and Tempo reagent (3.8 mg, 0.024 mmol, 0.089 equiv.) followed by the addition of bleach (i.e., aqueous NaOCl solution, 1.5 mL) in portions until the brownish color of the reaction mixture faded. The reaction mixture was then quenched with saturated aqueous Na$_2$S$_2$O$_3$ solution, diluted with EtOAc, and the organic and aqueous layers were separated. The organic layer was washed with saturated aqueous NaHCO$_3$ solution, and the aqueous layer was further extracted with EtOAc. The combined organic layers were dried over anhydrous Na$_2$SO$_4$, filtered and concentrated to give a crude product, which was purified by Prep. TLC to give Example 7 (43 mg, 29.5% yield). Electrospray MS [M+1]$^+$ 531.1.

Preparation of Example 8

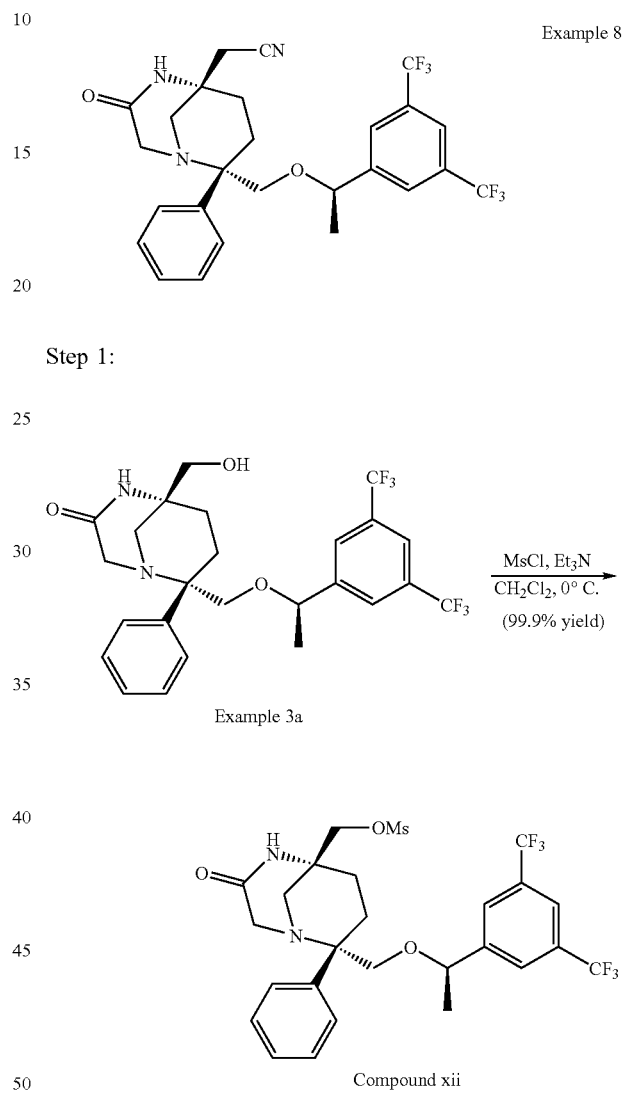

To a solution of Example 3a (149 mg, 0.288 mmol, 1 equiv.) in anhydrous CH$_2$Cl$_2$ (3 mL) at 0° C., was added Et$_3$N (90 μL, 0.646 mmol, 2.24 equiv.) followed by dropwise addition of MsCl (50 μL, 0.646 mmol, 2.24 equiv.). The reaction mixture was stirred at 0° C. for 2 h. TLC analysis (MeOH/CH$_2$Cl$_2$=5%) showed that the reaction was complete. The reaction mixture was then diluted with CH$_2$Cl$_2$, quenched with saturated aqueous NaHCO$_3$ solution, and the organic and aqueous layers were separated. The aqueous layer was further extracted with CH$_2$Cl$_2$, and the combined organic layers were dried over anhydrous Na$_2$SO$_4$, filtered and concentrated to give a crude product, which was purified with a BIOTAGE apparatus (MeOH/CH$_2$Cl$_2$=2%) to give Compound xii (171 mg, 99.9% yield).

Step 2:

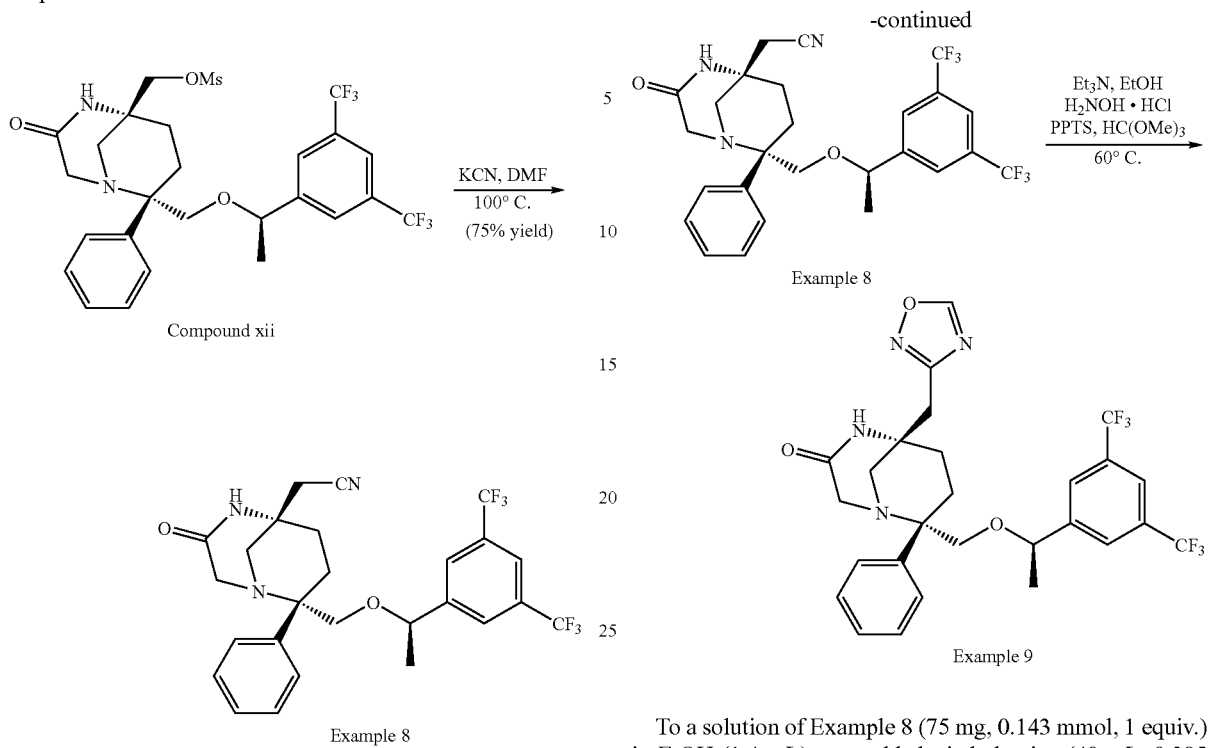

Example 8

To a solution of Compound xii (60 mg, 0.101 mmol, 1 equiv.) in DMF (1 mL), was added KCN (50 mg, 0.77 mmol, 7.6 equiv.). The resulting pale yellow suspension was heated at 100° C. overnight. LCMS analysis indicated that the reaction was complete. The reaction mixture was then diluted with EtOAC, quenched with saturated aqueous NaHCO$_3$ solution, and the organic and aqueous layers were separated. The aqueous layer was further extracted with EtOAc, and the combined organic layers were dried over anhydrous Na$_2$SO$_4$, filtered and concentrated to give a crude product, which was purified by Prep. TLC (MeOH/CH$_2$Cl$_2$=5%) to give Example 8 (40 mg, 75% yield). Electrospray MS [M+1]$^+$ 526.3.

Preparation of Example 9

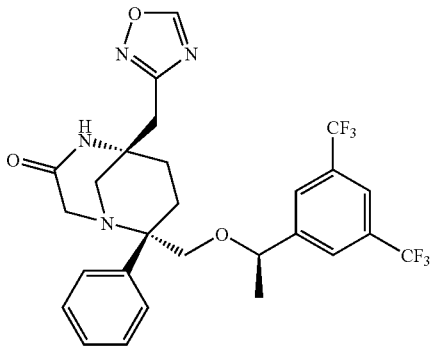

Example 9

To a solution of Example 8 (75 mg, 0.143 mmol, 1 equiv.) in EtOH (1.4 mL), was added triethylamine (40 mL, 0.285 mmol, 2 equiv.) and hydroxyamine HCl salt (20 mg, 0.285 mmol, 2 equiv.), and the resulting solution was stirred for 1 h, then heated at 60° C. for 16 h. The solvent was then removed and the resulting residue was dissolved in 2 mL HC(OMe)$_3$ followed by addition of PPTS and further heated for 1 h. Then the reaction mixture was partitioned between 10 mL of EtOAc and 10 mL of water. The organic layer was separated and dried over anhydrous Na$_2$SO$_4$, filtered and concentrated to give a crude product, which was purified by Prep. TLC (100% EtOAc) to give Example 9. Electrospray MS [M+1]$^+$ 569.1

Preparation of Example 10

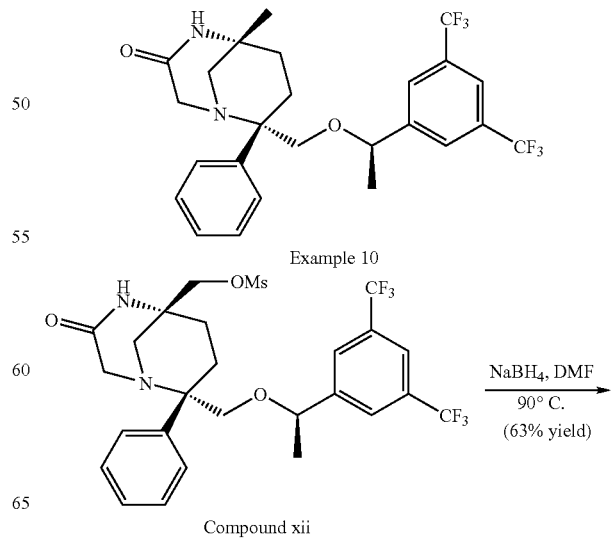

-continued

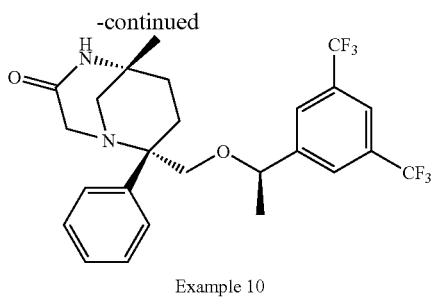

Example 10

To a solution of Compound xii (25 mg, 0.042 mmol, 1 equiv.) in anhydrous DMF (1 mL), was added $NaBH_4$ (8 mg, 0.21 mmol, 5 equiv.). The reaction mixture was heated at 90° C. for 1 h, until LCMS analysis only showed the presence of product. The reaction mixture was then diluted with $Et_2O$, washed with aqueous 1N HCl solution, then neutralized by adding $K_2CO_3$ until the pH of the solution was 7. The organic and aqueous layers were then separated, and the aqueous layer was further extracted with $Et_2O$. The combined organic layers were dried over anhydrous $MgSO_4$, filtered and concentrated to give a crude product, which was purified by Prep. TLC ($MeOH/CH_2Cl_2$=5%) to give Example 10 (13.3 mg, 63% yield). Electrospray MS $[M+1]^+$ 501.3.

Preparation of Examples 11 and 12

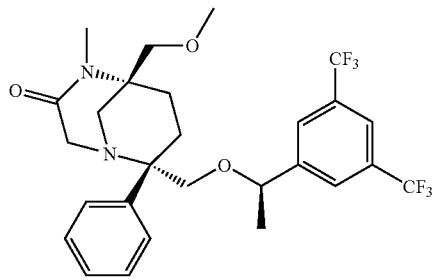

Example 11

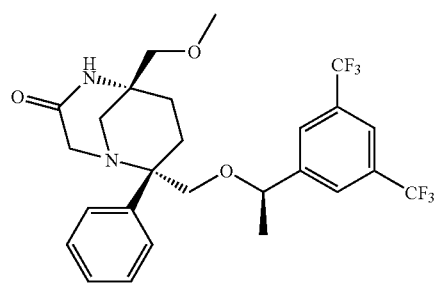

Example 12

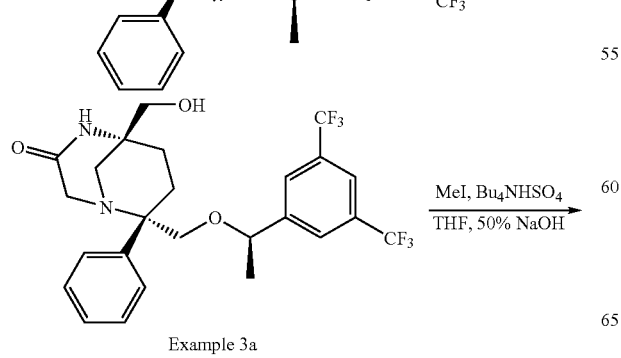

Example 3a

MeI, $Bu_4NHSO_4$ / THF, 50% NaOH →

-continued

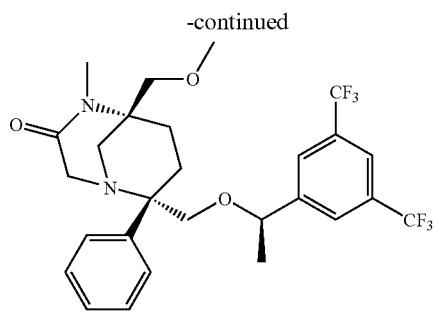

Example 11
(69%)

+

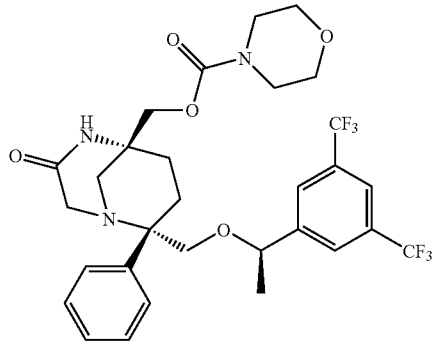

Example 12
(17%)

To a solution of Example 3a (28.8 mg, 0.0558 mmol, 1 equiv.) in anhydrous THF (0.4 mL) and 50 wt. % aqueous NaOH solution (0.2 mL), was added $Bu_4NHSO_4$ (8.9 mg, 0.022 mmol, 0.4 equiv.) and MeI (5.22 μL, 0.0836 mmol, 1.5 equiv.). The resulting pale yellow mixture was stirred at room temperature overnight. TLC analysis (MeOH/$CH_2Cl_2$=5%) showed that no starting material remained in the reaction mixture. The reaction mixture was then diluted with EtOAc, washed with water, and the organic and aqueous layers were separated. The aqueous layer was further extracted with EtOAc, and the combined organic layers were dried over anhydrous $Na_2SO_4$, filtered and concentrated to give a crude product, which was purified by Prep. TLC (MeOH/$CH_2Cl_2$=5%) to give Example 11 (21 mg, 69% yield), Electrospray MS $[M+1]^+$ 545.1; and Example 12 (5 mg, 17% yield). Electrospray MS $[M+1]^+$ 531.1.

Preparation of Example 13

Example 13

-continued

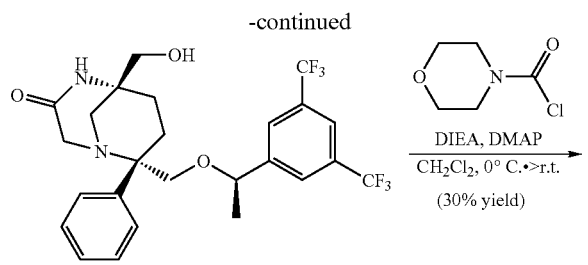

Example 3a

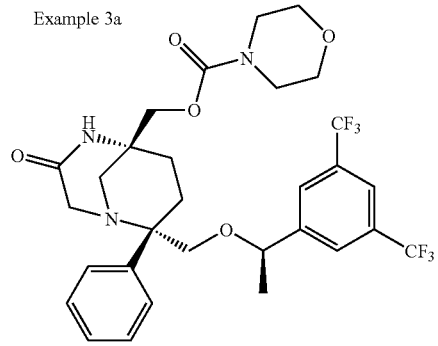

Example 13

To a solution of Example 3a (50 mg, 0.096 mmol, 1 equiv.) in anhydrous CH$_2$Cl$_2$ (1 mL) at 0° C., was added 4-morpholinecarbonyl chloride (12.4 μL, 0.106 mmol, 1.1 equiv.) and DIEA (18.5 μL, 0.106 mmol, 1.1 equiv.). The reaction mixture was stirred at 0° C. for 1.5 h, at which time TLC analysis (MeOH/CH$_2$Cl$_2$=5%) showed that no reaction had occurred. DMAP (6 mg, 0.048 mmol, 0.5 equiv.) was then added and the reaction mixture was stirred at room temperature overnight. The solvent was evaporated and the residue was purified twice by Prep. TLC (MeOH/CH$_2$Cl$_2$=5%) to give Example 13 (18.2 mg, 30% yield). Electrospray MS [M+1]$^+$ 630.3.

Preparation of Example 14

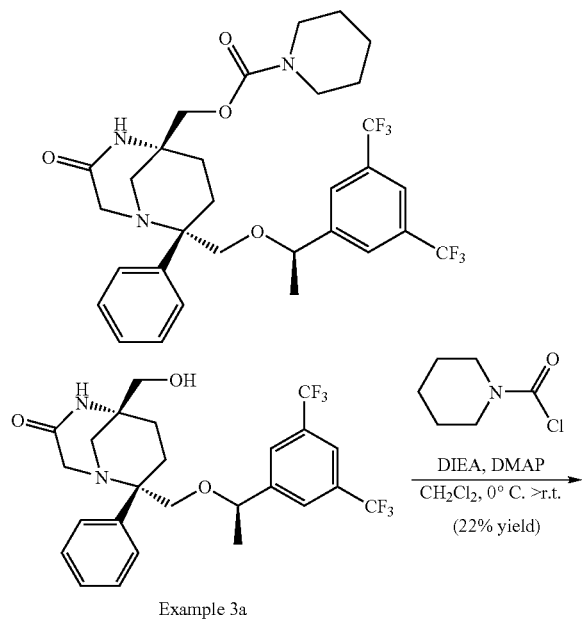

Example 14

-continued

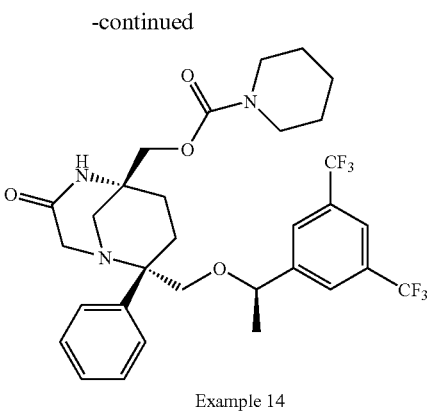

Example 14

Example 14 was prepared using a procedure similar to the procedure used for preparing Example 13, except that 4-piperidinecarbonyl chloride was used in place of 4-morpholinecarbonyl chloride (22% yield). Electrospray MS [M+1]$^+$ 628.1.

Preparation of Example 15

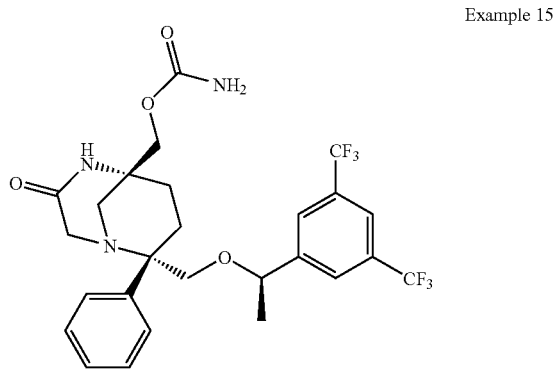

Example 15

Example 15 was prepared by a procedure similar to the procedure used for preparing Example 13, except that trimethylsilylisocyanate was used in place of morpholinecarbonyl chloride. Electrospray MS [M+1]$^+$ 560.1.

Preparation of Example 16

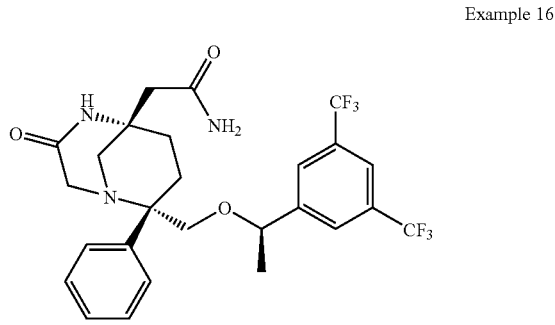

Example 16

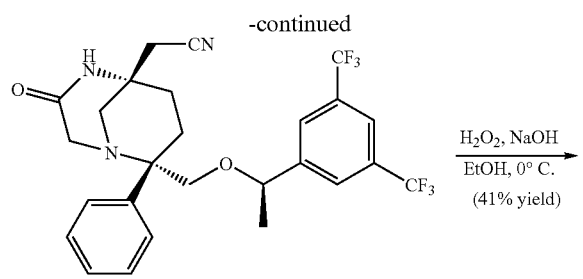

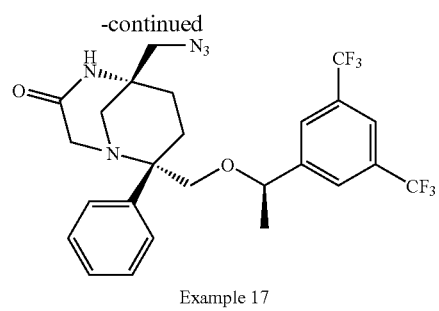

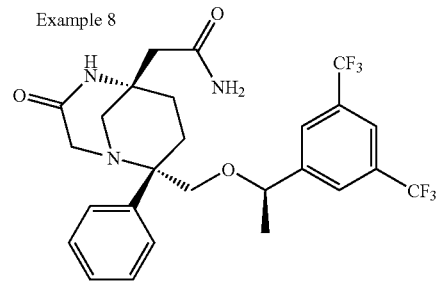

Example 16

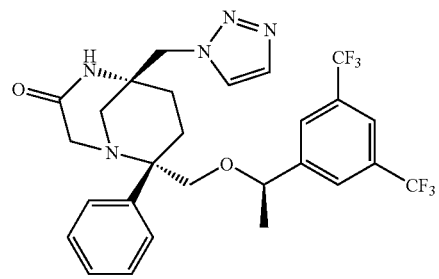

Example 17 was prepared using procedures similar to the procedures used to prepare Example 8, except that NaN₃ was used in place of KCN in Step 2 (63% yield for Step 2). Electrospray MS [M+1]⁺ 542.1.

Preparation of Example 18

To a solution of Example 8 (40.5 mg, 0.077 mmol, 1 equiv.) in EtOH (2.5 mL) at 0° C., was added an aqueous 2N NaOH solution (0.2 mL, 0.39 mmol, 5 equiv.) followed by a 30 wt. % aqueous H₂O₂ solution (1.6 mL, 14.1 mmol). The mixture was stirred at 0° C. for about 2 h at which time TLC analysis (MeOH/CH₂Cl₂=5%) showed that the reaction was complete. The reaction mixture was maintained at 0° C., then quenched with NaBH₄ (400 mg). The solvent was evaporated from the reaction mixture under vacuum. The resulting residue was then partitioned between EtOAc and water, and the organic and aqueous layers were separated. The aqueous layer was further extracted with EtOAc, and the combined organic layers were dried over anhydrous Na₂SO₄, filtered, and concentrated to give a crude product, which was purified by Prep. TLC (MeOH/CH₂Cl₂=5%) to give Example 16 (17 mg, 41% yield). Electrospray MS [M+1]⁺ 544.1.

Preparation of Example 17

Example 17

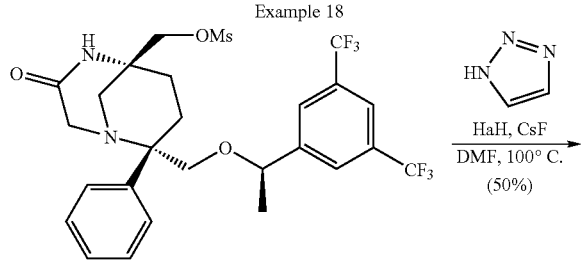

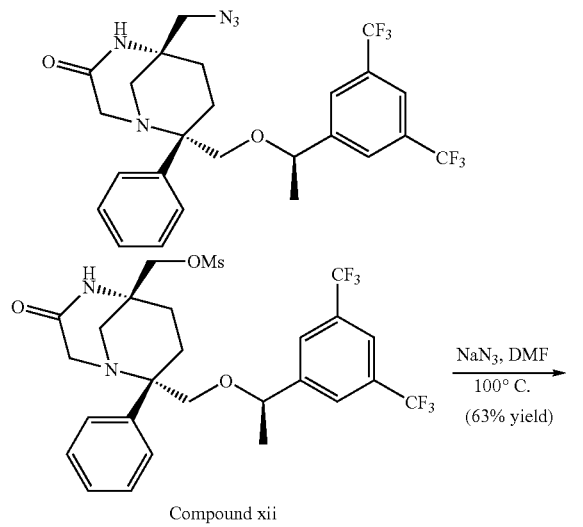

Compound xii

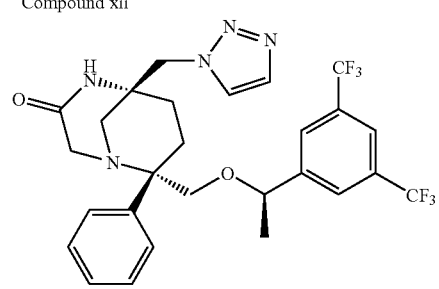

Example 18

To a solution of 1,2,3-triazole in anhydrous DMF (2 mL) at 0° C., was added NaH (10 mg, 60% dispersion in mineral oil, 0.25 mmol, 5 equiv.) and CsF (47 mg, 0.25 mmol, 5 equiv.). The resulted cloudy solution was stirred at 0° C. for 1.5 h before Compound xii (30 mg, 0.05 mmol, 1 equiv.) was added. The reaction mixture was heated at 100° C. for 16 h at which time LCMS analysis indicated that the reaction was complete. DMF was evaporated, the resulting residue was dissolved in EtOAc, and the organic and aqueous layers were separated. The aqueous layer was further extracted with EtOAc, and the combined organic layers were dried over anhydrous Na₂SO₄, filtered, and concentrated to give a crude product, which was purified by Prep. TLC (MeOH/CH₂Cl₂=5%) to give Example 18 (14.2 mg, 50% yield). Electrospray MS [M+1]⁺ 568.3.

Preparation of Example 19

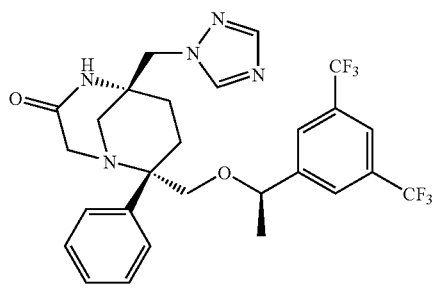

Example 19

Example 19 was prepared using procedures similar to the procedures used to prepare Example 18, except that 1,2,4-triazole was used instead of 1,2,3-triazole. Electrospray MS [M+1]⁺ 568.3.

Preparation of Example 20

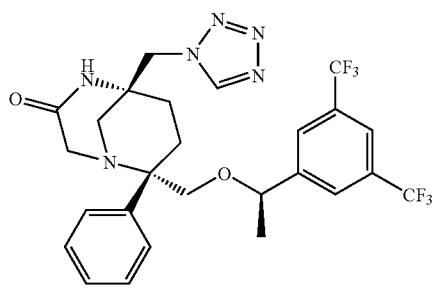

Example 20

Example 20 was prepared using procedures similar to the procedures used to prepare Example 18, except that tetrazole was used instead of 1,2,3-triazole. Electrospray MS [M+1]⁺ 569.1.

Preparation of Example 21

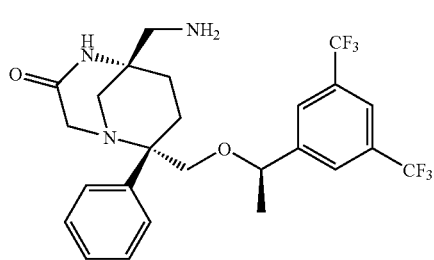

Example 21

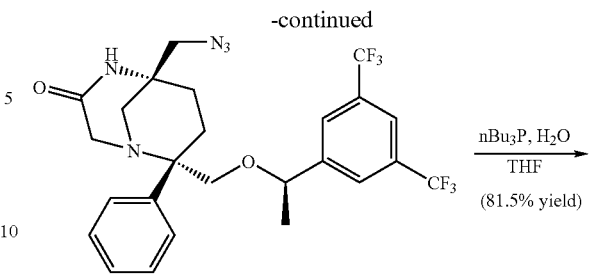

Example 17

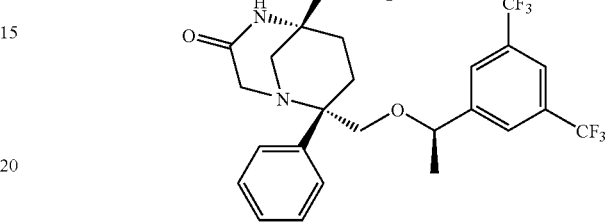

Example 21

To a solution of Example 17 in anhydrous THF (4 mL), was added n-Bu₃P (0.1 mL, 0.756 mmol, 2.25 equiv.) and water (0.08 mL). The mixture was stirred at room temperature over a weekend, at which time TLC analysis (MeOH/CH₂Cl₂=5%) showed that only product was present in the mixture. The solvent was then evaporated under vacuum, and the resulting residue was dissolved in EtOAc, washed with water and the organic and aqueous layers were separated. The aqueous layer was further extracted with EtOAc, and the combined organic layers were dried over anhydrous Na₂SO₄, filtered, and concentrated to give a crude product, which was purified by Prep. TLC (MeOH/CH₂Cl₂=10%) to give Example 21 (142.9 mg, 81.5% yield). Electrospray MS [M+1]⁺ 516.1.

Preparation of Example 22

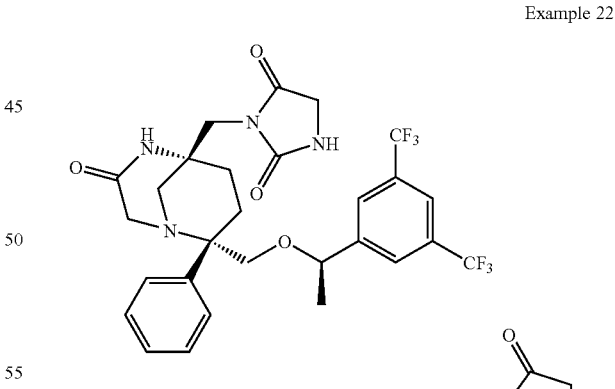

Example 22

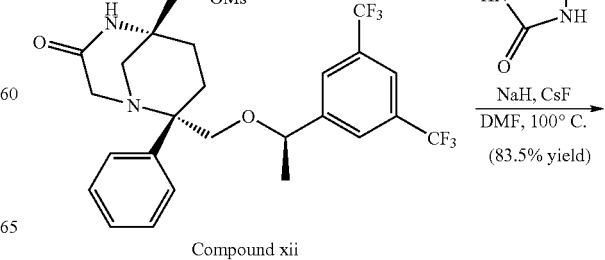

Compound xii

-continued

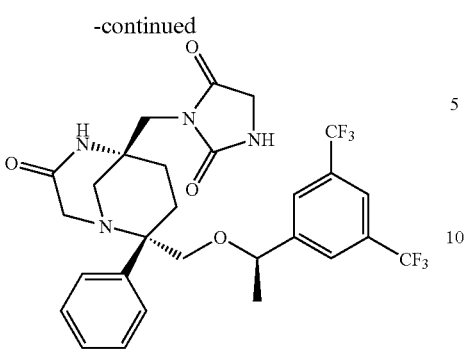

Example 22

Example 22 was prepared using procedures similar to the procedures used to prepare Example 18, except that hydantoin was used in place of 1,2,3-triazole (83.5% yield). Electrospray MS [M+1]+ 599.1.

Preparation of Example 23

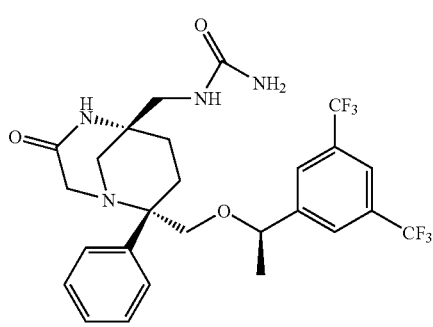

Example 23

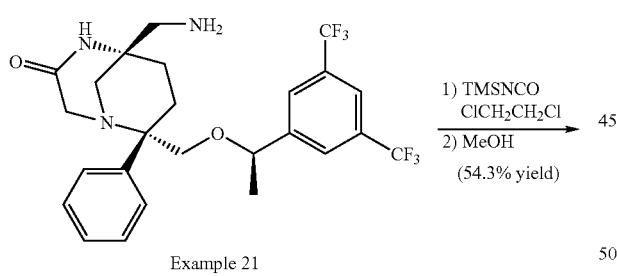

Example 21

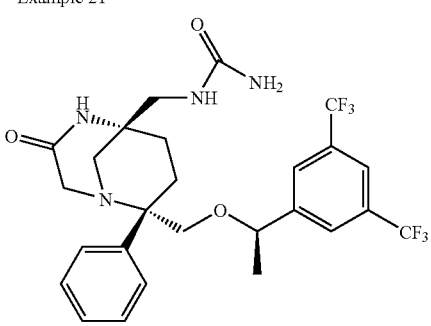

Example 23

To a solution of Example 21 (17.2 mg, 0.033 mmol, 1 equiv.) in anhydrous ClCH$_2$CH$_2$Cl (1 mL), was added trimethylsilylisocyanate (13.6 μL, 0.1 mmol, 3 equiv.). The solution was stirred at room temperature for 5 h. At that time, TLC analysis (MeOH/CH$_2$Cl$_2$=10%) showed only product. The solution was then treated with MeOH (1 mL) and stirred for 1 h. The solvent was evaporated under vacuum, and the residue was purified by Prep. TLC (MeOH/CH$_2$Cl$_2$=10%) to give Example 23 (10 mg, 54.3% yield). Electrospray MS [M+1]+ 559.1.

Preparation of Example 24

Example 24

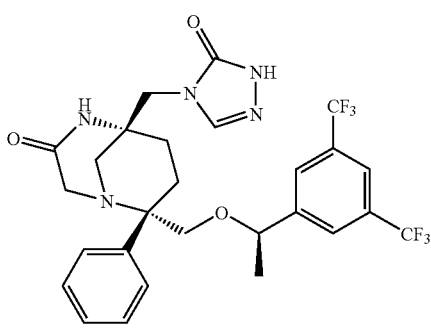

Example 21

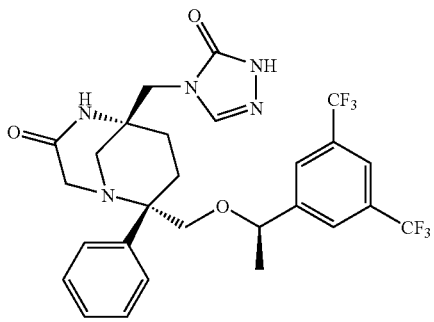

Example 24

To a solution of Example 21 (17.4 mg, 0.034 mmol, 1 equiv.) in EtOH (2 mL), was added Compound xiii (i.e., EtOC(H)C=NNHCO$_2$Me) (14.8 mg, 0.1 mmol, 3 equiv.). The solution was heated at 60° C. over a weekend, at which time LCMS analysis showed that the starting material (i.e., Example 21) was completely consumed. The solution was then diluted with anhydrous MeOH (5 mL), treated with anhydrous NaOMe (25 mg, 0.463 mmol, 13.6 equiv.), heated at 88° C. overnight, and concentrated to dryness. The resulting residue was dissolved in EtOAc, washed with saturated aqueous NH$_4$Cl solution, and water. The organic layer was dried over anhydrous Na$_2$SO$_4$, filtered and concentrated to give a crude product, which was purified by Prep. TLC (MeOH/EtOAc=10%) to give Example 24 (6.6 mg, 33.2% yield). Electrospray MS [M+1]$^+$ 584.1.

Preparation of Example 25

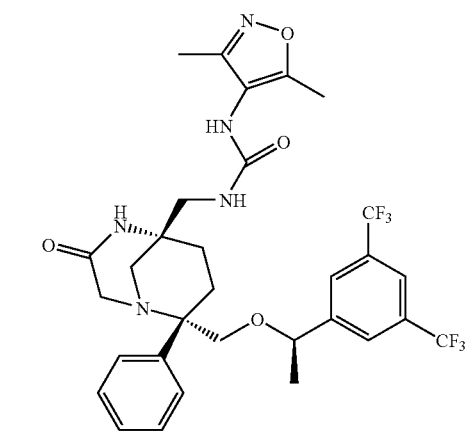

Example 25

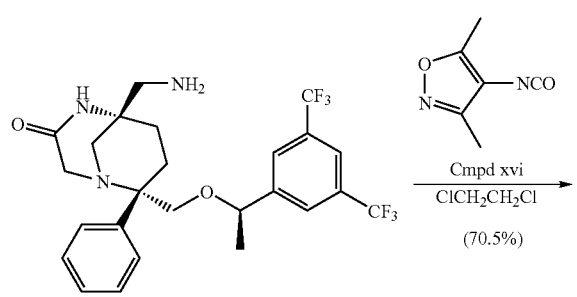

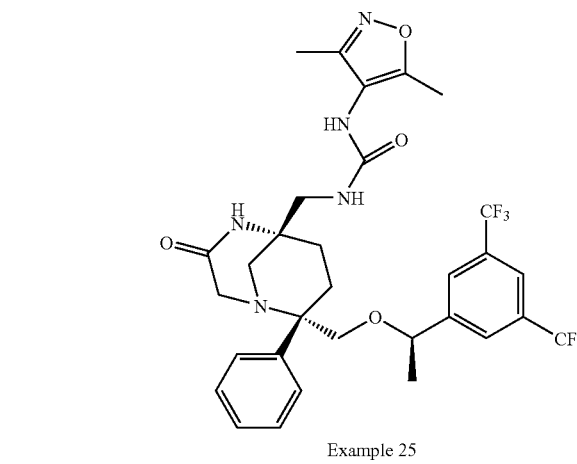

Example 25

Example 25 was prepared using procedures similar to the procedures used to prepare Example 23, except that Compound xiv was used in place of trimethylsilylisocyanate (70.5% yield). Electrospray MS [M+1]$^+$ 654.2.

Preparation of Examples 26 and 27

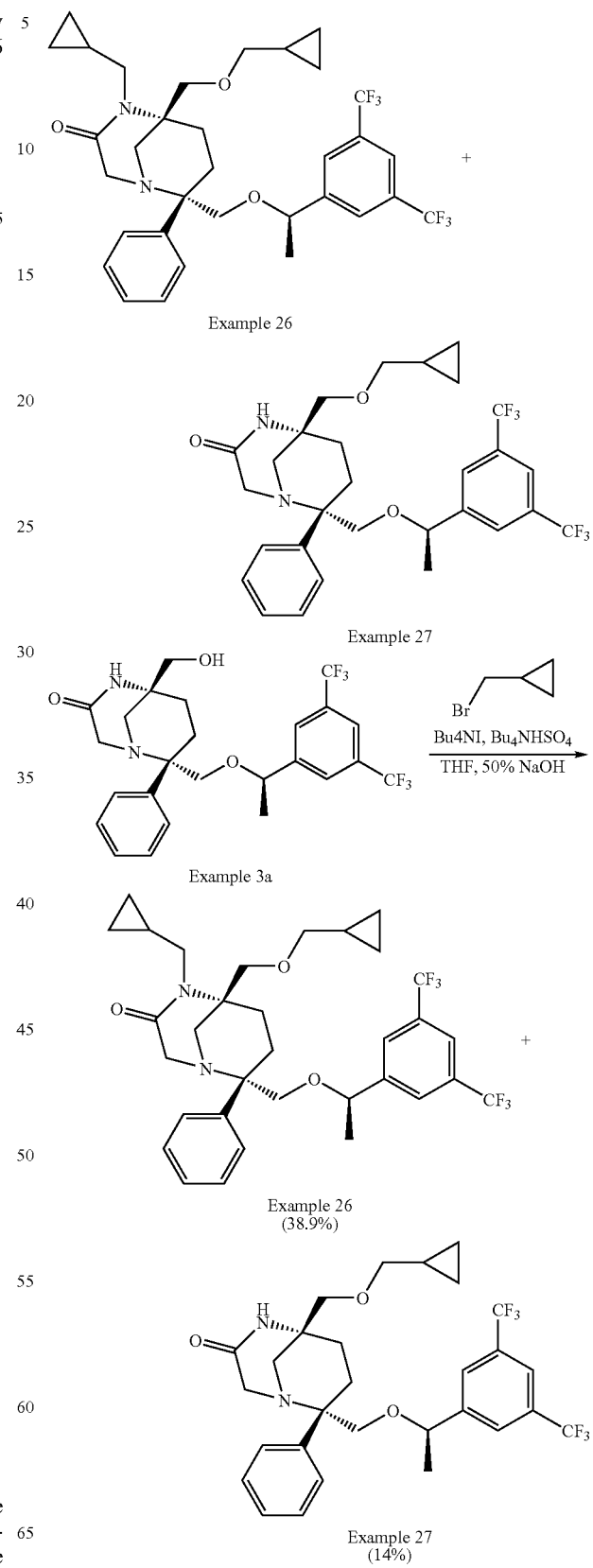

Examples 26 and 27 were prepared using procedures similar to the procedures used to prepare Examples 11 and 12, except that cyclopropyl bromide and tetrabutyl-ammonium iodide were used in place of methyliodide. Example 26 (38.9% yield). Electrospray MS [M+1]$^+$ 625.3. Example 27 (14% yield). Electrospray MS [M+1]$^+$ 571.3.

Preparation of Examples 28 and 29

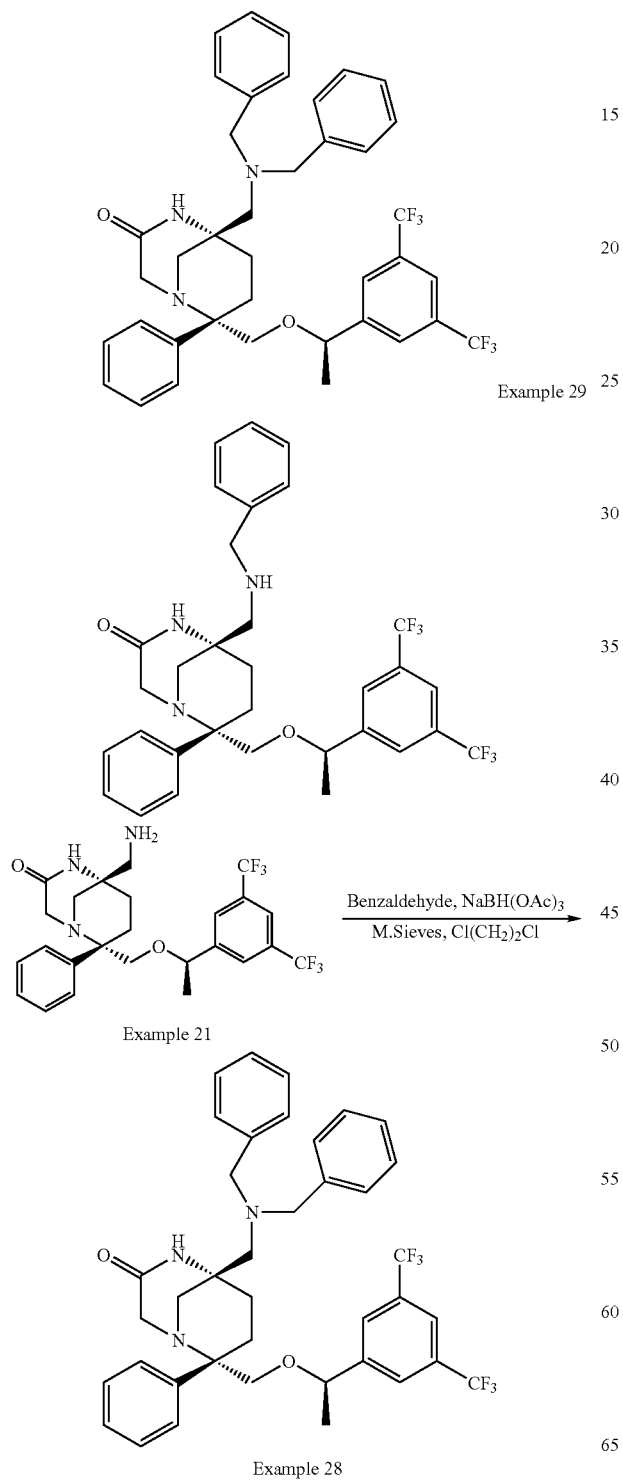

-continued

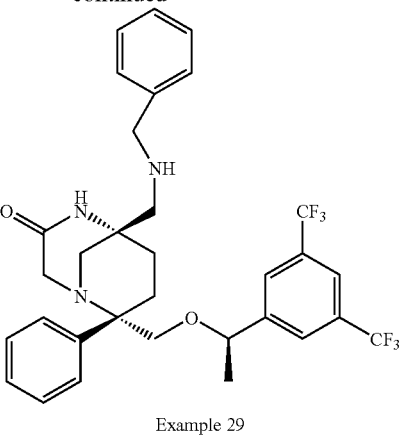

Example 29

In a 25 mL round-bottomed flask, Example 21 (0.035 g, 0.00007 mol, 1.0 equiv.) was taken up in 3 mL of dichloroethane. Benzaldehyde (0.008 mL, 0.000075 mol, 1.1 equiv.) was added, followed by molecular sieves (0.04 g). The reaction mixture was stirred for 1 h, and then NaBH(OAc)$_3$ (0.04 g, 0.00016 mol, 2.6 equiv.) was added, and the reaction mixture was stirred overnight. Upon completion of the reaction, the reaction mixture was filtered through a CELITE pad, which was then washed with EtOAc. The organic layer was washed with H$_2$O, dried over Na$_2$SO$_4$, and concentrated to give a crude product. Prep. TLC purification was carried out using 60/40 EtOAc/hexane, to isolate two compounds. The first compound eluted was the di-benzylated product Example 28 (0.007 g), and the second product eluted was the mono-benzylated product Example 29 (0.005 g).

Preparation of Example 30

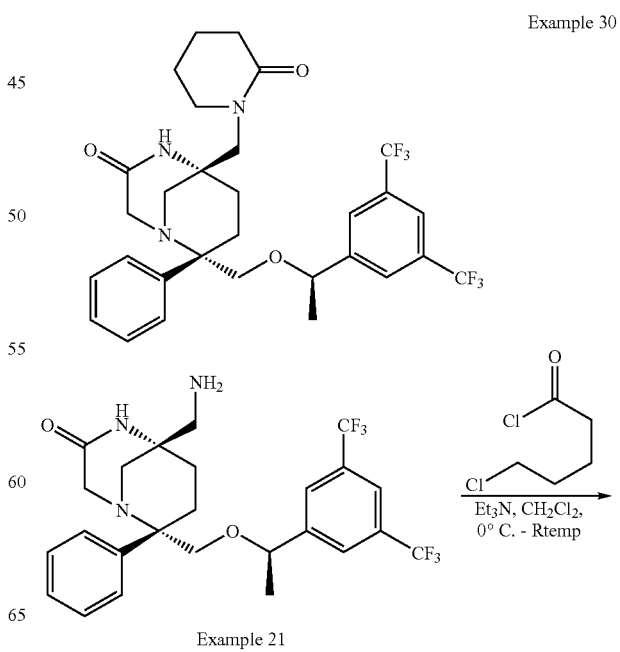

-continued

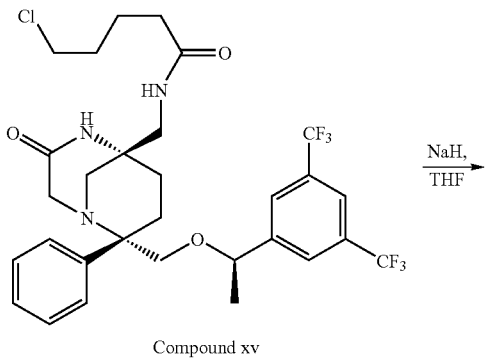

Compound xv

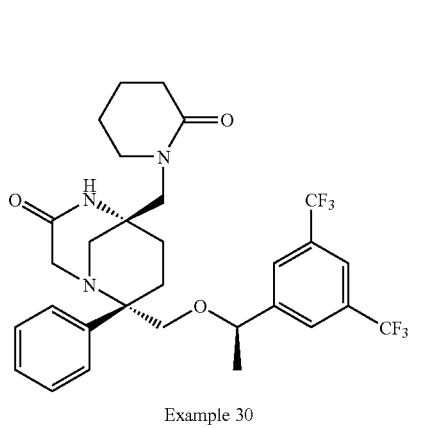

Example 30

Step 1:

In a 10 mL round-bottomed flask, Example 21 (0.085 g, 0.0016 mol, 1.0 equiv.) was taken up in 1 mL of anhydrous $CH_2Cl_2$. The reaction mixture was then cooled to 0° C. in an ice bath. $Et_3N$ (0.035 mL, 0.0025 mol, 1.5 equiv.) followed by chlorovaleryl chloride (0.025 mL, 0.00019 mol, 1.2 equiv.) were then added. The reaction mixture was slowly warmed to room temperature and was stirred for 14 h. The reaction was monitored by TLC (60:40 EtOAc/hexane) and MS. Upon completion of the reaction, the reaction was diluted with $CH_2Cl_2$, quenched with saturated aqueous $NaHCO_3$, followed by brine. The organic layer was dried over $Na_2SO_4$ and concentrated to give Compound xv (0.085 g) as a crude product.

Step 2:

In a flame-dried 15 mL round-bottomed flask, Compound xv (0.085 g, 0.00013 mol, 1.0 equiv.) was taken up in dry THF. To this solution, 60% NaH (0.014 g, 0.0004 mol, 3.0 equiv.) was added, and reaction mixture was stirred at room temperature for 2 hrs. The reaction was monitored by TLC (95/5 EtOAC/MeOH) and MS. Upon completion of the reaction, the reaction mixture was diluted with EtOAc and quenched with a saturated aqueous $NaHCO_3$ solution. The organic layer was dried over $Na_2SO_4$ and concentrated to give a crude product. Prep. TLC purification was carried out using 2% MeOH/EtOAc to give Example 30 (0.025 g).

Preparation of Example 31

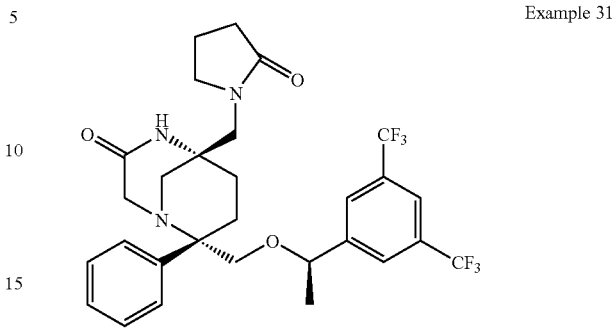

Example 31

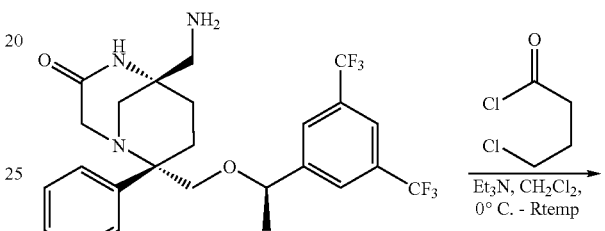

Example 21

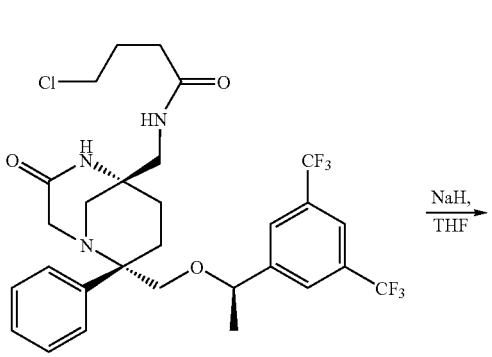

Compound xvi

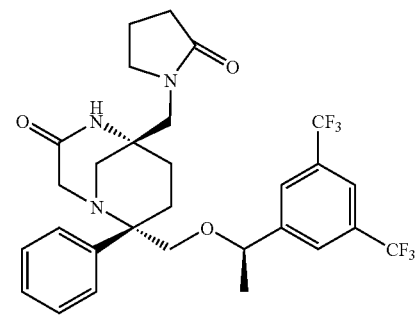

Example 31

Step 1:

In a 15 mL round-bottomed flask, Example 21 (0.085 g, 0.00016 mol, 1.0 equiv.) was taken up in 3 mL of $CH_2Cl_2$, and the reaction mixture was cooled to 0° C. in an ice bath. $Et_3N$ (0.035 mL, 0.00025 mol, 1.5 equiv.) followed by 4-chlorobutyryl chloride (0.023 mL, 0.00018 mol, 1.2 equiv.) was then added to the reaction mixture, which was then slowly warmed to room temperature and stirred for 14 hrs. The reaction was monitored by TLC (95/5 EtOAC/MeOH) and MS. Upon completion of the reaction, the reaction mixture was diluted with CH$_2$Cl$_2$, quenched with saturated aqueous NaHCO$_3$, followed by brine. The organic layer was dried over Na$_2$SO$_4$ and concentrated to give Compound xvi (0.075 g) as a crude product.

Step 2:

In a flame-dried 15 mL round-bottomed flask, Compound xvi (0.075 g, 0.00014 mol, 1.0 equiv.) was taken up in dry THF (1 mL). To this reaction mixture, 60% NaH (0.014 g, 0.00027 mol, 3.0 equiv.) was added, and the reaction mixture was stirred at room temperature for 2 hrs. The reaction was monitored by TLC (95/5 EtOAC/MeOH) and MS. Upon completion of the reaction, the reaction mixture was diluted with EtOAc and quenched with saturated aqueous NaHCO$_3$. The organic layer was dried over Na$_2$SO$_4$ and concentrated to give a crude product. Prep. TLC purification was carried out using 2% MeOH/EtOAc to give Example 31 (0.025 g).

Preparation of Example 32

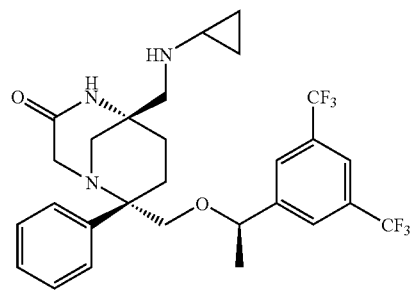

Example 32

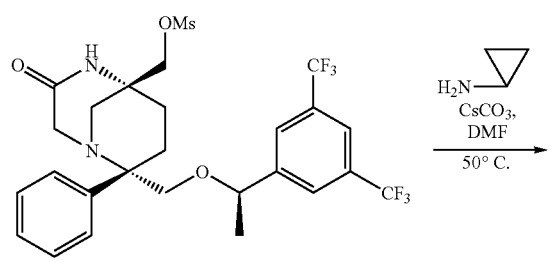

Compound xii

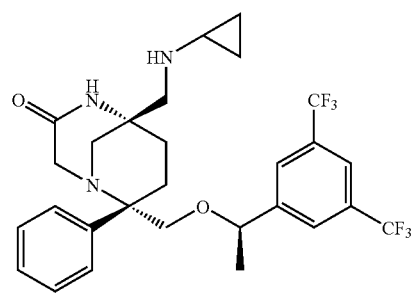

Example 32

In a 10 mL sealed tube, Compound xii (0.075 g, 0.000126 mol, 1.0 equiv.) was taken up in dry DMF, and cyclopropyl amine (0.026 mL, 0.00038 mol, 3.0 equiv.) followed by CsCO$_3$ (0.123 g, 0.00038 mol, 3.0 equiv.) was then added. The reaction mixture was heated to 50° C. for 12 h. The reaction was monitored by TLC (100% EtOAc) and MS. Upon completion of the reaction, the reaction mixture was diluted with EtOAc and washed with water. The organic layer was dried over Na$_2$SO$_4$ to give a crude product. Prep. TLC purification was carried out using 5% MeOH/CH$_2$Cl$_2$ to give Example 32 (0.029 g).

Preparation of Example 33

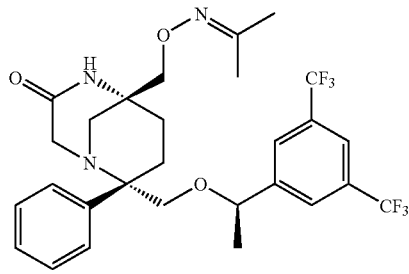

Example 33

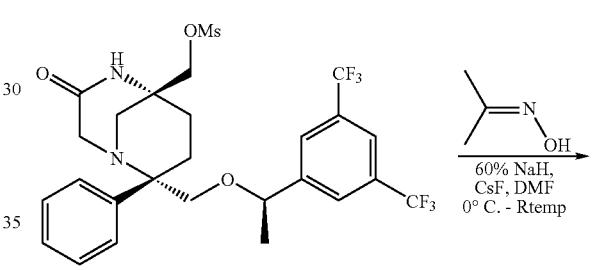

Compound xii

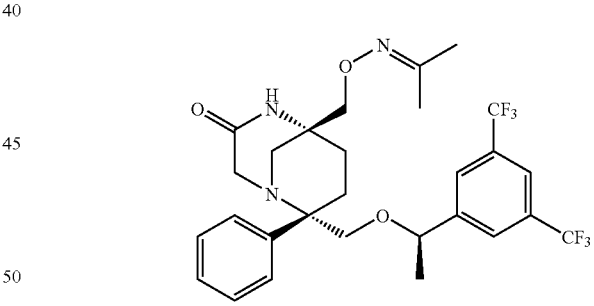

Example 33

To a flame-dried 15 mL round-bottomed flask maintained at 0° C., dry DMF (1 mL) was added 60% NaH (0.021 g, 0.00054 mol, 4.0 equiv.), CsF (0.082 g, 0.00054 mol, 4.0 equiv.) followed by acetoneoxime (0.02 g, 0.00027 mol, 2.0 equiv.). After 15 min., the reaction mixture was warmed to room temperature and was stirred for 1.5 h. Compound xii (0.08 g, 0.000134 mol, 1.0 equiv.) was then added to the reaction mixture, and the reaction mixture was stirred for 12 h. The reaction was monitored by TLC (10% MeOH/EtOAc) and MS. Upon completion of the reaction, the reaction mixture was diluted with EtOAc and washed with water. The organic layer was dried over Na$_2$SO$_4$ to give a crude product. Prep. TLC purification was carried out using 5% MeOH/CH$_2$Cl$_2$ to give Example 33 (0.035 g).

Preparation of Example 34

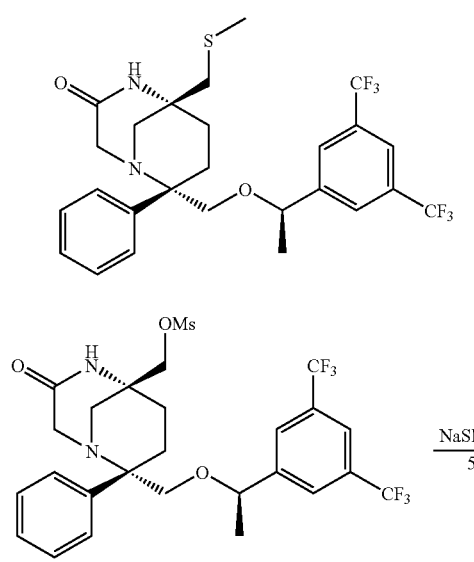

Example 34

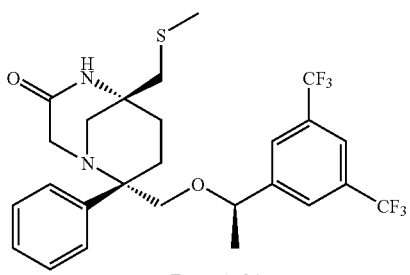

Compound xii

NaSMe, DMF
50° C.

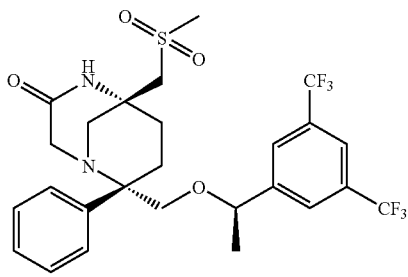

Example 34

In a flame-dried 15 mL round-bottomed flask, Compound xii (0.185 g, 0.00031 mol, 1.0 equiv.) was taken up in dry DMF (2 mL). To this mixture, sodium thiomethoxide (0.048 g, 0.000685 mol, 2.7 equiv.) was added and the reaction mixture was heated to 50° C. for 12 h. Purification was carried out using a BIOTAGE apparatus (30/70 EtOAc/Hexane to 60/40 EtOAc/Hexane), to give Example 34 (0.135 g, 80% yield).

Preparation of Example 35

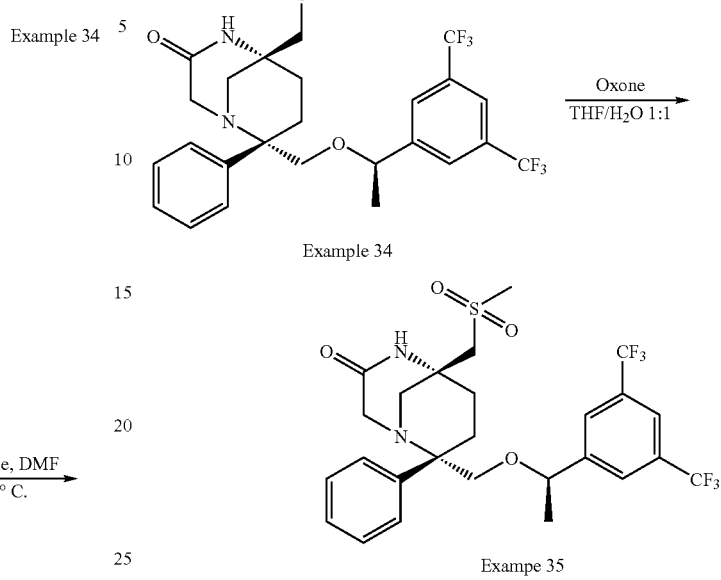

Example 34

Oxone
THF/H₂O 1:1

Exampe 35

In a flame-dried 15 mL round-bottomed flask, Example 34 (0.077 g, 0.00014 mol, 1.0 equiv.) was taken up in THF/H₂O (1:1, 1 mL each). Oxone (0.104 g, 0.00018 mol, 1.2 equiv.) was then added. The reaction mixture was stirred at room temperature for 3 h, and monitored by TLC (60/40 EtOAc/hexane). Upon completion of the reaction, the reaction mixture was concentrated, the residue was diluted with EtOAc, washed with H₂O, and dried over Na₂SO₄ to give a crude product. Prep. TLC purification was carried out using 5% MeOH/CH₂Cl₂ to give Example 35 (0.030 g).

Preparation of Example 36

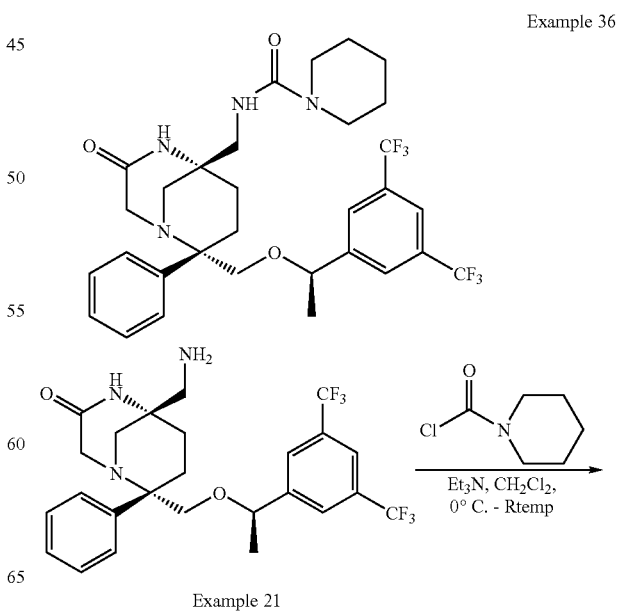

Example 36

Example 21

Et₃N, CH₂Cl₂,
0° C. - Rtemp

-continued

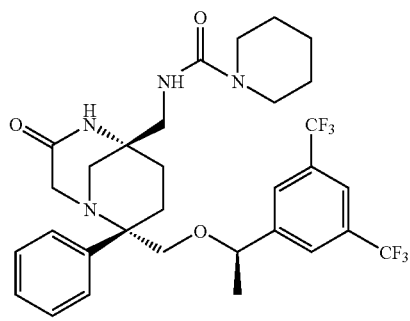

Example 36

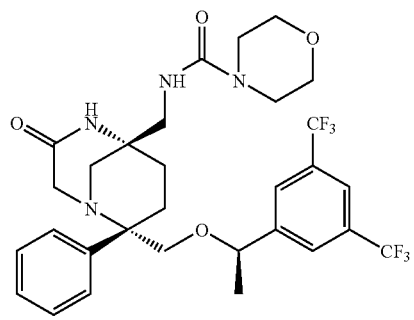

Example 37

In a 15 mL round-bottomed flask, Example 21 (0.185 g, 0.000366 mol, 1.0 equiv.) was taken up in 1 mL of CH₂Cl₂, and the reaction mixture was cooled to 0° C. in an ice bath. Et₃N (0.325 mL, 0.000726 mol, 2.0 equiv.) followed by piperidine carbonyl chloride (0.055 mL, 0.00044 mol, 1.2 equiv.) was then added to the reaction mixture, which was then slowly warmed to room temperature and stirred for 4 hrs. The reaction was monitored by TLC (85/5/10 EtOAC/MeOH/hexane) and MS. Upon completion of the reaction, the reaction mixture was diluted with CH₂Cl₂ and quenched with aqueous saturated NaHCO₃. The organic layer was dried over Na₂SO₄ and concentrated to give a crude product. Prep. TLC purification was carried out using 85/5/15 EtOAc/MeOH/Hexane to give Example 36 (0.090 g).

Preparation of Example 37

In a 15 mL round-bottomed flask, Example 20 (0.06 g, 0.000116 mol, 1.0 equiv.) was taken up in 1 mL of CH₂Cl₂, and the reaction mixture was then cooled to 0° C. in an ice bath. Et₃N (0.101 mL, 0.000232 mol, 2.0 equiv.) followed by morpholine carbonyl chloride (0.016 mL, 0.00014 mol, 1.2 equiv) was then added to the reaction mixture, which was slowly warmed to room temperature and stirred for 4 hrs. The reaction was monitored by TLC (85/5/10 EtOAC/MeOH/hexane) and MS. Upon completion of the reaction, the reaction mixture was diluted with CH₂Cl₂ and quenched with aqueous saturated NaHCO₃. The organic layer was dried over Na₂SO₄ and concentrated to give crude product. Prep. TLC purification was carried out using 85/5/15 EtOAc/MeOH/Hexane to give Example 37 (0.030 g).

Preparation of Example 38

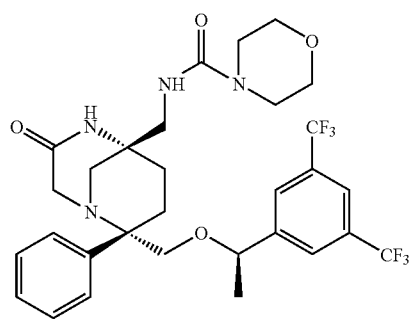

Example 37

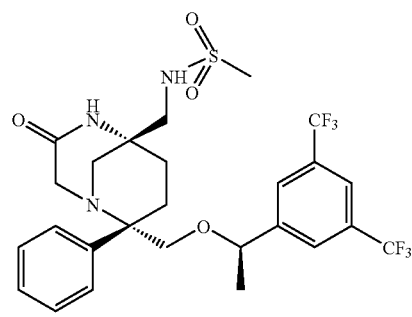

Example 38

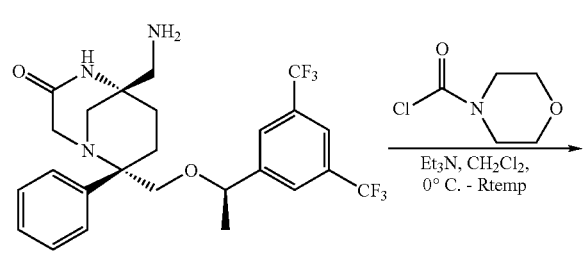

Example 21

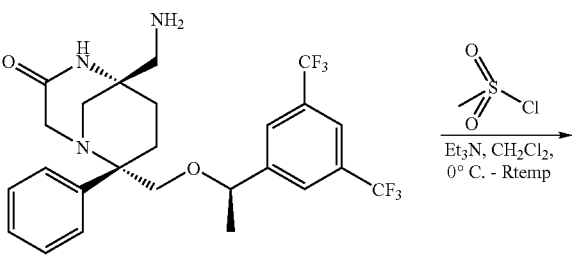

Example 21

-continued

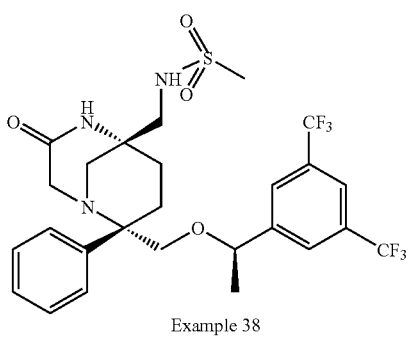

Example 38

In a 15 mL round-bottomed flask, Example 20 (0.06 g, 0.000116 mol, 1.0 equiv.) was taken up in 1 mL of CH₂Cl₂ and the reaction mixture was cooled to 0° C. in an ice bath. Et₃N (0.101 mL, 0.000232 mol, 2.0 equiv.) and methane sulfonyl chloride (0.011 mL, 0.00014 mol, 1.2 equiv) were then added, and the reaction mixture was then slowly warmed to room temperature and stirred for 4 h. The reaction was monitored by TLC (85/5/10 EtOAC/MeOH/hexane) and MS. Upon completion of the reaction, the reaction mixture was diluted with CH₂Cl₂ and quenched with saturated aqueous NaHCO₃. The organic layer was then dried over Na₂SO₄ and concentrated to give a crude product. Prep. TLC purification was carried out using 85/5/15 EtOAc/MeOH/hexane to give Example 38 (0.030 g).

Preparation of Example 39

-continued

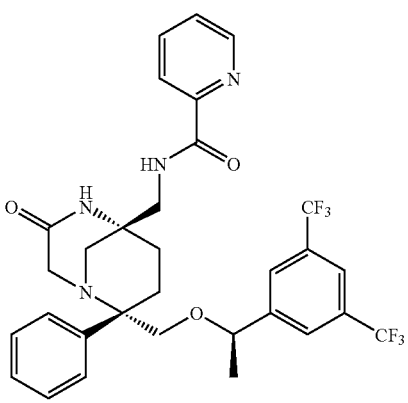

Example 39

In a 15 mL round-bottomed flask, Example 20 (0.06 g, 0.000116 mol, 1.0 equiv.) was taken up in 1 mL of CH₂Cl₂, and the reaction mixture was cooled to 0° C. in an ice bath. Et₃N (0.101 mL, 0.000232 mol, 2.0 equiv.) followed by picolinonyl chloride (0.025 g, 0.00014 mol, 1.2 equiv) were then added to the reaction mixture, which was then slowly warmed to room temperature and stirred for 4 h. The reaction was monitored by TLC (85/5/10 EtOAC/MeOH/hexane) and MS. Upon completion of the reaction, the reaction mixture was diluted with CH₂Cl₂ quenched with saturated aqueous NaHCO₃. The organic layer was then dried over Na₂SO₄ and concentrated to give a crude product. Prep. TLC purification was carried out using 85/5/15 EtOAc/MeOH/hexane to give Example 39 (0.035 g).

Preparation of Example 40

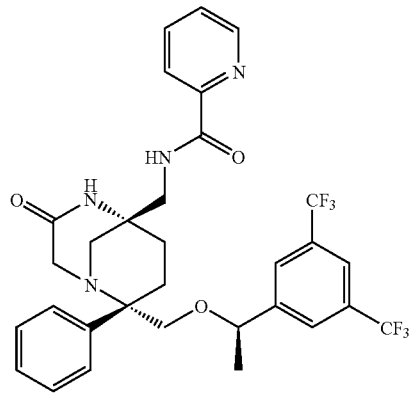

Example 39

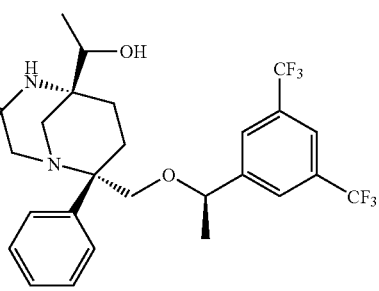

Example 40

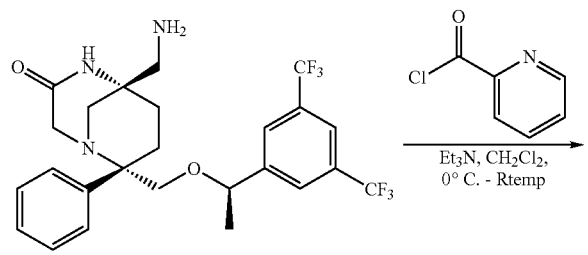

Example 21

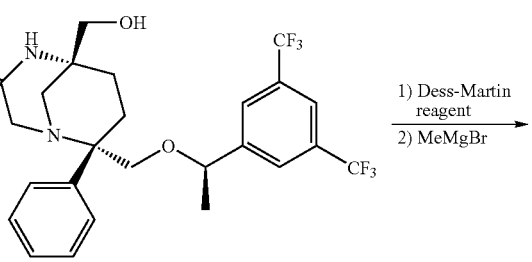

Example 3a

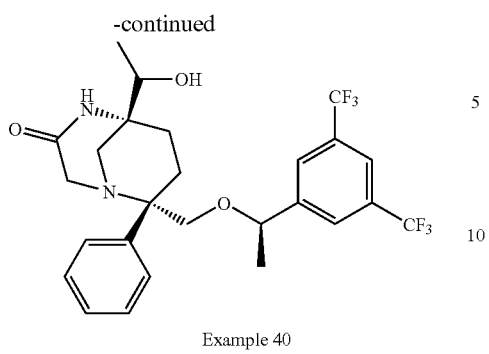

Example 40

To Example 3a (200 mg, 0.39 mmol) in 5 mL CH$_2$Cl$_2$ was added Dess-Martin reagent (231 mg, 0.55 mmol) and the reaction mixture was stirred for 1 h. The reaction mixture was then diluted with Et$_2$O (20 mL), washed with a mixture of 2 mL of saturated aqueous NaHCO$_3$ and 2 mL of saturated aqueous Na$_2$S$_2$O$_3$, and the organic layer was dried and concentrated. Half of the resulting mixture (98 mg) was dissolved in 3 mL of THF, and was cooled to 0° C. This solution was treated with MeMgBr (3.0 M in Et$_2$O, 0.2 mL) at 0° C., then slowly warmed to 23° C., and stirred for 2 h. The reaction mixture was then quenched with aqueous NH$_4$Cl and extracted with EtOAc. The organic layer was dried and concentrated to give a crude product, which was purified by silica gel chromatography (20-50% EtOAc/hexane) to give Example 40. Electrospray MS [M+1]$^+$ 531.1.

Preparation of Example 41

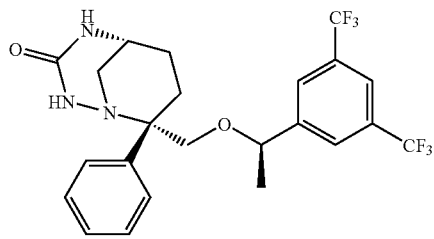

Example 41

Step 1:

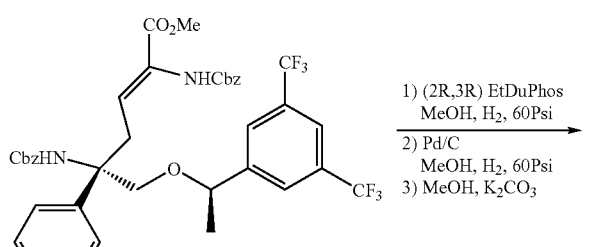

Compound xvii

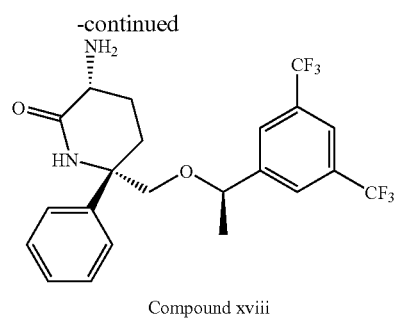

Compound xviii

N$_2$ was bubbled through a solution of Compound xvii (i.e., Compound 24 of U.S. Published Application 2003/0158173 A1, Ser. No. 10/321,687) (3.7 g, 4.88 mmol) in 40 mL of anhydrous MeOH in a PARR shaker, for 15 min. Then 1,2-bis((2R,5R)-2,5-diethylphospholano)benzene (cyclooctadiene)rhodium (I) trifluoromethanesulfonate (140 mg, 0.20 mmol) was added, and the reaction mixture was hydrogenated at 60 psi for 60 h. The reaction mixture was then treated with Pd(OH)$_2$/C (20% on carbon, 730 mg) and was hydrogenated at 40 psi for 16 h. The mixture was filtered through a pad of CELITE and washed twice with 10 mL of MeOH. The MeOH solution was then heated at 60° C. for 4 h, and concentrated to give Compound xviii (2.1 g, 93% yield).

Step 2:

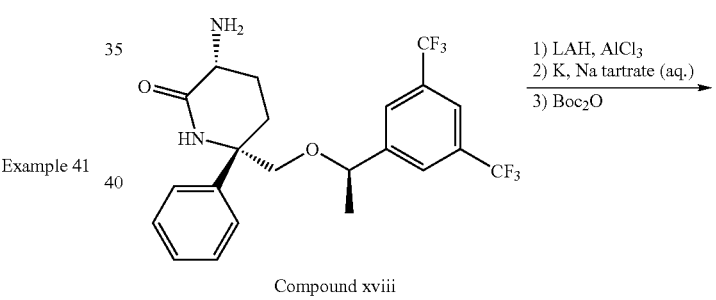

Compound xviii

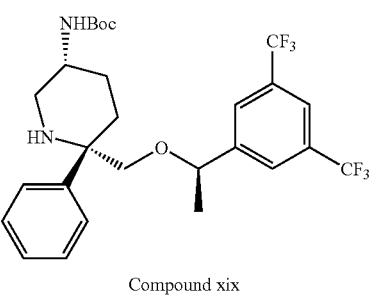

Compound xix

A flame-dried flask containing AlCl$_3$ (450 mg, 0.337 mmol) was cooled to 0° C., and then a LiAlH$_4$ solution (1.0 M in Et$_2$O, 9.77 mL, 9.77 mmol) was added, dropwise. The suspension was stirred at 0° C. for 30 min, and then cooled to −78° C. A solution of Compound xviii (1.0 g, 2.17 mmol) in dry THF (30 mL) was added via a cannula. The solution was then stirred at −78° C. for 1 h, and was then allowed to warm up to 23° C. and stirred for additional 1 h. The reaction mixture was again cooled to 0° C., then 15 mL of aqueous K, Na tartrate solution was added, dropwise. The solution was stirred at 23° C. for 2 h, then Boc anhydride (947 mg, 4.34 mmol) was added and the reaction was stirred overnight. The organic and aqueous layers were separated and the aqueous layer was extracted with 20 mL of EtOAc, three times. The combined organic layers were dried and concentrated, and the resulting residue was subjected to silica gel chromatography (20%-60% EtOAc/hexane) to give Compound xix (914 mg, 77% yield), Electrospray MS [M+1]$^+$ 547.1.

Step 3:

Compound xix

To a solution of Compound xix (245 mg, 0.448 mmol) in THF (2 mL), was added NaNO$_2$ (37 mg, 0.538 mmol) in 1 mL water, followed by the addition of HOAc (39 mL). The reaction mixture was stirred for 2 h, then NaNO$_2$ (14 mg) and HOAc (15 μL) were added and the reaction mixture was stirred for 30 min. Then another portion of NaNO$_2$ (14 mg) and HOAc (15 μL) was added, and the reaction mixture was stirred for an additional 1 h. The reaction mixture was then diluted with Et$_2$O, washed with aqueous NaHCO$_3$ and brine, dried, and concentrated. The resulting residue was dissolved in THF (2 mL) cooled to 0° C. and an LAH solution (1.0 M in Et$_2$O, 0.92 mL) was added and the reaction was stirred for 4 h at 23° C. The reaction was further treated with an LAH solution (1.0 M in Et$_2$O, 0.92 mL) and stirred at 23° C. for 16 h. The reaction was diluted with 20 mL Et$_2$O, quenched with Na, K tartrate (saturated aq.), and stirred for 1 h. The organic and aqueous layers were separated, and the organic layer was washed with brine, dried, and concentrated. The resulting residue was purified by chromatography on a silica gel column (EtOAc/Hexane=2/1) to give Compound xx (180 mg, 71% yield), Electrospray MS [M+1]$^+$ 562.1.

Step 4:

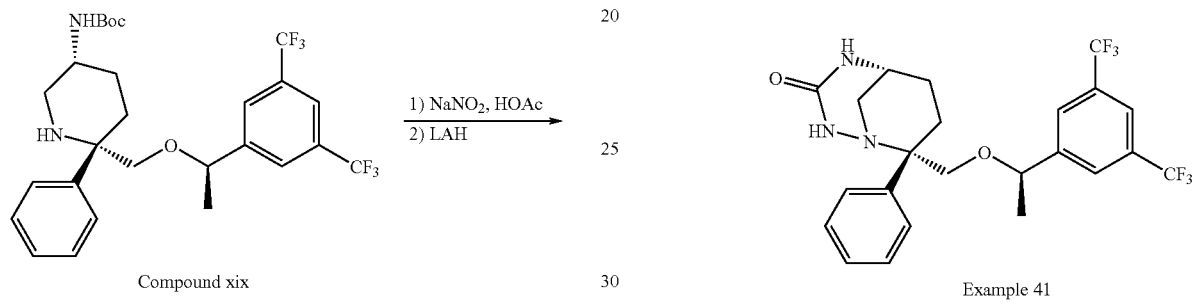

Compound xx

To a solution of Compound xx (80 mg, 0.14 mmol) in CH$_2$Cl$_2$ (2 mL), was added HCl in dioxane (4 M, 1 mL), and the resulting mixture was stirred at 23° C. for 16 h. The solvent was then removed and the residue was dissolved in CH$_2$Cl$_2$ (3 mL). The solution was cooled to 0° C. and DIEA (78.4 μL, 0.45 mmol) was added followed by triphosgene (11 mg, 0.036 mmol). After stirring for 5 min., the reaction mixture was allowed to warm to 23° C. and stirred for an additional 2 h. The solvent was removed and the residue was partitioned between EtOAc (10 mL) and water (5 mL). The organic layer was then dried and concentrated. The resulting residue was purified using Prep. TLC (5% MeOH/CH$_2$Cl$_2$) to give Example 41 (45 mg, 65% yield), Electrospray MS [M+1]$^+$ 488.3.

Preparation of Compound of Example 42

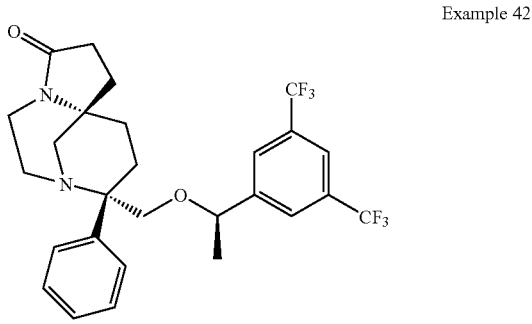

Example 42

Step 1:

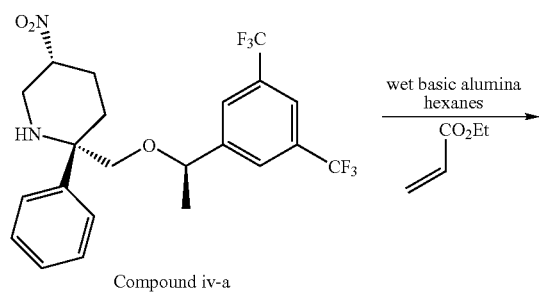

Compound iv-a

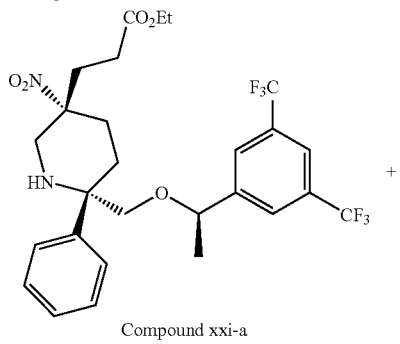

Compound xxi-a

Compound xxi-b

In a 100 mL round bottomed flask, Compound iv-a (1.0 g, 2.1 mmol) was taken up in 40 mL of hexanes. Wet basic alumina (10 wt % water) (10.0 g, 10 wt. equiv) was added, followed by ethyl acrylate (1.14 mL, 10.5 mmol, 5 equiv). The reaction mixture was allowed to stir at room temperature overnight. After the reaction was complete, the reaction mixture was filtered to remove the alumina, washed with EtOAc (4×25 mL), and concentrated. The crude mixture was purified using a BIOTAGE apparatus (5% EtOAc/hexanes) to give 0.535 g (45% yield) of Compound xxi-a (which was separated from Compound xxi-b).

Step 2:

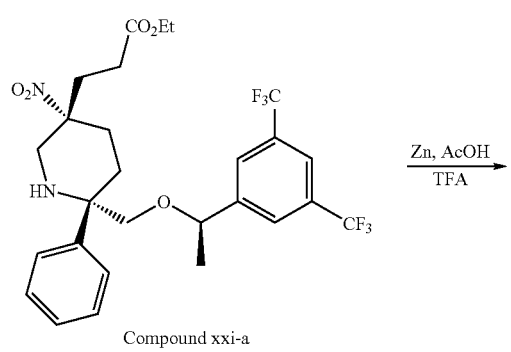

Compound xxi-a

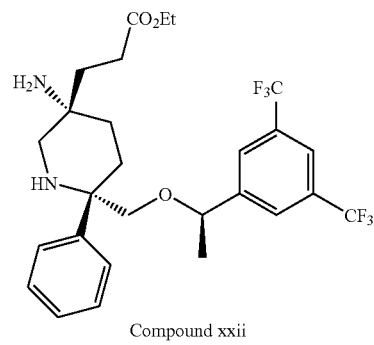

Compound xxii

In a 25 mL round-bottomed flask, Compound xxi-a (0.2 g, 0.35 mmol) was dissolved in 10 mL acetic acid. 1 mL of TFA was then added, and the reaction mixture was cooled to 0° C. Zn dust (0.227 g, 3.5 mmol, 10 equiv) was added, and the reaction was slowly allowed to warm to room temperature and left to stir overnight. The reaction mixture was filtered through CELITE and diluted with $CH_2Cl_2$ (25 mL). The filtrate was concentrated and the crude Compound xxii was used without any further purification.

Step 3:

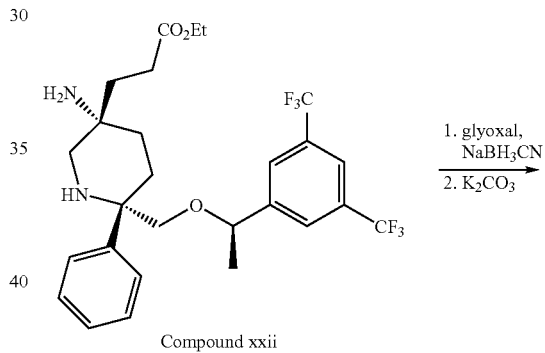

Compound xxii

Example 42

In a 25 mL round bottomed flask, Compound xxii (0.095 g, 0.17 mmol) was dissolved in 5 mL of $CH_3OH$. Glyoxal (40% in $H_2O$) (0.026 mL, 0.23 mmol, 1.3 equiv) was then added and the reaction stirred for 30 min, and then $NaBH_3CN$ (0.021 g, 0.34 mmol, 2 equiv) was added, and the reaction mixture was refluxed for 1 h. The reaction was allowed to cool to room temperature, diluted with 2 mL of MeOH, and then K$_2$CO$_3$ (0.117 g, 0.85 mmol, 5 equiv) was added. The reaction mixture was allowed to reflux overnight. After the reaction was complete, the mixture was concentrated, diluted with H$_2$O, and extracted with EtOAc (2×10 mL). The organic layer was dried over MgSO$_4$, concentrated and purified by Prep. TLC (4:1 EtOAc:hexanes) to give 0.021 g of Example 42. HRMS calcd. for C$_{27}$H$_{29}$N$_2$O$_2$F$_6$ (M+H) 527.2133, found 527.2139.

Preparation of Example 43

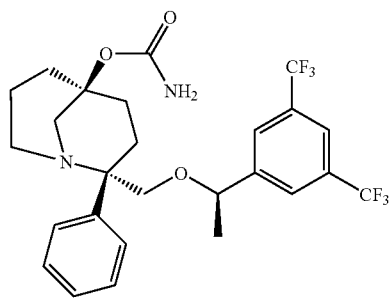

Example 43

Step 1:

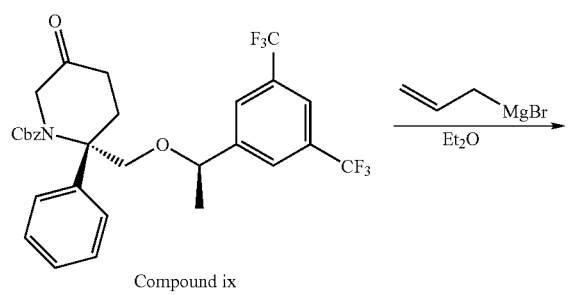

Compound ix

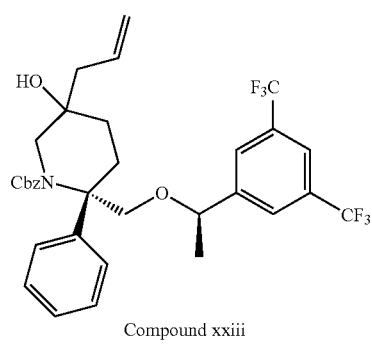

Compound xxiii

In a 25 mL round-bottomed flask equipped with an argon balloon, was placed Compound ix (0.5 g, 0.86 mmol) in 5 mL of Et$_2$O. The solution was cooled to 0° C. with an ice bath. Allylmagnesium bromide (0.95 mL, 0.95 mmol, 1.1 equiv, 1 M solution in Et$_2$O) was added, and the reaction was stirred at 0° C. for 2 h. After the reaction was complete, the reaction mixture was quenched with saturated aqueous NH$_4$Cl and extracted with EtOAc (2×10 mL). The organic layers were combined, dried over MgSO$_4$, and concentrated to give 0.53 g of crude Compound xxiii. The crude Compound xxiii was used without further purification in the next step.

Step 2:

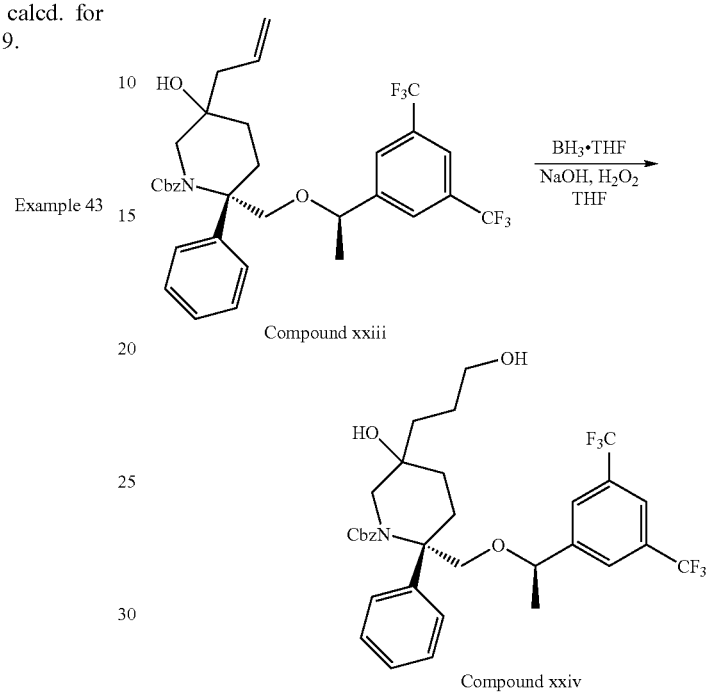

Compound xxiii

Compound xxiv

In a 25 mL round-bottomed flask, Compound xxiii (0.51 g, 0.82 mmol) was dissolved in 5 mL of THF and cooled to 0° C. in an ice bath. BH$_3$.THF complex (1.0 M in THF, 1.64 mL, 1.64 mmol, 2.0 equiv) was added, and the reaction mixture was stirred at 0° C. for 3 h, at which time 2 N NaOH (1.23 mL, 2.46 mmol, 3 equiv) was rapidly introduced followed by H$_2$O$_2$ (30 wt %, 0.29 g, 2.54 mmol, 3.1 equiv). Stirring was maintained at 0° C. for an additional hour. After the reaction was complete, the mixture was diluted with EtOAc (10 mL), extracted with EtOAc (2×5 mL), and the combined organic layers were dried over MgSO$_4$ and concentrated. The crude product was purified with a BIOTAGE apparatus (20% EtOAc/hexanes to 100% EtOAc) to give 0.18 g of Compound xxiv.

Step 3:

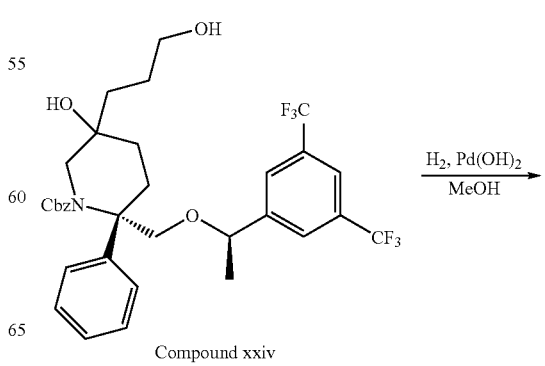

Compound xxiv

-continued

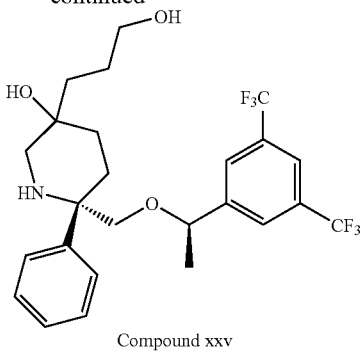

Compound xxv

In a 25 mL round-bottomed flask, Compound xxiv (0.18 g, 0.28 mmol) was dissolved in 5 mL MeOH. The reaction vessel was flushed with nitrogen, and then Pd(OH)$_2$ (0.016 g, 0.11 mmol, 40 wt %) was added. The mixture was hydrogenated at room temperature using a hydrogen-filled balloon. The reaction mixture was filtered through CELITE after 40 min of reaction and concentrated to give crude Compound xxv, which was used in the next step without any further purification.

Step 4:

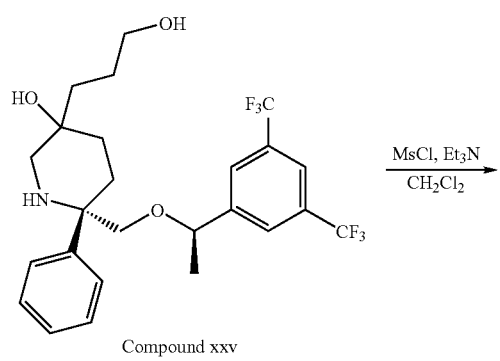

Compound xxv

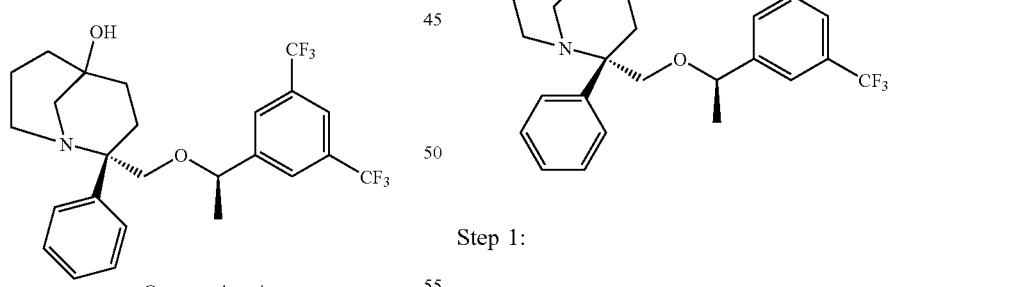

Compound xxvi

In a 10 mL round-bottomed flask, Compound xxv (0.07 g, 0.138 mmol) was dissolved in 2 mL of CH$_2$Cl$_2$ and 1 mL of Et$_3$N. The solution was cooled to 0° C., followed by the addition of MsCl (0.012 mL, 0.152 mmol, 1.1 equiv). The reaction mixture was allowed to stir overnight at room temperature. After the reaction was complete, the reaction mixture was quenched by the addition of saturated aqueous NaHCO$_3$, and extracted with CH$_2$Cl$_2$ (10 mL). The organic layer was isolated, dried over MgSO$_4$, concentrated, and purified by Prep. TLC to give 0.020 g of Compound xxvi.

Step 5:

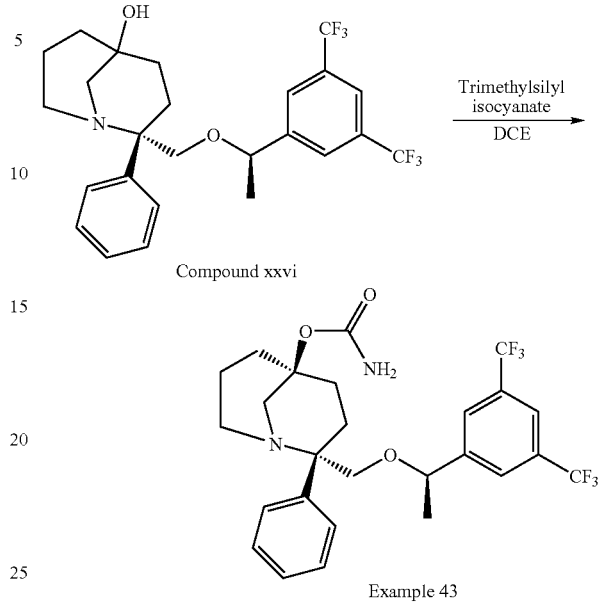

Compound xxvi

Example 43

In a 10 mL round-bottomed flask, Compound xxvi was taken up in 2 mL of DCE. TMS isocyanate (0.112 mL, 0.84 mmol, 20 equiv) was then added, and the reaction mixture was refluxed at 80° C., overnight. The reaction mixture was quenched by the addition of saturated aqueous NaHCO$_3$, diluted with EtOAc (10 mL) and extracted with EtOAc (2×5 mL). The organic layers were combined, dried over MgSO$_4$, and concentrated. The resulting crude mixture was purified by Prep. TLC to give 0.007 g of Example 43. HRMS calcd. for C$_{26}$H$_{29}$N$_2$O$_3$F$_6$ (M+H) 531.2082, found 531.2080.

Preparation of Compound of Example 44

Example 44

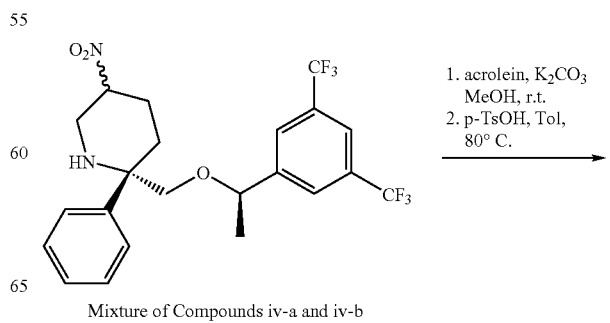

Step 1:

Mixture of Compounds iv-a and iv-b 1. acrolein, K$_2$CO$_3$
   MeOH, r.t.
2. p-TsOH, Tol,
   80° C.

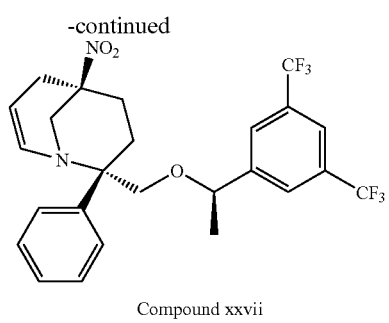

Compound xxvii

To a solution of nitropiperidine Compounds iv-a and iv-b (1.0 g, 2.1 mmol) in methanol (50 mL) maintained at room temperature, acrolein (0.31 mL, 4.2 mmol) was added, followed by a catalytic amount of potassium carbonate. After being stirred at room temperature overnight, the mixture was quenched with a saturated ammonium chloride solution and then ethyl acetate was added. The organic and aqueous layers were separated and the aqueous layer was extracted with ethyl acetate (two times). The combined organic layers were dried (MgSO$_4$) and filtered. The solvents were removed under vacuum too give a yellow oil. The yellow oil was then dissolved in toluene (50 mL) and a catalytic amount of p-toluenesulfonic acid was added. The mixture was heated at 80° C. overnight, and then cooled to room temperature. Excess triethylamine was then added, and the reaction mixture was filtered through a pad of silica and eluted with ethyl acetate. The solvents in the filtrate were removed under vacuum, and the resulting residue was purified by chromatography (silica column, hexanes-ethyl acetate, 9:1 (v/v)) to give enamine Compound xxvii (540 mg, 50% yield) as a colorless oil.

Step 2:

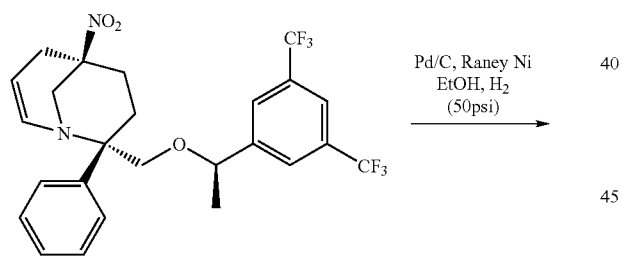

Compound xxvii

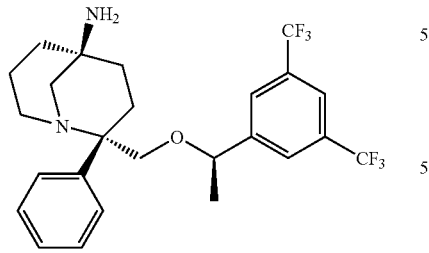

Example 44

A solution of enamine Compound xxvii (100 mg, 0.19 mmol) in methanol (10 mL) was hydrogenated at 50 psi with a catalytic amount of Pd/C and a catalytic amount of Raney Nickel, overnight. The catalyst was then removed by filtration through a pad of CELITE. The solvents were removed under vacuum to give diamine Example 44 (92 mg, 100% yield) as a colorless oil. Electrospray MS [M+1]$^+$=487.

Preparation of Example 45

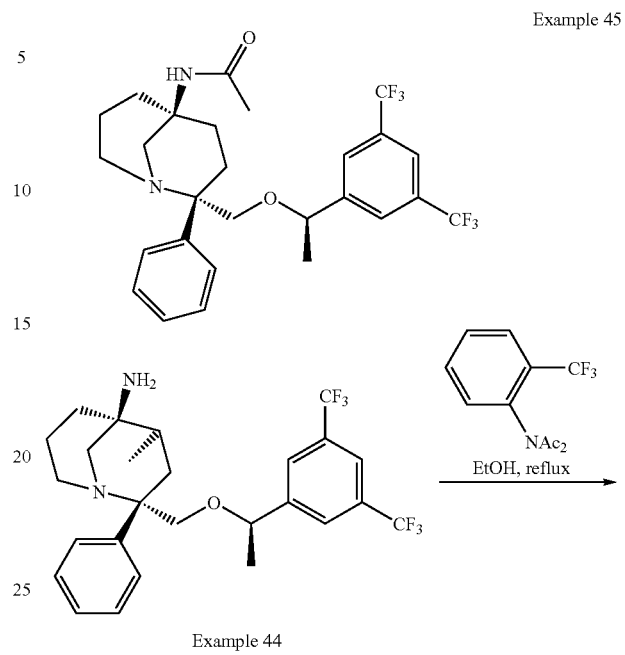

Example 45

To a solution of diamine Example 44 (92 mg, 0.19 mmol) in ethanol (5 mL), trifluorodiacetylaniline was added and the mixture was heated at reflux overnight. After being cooled to room temperature, the solvents were removed under vacuum, and the crude product was purified by column chromatography (silica, ethyl acetate) to give acetate Example 45 (80 mg, 80% yield) as a colorless oil. Electrospray MS [M+1]$^+$=529.

Preparation of Example 46

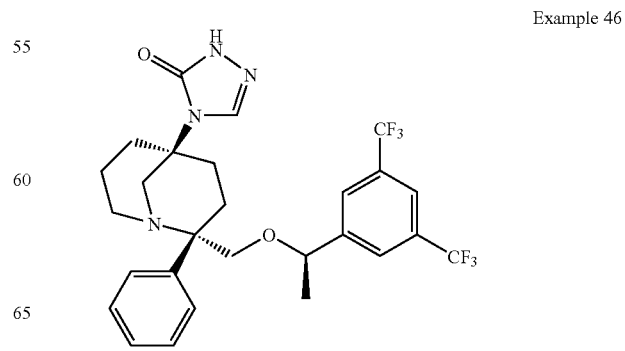

Example 46

-continued

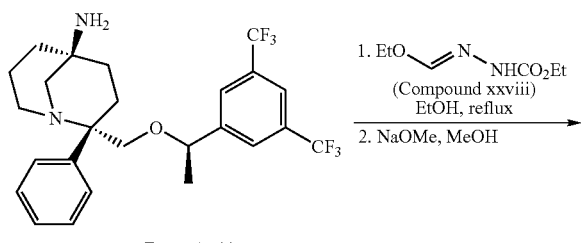

Example 44

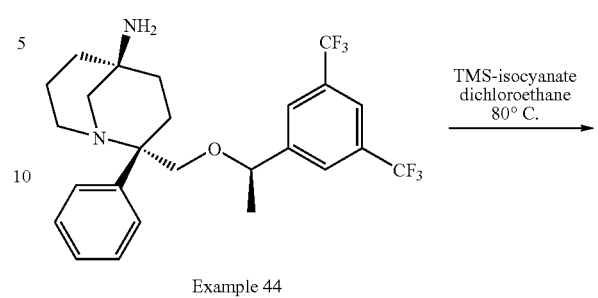

Example 44

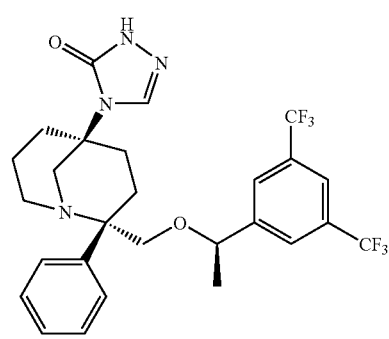

Example 46

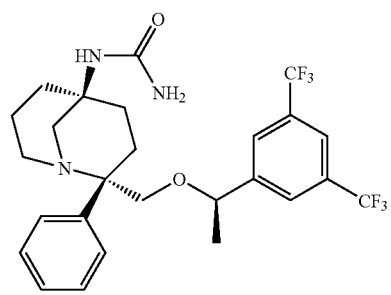

Example 47

To a solution of diamine Example 46 (92 mg, 0.19 mmol) in ethanol (5 mL), ester Compound xxviii (85 mg, 0.53 mmol) was added and the mixture was heated at reflux overnight. Sodium methoxide (1 mL, 30% in methanol) was added, and the mixture was again heated at reflux overnight. After being cooled to room temperature, the mixture was quenched with saturated ammonium chloride solution, and ethyl acetate was added. The organic and aqueous layers were separated, and the aqueous layer was extracted twice with ethyl acetate. The combined organic layers were dried (MgSO$_4$) and filtered. The solvents were removed under vacuum, and the resulting residue was purified by column chromatography (silica, ethyl acetate) to give triazolone Example 46 (68 mg, 65% yield) as a white solid. Electrospray MS [M+1]$^+$=555.

Preparation of Example 47

To a solution of diamine Example 44 (40 mg, 0.082 mmol) in dichloroethane (1 mL), trimethylsilylisocyanate (0.13 mL, 0.82 mmol) was added and the mixture was heated at 80° C. overnight. After being cooled to room temperature, the mixture was quenched with saturated ammonium chloride solution and ethyl acetate was then added. The organic and aqueous layers were separated, and the aqueous layer was extracted twice with ethyl acetate. The combined organic layers were dried (MgSO$_4$) and filtered. The solvents were removed under vacuum, and the resulting residue was purified by column chromatography (silica, ethyl acetate) to give urea Example 47 (37 mg, 85% yield) as a colorless oil. Electrospray MS [M+1]$^+$=530.

Preparation of Examples 48a and 48b

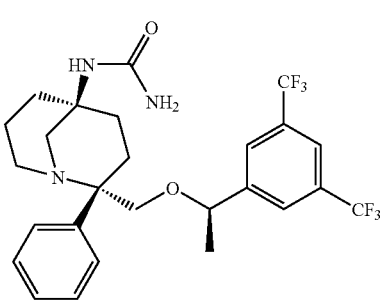

Example 47

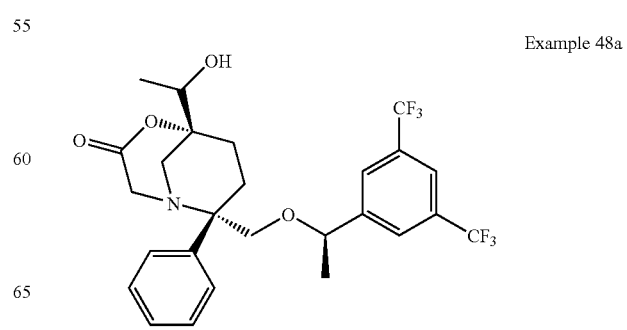

Example 48a

Example 48b

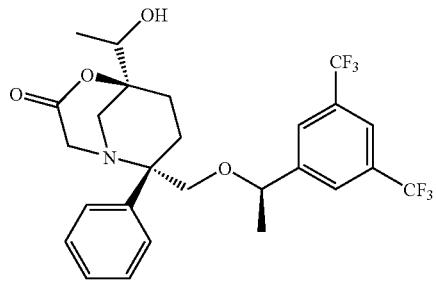

Step 1:

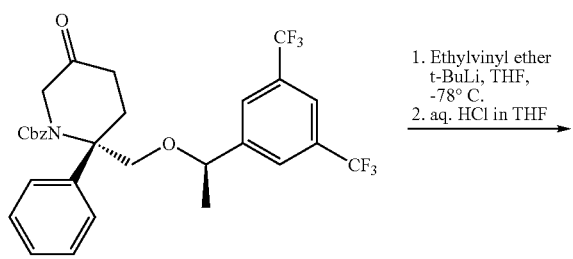

Compound ix

1. Ethylvinyl ether t-BuLi, THF, -78° C.
2. aq. HCl in THF

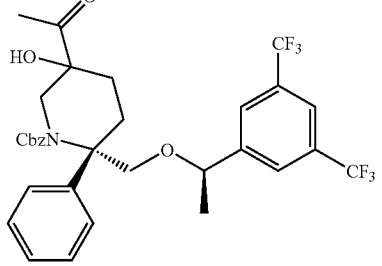

Compound xxix

To a solution of ethylvinyl ether (1.74 mL, 0.018 mol) in THF (50 mL) cooled to −78° C. with a cooling bath, t-butyllithium (4.6 mL, 0.0078 mol) was added. The cooling bath was then removed and the reaction mixture temperature was raised to −10° C. The reaction mixture was then stirred at −10° C. until the yellow color disappeared. The reaction mixture was then cooled to −78° C. and ketone Compound ix (1.5 g, 0.0026 mol) in THF (10 mL) was added. The reaction mixture was stirred at −78° C. for 1 h before it was quenched with a saturated aqueous ammonium chloride solution. Ethyl acetate was then added to the reaction mixture, and the organic and aqueous layers were separated. The aqueous layer was extracted twice with ethyl acetate. The combined organic layers were dried (MgSO$_4$) and filtered. The solvents were removed under vacuum to give a yellow oil. The yellow oil was dissolved in THF (20 mL) and hydrochloric acid (10 mL, 10% in water) was added. The mixture was stirred at room temperature overnight before it was quenched with saturated sodium bicarbonate solution. Ethyl acetate was then added and the organic and aqueous layers were separated. The aqueous layer was extracted twice with ethyl acetate. The combined organic layers were dried (MgSO$_4$) and filtered. The solvents were removed under vacuum and the resulting residue was purified by column chromatography (silica, dichloromethane-methanol, 99:1 (v/v)) to give alcohol Compound xxix (810 mg, 50% yield) as a yellow oil.

Step 2:

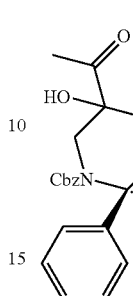

Pd(OH)$_2$, MeOH
H$_2$ (45psi)

Compound xxix

Compound xxx

A solution of alcohol Compound xxix (751 mg, 1.2 mmol) in ethanol (10 mL) was hydrogenated overnight using a hydrogen-filled balloon and a catalytic amount of Pd/C. The catalyst was then removed by filtration of the reaction mixture through a pad of CELITE. Solvents were removed under vacuum to give piperidine Compound xxx as a yellow oil (587 mg, 100% yield).

Step 3:

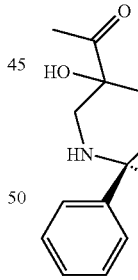

Compound xxx (OHCCO$_2$Et)$_n$,
HOAc
NaCNBH$_3$, r.t.

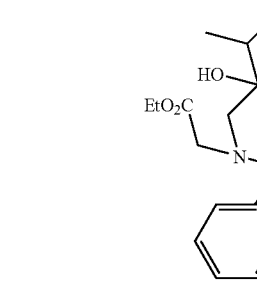

Compound xxxi

To a solution of piperidine Compound xxx (410 mg, 0.84 mmol) and ethyl glyoxalate (0.83 mL, 4.19 mmol, 40-50% in toluene) in acetic acid (20 mL) at room temperature, sodium cyanoborohydride (792 mg, 12.6 mmol) was added in small portions. The mixture was stirred at room temperature overnight. The solvents were removed under vacuum, and the resulting residue was purified by column chromatography (silica, ethyl acetate) to give diol Compound xxxi (363 mg, 75% yield) as a colorless oil.

Step 4:

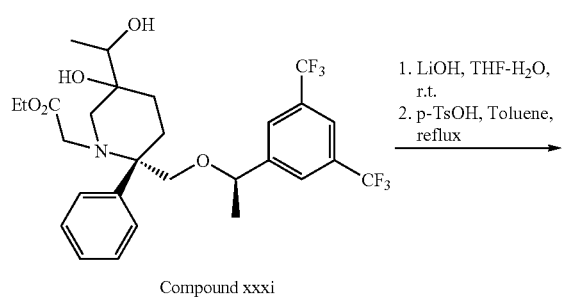

Compound xxxi

1. LiOH, THF-H$_2$O, r.t.
2. p-TsOH, Toluene, reflux

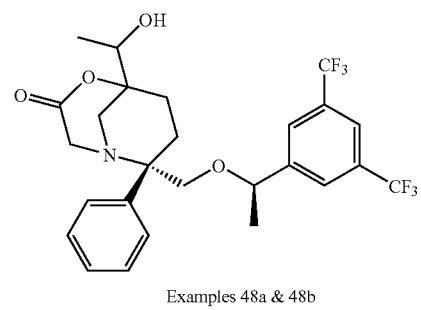

Examples 48a & 48b

To a solution of diol Compound xxxi (363 mg, 0.63 mmol) in THF (5 mL) at room temperature, lithium hydroxide (76 mg, 3.15 mmol) in water (5 mL) was added. The reaction mixture was stirred at room temperature overnight before it was quenched with citric acid (10% in water). Ethyl acetate was then added and the organic and aqueous layers were separated. The aqueous layer was extracted twice with ethyl acetate. The combined organic layers were dried (MgSO$_4$) and filtered. The solvents were removed under vacuum to give a yellow oil. The oil was dissolved in toluene and a catalytic amount of p-toluenesulfonic acid was added. The resulting mixture was heated at reflux overnight. After being cooled to room temperature, ethyl acetate was added and the reaction mixture was quenched with a saturated aqueous sodium bicarbonate solution. The organic and aqueous layers were then separated and the aqueous layer was extracted twice with ethyl acetate. The combined organic layers were dried (MgSO$_4$) and filtered. The solvents were removed under vacuum and the resulting residue was purified by column chromatography (silica, hexanes-ethyl acetate, 4:1 (v/v)) to give less polar lactones, Example 48a (74 mg, 22%) as a colorless oil. Electrospray MS [M+1]$^+$ = 532. Continuous elution with the same solvents system gave more polar lactones, Example 48b (67 mg, 20%) also as colorless oil. Electrospray MS [M+1]$^+$=532.

Preparation of Example 49

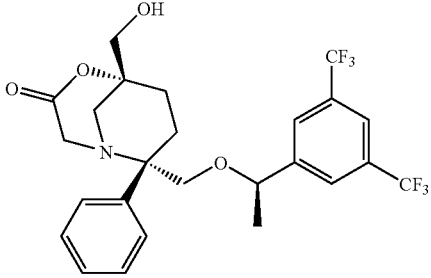

Example 49

Step 1:

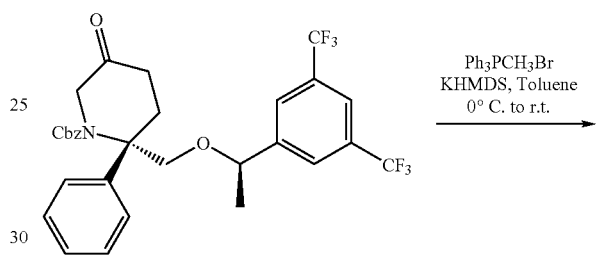

Compound ix

Ph$_3$PCH$_3$Br
KHMDS, Toluene
0° C. to r.t.

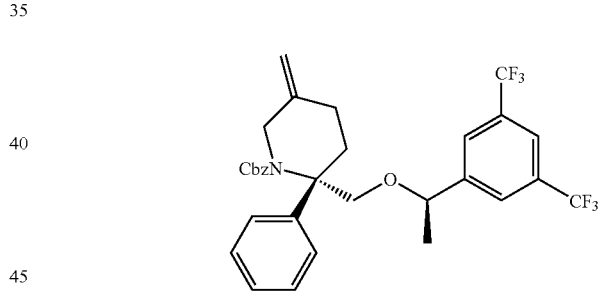

Compound xxxii

To a solution of methyltriphenylphosphonium bromide (1.85 g, 5.18 mmol) in toluene (10 mL) maintained at 0° C. with a cooling bath under a nitrogen atmosphere, a solution of potassium bis(trimethylsilyl)amide (10.4 mL, 5.18 mmol) was added. The reaction mixture was stirred at 0° C. for 1 h and a solution of ketone Compound ix (1.0 g, 1.72 mmol) in toluene (5 mL) was added. The cooling bath was removed and the reaction mixture was warmed to room temperature before it was quenched with a saturated aqueous ammonium chloride solution. Ethyl acetate was added, and the organic and aqueous layers were separated. The aqueous layer was extracted twice with ethyl acetate. The combined organic layers were dried (MgSO$_4$) and filtered. The solvents were removed under vacuum, and the resulting residue was purified by column chromatography (silica, hexanes-ethyl acetate, 19:1 (v/v)) to give alkene Compound xxxii (1.0 g, 100% yield) as a colorless oil.

Step 2:

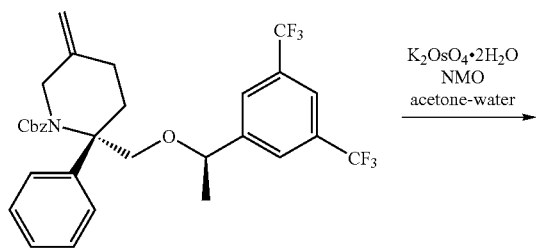

Compound xxxii

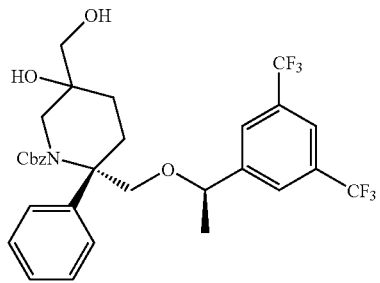

Compound xxxiii

A mixture of alkene Compound xxxii (1.0 g, 1.73 mmol), 4-methylmorpholine N-oxide (304 mg, 2.6 mmol) and potassium osmate dihydrate (96 mg, 0.26 mmol) in an acetone (20 mL)/water (10 mL) mixture were stirred at room temperature overnight. A saturated aqueous sodium thiosulfite solution and ethyl acetate were then added. The organic and aqueous layers were separated, and the aqueous layer was extracted twice with ethyl acetate. The combined organic layers were dried (MgSO₄) and filtered. The solvents were removed under vacuum and the resulting residue was purified by column chromatography (silica, hexanes-ethyl acetate, 1:1 (v/v)) to give diol Compound xxxiii (782 mg, 74% yield) as a yellow oil.

Step 3:

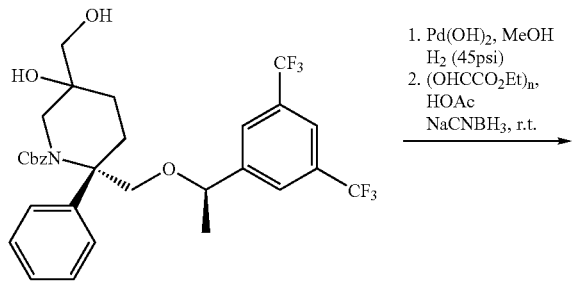

Compound xxxiii

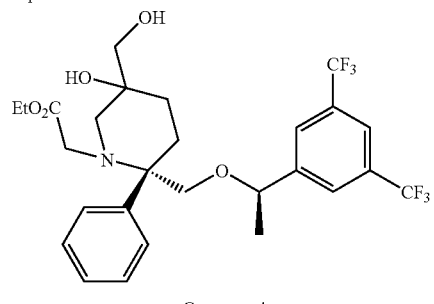

Compound xxxv

A solution of diol Compound xxxiii (715 mg, 1.17 mmol) in methanol (20 mL) was hydrogenated (45 psi hydrogen) in the presence of a catalytic amount of Pd(OH)₂/C (62 mg, 0.12 mmol) for 2 h. The catalyst was then removed by filtration of the reaction mixture through a pad of CELITE. The solvents were removed under vacuum to give a crude piperidine Compound xxxiv as a colorless oil. To a solution of the crude piperidine Compound xxxiv and ethyl glyoxalate (0.5 mL, 2.34 mmol, 40-50% in toluene) in acetic acid (10 mL) at room temperature, sodium cyanoborohydride (368 mg, 5.58 mmol) was added in small portions. The mixture was stirred at room temperature overnight. The solvents were then removed under vacuum and the resulting residue was purified by column chromatography (silica, ethyl acetate) to give ester Compound xxxv (428 mg, 65% yield) as a colorless oil.

Step 4:

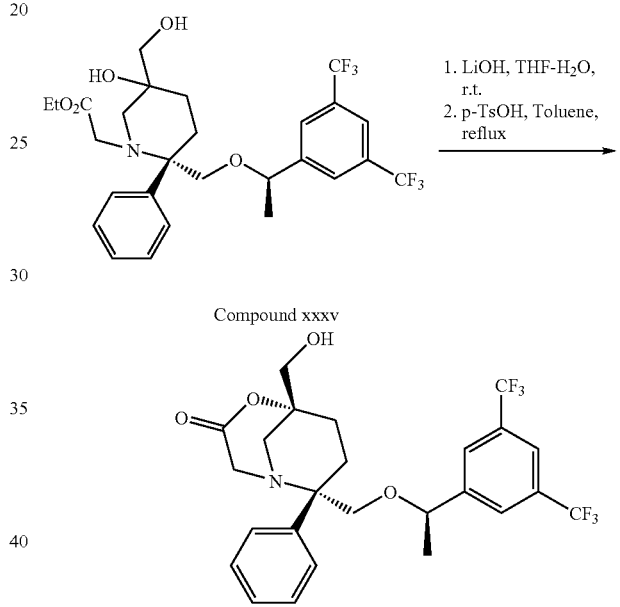

Example 49

To a solution of ester Compound xxxv (400 mg, 0.71 mmol) in THF (10 mL)/MeOH (10 mL) at room temperature, lithium hydroxide (1.42 mL, 1.42 mmol, 1 M in water) was added. The reaction mixture was stirred at room temperature for 4 h before it was quenched with citric acid (10% in water). Ethyl acetate was then added and the organic and aqueous layers were separated. The aqueous layer was extracted twice with ethyl acetate. The combined organic layers were dried (MgSO₄) and filtered. The solvents were removed under vacuum to give a yellow oil. The oil was dissolved in toluene and a catalytic amount of p-toluenesulfonic acid was added. The reaction mixture was heated at reflux overnight. After being cooled to room temperature, ethyl acetate was added, and the mixture was quenched with a saturated aqueous sodium bicarbonate solution. The organic and aqueous layers were separated and the aqueous layer was extracted twice with ethyl acetate. The combined organic layers were dried (MgSO₄) and filtered. The solvents were removed under vacuum and the resulting residue was purified by column chromatography (silica, hexanes-ethyl acetate, 4:1 (v/v)) to give lactone Example 49 (152 mg, 41% yield) as a colorless oil. Electrospray MS [M+1]⁺=518.

Preparation of Example 50

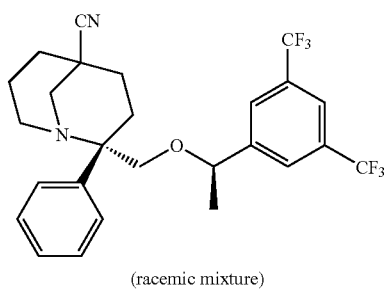

Example 50 (racemic mixture)

Step 1:

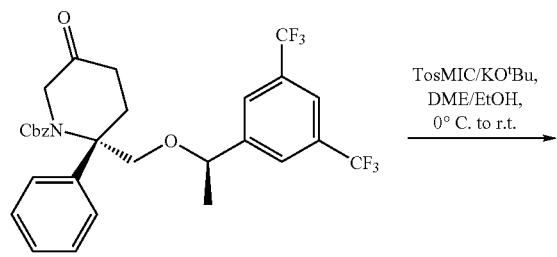

Compound ix

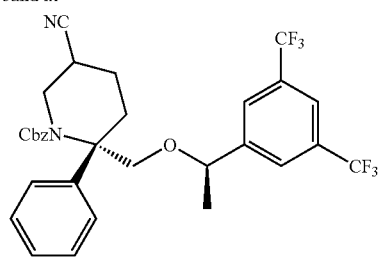

Compound xxxvi

KOtBu powder (0.93 g, 8.28 mmol) was added portion-wise within 5 minutes to a solution of Compound ix and TosMIC (0.88 g, 4.48 mmol) in DME (12.0 mL) and EtOH (0.33 mL) at room temperature. The resulting reaction mixture was stirred for 45 minutes before it was heated at 40° C. for another 45 minutes. The reaction mixture was then cooled to room temperature and filtered through a sintered funnel. The residue was washed with ether (3×50 mL), and the combined ether phases were washed with water (20 mL), brine (20 mL), and dried over $MgSO_4$. After filtration and concentration, the crude product was purified using a BIOTAGE apparatus, eluting with hexane/EtOAc (v/v=6/1) to give Compound xxxvi (0.5 g, 24% yield).

Step 2:

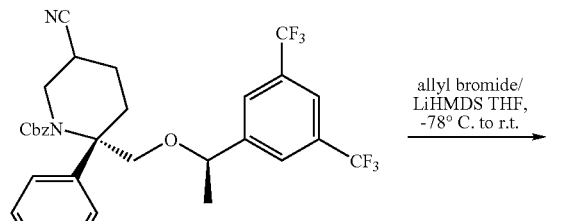

Compound xxxvi

-continued

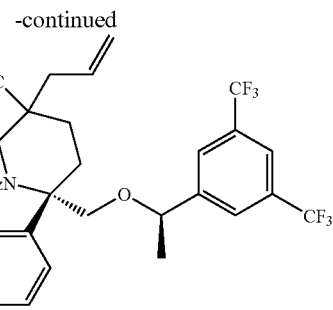

Compound xxxvii

LiHMDS (1.38 mL, 1.38 mmol) was added to a stirred solution of Compound xxxvi (0.65 g, 1.10 mmol) in THF (7.5 mL) at −78° C. The reaction mixture was stirred for 45 minutes before allyl bromide (0.286 mL, 3.31 mmol) was added dropwise at −78° C. The reaction mixture was stirred for 0.5 h before it was slowly brought to room temperature. The reaction mixture was quenched by the addition of an aqueous $NH_4Cl$ solution (15 mL) and was then diluted with the addition of EtOAc (50 mL). The aqueous phase was extracted with EtOAc (3×15 mL). The combined organic layers were washed with water (15 mL), brine (20 mL), and dried over $MgSO_4$. After filtration and concentration, the crude product was purified with a BIOTAGE apparatus, eluting with hexane/EtOAc (v/v=7/1) to give Compound xxxvii (0.34 g, 49% yield, diastereomer ratio 6/1).

Step 3:

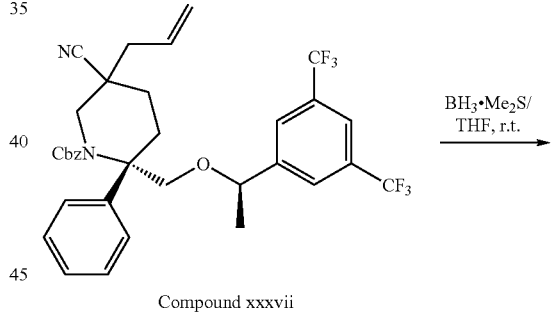

Compound xxxvii

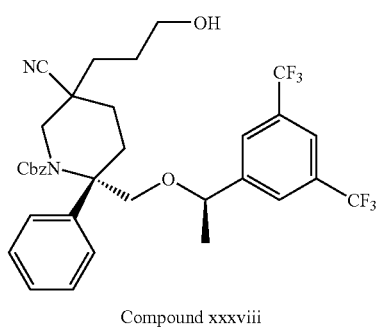

Compound xxxviii $BH_3 \cdot Me_2S$ (37.8 μL, 0.369 mmol) was added dropwise to a solution of Compound xxxvii (0.155 g, 0.246 mmol) in THF (3.0 mL) at room temperature. The resulting mixture was stirred for 6 h before it was cooled to 0° C. and quenched by the careful addition of NaOH (0.75 mL, 2.0 M) followed by the addition of $H_2O_2$ (0.75 mL, 30%). The reaction mixture was then stirred at room temperature overnight, and then diluted with EtOAc (50 mL) and water (15 mL). The aqueous phase was extracted with EtOAc (3×15 mL). The combined organic layers were washed with water (15 mL), brine (20 mL), and dried over $MgSO_4$. After filtration and concentration, the crude product was purified using a BIOTAGE apparatus, eluting with hexane/EtOAc (v/v=1/1) to give Compound xxxviii (0.052 g, 33%).

Step 4:

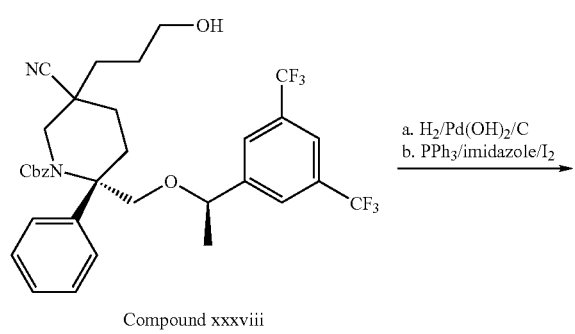

Compound xxxviii

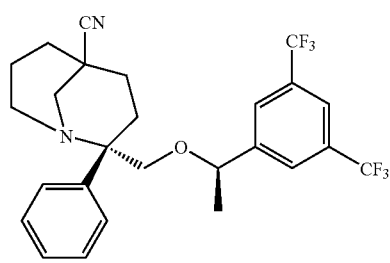

Example 50
(one isomer)

Compound xxxviii (26.4 mg, 0.0407 mmol) in EtOH (2.0 mL) was treated at room temperature with $Pd(OH)_2/C$ (10.5 mg, 10 wt %) and was hydrogenated using a $H_2$ balloon for 30 minutes. The reaction mixture was filtered through a short pad of Celite, and the residue was washed with EtOH (15 mL). The solvent was removed under reduced pressure to give a crude product, which was taken up in ether (1.0 mL) and $CH_3CN$ (0.5 mL). The resulting solution was treated with $PPh_3$ (20.8 mg, 0.0792 mmol), imidazole (8.1 mg, 0.119 mmol) and $I_2$ (20.1 mg, 0.0792 mmol), successively, at 0° C. After stirring for 1 h, the reaction mixture was diluted with EtOAc (20 mL), and then $NaHCO_3$ (10 mL) and $Na_2S_2O_3$ solutions (5 mL) were added. The aqueous phase was then extracted with EtOAc (3×5 mL). The combined organic layers were washed with water (10 mL), brine (10 mL), and dried over $MgSO_4$. After filtration and concentration, the crude intermediate was dissolved in acetone (1.0 mL) and treated with $K_2CO_3$ (5 mg). The reaction mixture was stirred and heated at 70° C. overnight, and then cooled to room temperature and filtered through a short pad of Celite. The solvent was removed under reduced pressure, and the crude product was purified using preparative TLC with hexane/EtOAc (v/v=4/1) as the eluent to give a pure isomer Compound 50 (8 mg, 40% yield) and another minor isomer (2 mg, 10%). Electrospray MS [M+1]$^+$ 497.1.

Preparation of Example 51

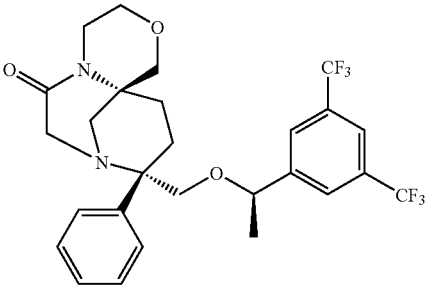

Example 51

Step 1:

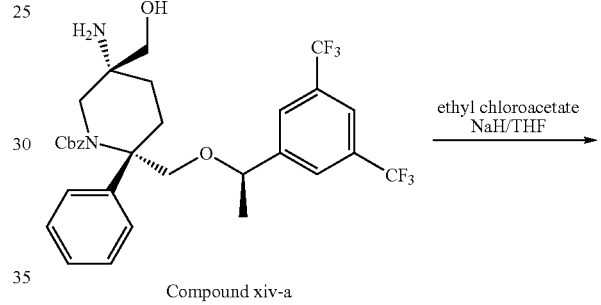

Compound xiv-a

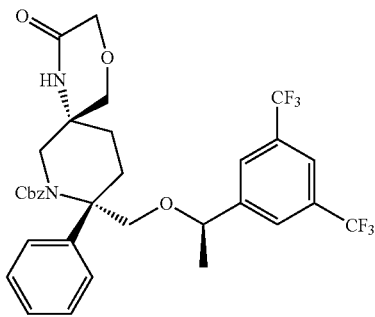

Compound xxxix

NaH (56.9 mg, 1.30 mmol, 55% in mineral oil) was added to a solution of Compound xlv-a (prepared as described in Step 2 of the procedure for preparing Examples 53a and 53b, below) (0.663 g, 1.09 mmol) in THF (5.0 mL) at room temperature. The mixture was stirred for 30 minutes before ethyl chloroacetate (0.128 mL, 1.2 mmol) was added. The reaction was quenched by the addition of an aqueous $NH_4Cl$ solution (15 mL) and was then diluted with EtOAc (75 mL). The aqueous phase was extracted with EtOAc (3×15 mL). The combined organic layers were washed with water (15 mL), brine (20 mL), and dried over $MgSO_4$. After filtration and concentration, the crude product was purified with a BIOTAGE apparatus, eluting with hexane/EtOAc (v/v=1/4) to give Compound xxxix (0.35 g, 49% yield).

Step 2:

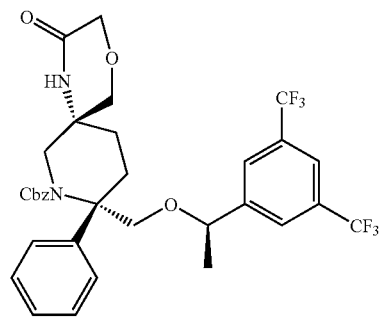

Compound xxxix

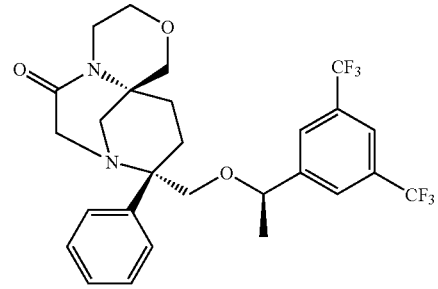

Example 51

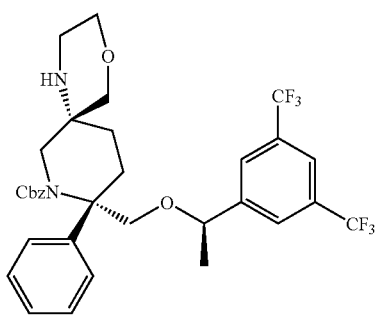

Compound xl

BH$_3$.Me$_2$S (0.151 mL, 1.48 mmol) was added to a solution of Compound xxxix (0.16 g, 0.246 mmol) in THF (2.0 mL) at room temperature. The reaction mixture was then heated under reflux overnight before it was cooled to room temperature. The solvent was removed under reduced pressure, and the residue was taken up in MeOH (4.0 mL) and aqueous HCl (8.0 mL, 2 N). The resulting mixture was heated at 90° C. for 1.5 h before it was cooled to room temperature, diluted with EtOAc (50 mL), and neutralized by the addition of NaOH (10 mL, 2 N). The aqueous phase was extracted with EtOAc (3×15 mL). The combined organic layers were washed with water (15 mL), brine (20 mL), and dried over MgSO$_4$. After filtration and concentration, the crude product was purified with a BIOTAGE apparatus, eluting with EtOAc/MeOH (v/v=10/1) to give Compound xl (0.11 g, 70%).

Step 3:

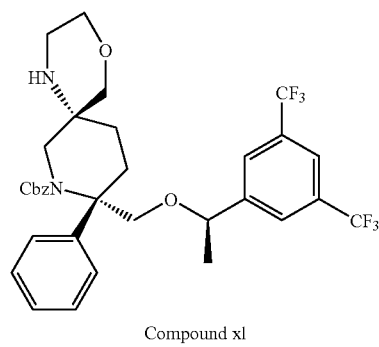

Compound xl

Compound xl (48.7 mg, 0.0766 mmol) in EtOH (3.0 mL) was treated at room temperature with Pd(OH)$_2$/C (24.3 mg, 10 wt %), and was hydrogenated with a H$_2$ balloon for 30 minutes. The reaction mixture was filtered through a short pad of CELITE, and the residue was washed with EtOH (15 mL). The solvent was removed under reduced pressure to give the crude product, which was taken up in CH$_2$Cl$_2$ (2.0 mL) and treated with chloroacetyl chloride (7.3 µL, 0.092 mmol) and NEt$_3$ (25.6 µL, 0.184 mmol) at room temperature. The reaction mixture was stirred for 30 minutes, and then diluted with CH$_2$Cl$_2$ (30 mL), washed with NaHCO$_3$ (10 mL), water (10 mL) and brine (10 mL). The organic layer was dried over MgSO$_4$. After filtration and concentration, the crude mixture was dissolved in ClCH$_2$CH$_2$Cl (1.5 mL) and treated with NEt$_3$ (42.6 µL, 0.306 mmol). The resulting mixture was heated at 50° C. overnight. The mixture was then cooled to room temperature, diluted with CH$_2$Cl$_2$ (30 mL), and washed with NaHCO$_3$ (10 mL), water (10 mL) and brine (10 mL). The organic layer was dried over MgSO$_4$. After filtration and concentration, the crude product was purified using preparative TLC with hexane/EtOAc (v/v=1/2) as the eluent, to give pure isomer Example 51 (17.5 mg, 42% yield). Electrospray MS [M+1]$^+$ 543.1.

Preparation of Example 52a

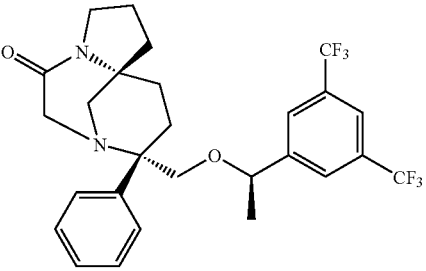

Example 52a a. H$_2$/Pd(OH)$_2$/C
b. ClCH$_2$COCl/NEt$_3$

Step 1:

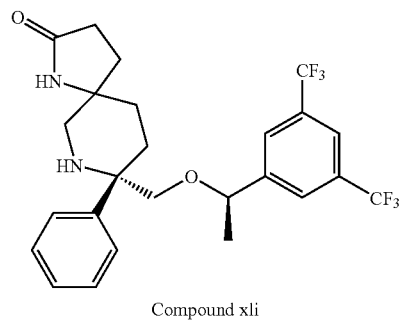

Compound xli

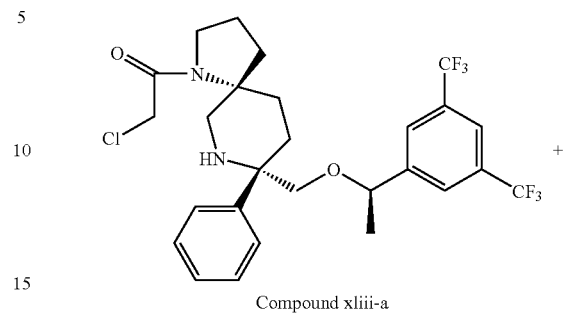

Compound xliii-a

+

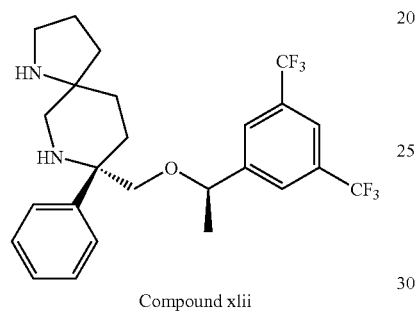

Compound xlii

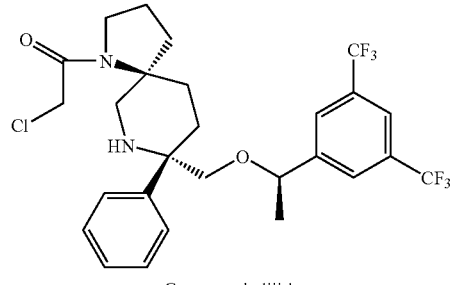

Compound xliii-b

BH$_3$.Me$_2$S (0.321 mL, 3.34 mmol) was added to a solution of Compound xli (i.e., a mixture of Examples 72a and 72b of U.S. Published Application 2003/158173 A1, Ser. No. 10/321,687) (0.209 g, 0.417 mmol) in THF (3.0 mL) at room temperature. The reaction mixture was then heated under reflux overnight before it was cooled to room temperature. The solvent was removed under reduced pressure, and the residue was taken up in MeOH (7.0 mL) and aqueous HCl (14.0 mL, 2 N). The resulting mixture was heated at 90° C. for 1.5 h, and then cooled to room temperature, diluted with EtOAc (75 mL) and neutralized with NaOH (20 mL, 2N). The aqueous phase was extracted with EtOAc (3×20 mL). The combined organic layers were washed with water (20 mL), brine (20 mL), and dried over MgSO$_4$. After filtration and concentration, the crude Compound xlii was obtained in quantitative yield, and used without further purification.

Step 2:

A solution of Compound xlii (0.203 g, 0.417 mmol) in CH$_2$Cl$_2$ (3.0 mL) was treated with chloroacetyl chloride (7.3 μL, 0.092 mmol) and NEt$_3$ (25.6 μL, 0.184 mmol) at room temperature. The reaction mixture was stirred for 30 minutes, and then diluted with CH$_2$Cl$_2$ (50 mL) and washed with NaHCO$_3$ (10 mL), water (10 mL) and brine (10 mL). The organic layer was dried over MgSO$_4$. After filtration and concentration, the crude product was purified with a BIOTAGE apparatus, eluting with hexane/EtOAc (v/v=9/1 to 1/3 gradient) to give separable isomers Compound xliii-a (80 mg, 34%) and Compound xliii-b (45 mg, 19%).

Step 3:

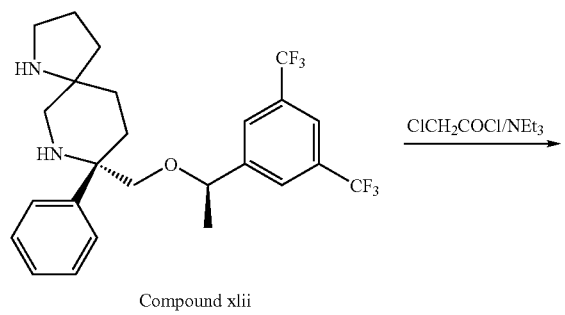

Compound xlii

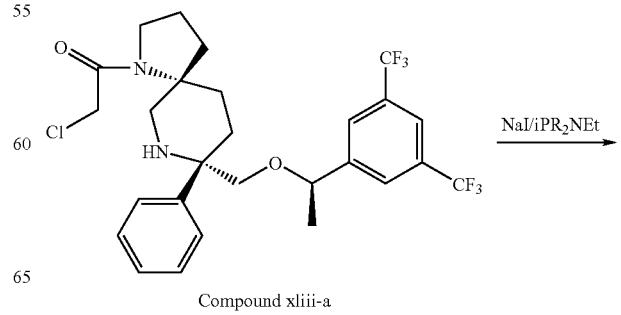

Compound xliii-a

-continued

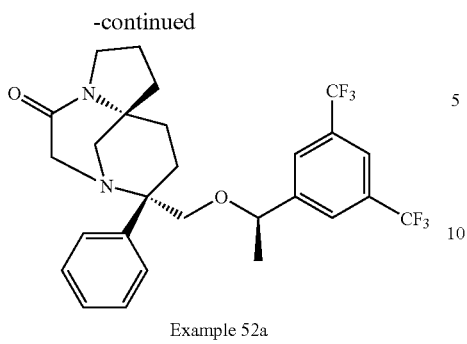

Example 52a

A solution of Compound xliii-a (10.9 mg, 0.019 mmol) in CH$_3$CN (0.5 mL) was treated with NaI (2.9 mg, 0.019 mmol) and i-Pr$_2$NEt (5.1 µL, 0.0291 mmol) at room temperature. The resulting reaction mixture was heated at 85° C. overnight, and then cooled to room temperature. The reaction mixture was then diluted with EtOAc (20 mL) and washed with aqueous NaHCO$_3$ (5 mL). The aqueous phase was extracted with EtOAc (3×10 mL). The combined organic layers were washed with water (10 mL) and brine (10 mL), and dried over MgSO$_4$. After filtration and concentration, the crude product was purified using preparative TLC with hexane/EtOAc (v/v=1/6) as the eluent, to give Example 52a (7.5 mg, 73%). Electrospray MS [M+1]$^+$ 527.1.

Preparation of Compound of Example 52b

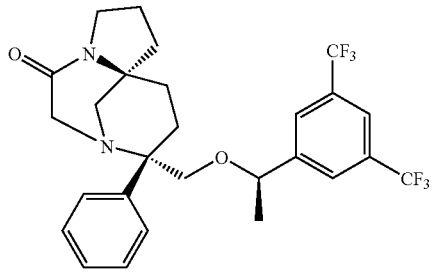

Example 52b

Step 1:

-continued

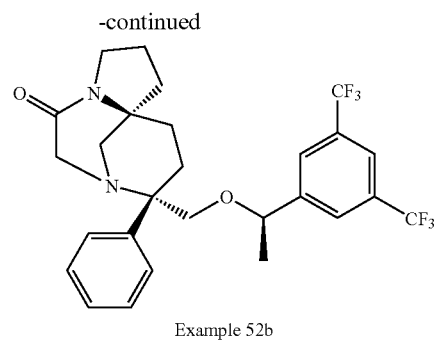

Example 52b

A solution of Compound xli-b (24.2 mg, 0.043 mmol) in CH$_3$CN (0.5 mL) was treated with NaI (6.4 mg, 0.043 mmol) and i-Pr$_2$NEt (11.3 µL, 0.0646 mmol) at room temperature. The resulting reaction mixture was heated at 85° C. overnight, and then cooled to room temperature. The reaction mixture was then diluted with EtOAc (30 mL) and washed with aqueous NaHCO$_3$ (5 mL). The aqueous phase was extracted with EtOAc (3×10 mL). The combined organic layers were washed with water (10 mL), brine (10 mL), and dried over MgSO$_4$. After filtration and concentration, the crude product was purified using preparative TLC with hexane/EtOAc (v/v=1/6) as the eluent, to give Example 52b (11.0 mg, 49% yield). Electrospray MS [M+1]$^+$ 527.1.

Preparation of Examples 53a and 53b

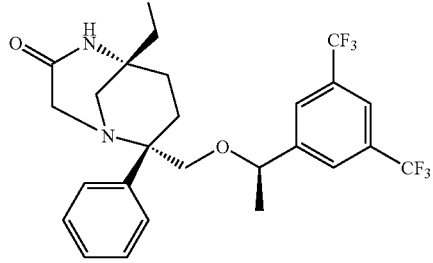

Example 53a

Example 53b

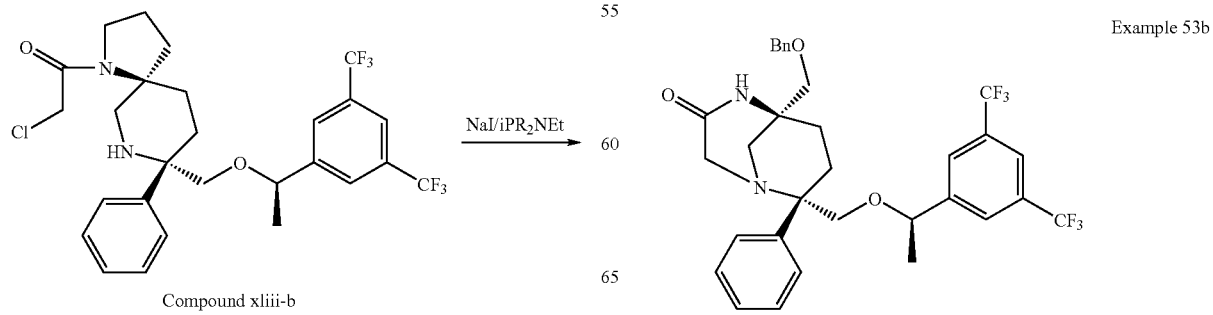

Compound xliii-b

Step 1:

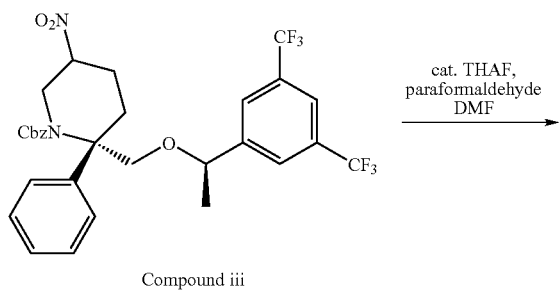

Step 2:

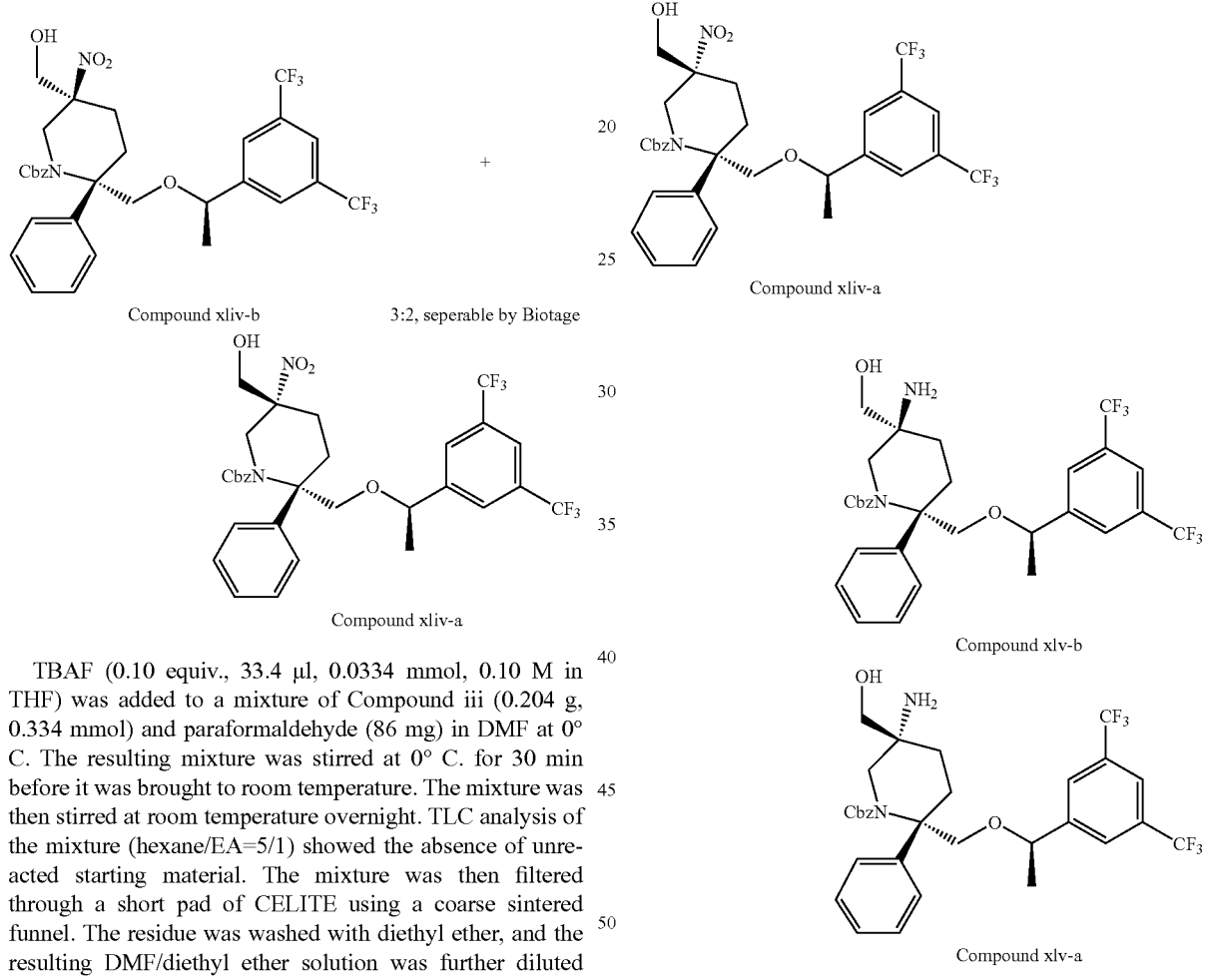

TBAF (0.10 equiv., 33.4 µl, 0.0334 mmol, 0.10 M in THF) was added to a mixture of Compound iii (0.204 g, 0.334 mmol) and paraformaldehyde (86 mg) in DMF at 0° C. The resulting mixture was stirred at 0° C. for 30 min before it was brought to room temperature. The mixture was then stirred at room temperature overnight. TLC analysis of the mixture (hexane/EA=5/1) showed the absence of unreacted starting material. The mixture was then filtered through a short pad of CELITE using a coarse sintered funnel. The residue was washed with diethyl ether, and the resulting DMF/diethyl ether solution was further diluted with diethyl ether, and washed with water (3×) to remove the DMF. The aqueous layer was extracted with diethyl ether (2×) and the combined organic layers were washed with water (1×), brine and then dried over MgSO$_4$. Solvent was removed under reduced pressure to give a crude product, which was purified with a BIOTAGE column (slow flow, CH$_2$Cl$_2$ as eluent) to give the two separable diastereomers, Compounds xliv-a and xliv-b in a ratio of 3/2, where Compound xliv-b is the isomer which is more polar by TLC. Yield: quantitative.

When Step 1, above, is carried out in THF, the ratio of Compounds xliv-a/xliv-b=5/2. The isomers can be separated after Step 1, or after Step X. The reaction was carried out at 10 grams scale without any significant difficulties.

A mixture of Compound xliv-a and xliv-b (7.54 g, 11.76 mmol) and Zn powder (10 equiv., 7.68 g, 117.6 mmol) in acetic acid (120 mL) was heated at 60° C. with stirring. The reaction was complete in 2 hrs. After cooling, the system was filtered through a short pad of CELITE, and the residue was washed with ethanol. The solvent was removed under vacuum and the resulting residue was taken up in ethyl acetate. The ethyl acetate layer was washed with NaOH (4 M) until the aqueous layer was basic to pH paper. The aqueous phase was extracted with ethyl acetate (3×). The combined organic layers were washed with water (1×), brine and dried (MgSO$_4$). The solvent was removed under reduced pressure to give a free amino alcohol crude product which sufficiently pure to be used in the next step without additional purification. Alternatively, the crude product could be purified with a fast Biotage column (hexane/EA 9/1-1/1-1/5, then ethyl acetate/CH$_3$OH 4/1) to give pure product, Compounds xlv-a and xlv-b (6.4 g, 89%).

Step 3:

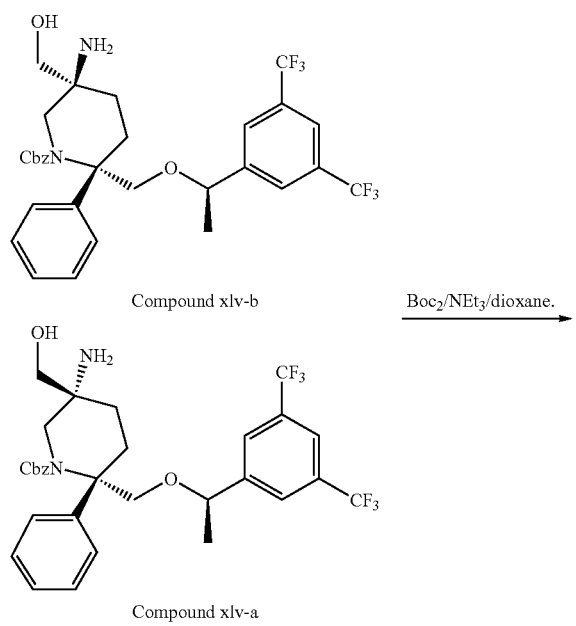

Compound xlv-b

Compound xlv-a

Boc$_2$/NEt$_3$/dioxane.

Compound xlvi-b

Compound xlvi-a

A solution of the free amino alcohol product, Compounds xlv-a and xlv-b, prepared above (0.472 g, 0.77 mmol) in dioxane (3.0 mL) was treated with Boc$_2$O (1.05 equiv., 0.176 g, 0.808 mmol) and NEt$_3$ (1.2 equiv., 0.129 mL, 0.93 mmol) at room temperature. The reaction was complete in 6 hrs, based on TLC analysis (hexane/EA=1/3). The mixture was diluted with ethyl acetate and washed with HCl (1×, 0.25 N), water (1×) and brine. The organic layer was dried (MgSO$_4$), and solvent was removed under reduced pressure to give crude product which was purified with flash silica gel column (hexane/EA 9/1-5/1-1/1-1/2) to give pure product, Compounds xlvi-a and xlvi-b (0.465 g, 85%).

Step 4:

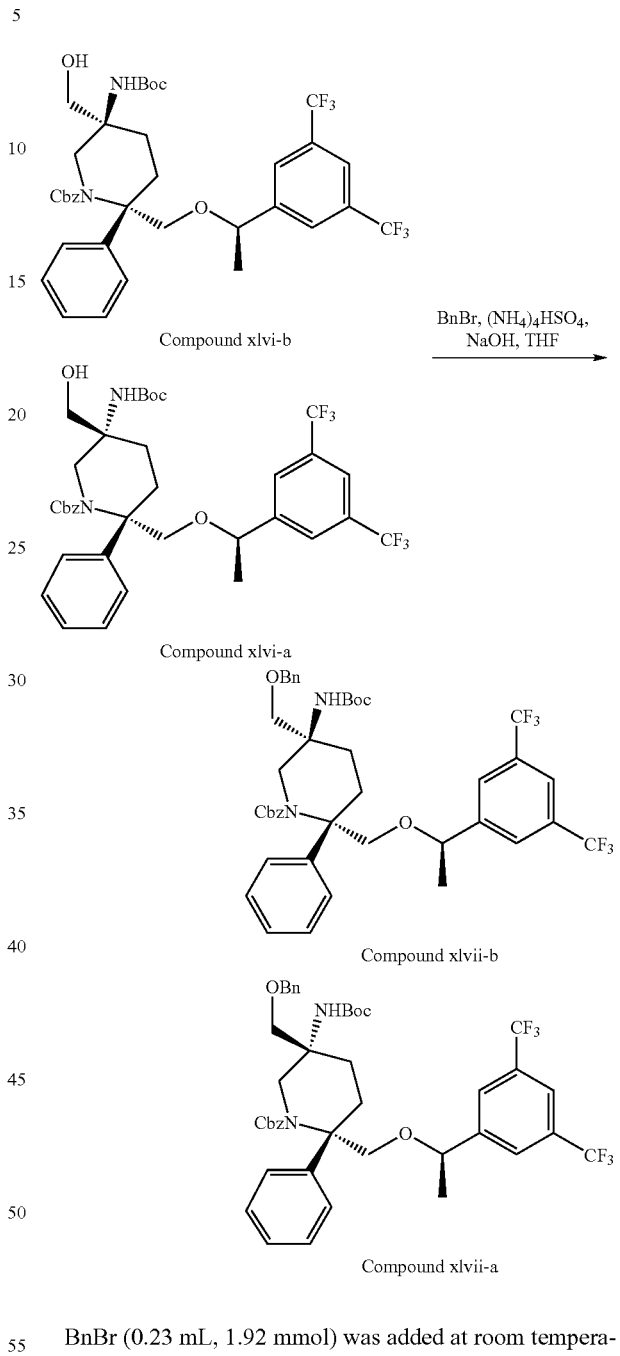

Compound xlvi-b

Compound xlvi-a

BnBr, (NH$_4$)$_4$HSO$_4$, NaOH, THF

Compound xlvii-b

Compound xlvii-a

BnBr (0.23 mL, 1.92 mmol) was added at room temperature to a vigorously stirred mixture of Compounds xlvi-a and xlvi-b (0.91 g, 1.28 mmol), Bu$_4$NHSO$_4$ (0.174 g, 0.512 mmol) in THF (8.0 mL), and an aqueous NaOH solution (4.0 mL, 50 wt %). The reaction mixture was stirred at room temperature for 12 h and then diluted with EtOAc (100 mL) and washed with water (30 mL). The aqueous phase was extracted with EtOAc (3×20 mL). The combined organic layers were washed with water (20 mL), brine (20 mL), and dried over MgSO$_4$. After filtration and concentration, the crude product was purified with a BIOTAGE apparatus, eluting with hexane/EtOAc (v/v=10/1) to give Compounds xlvii-a and xlvii-b (0.81 g, 79%).

Step 5:

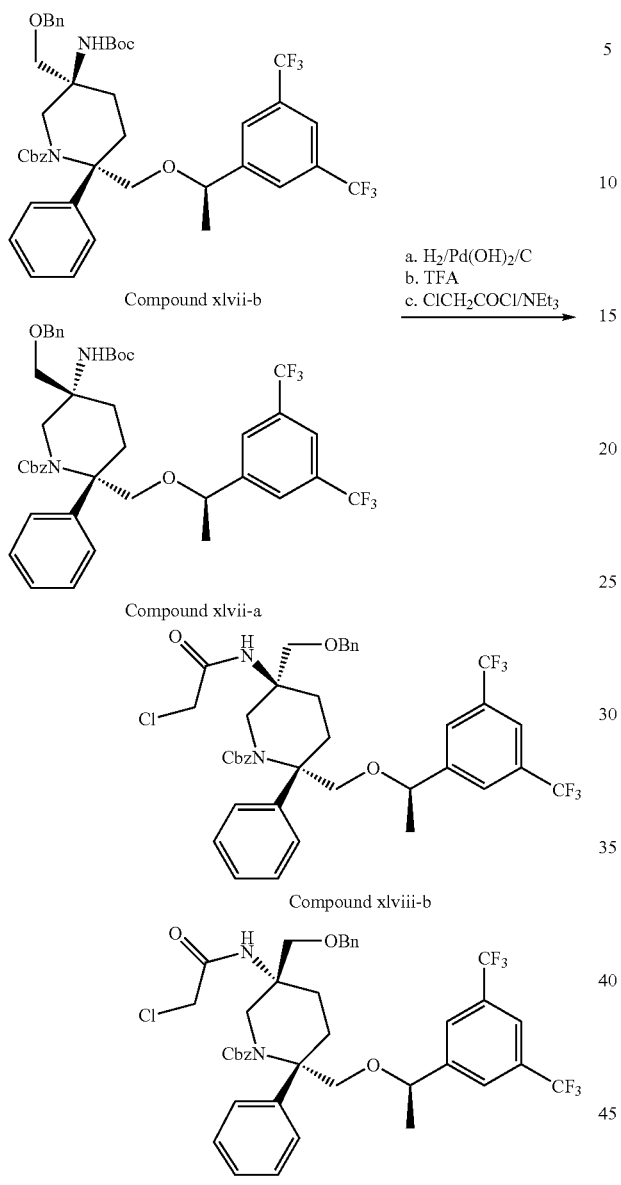

A solution of Compounds xlvii-a and xlvii-b (111 mg, 0.139 mmol) in EtOH (3.0 mL) was treated at room temperature with Pd(OH)₂/C (33 mg, 10 wt %) and hydrogenated with a hydrogen balloon for 30 minutes. The reaction mixture was filtered through a short pad of CELITE, and the residue was washed with EtOH (15 mL). The solvent was removed under reduced pressure to give the crude product, which was dissolved in TFA (2.0 mL). The reaction mixture was then stirred at room temperature for 20 minutes before the solvent was removed under reduced pressure. The residue was taken up in EtOAc (50 mL) and washed with NaOH solution (4.0 N, 15 mL). The aqueous phase was extracted with EtOAc (3×10 mL). The combined organic layers were washed with water (15 mL), brine (15 mL), and dried over MgSO₄. After filtration and concentration, the crude diamine was dissolved in CH₂Cl₂ (2.0 mL) and treated with chloroacetyl chloride (16.6 μL, 0.208 mmol) and NEt₃ (58 μL, 0.416 mmol) at room temperature. The reaction mixture was stirred for 30 minutes, and then diluted with CH₂Cl₂ (50 mL) and washed with NaHCO₃ (10 mL), water (10 mL) and brine (10 mL). The organic layer was dried over MgSO₄. After filtration and concentration, the crude Compounds xlviii-a and xlviii-b were obtained in quantitative yield.

Step 6:

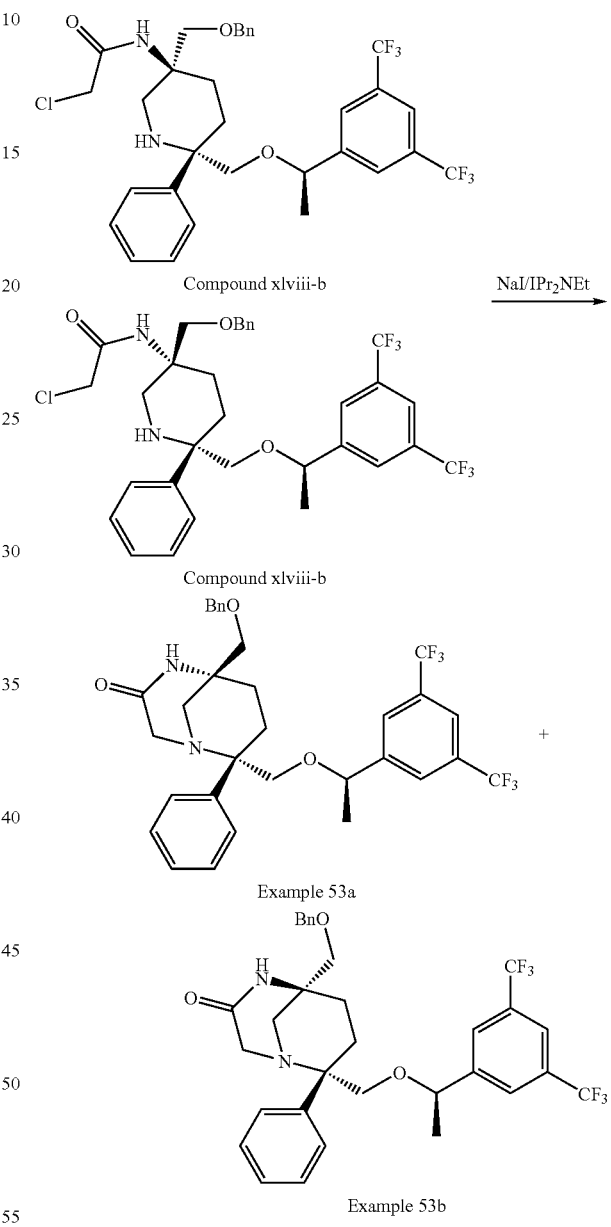

A solution of Compounds xlviii-a and xlviii-b (89 mg, 0.139 mmol) in CH₃CN (0.5 mL) was treated with NaI (0.208 g, 1.39 mmol) and i-Pr₂NEt (72.8 μL, 0.417 mmol) at room temperature. The resulting reaction mixture was heated at 85° C. for 48 h, and then cooled to room temperature. The reaction mixture was then diluted with EtOAc (30 mL) and washed with aqueous NaHCO₃ (5 mL). The aqueous phase was extracted with EtOAc (3×10 mL). The combined organic layers were washed with water (10 mL), brine (10 mL), and dried over MgSO₄. After filtration and concentration, the crude product was purified by preparative TLC with hexane/EtOAc (v/v=1/1) as eluent, to give Example 53a (16 mg, 19% yield for 4 steps), Electrospray MS [M+1]+ 607.1, and Example 53b (12 mg, 14% yield for 4 steps), Electrospray MS [M+1]+ 607.1.

Preparation of Examples 54a and 54b

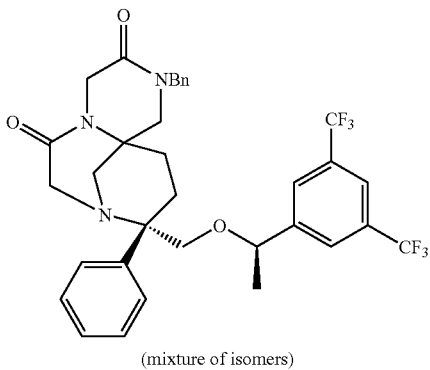

Examples 54a and 54b
(mixture of isomers)

Step 1:

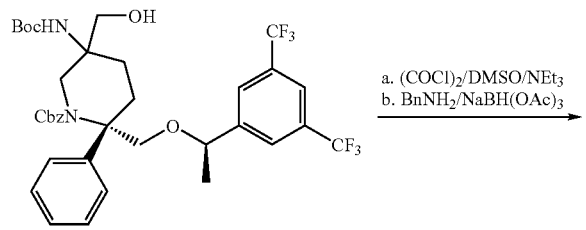

Mixture of Compounds xlvi-a and xlvi-b

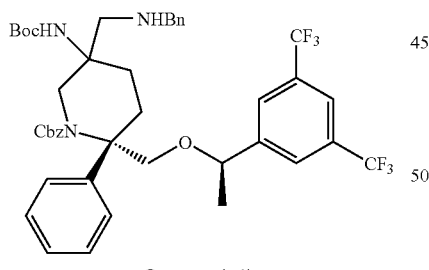

Compound xlix
(mixture of isomes)

Oxalyl chloride (0.134 ml, 1.56 mmol) was added to a solution of DMSO (0.222 mL, 3.12 mmol) in dichloromethane (4.0 mL), cooled to −78° C. with a cooling bath, and maintained under a nitrogen atmosphere. The mixture was stirred at −78° C. for 15 min, and then a solution of Compounds xlvi-a and xlvi-b (i.e., an isomeric mixture) (0.444 g, 0.625 mmol) in dichloromethane (1.0 mL) was added. The mixture was stirred at −78° C. for an additional 1 h, and then trimethylamine (0.76 mL, 5.47 mmol) was added. The cooling bath was removed, and the mixture was warmed to room temperature, and then quenched with HCl (15 mL, 0.5 N). The mixture was then diluted with CH$_2$Cl$_2$ (50 mL) and the aqueous layer was extracted with dichloromethane (2×15 mL). The combined organic layers were dried (MgSO$_4$) and filtered. The solvent was removed under reduced pressure to give a crude aldehyde (0.44 g, 100%), which was taken up in ClCH$_2$CH$_2$Cl (4.0 mL), treated with 4 Å molecular sieves (100 mg) and benzyl amine (0.196 mL, 1.86 mmol), followed by the addition of NaBH(OAc)$_3$ (0.79 g, 3.73 mmol). The resulting reaction mixture was stirred at room temperature for 12 h, and then diluted with EtOAc (100 mL) and washed with aqueous NaHCO$_3$ (30 mL). The aqueous phase was extracted with EtOAc (3×20 mL). The combined organic layers were washed with water (20 mL), brine (20 mL), and dried over MgSO$_4$. After filtration and concentration, the crude product was purified using a BIOTAGE apparatus, eluting with hexane/EtOAc (v/v=2/1) to give Compound xlix (mixture of isomers) (0.365 g, 74% yield for 2 steps).

Step 2:

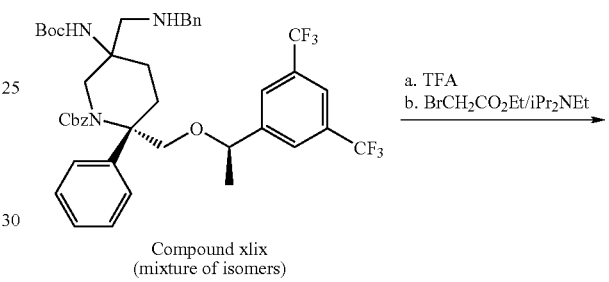

Compound xlix
(mixture of isomers)

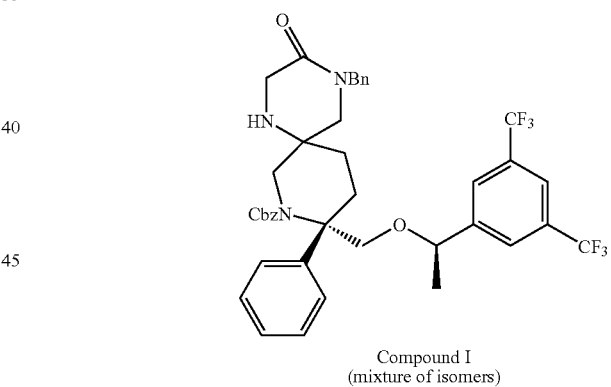

Compound I
(mixture of isomers)

A solution of Compound xlix (mixture of isomers) (0.257 g, 0.322 mmol) in TFA (2.5 mL) was stirred at room temperature for 20 minutes, and then the solvent was removed under reduced pressure. The resulting residue was taken up in EtOAc (50 mL) and washed with an aqueous NaOH solution (4.0 N, 15 mL). The aqueous phase was extracted with EtOAc (3×10 mL). The combined organic layers were washed with water (15 mL), brine (15 mL), and dried over MgSO$_4$. After filtration and concentration, the crude diamine was dissolved in CH$_2$Cl$_2$ (2.0 mL) and treated with ethyl bromoacetate (37.5 µL, 0.338 mmol) and i-Pr$_2$NEt (118 µL, 0.676 mmol) at room temperature. The reaction mixture was stirred at reflux for 48 h, and then cooled to room temperature and diluted with CH$_2$Cl$_2$ (50 mL). The organic phase was washed with NaHCO$_3$ (10 mL), water (10 mL), brine (10 mL) and dried over MgSO$_4$. After filtration and concentration, the crude product was purified using a BIOTAGE apparatus, eluting with hexane/EtOAc (v/v=1/1 to 0/100) to give Compound I (mixture of isomers) (58 mg, 24% yield for 2 steps).

Step 3:

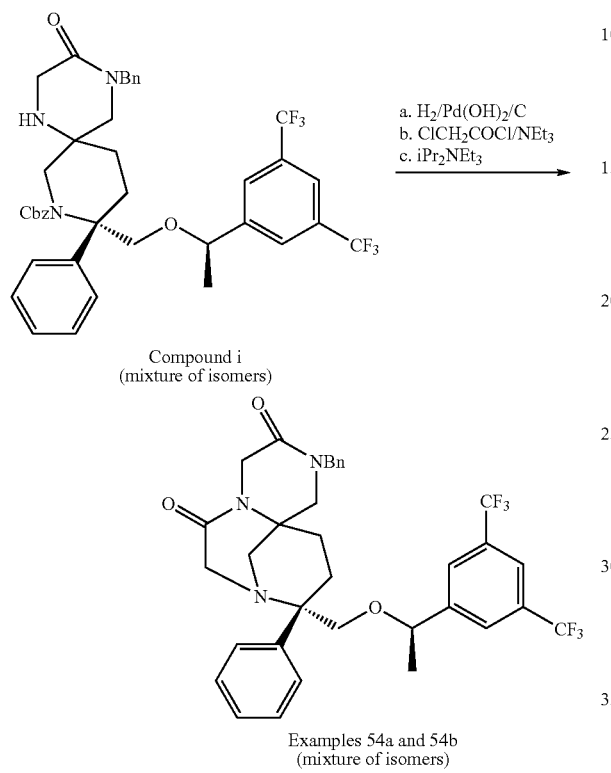

Compound i
(mixture of isomers)

Examples 54a and 54b
(mixture of isomers)

Compound I (mixture of isomers) (55.7 mg, 0.075 mmol) in EtOH (2.5 mL) was treated at room temperature with Pd(OH)$_2$/C (33.3 mg, 10 wt %) and hydrogenated with a hydrogen balloon for 30 minutes. The reaction mixture was filtered through a short pad of CELITE, and the residue was washed with EtOH (15 mL). The solvent was removed under reduced pressure to give a crude product, which was taken up in CH$_2$Cl$_2$ (0.75 mL) and treated with chloroacetyl chloride (9.0 μL, 0.112 mmol) and NEt$_3$ (31.4 μL, 0.225 mmol) at room temperature. The reaction mixture was stirred for 30 minutes, and then diluted with CH$_2$Cl$_2$ (30 mL) and washed with NaHCO$_3$ (10 mL), water (10 mL) and brine (10 mL). The organic layer was dried over MgSO$_4$. After filtration and concentration, the crude mixture was dissolved in ClCH$_2$CH$_2$Cl (2.0 mL) and treated with i-Pr$_2$NEt (52.4 μL, 0.30 mmol). The resulting mixture was heated at 60° C. overnight. The mixture was cooled to room temperature, diluted with CH$_2$Cl$_2$ (30 mL), and washed with NaHCO$_3$ (10 mL), water (10 mL) and brine (10 mL). The organic layer was dried over MgSO$_4$. After filtration and concentration, the crude product was purified using preparative TLC with hexane/EtOAc (v/v=1/2) as eluent to give pure isomer Example 54a (13 mg, 27% yield), Electrospray MS [M+1]$^+$ 646.2 and Example 54b (14 mg, 29% yield). Electrospray MS [M+1]$^+$ 646.2.

Preparation of Example 55

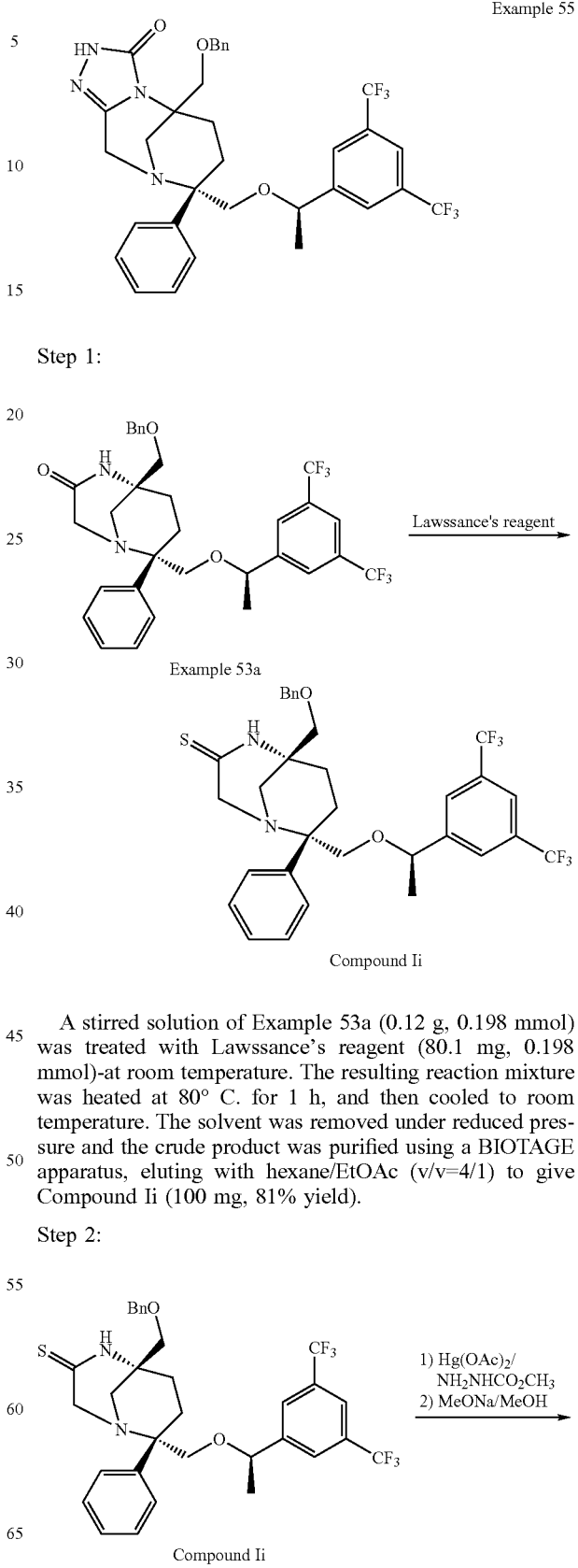

Example 55

Step 1:

Example 53a

Compound Ii

A stirred solution of Example 53a (0.12 g, 0.198 mmol) was treated with Lawssance's reagent (80.1 mg, 0.198 mmol)-at room temperature. The resulting reaction mixture was heated at 80° C. for 1 h, and then cooled to room temperature. The solvent was removed under reduced pressure and the crude product was purified using a BIOTAGE apparatus, eluting with hexane/EtOAc (v/v=4/1) to give Compound Ii (100 mg, 81% yield).

Step 2:

Compound Ii

-continued

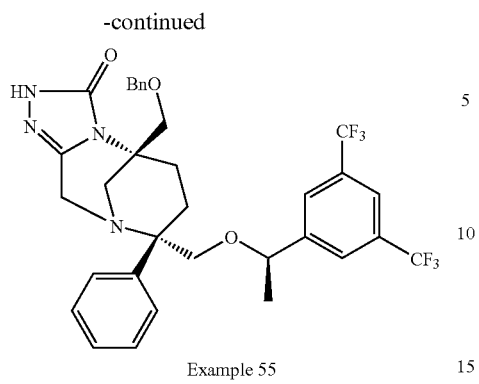

Example 55

Hg(OAc)$_2$ (76.8 mg, 0.24 mmol) was added to a stirred mixture of Compound Ii (0.10 g, 0.16 mmol) and NH$_2$NHCO$_2$CH$_3$ (72.1 mg, 0.80 mmol) in CH$_3$CN (1.5 mL) at room temperature. The reaction mixture was stirred for 2 h, and then it was filtered through a short pad of CELITE. The residue was washed with EtOAc (20 mL). The solvent was removed under reduced pressure to give a crude product, which was taken up in MeOH (1.0 mL) and treated with NaOCH$_3$ (0.25 mL, 30% in MeOH). The resulting reaction mixture was heated at 80° C. for 1.5 h, and then cooled to room temperature. The reaction mixture was diluted with EtOAc (20 mL) and aqueous NaHCO$_3$ solution (10 mL). The aqueous phase was extracted with EtOAc (3×10 mL). The combined organic layers were washed with water (10 mL), brine (10 mL), and dried over MgSO$_4$. After filtration and concentration, the crude product was purified by preparative TLC with hexane/EtOAc (v/v=1/4) as eluent, to give Example 55 (24 mg, 23%), Electrospray MS [M+1]$^+$ 647.4.

Preparation of Example 56

-continued

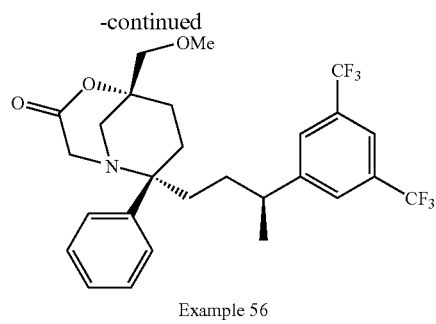

Example 56

Into a solution of Example 49 (50 mg, 0.1 mmol, 1 equiv.) in anhydrous CH$_2$Cl$_2$ (2 mL) was added Proton Sponge (26 mg, 0.12 mmol, 1.2 equiv.) and trimethyloxonium tetrafluoroborate (15 mg, 0.1 mmol, 1 equiv.). After the reaction mixture was stirred under N$_2$ at room temperature for 5 hours, the reaction was quenched with iced water (10 mL) and saturated NH$_4$Cl (10 mL). The reaction mixture was then extracted with ethyl acetate (20 mL×2), and the organic and aqueous layers were separated. The organic layer was dried with Na$_2$SO$_4$ and concentrated under vacuum to give a yellow solid. The solid was purified by preparative TLC with hexanes/ethyl acetate (2:1) to give Example 56 (30 mg, 59%).

Preparation of Example 57

Example 57

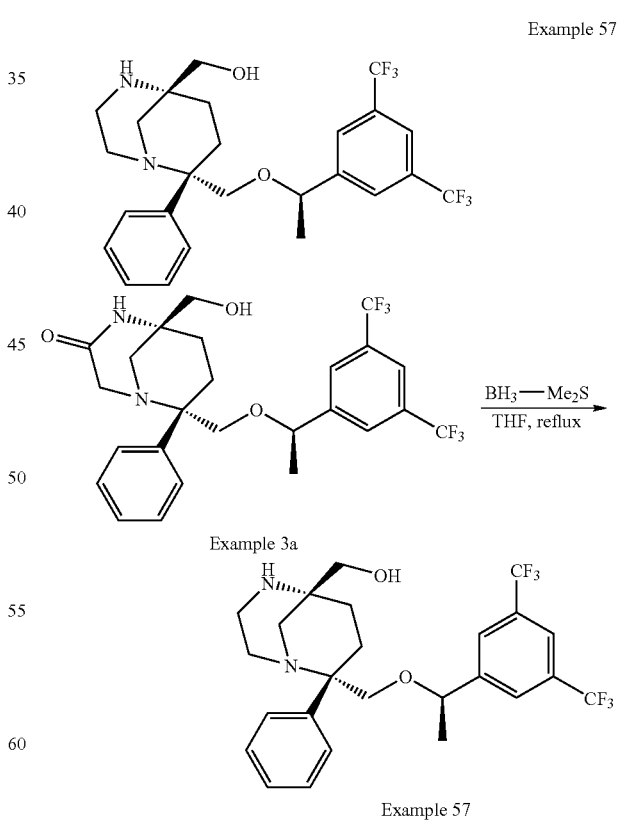

Example 57

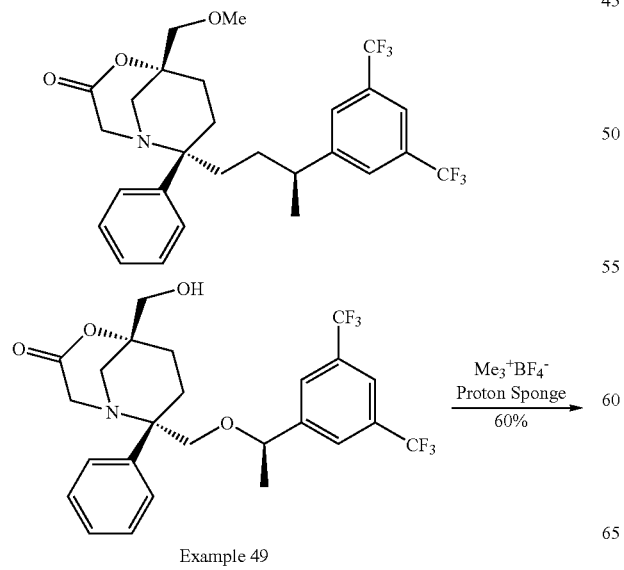

Example 49

A mixture of Example 3a (0.5 g, 0.97 mmol, 1 equiv.) in anhydrous THF (50 mL) and BH$_3$.Me$_2$S (0.56 mL, 5.8 mmol, 6 equiv.) was stirred and heated to reflux for 16 hours.

The solvent was removed and the resulting residue was mixed with MeOH (8 mL) and 2 M HCl (8 mL). The reaction mixture was heated to reflux for 1.5 hours. The reaction mixture was then concentrated and mixed with ethyl acetate (100 mL) and saturated NH₄Cl (60 mL), and neutralized with 2 N NaOH to pH 10. The aqueous layer was extracted with CH₂Cl₂ (50 mL×2). The organic layer was dried with Na₂SO₄ and concentrated under vacuum to give a white solid. The solid was purified by Biotage chromatography with 8% NH₄OH in MeOH/CH₂Cl₂ to give Example 57 (0.43 g, 88%).

Preparation of Example 58

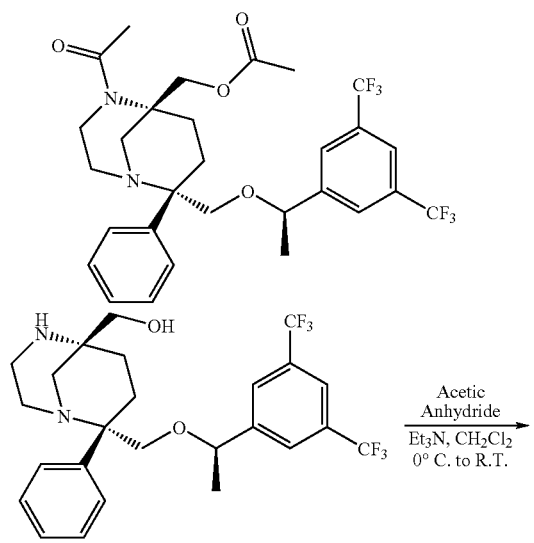

Example 58

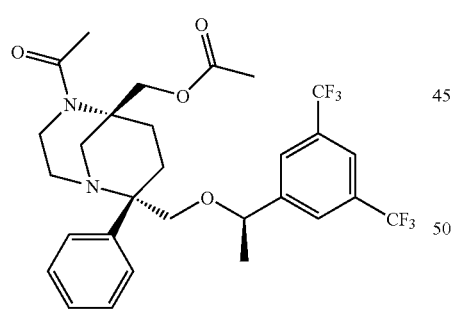

Example 58

Into a solution of Example 57 (100.5 mg, 0.2 mmol, 1 equiv.) in anhydrous CH₂Cl₂ (1 mL), which cooled to 0° C., was added triethylamine (26 mg, 0.6 mmol, 3 equiv.) and acetic anhydride (51 mg, 2.5 equiv.). After stirring under N₂ at 0° C. for 1 hour then at room temperature for 16 hours, the reaction mixture was diluted with ethyl acetate (30 mL), and then washed with saturated NaHCO₃ (20 mL×2). The organic layer was isolated and dried with Na₂SO₄ and concentrated under vacuum to give a white solid. The solid was purified by Biotage chromatography with 40% ethyl acetate in hexanes to give Example 58 (100 mg, 83%).

Preparation of Example 59

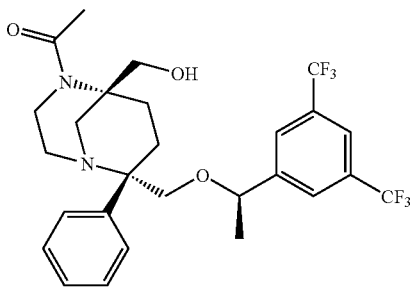

Example 59

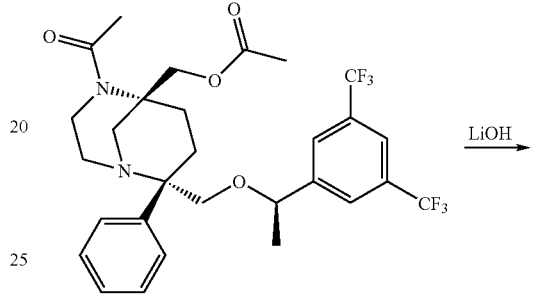

Example 58

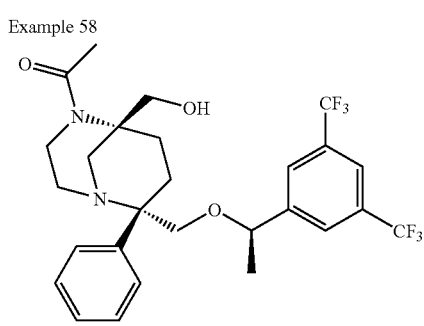

Example 59

A mixture of Example 58 (60 mg, 0.102 mmol, 1 equiv.) in THF/H₂O (2:1, 2 mL) and LiOH (14.5 mg, 0.205 mmol, 2 equiv.) was stirred at room temperature for 16 hours. The reaction mixture was then diluted with ethyl acetate (30 mL) and washed with saturated NH₄Cl (20 mL×2). The organic layer was isolated, dried with Na₂SO₄ and concentrated under vacuum to give a solid. The solid was purified by preparative TLC with 5% NH₄OH in MeOH/CH₂Cl₂ to give Example 59 (40 mg, 73%).

Preparation of Example 60

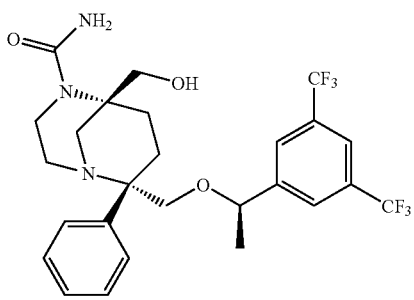

Example 60

-continued

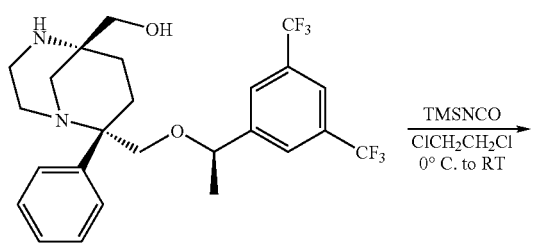

Example 57

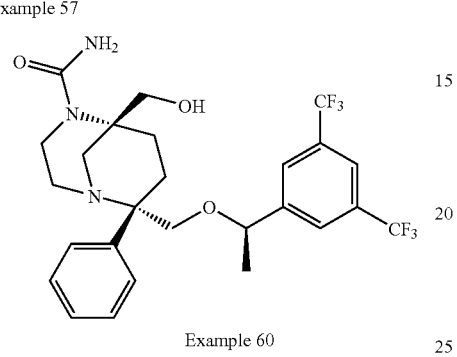

Example 60

Into a solution of Example 57 (30 mg, 0.06 mmol, 1 equiv.) in anhydrous 1,2-dichloroethane (2 mL), which was cooled to 0° C., was added TMSNCO (7 mg, 0.12 mmol, 2 equiv.). After stirring under N₂ at 0° C. for 30 min., then at room temperature for 1 hour, the reaction was quenched with MeOH (1 mL). The reaction mixture was then concentrated under vacuum to give an off-white solid. The solid was purified by preparative TLC with 8% NH₄OH in MeOH/ CH₂Cl₂ to give Example 60 (14 mg, 44%).

Preparation of Examples 61a and 61b

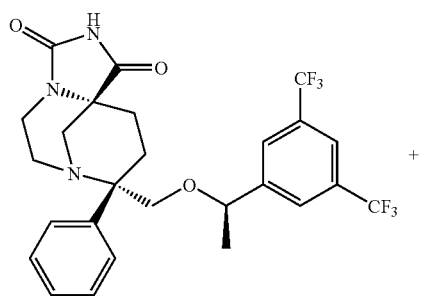

Example 61a

+

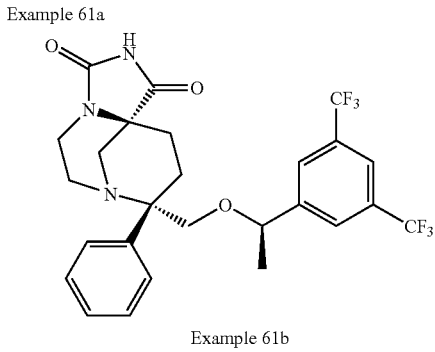

Example 61b

Step 1:

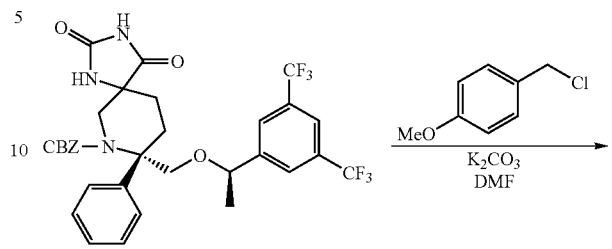

Compound Iii

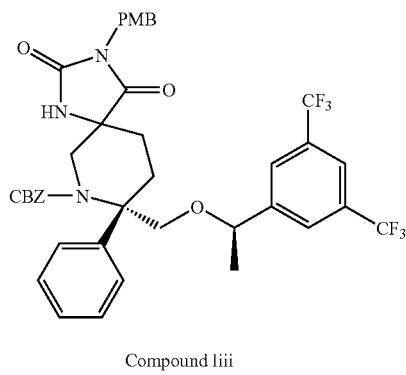

Compound Iiii

A mixture of Compound Iii (i.e., Compound 48 of U.S. Published Application 2003/158173 A1, Ser. No. 10/321, 687) (1.3 g, 2 mmol, 1 equiv.) in DMF (10 mL), p-methoxybenzyl chloride (PMB chloride) (0.34 g, 2.2 mmol, 1.2 equiv.), and K₂CO₃ (1.1 g, 8 mmol, 4 equiv.) was stirred at room temperature for 16 hours. The reaction mixture was diluted with ethyl acetate (100 mL), and then washed with saturated NH₄Cl (100 mL×2). The organic layer was isolated and dried with Na₂SO₄ and concentrated under vacuum to give a solid. The solid was purified by Biotage chromatography with 20% ethyl acetate in hexanes to give Compound Iiii (1.4 g, 93%).

Step 2:

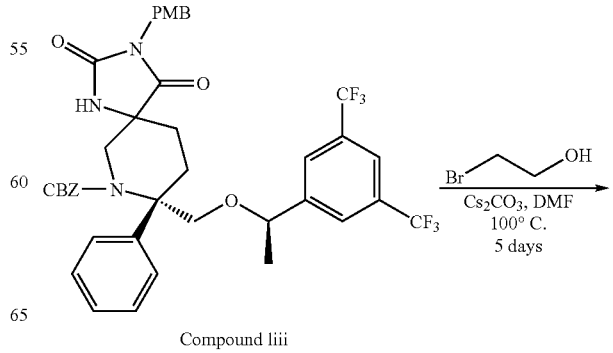

Compound Iiii

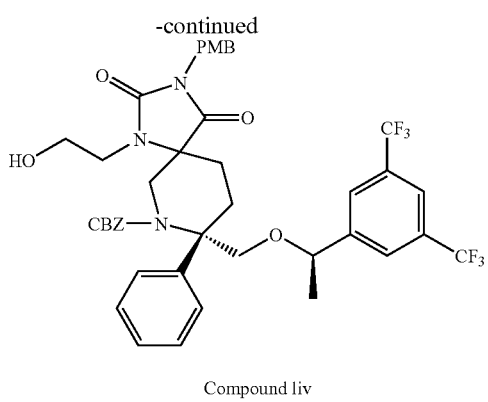

Compound liv

A mixture of Compound liii (1.3 g, 1.69 mmol, 1 equiv.) in anhydrous DMF (15 mL), 2-bromoethanol (0.42 g, 3.4 mmol, 2 equiv.), Cs$_2$CO$_3$ (2.2 g, 6.8 mmol, 4 equiv.), and NaI (0.4 g) was stirred and heated to 100° C. for 5 days. The reaction mixture was then diluted with ethyl acetate (150 mL) and washed with saturated NH$_4$Cl (100 mL×2). The organic solution was dried with Na$_2$SO$_4$ and concentrated under vacuum to give a solid. The solid was purified by Biotage chromatography with 30% ethyl acetate in hexanes to give Compound liv (0.85 g, 61%).

Step 3:

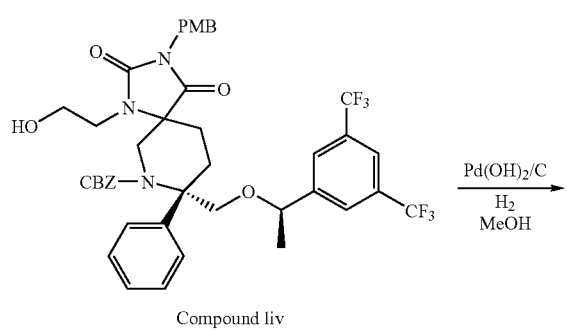

Compound liv

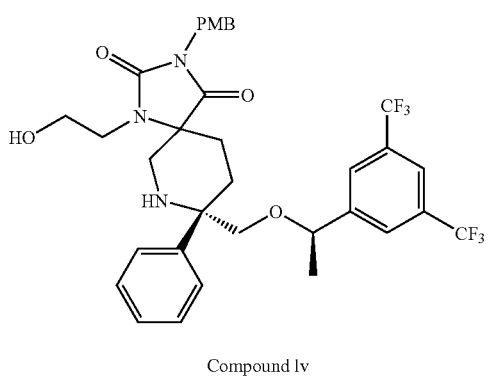

Compound lv

A mixture of Compound liv (2.85 g, 3.5 mmol, 1 equiv.) in MeOH (30 mL) and 20% Pd(OH)$_2$/C (0.57 g, 20% by weight) was hydrogenated with a H$_2$ balloon for 5 hours. The catalyst was filtered off, and the resulting filtrate was concentrated under vacuum to give Compound lv (2.23 g, 94%).

Step 4:

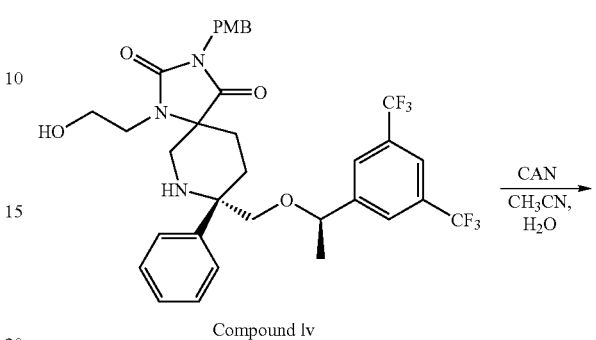

Compound lv

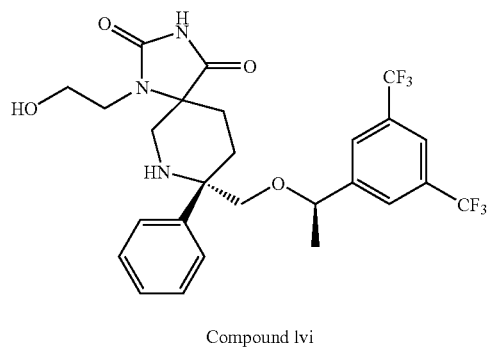

Compound lvi

Into a solution of Compound lv (2.23 g, 3.28 mmol, 1 equiv.) in CH$_3$CN/H$_2$O(3:1, 40 mL), which was cooled to 0° C., was added ammonium cerium nitrate (7.7 g, 13.1 mmol, 4 equiv.). After stirring under N$_2$ at 0° C. for 5 hours, then at room temperature for 16 hours, the reaction mixture was taken up in H$_2$O (200 mL)/ethyl acetate (200 mL). The organic layer was washed with saturated NaHCO$_3$ (200 mL×2) and brine (100 ml), isolated, dried with Na$_2$SO$_4$, and concentrated under vacuum to give a foamy solid. The solid was purified by Biotage chromatography with 4.5% NH$_4$OH in MeOH/CH$_2$Cl$_2$ to give Compound lvi (1.48 g, 82%).

Step 5:

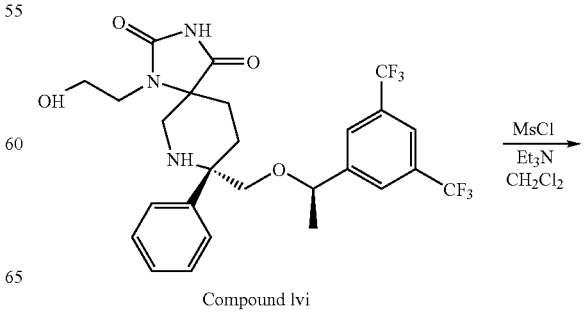

Compound lvi

-continued

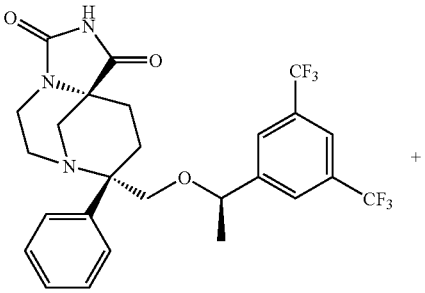

Example 61a

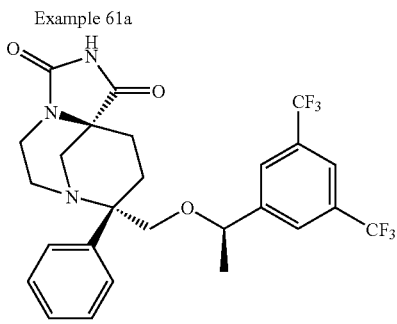

Example 61b

Into a solution of Compound lvi (55 mg, 0.098 mmol, 1 equiv.) in anhydrous $CH_2Cl_2$ (1 mL) and triethyl amine (12 mg, 0.12 mmol, 1.2 equiv.), which was cooled to 0° C., was added methanesulfonyl chloride (14 mg, 0.12 mmol, 1.2 equiv.). After stirring under $N_2$ at 0° C. for 2 hours, then at room temperature for 16 hours, the reaction mixture was concentrated under vacuum to give a foamy solid. The solid was purified on prep TLC with 4% $NH_4OH$ in MeOH/$CH_2Cl_2$ to give Example 61a (20 mg, 38%) and Example 61b (14 mg, 26%).

While the present invention has been described in conjunction with the specific embodiments set forth above, many alternatives, modifications, and variations thereof will be apparent to those of ordinary skill in the art. All such alternatives, modifications, and variations are intended to fall within the spirit and scope of the present invention.

What is claimed is:
1. A compound of Formula (I):

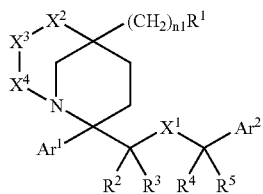

or a pharmaceutically acceptable salt, thereof, wherein:
$Ar^1$ and $Ar^2$ are each independently selected from the group consisting of aryl substituted with 0 to 3 substituents $R^6$ and heteroaryl substituted with 0 to 3 substituents $R^6$;
$X^1$ is —O—;
$X^2$ is —N($R^8$)—;
$X^3$ is —C(O)—;
$X^4$ is —C($R^9$)$_2$—;
n1 is an integer of from 0 to 4;

$R^1$ is selected from the group consisting of H, —OH, alkyl, alkyl substituted with one or more hydroxyl groups, —O-alkyl, —O-alkyl-cycloalkyl, heteroaryl or aryl substituted with 0 to 3 substituents $R^6$, —N($R^7$)$_2$, —N($R^{11}$)C(O)$R^{12}$, heterocyclyl substituted with 0 to 3 substituents $R^{13}$, —N($R^{11}$)C(O)N($R^{14}$)$_2$, —OC(O)N($R^{14}$)$_2$, —C(O)N($R^{14}$)$_2$, —C(O)$R^{12}$, —OC(O)$R^{12}$, —C(O)O$R^{15}$, —CN, —CH$_2$N$_3$, —O-alkyl-aryl, —O—N=C($R^{12}$)$_2$, —S—$R^{12}$, —S(O)—$R^{12}$, —S(O$_2$)—$R^{12}$, and N($R^{11}$)S(O$_2$)—$R^{12}$; or
when $X^2$ is —N($R^8$)—, $R^1$ and $R^8$ together can form a group $X^5$ as shown in Formula (IA):

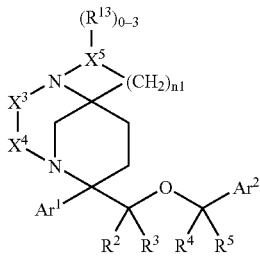

wherein $X^5$ is selected from the group consisting of —C(O)—, —(CH$_2$)$_{n2}$—O—, —(CH$_2$)$_{n2}$—, —(CH$_2$)$_{n2}$—C(O)—N($R^{13}$)—, —(CH$_2$)$_{n2}$—N($R^{13}$)—, and —C(O)—N($R^{13}$)—C(O)—;
n2 is an integer of from 1 to 3;
with the proviso that:
(a) when $X^5$ is —C(O)—, n1 is 2 or 3;
(b) when $X^5$ is —(CH$_2$)$_{n2}$—O—, n2 is 2 or 3; and
(c) when $X^5$ is —(CH$_2$)$_{n2}$—, n1 is 2 or 3;
$R^2$, $R^3$, $R^4$, and $R^5$ are each independently selected from the group consisting of H, alkyl, haloalkyl, cycloalkyl, heterocyclyl substituted with 0 to 3 substituents $R^{13}$, and aryl or heteroaryl substituted with 0 to 3 substituents $R^6$;
each $R^6$ is independently selected from the group consisting of halogen, alkyl, —O-alkyl, haloalkyl, —O-haloalkyl, —CN, —OH, unsubstituted heteroaryl, and heteroaryl substituted with at least one alkyl or haloalkyl;
$R^7$ is selected from the group consisting of H, alkyl, haloalkyl, cycloalkyl, heterocyclyl substituted with 0 to 3 substituents $R^{13}$, aryl substituted with 0 to 3 substituents $R^6$, -alkyl-aryl wherein the aryl moiety is substituted with 0 to 3 substituents $R^6$, and heteroaryl substituted with 0 to 3 substituents $R^6$;
$R^8$ is selected from the group consisting of H, alkyl, -alkyl-cycloalkyl, —C(O)N($R^{14}$)$_2$, —C(O)$R^{12}$, and aryl or heteroaryl substituted with 0 to 3 substituents $R^6$;
each $R^9$ is independently selected from the group consisting of H, alkyl, haloalkyl, cycloalkyl, heterocyclyl, aryl, and heteroaryl;
$R^{10}$ is alkyl or aryl.
2. The compound of claim 1, wherein:
$Ar^1$ is aryl;
$Ar^2$ is aryl substituted with 0 to 3 substituents $R^6$;
$X^1$ is —O—;
$X^2$ is —N($R^8$)—;
$X^3$ is —C(O)—;
$X^4$ is —C($R^9$)$_2$—;
n1 is an integer of from 0 to 3;

$R^1$ is selected from the group consisting of H, —OH, $(C_{1-6})$alkyl, $(C_{1-6})$alkyl substituted with one or more hydroxyl groups, —O-alkyl, —O—$(C_{1-6})$alkyl-$(C_{3-6})$cycloalkyl, heteroaryl substituted with 0 to 3 substituents $R^6$, —$N(R^7)_2$, —$N(R^{11})C(O)R^{12}$, heterocyclyl substituted with 0 to 3 substituents $R^{13}$, —$N(R^{11})C(O)N(R^{14})_2$, —$OC(O)N(R^{14})_2$, —$C(O)N(R^{14})_2$, —$OC(O)R^{12}$, —$C(O)R^{12}$, —$C(O)OR^{15}$, —CN, —$CN_3$, —O-alkyl-aryl, —O—N=$C(R^{12})_2$, —S—$R^{12}$, —$S(O_2)$—$R^{12}$, and $N(R^{11})S(O_2)$—$R^{12}$; or when $X^2$ is —$N(R^8)$—, $R^1$ and $R^8$ together can form a group $X^5$ as shown in Formula (IA):

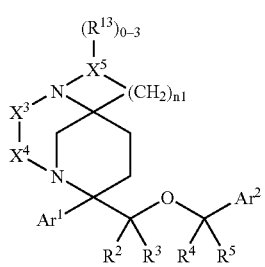

(IA)

wherein $X^5$ is selected from the group consisting of —C(O)—, —$(CH_2)_{n2}$—O—, a covalent bond, —$(CH_2)_{n2}$—C(O)—$N(R^{13})$—, and —C(O)—N$(R^{13})$—C(O)—;

n2 is an integer of from 1 to 3;

with the proviso that:
(a) when $X^5$ is —C(O)—, n1 is 2;
(b) when $X^5$ is —$(CH_2)_{n2}$—O—, n1 is 1 and n2 is 2;
(c) when $X^5$ is —$(CH_2)_{n2}$—, n1 is 2 and n2 is 1;
(d) when $X^5$ is —$(CH_2)_{n2}$—C(O)—$N(R^{13})$—, n1 and n2 are both 1; and
(e) when $X^5$ is —C(O)—$N(R^{13})$—C(O)—, n1 is 0;

$R^2$ and $R^3$ are H;
$R^4$ and $R^5$ are each independently H or $(C_{1-6})$alkyl;
each $R^6$ is independently $(C_{1-6})$alkyl or halo$(C_{1-6})$alkyl;
$R^7$ is selected from the group consisting of H, $(C_{3-6})$cycloalkyl, and —$(C_{1-6})$alkyl-aryl wherein the aryl moiety is substituted with 0 to 3 substituents $R^6$;
$R^8$ is selected from the group consisting of H, $(C_{1-6})$alkyl, —$(C_{1-6})$alkyl-$(C_{3-6})$cycloalkyl, —$C(O)N(R^{14})_2$, and —$C(O)R^{12}$;
$R^9$ is H;
$R^{10}$ is $(C_{1-6})$alkyl or aryl.

3. The compound of claim 1, wherein:
$X^2$ is —$N(R^8)$—, $X^3$ is —C(O)—, and $X^4$ is —$C(R^9)_2$—.

4. The compound of claim 1 having the structure of Formula (IA):

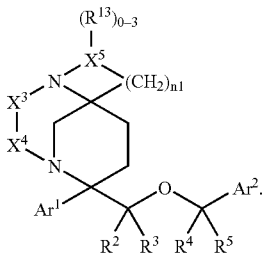

5. The compound of claim 4, wherein:
$X^5$ is —C(O)—.

6. The compound of claim 4, wherein:
$X^5$ is —$(CH_2)_{n2}$—O—.

7. The compound of claim 4, wherein:
$X^5$ is —$(CH_2)_{n2}$—.

8. The compound of claim 4, wherein:
$X^5$ is —$(CH_2)_{n2}$—C(O)—$N(R^{13})$—.

9. The compound of claim 4, wherein:
$X^5$ is —$(CH_2)_{n2}$—$N(R^{13})$—.

10. The compound of claim 4, wherein:
$X^5$ is —C(O)—$N(R^{13})$—C(O)—.

11. The compound of claim 1, wherein said compound has a structure according to the following Formula (II):

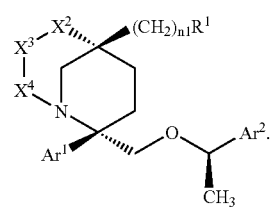

(II)

12. The compound of claim 1, wherein said compound has a structure according to the following Formula (III):

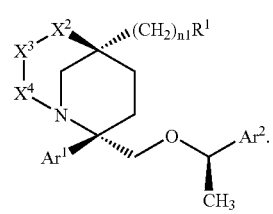

(III)

13. The compound of claim 1, wherein said compound has a structure selected from the group consisting of:

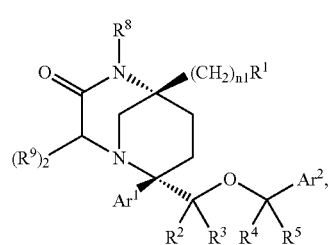

(IV)

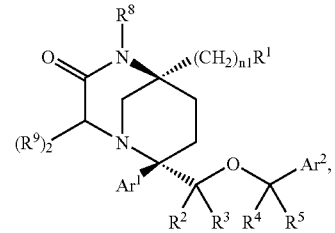

(V)

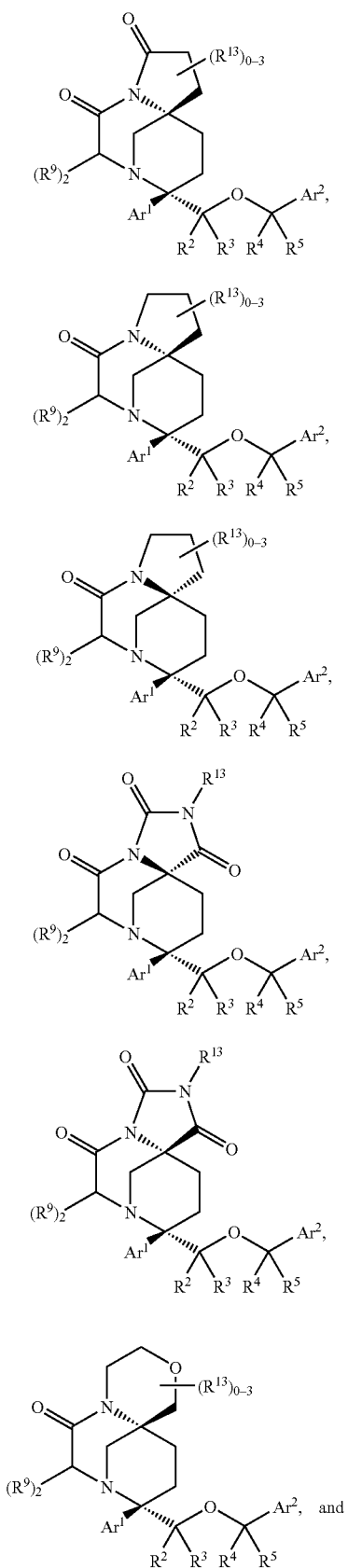

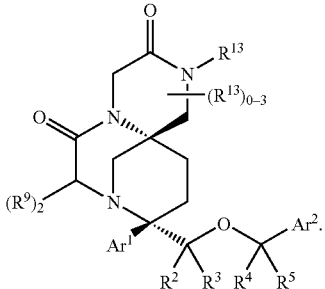

14. The compound of claim 13 having the structure of Formula (IV), wherein:

Ar$^1$ and Ar$^2$ are both phenyl substituted with 0 to 3 substituents R$^6$;

R$^1$ is selected from the group consisting of H, —OH, (C$_{1-6}$)alkyl, —(C$_{1-6}$)alkyl-OH, —O—(C$_{1-6}$)alkyl, —O—(C$_{1-6}$)alkyl-(C$_{3-6}$)cycloalkyl, —N(R$^7$)$_2$, —N(R$^{11}$)C(O)N(R$^{14}$)$_2$, —OC(O)N(R$^{14}$)$_2$, —OC(O)—(C$_{1-6}$)alkyl, —C(O)OH, —C(O)—O—(C$_{1-6}$)alkyl, —CN, —CN$_3$, —O—(C$_{1-6}$)alkyl-phenyl, —O—N=C((C$_{1-6}$)alkyl)$_2$, —S—(C$_{1-6}$)alkyl, —S(O$_2$)—(C$_{1-6}$)alkyl, and N(R$^{11}$)S(O$_2$)—(C$_{1-6}$)alkyl,

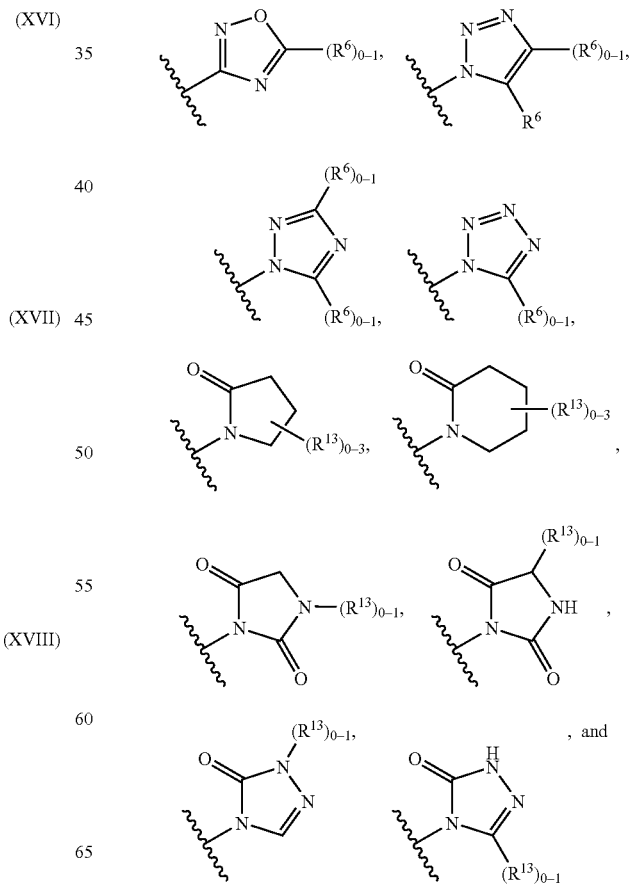

-continued

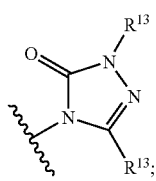

R², R³ and R⁴ are each H;

R⁵ is (C$_{1-6}$)alkyl;

each R⁶ is independently H, (C$_{1-6}$)alkyl, or (C$_{1-6}$)haloalkyl;

R⁷ is H, (C$_{1-6}$)alkyl, (C$_{3-6}$)cycloalkyl, or —(C$_{1-6}$)alkyl-phenyl;

R⁸ is H, (C$_{1-6}$)alkyl, or —(C$_{1-6}$)alkyl-(C$_{3-6}$)cycloalkyl;

each R⁹ is independently H or (C$_{1-6}$)alkyl;

R¹¹ is H or (C$_{1-6}$)alkyl;

R¹³ is H or (C$_{1-6}$)alkyl;

R¹⁴ is H, (C$_{1-6}$)alkyl, or 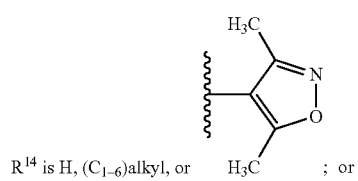 ; or two R¹⁴ groups, together with the nitrogen atom to which they are shown attached, form

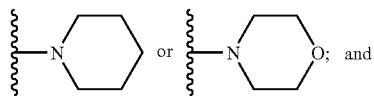 and n is 0 or 1.

15. The compound of claim 13 having the structure of Formula (V), wherein:

Ar¹ and Ar² are both phenyl substituted with 0 to 3 substituents R⁶;

R¹ is selected from the group consisting of H, —OH, (C$_{1-6}$)alkyl, —(C$_{1-6}$)alkyl-OH, —O—(C$_{1-6}$)alkyl, —O—(C$_{1-6}$)alkyl-(C$_{3-6}$)cycloalkyl, —N(R⁷)$_2$, —N(R¹¹)C(O)N(R¹⁴)$_2$, —OC(O)N(R¹⁴)$_2$, —OC(O)—(C$_{1-6}$)alkyl, —C(O)OH, —C(O)—O—(C$_{1-6}$)alkyl, —CN, —CN$_3$, —O—(C$_{1-6}$)alkyl-phenyl, —O—N=C((C$_{1-6}$)alkyl)$_2$, —S—(C$_{1-6}$)alkyl, —S(O$_2$)—(C$_{1-6}$)alkyl, and N(R¹¹)S(O$_2$)—(C$_{1-6}$)alkyl,

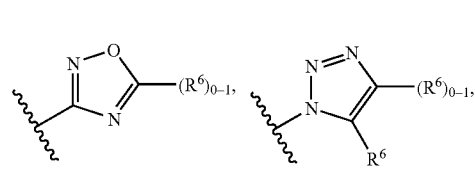

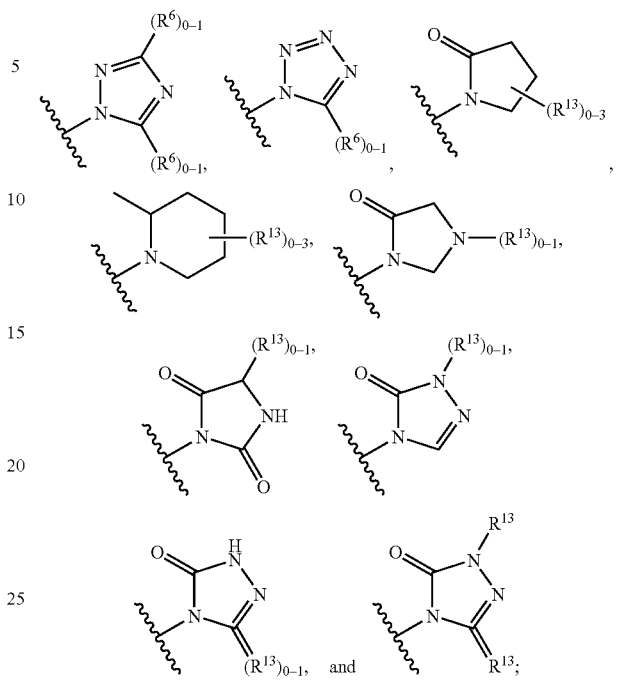

R², R³ and R⁴ are each H;

R⁵ is (C$_{1-6}$)alkyl;

each R⁶ is independently H, (C$_{1-6}$)alkyl, or (C$_{1-6}$)haloalkyl;

R⁷ is H, (C$_{1-6}$)alkyl, (C$_{3-6}$)cycloalkyl, or —(C$_{1-6}$)alkyl-phenyl;

R⁸ is H, (C$_{1-6}$)alkyl, or —(C$_{1-6}$)alkyl-(C$_{3-6}$)cycloalkyl;

each R⁹ is independently H or (C$_{1-6}$)alkyl;

R¹¹ is H or (C$_{1-6}$)alkyl;

R¹³ is H or (C$_{1-6}$)alkyl;

R¹⁴ is H, (C$_{1-6}$)alkyl, or 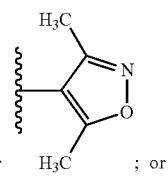 ; or two R¹⁴ groups, together with the nitrogen atom to which they are shown attached, form

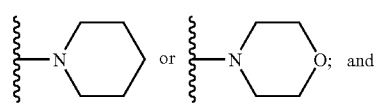 and n is 0 or 1.

16. The compound of claim 13 having the structure of Formula (XIII), wherein:

Ar¹ and Ar² are both phenyl substituted with 0 to 3 substituents R⁶;

R², R³ and R⁴ are each H;
R⁵ is (C₁₋₆)alkyl;
each R⁶ is independently H, (C₁₋₆)alkyl, or (C₁₋₆)haloalkyl;
each R⁹ is independently H or (C₁₋₆)alkyl; and
each R¹³ is independently H or (C₁₋₆)alkyl.

17. The compound of claim 13 having the structure of Formula (XIV), wherein:
Ar¹ and Ar² are both phenyl substituted with 0 to 3 substituents R⁶;
R², R³ and R⁴ are each H;
R⁵ is (C₁₋₆)alkyl;
each R⁶ is independently H, (C₁₋₆)alkyl, or (C₁₋₆)haloalkyl;
each R⁹ is independently H or (C₁₋₆)alkyl; and
each R¹³ is independently H or (C₁₋₆)alkyl.

18. The compound of claim 13 having the structure of Formula (XV), wherein:
Ar¹ and Ar² are both phenyl substituted with 0 to 3 substituents R⁶;
R², R³ and R⁴ are each H;
R⁵ is (C₁₋₆)alkyl;
each R⁶ is independently H, (C₁₋₆)alkyl, or (C₁₋₆)haloalkyl;
each R⁹ is independently H or (C₁₋₆)alkyl; and
each R¹³ is independently H or (C₁₋₆)alkyl.

19. The compound of claim 13 having the structure of Formula (XVI), wherein:
Ar¹ and Ar² are both phenyl substituted with 0 to 3 substituents R⁶;
R², R³ and R⁴ are each H;
R⁵ is (C₁₋₆)alkyl;
each R⁶ is independently H, (C₁₋₆)alkyl, or (C₁₋₆)haloalkyl;
each R⁹ is independently H or (C₁₋₆)alkyl; and
each R¹³ is independently H or (C₁₋₆)alkyl.

20. The compound of claim 13 having the structure of Formula (XVII), wherein:
Ar¹ and Ar² are both phenyl substituted with 0 to 3 substituents R⁶;
R², R³ and R⁴ are each H;
R⁵ is (C₁₋₆)alkyl;
each R⁶ is independently H, (C₁₋₆)alkyl, or (C₁₋₆)haloalkyl;
each R⁹ is independently H or (C₁₋₆)alkyl; and
each R¹³ is independently H or (C₁₋₆)alkyl.

21. The compound of claim 13 having the structure of Formula (XVIII), wherein:
Ar¹ and Ar² are both phenyl substituted with 0 to 3 substituents R⁶;
R², R³ and R⁴ are each H;
R⁵ is (C₁₋₆)alkyl;
each R⁶ is independently H, (C₁₋₆)alkyl, or (C₁₋₆)haloalkyl;
each R⁹ is independently H or (C₁₋₆)alkyl; and
each R¹³ is independently H or (C₁₋₆)alkyl.

22. The compound of claim 13 having the structure of Formula (XIX), wherein:
Ar¹ and Ar² are both phenyl substituted with 0 to 3 substituents R⁶;
R², R³ and R⁴ are each H;
R⁵ is (C₁₋₆)alkyl;
each R⁶ is independently H, (C₁₋₆)alkyl, or (C₁₋₆)haloalkyl;
each R⁹ is independently H or (C₁₋₆)alkyl; and
each R¹³ is independently H, (C₁₋₆)alkyl, or —(C₁₋₆)alkyl-(C₆₋₁₂)aryl.

23. A compound, or a pharmaceutically acceptable salt thereof, selected from the group consisting of:

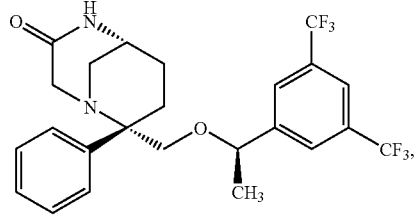

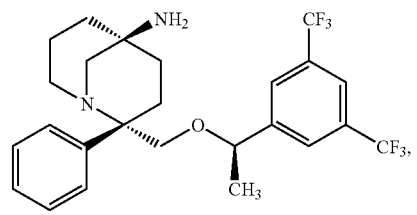

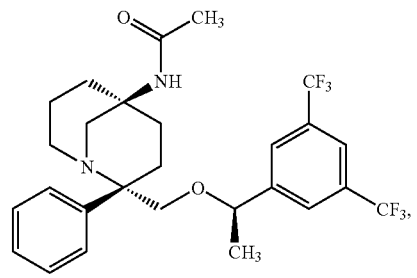

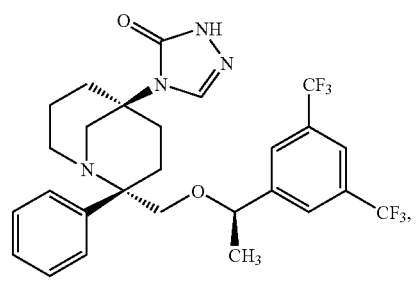

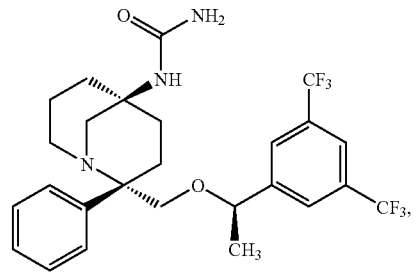

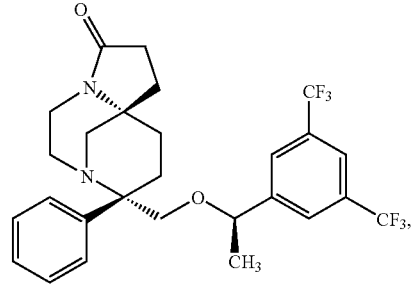

-continued
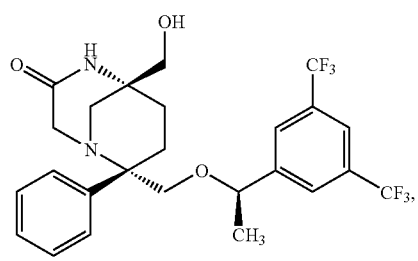
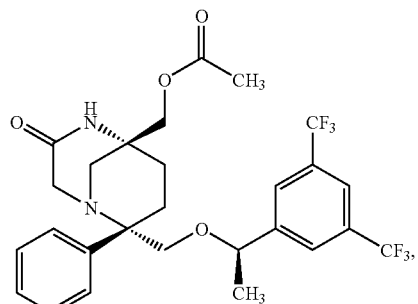
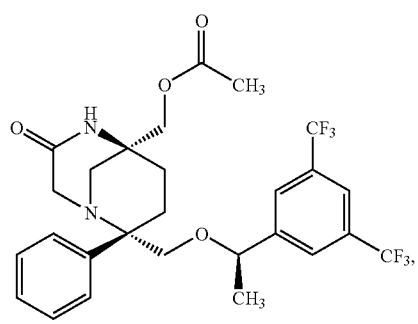
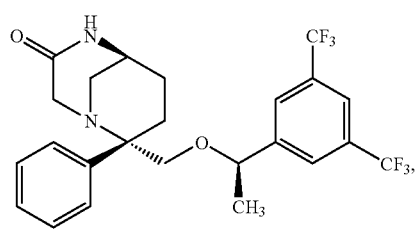
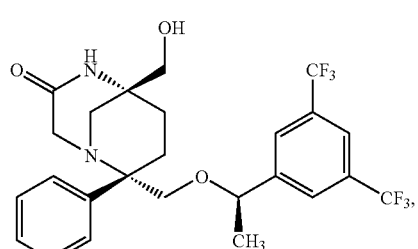
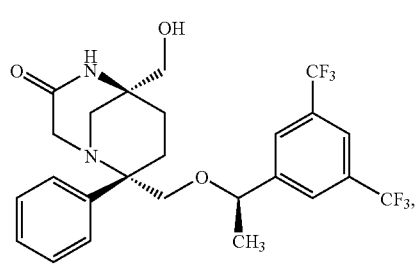
-continued
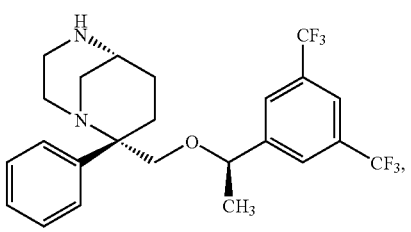
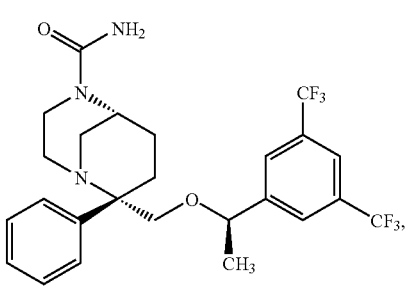
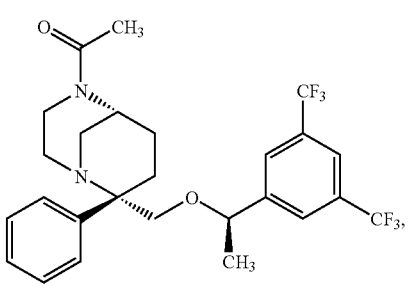
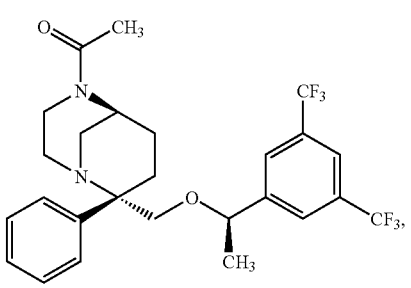
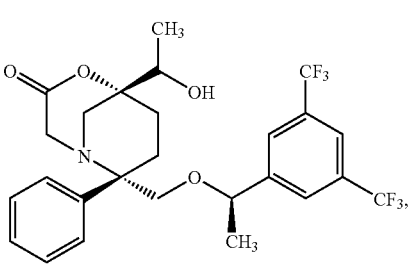
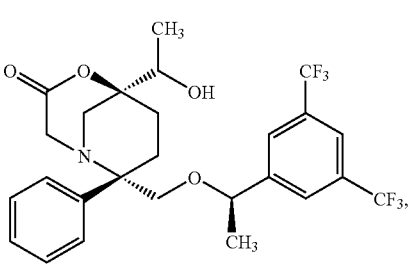

-continued
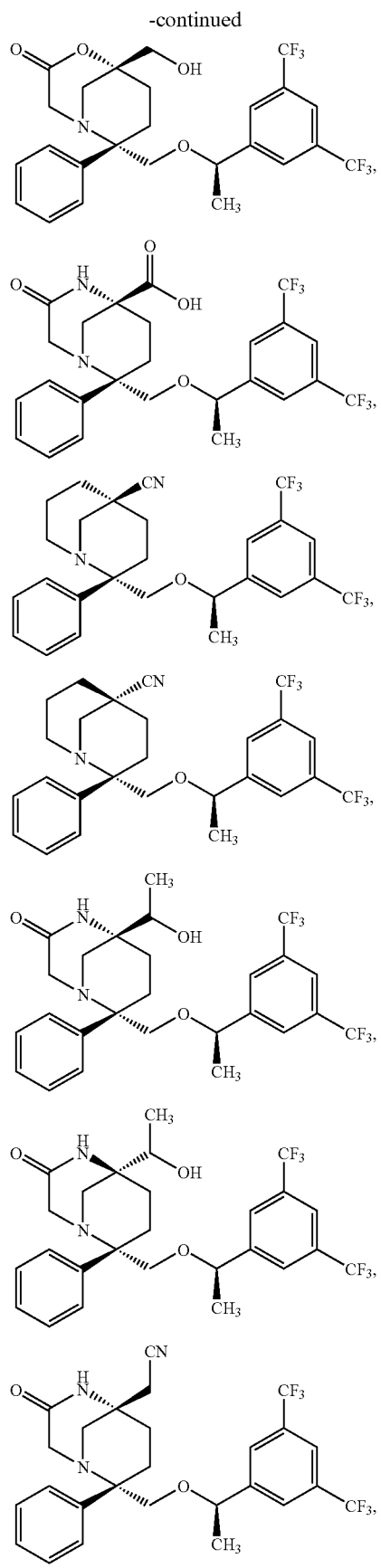
-continued
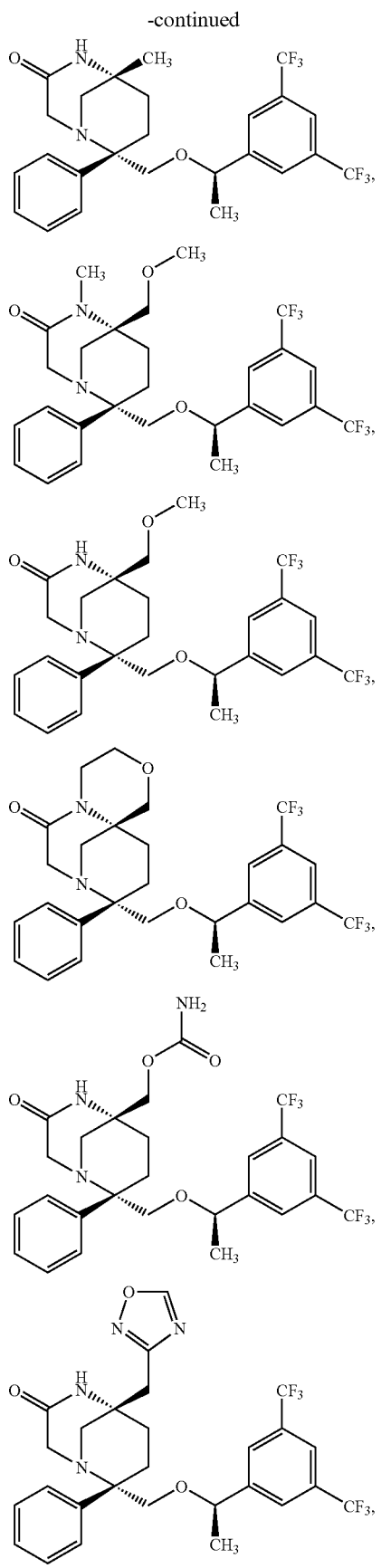

-continued
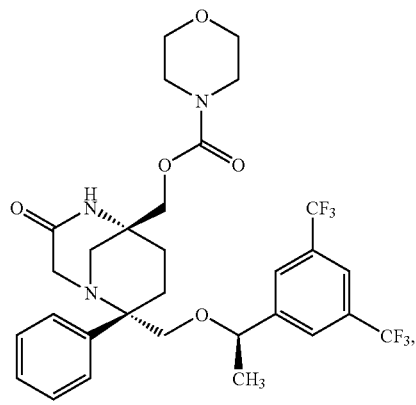
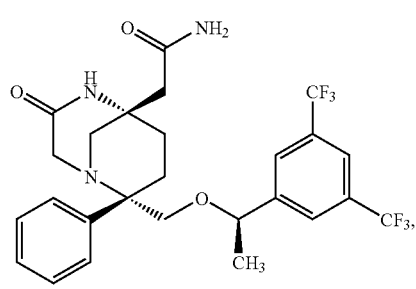
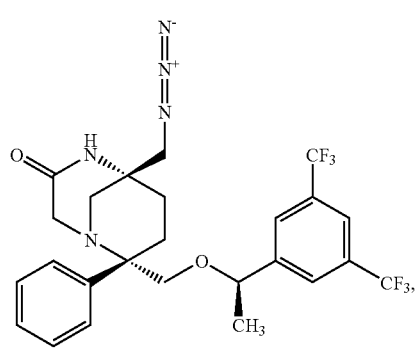
-continued
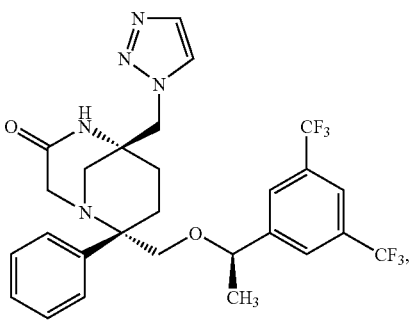
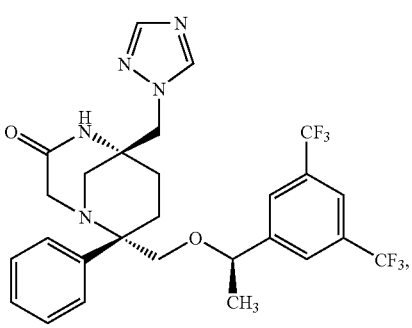
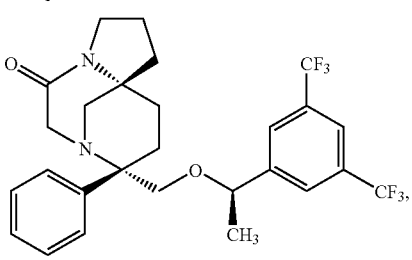
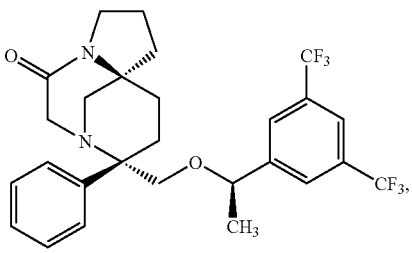
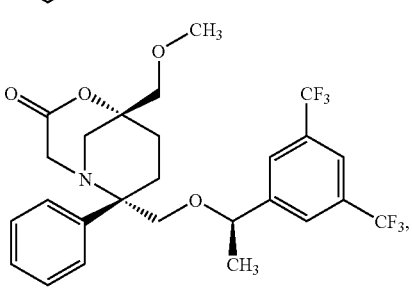
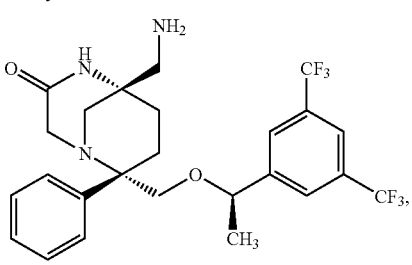

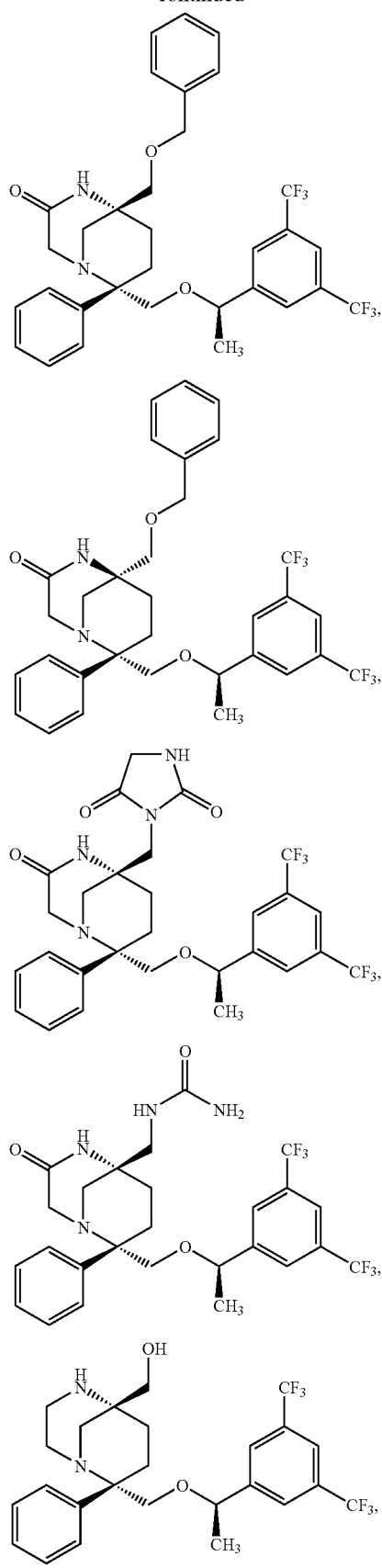
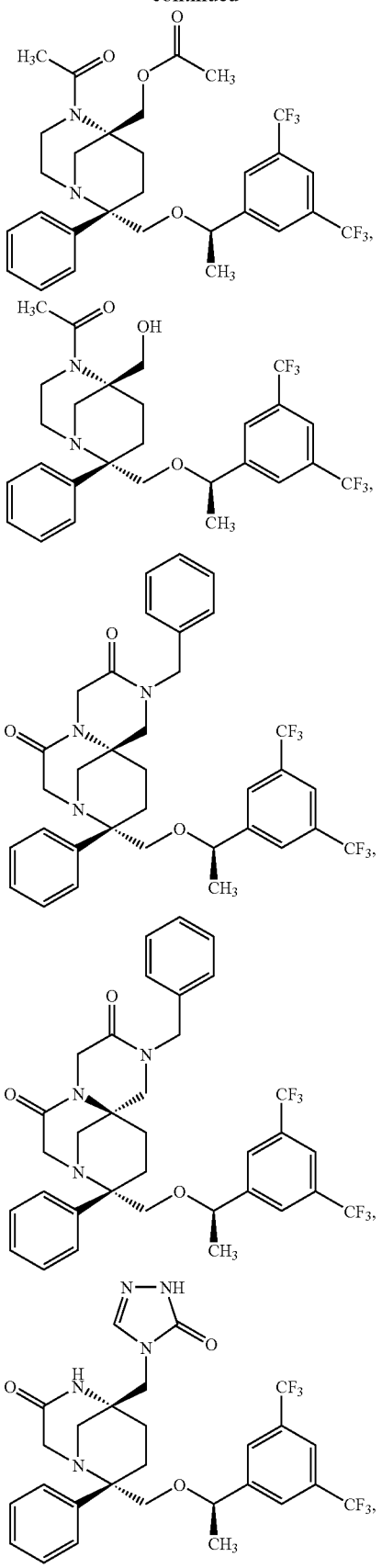

-continued
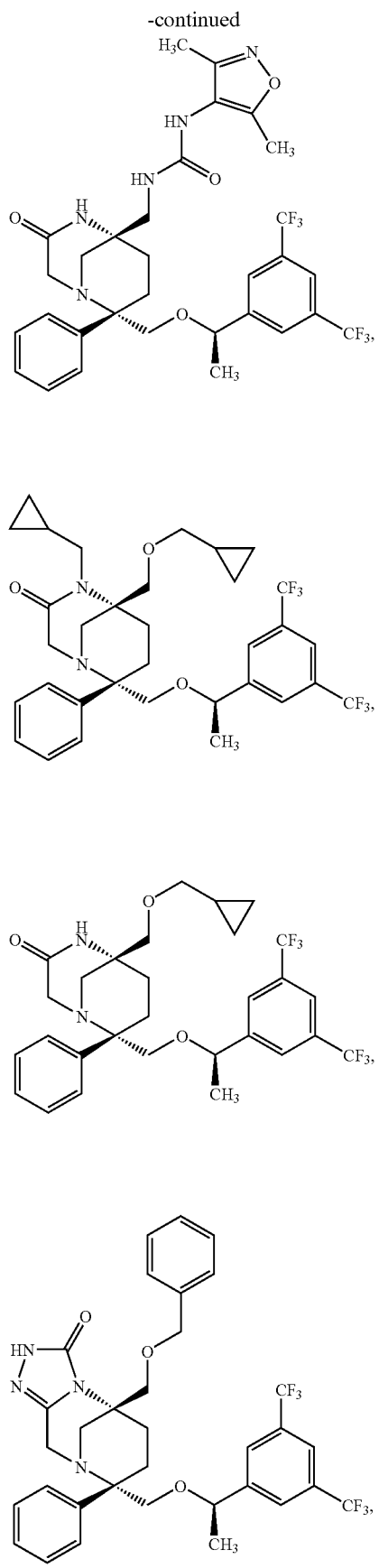
-continued
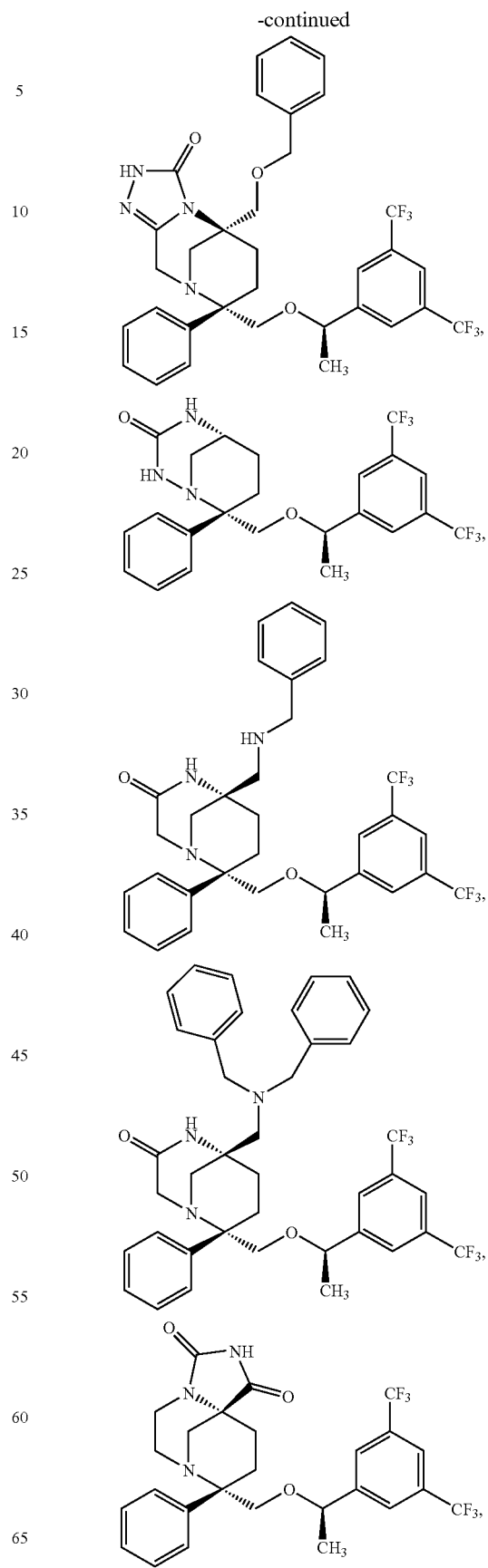

161
-continued
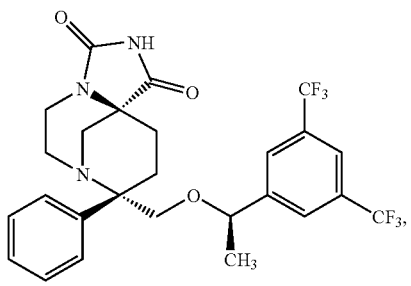
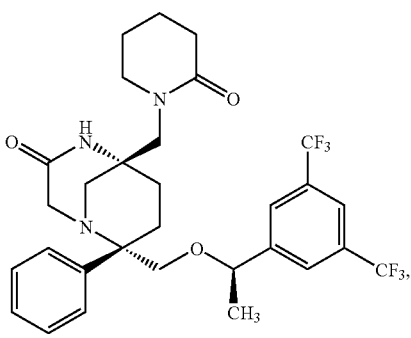
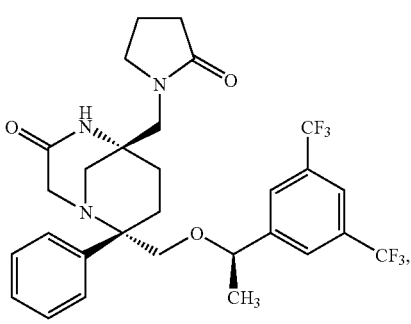
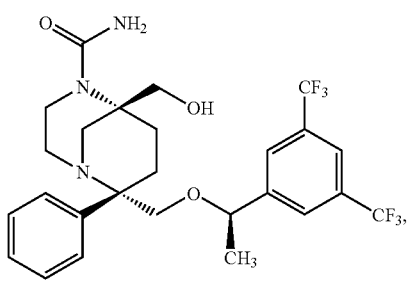
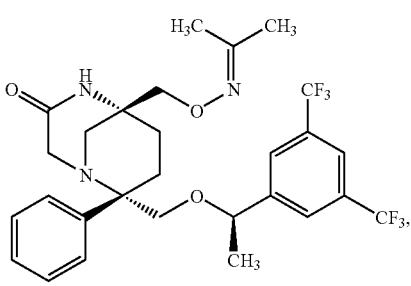
162
-continued
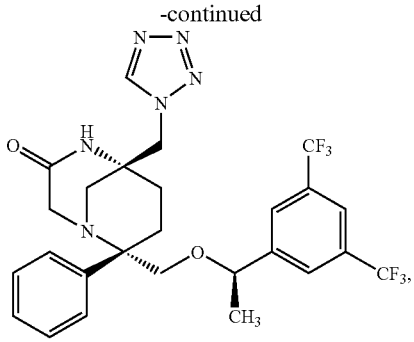
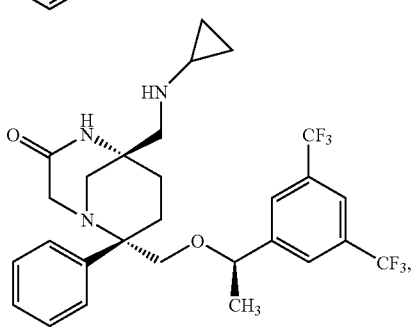
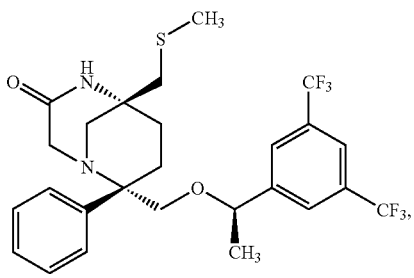
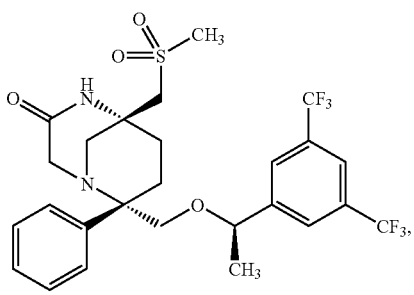
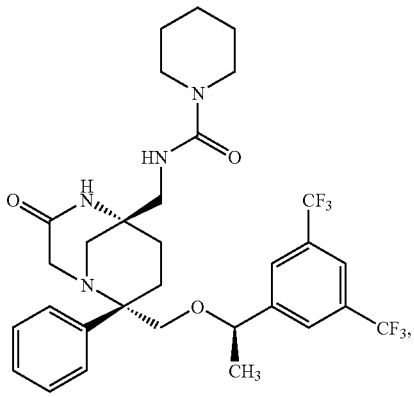

-continued

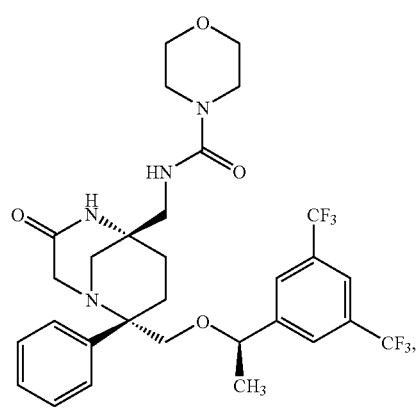

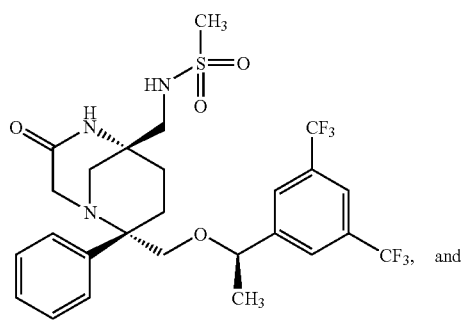

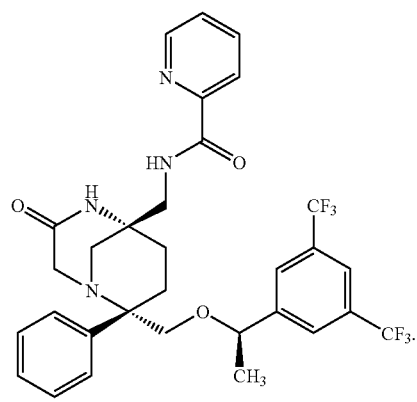

24. A compound, or a pharmaceutically acceptable salt, thereof, having the following structure:

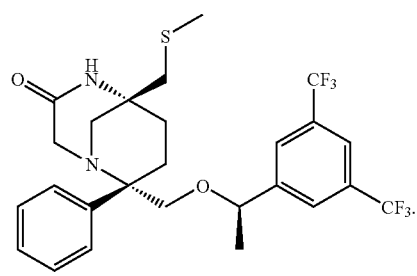

25. A compound, or a pharmaceutically acceptable salt, thereof, having the following structure:

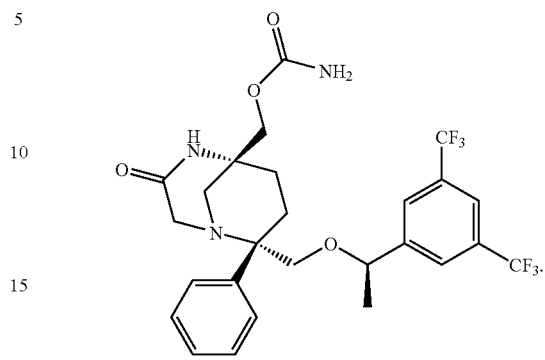

26. A compound, or a pharmaceutically acceptable salt, thereof, having the following structure:

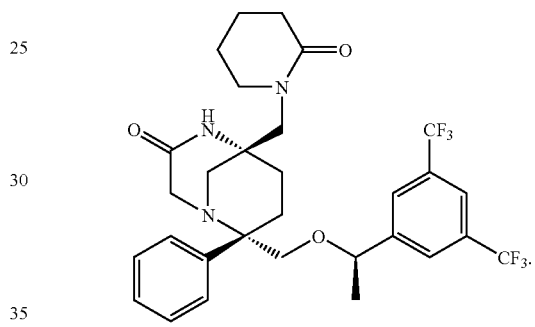

27. A compound, or a pharmaceutically acceptable salt, thereof, having the following structure:

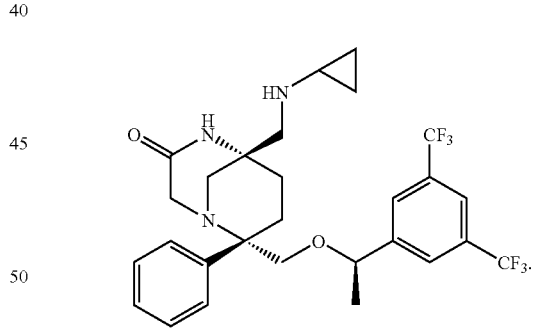

28. A mixture comprising two or more compounds of claim 23.

29. A pharmaceutical composition comprising:
   at least one compound of claim 1; and
   at least one pharmaceutically acceptable carrier.

30. A isolated compound according to claim 1.

* * * * *

UNITED STATES PATENT AND TRADEMARK OFFICE
CERTIFICATE OF CORRECTION

PATENT NO. : 7,354,922 B2 Page 1 of 1
APPLICATION NO. : 11/291363
DATED : April 8, 2008
INVENTOR(S) : Xiao et al.

It is certified that error appears in the above-identified patent and that said Letters Patent is hereby corrected as shown below:

Column 146

Claim 13, Lines 5-15, replace

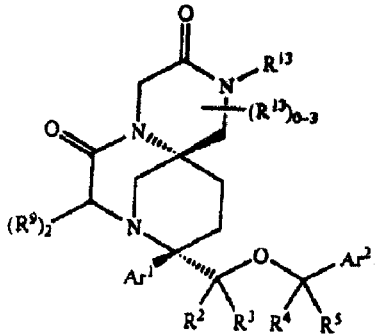

with

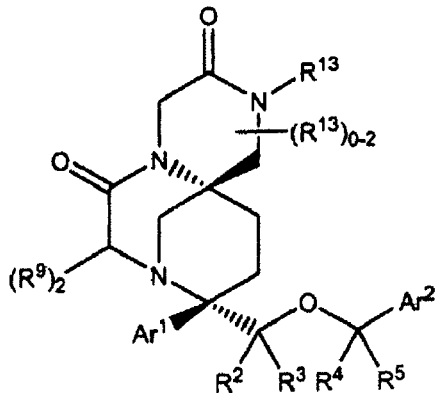

Signed and Sealed this

First Day of July, 2008

JON W. DUDAS
*Director of the United States Patent and Trademark Office*

UNITED STATES PATENT AND TRADEMARK OFFICE
CERTIFICATE OF CORRECTION

PATENT NO. : 7,354,922 B2  Page 1 of 1
APPLICATION NO. : 11/291363
DATED : April 8, 2008
INVENTOR(S) : Xiao et al.

It is certified that error appears in the above-identified patent and that said Letters Patent is hereby corrected as shown below:

Column 148, Lines 23-28,
Claim 15, replace with

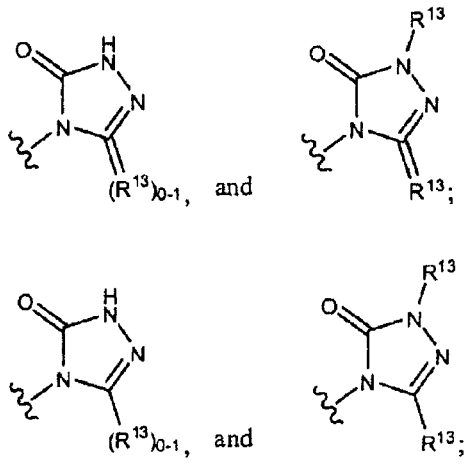

Signed and Sealed this

Twentieth Day of January, 2009

JON W. DUDAS
*Director of the United States Patent and Trademark Office*